(12) United States Patent
Wonders et al.

(10) Patent No.: US 8,114,356 B2
(45) Date of Patent: Feb. 14, 2012

(54) OPTIMIZED LIQUID-PHASE OXIDATION

(75) Inventors: Alan George Wonders, Kingsport, TN (US); Lee Reynolds Partin, Kingsport, TN (US); Wayne Scott Strasser, Kingsport, TN (US)

(73) Assignee: Grupo Pretrotemex, S.A. de C.V., San Pedro Garza Garcia (MX)

( * ) Notice: Subject to any disclaimer, the term of this patent is extended or adjusted under 35 U.S.C. 154(b) by 0 days.

(21) Appl. No.: 12/490,442

(22) Filed: Jun. 24, 2009

(65) Prior Publication Data

US 2009/0257930 A1    Oct. 15, 2009

Related U.S. Application Data

(62) Division of application No. 11/154,396, filed on Jun. 16, 2005, now Pat. No. 7,572,936.

(60) Provisional application No. 60/606,731, filed on Sep. 2, 2004, provisional application No. 60/631,499, filed on Nov. 29, 2004.

(51) Int. Cl.
*B01J 19/24* (2006.01)
(52) U.S. Cl. .................................. 422/231; 422/230
(58) Field of Classification Search ............ 422/230, 422/231
See application file for complete search history.

(56) References Cited

U.S. PATENT DOCUMENTS

| | | | |
|---|---|---|---|
| 1,902,550 A | 3/1933 | Forrest et al. | |
| 1,936,427 A | 11/1933 | Forrest et al. | |
| 2,572,575 A | 10/1951 | Shafer et al. | |
| 2,572,710 A | 10/1951 | Emerson et al. | |
| 3,029,278 A | 4/1962 | Spiller, Jr. et al. | |
| 3,064,044 A | 11/1962 | Baldwin | |
| 3,071,447 A | 1/1963 | Bernhardi | |
| 3,082,250 A | 3/1963 | Baldwin et al. | |
| 3,216,481 A | 11/1965 | Henze | |
| 3,240,803 A | 3/1966 | Thompson et al. | |
| 3,244,744 A | 4/1966 | Bowman et al. | |
| 3,255,243 A | 6/1966 | Saur et al. | |
| 3,257,363 A | 6/1966 | Miller et al. | |
| 3,293,288 A | 12/1966 | Cier et al. | |
| 3,313,849 A | 4/1967 | List et al. | |
| 3,361,803 A | 1/1968 | Augustynowicz | |

(Continued)

FOREIGN PATENT DOCUMENTS

AT        236 346        10/1964

(Continued)

OTHER PUBLICATIONS

USPTO Notice of Allowance dated Dec. 31, 2009 for copending U.S. Appl. No. 11/154,253.

(Continued)

*Primary Examiner* — Walter D Griffin
*Assistant Examiner* — Lessanework Seifu
(74) *Attorney, Agent, or Firm* — Oblon, Spivak, McClelland, Maier & Neustadt, L.L.P.

(57) ABSTRACT

Disclosed is an optimized process and apparatus for more efficiently and economically carrying out the liquid-phase oxidation of an oxidizable compound. Such liquid-phase oxidation is carried out in a bubble column reactor that provides for a highly efficient reaction at relatively low temperatures. When the oxidized compound is para-xylene and the product from the oxidation reaction is crude terephthalic acid (CTA), such CTA product can be purified and separated by more economical techniques than could be employed if the CTA were formed by a conventional high-temperature oxidation process.

8 Claims, 33 Drawing Sheets

U.S. PATENT DOCUMENTS

| | | |
|---|---|---|
| 3,388,157 A | 6/1968 | Barona |
| 3,410,897 A | 11/1968 | Shigeyasu |
| 3,452,088 A | 6/1969 | Baldwin et al. |
| 3,497,552 A | 2/1970 | Olsen |
| 3,531,944 A | 10/1970 | Lindley |
| 3,534,090 A | 10/1970 | Bryant, Jr. et al. |
| 3,549,695 A | 12/1970 | Bryant, Jr. et al. |
| 3,556,733 A | 1/1971 | Hedrick |
| 3,584,039 A | 6/1971 | Meyer |
| 3,617,033 A | 11/1971 | Ichikawa et al. |
| 3,626,001 A | 12/1971 | Keith et al. |
| 3,629,321 A | 12/1971 | Longland |
| 3,644,192 A * | 2/1972 | Li et al. ............ 208/408 |
| 3,652,445 A | 3/1972 | Senolt et al. |
| 3,660,476 A | 5/1972 | Ichikawa et al. |
| 3,663,611 A | 5/1972 | Leuck et al. |
| 3,683,018 A | 8/1972 | Longland, Jr. |
| 3,686,293 A | 8/1972 | Gualdi et al. |
| 3,700,731 A | 10/1972 | Sullivan |
| 3,708,532 A | 1/1973 | Ichikawa et al. |
| 3,759,669 A | 9/1973 | Aaron et al. |
| 3,785,779 A | 1/1974 | Li et al. |
| 3,839,435 A | 10/1974 | Shigeyasu et al. |
| 3,839,436 A | 10/1974 | Longland, Jr. |
| 3,845,117 A | 10/1974 | Kollar |
| 3,850,981 A | 11/1974 | Trebellas et al. |
| 3,850,983 A | 11/1974 | Park |
| 3,873,275 A | 3/1975 | Bennett |
| 3,880,921 A | 4/1975 | Hellemanns et al. |
| 3,883,311 A | 5/1975 | Kanai et al. |
| 3,887,612 A | 6/1975 | Shigeyasu et al. |
| 3,899,530 A | 8/1975 | Syoji et al. |
| 3,931,305 A | 1/1976 | Fisher |
| 3,996,271 A | 12/1976 | Yokota et al. |
| 3,997,620 A | 12/1976 | Neuzil |
| 4,053,506 A | 10/1977 | Park et al. |
| 4,062,654 A | 12/1977 | Shigeyasu et al. |
| 4,081,464 A | 3/1978 | Marsh et al. |
| 4,158,738 A | 6/1979 | Scott et al. |
| 4,185,073 A | 1/1980 | Marsh et al. |
| 4,233,269 A | 11/1980 | Kaye et al. |
| 4,255,590 A | 3/1981 | Allen |
| 4,263,448 A | 4/1981 | Leacock |
| 4,269,805 A | 5/1981 | Schoengen et al. |
| 4,271,127 A | 6/1981 | Borner et al. |
| 4,278,810 A | 7/1981 | Hanotier |
| 4,327,226 A | 4/1982 | Shigeyasu et al. |
| 4,332,592 A | 6/1982 | Miller |
| 4,334,086 A | 6/1982 | Hanotier et al. |
| 4,342,876 A | 8/1982 | Klingman |
| 4,356,319 A | 10/1982 | Roffia et al. |
| 4,357,475 A | 11/1982 | Hanotier et al. |
| 4,370,496 A | 1/1983 | Shigeyasu et al. |
| 4,391,985 A | 7/1983 | Hook et al. |
| 4,456,767 A | 6/1984 | Giacobbe et al. |
| 4,459,365 A | 7/1984 | Suzuki et al. |
| 4,482,524 A | 11/1984 | Hardison |
| 4,500,732 A | 2/1985 | Pett-Weeks et al. |
| 4,507,253 A | 3/1985 | Wiesmann |
| 4,545,945 A | 10/1985 | Prave et al. |
| 4,593,122 A | 6/1986 | Hashizume et al. |
| 4,594,449 A | 6/1986 | Takuma et al. |
| 4,605,763 A | 8/1986 | Kiefer et al. |
| 4,648,999 A | 3/1987 | Armstrong et al. |
| 4,769,487 A | 9/1988 | Hundley et al. |
| 4,769,489 A | 9/1988 | Abrams et al. |
| 4,772,748 A | 9/1988 | Hashizume et al. |
| 4,777,287 A | 10/1988 | Zeitlin et al. |
| 4,778,929 A | 10/1988 | Zehner et al. |
| 4,782,024 A | 11/1988 | Scott et al. |
| 4,827,025 A | 5/1989 | Shiraki et al. |
| 4,833,269 A | 5/1989 | Schroeder |
| 4,835,307 A | 5/1989 | Lindahl et al. |
| 4,855,491 A | 8/1989 | Chew et al. |
| 4,855,492 A | 8/1989 | Hundley |
| 4,863,888 A | 9/1989 | Melville et al. |
| 4,877,900 A | 10/1989 | Tamaru et al. |
| 4,892,970 A | 1/1990 | Nowicki et al. |
| 4,900,480 A | 2/1990 | Litz et al. |
| 4,908,471 A | 3/1990 | Leuck et al. |
| 4,914,230 A | 4/1990 | Abrams et al. |
| 4,939,297 A | 7/1990 | Browder et al. |
| 5,004,830 A | 4/1991 | Park et al. |
| 5,055,630 A | 10/1991 | Puppel |
| 5,068,406 A | 11/1991 | Holzhauer et al. |
| 5,095,142 A | 3/1992 | Janulis |
| 5,095,145 A | 3/1992 | Rosen |
| 5,099,064 A | 3/1992 | Huber, Jr. |
| 5,126,037 A | 6/1992 | Showalter |
| 5,132,450 A | 7/1992 | Tanaka et al. |
| 5,157,157 A | 10/1992 | Choi et al. |
| 5,166,420 A | 11/1992 | Shiraki et al. |
| 5,175,355 A | 12/1992 | Streich et al. |
| 5,198,362 A | 3/1993 | Forsyth et al. |
| 5,211,924 A | 5/1993 | Lee et al. |
| 5,227,570 A | 7/1993 | Tan |
| 5,292,934 A | 3/1994 | Sikkenga et al. |
| 5,304,676 A | 4/1994 | Hindmarsh et al. |
| 5,356,600 A | 10/1994 | Kiyonaga et al. |
| 5,359,133 A | 10/1994 | Nazimok et al. |
| 5,518,700 A | 5/1996 | Ayoub et al. |
| 5,523,474 A | 6/1996 | Kingsley et al. |
| 5,527,957 A | 6/1996 | Hindmarsh et al. |
| 5,563,293 A | 10/1996 | Hindmarsh et al. |
| 5,567,842 A | 10/1996 | Izumisawa et al. |
| 5,580,531 A | 12/1996 | Vassiliou et al. |
| 5,583,254 A | 12/1996 | Turner et al. |
| 5,679,846 A | 10/1997 | Hindmarsh et al. |
| 5,679,847 A | 10/1997 | Ohkoshi et al. |
| 5,684,187 A | 11/1997 | Ohkoshi et al. |
| 5,693,856 A | 12/1997 | Ramachandran et al. |
| 5,696,285 A | 12/1997 | Roby |
| 5,712,412 A | 1/1998 | Inary et al. |
| 5,739,384 A | 4/1998 | Albillos et al. |
| 5,756,833 A | 5/1998 | Rosen et al. |
| 5,763,648 A | 6/1998 | Hashizume et al. |
| 5,767,311 A | 6/1998 | Lee et al. |
| 5,770,629 A | 6/1998 | Degeorge et al. |
| 5,770,765 A | 6/1998 | Ohkoshi |
| 5,777,161 A | 7/1998 | Inary |
| 5,801,282 A | 9/1998 | Dassel et al. |
| 5,811,363 A | 9/1998 | Leviness et al. |
| 5,811,468 A | 9/1998 | Chang et al. |
| 5,817,702 A | 10/1998 | Behrmann et al. |
| 5,824,207 A | 10/1998 | Lyapin et al. |
| 5,824,819 A | 10/1998 | Dassel et al. |
| 5,840,968 A | 11/1998 | Lee et al. |
| RE36,008 E | 12/1998 | Hindmarsh et al. |
| 5,843,307 A | 12/1998 | Faivre et al. |
| 5,877,346 A | 3/1999 | Hindmarsh et al. |
| 5,883,292 A | 3/1999 | Dassel et al. |
| 5,898,254 A | 4/1999 | Kostov et al. |
| 5,928,521 A | 7/1999 | Levee |
| 5,928,615 A | 7/1999 | Strock et al. |
| 5,929,274 A | 7/1999 | Lamshing et al. |
| 5,939,313 A | 8/1999 | Cheng |
| 5,973,196 A | 10/1999 | Takano et al. |
| 5,980,801 A | 11/1999 | Dassel et al. |
| 5,994,567 A | 11/1999 | Kingsley et al. |
| 5,998,572 A | 12/1999 | Rostami et al. |
| 6,004,452 A | 12/1999 | Ash et al. |
| 6,013,835 A | 1/2000 | Lee et al. |
| 6,022,755 A | 2/2000 | Kinnari et al. |
| 6,037,491 A | 3/2000 | Vassiliou et al. |
| 6,057,475 A | 5/2000 | Colman et al. |
| 6,060,634 A | 5/2000 | Mikitenko et al. |
| 6,080,372 A | 6/2000 | Machado |
| 6,084,125 A | 7/2000 | Kingsley et al. |
| 6,133,470 A | 10/2000 | Beck et al. |
| 6,133,476 A | 10/2000 | Lin |
| 6,143,926 A | 11/2000 | Parten |
| 6,147,272 A | 11/2000 | Mikitenko et al. |
| 6,153,790 A | 11/2000 | June et al. |
| 6,232,495 B1 | 5/2001 | Vassiliou et al. |
| 6,288,270 B1 | 9/2001 | Dassel et al. |
| 6,288,273 B1 | 9/2001 | Heidemann et al. |
| 6,288,274 B1 | 9/2001 | DeCoster et al. |

| | | |
|---|---|---|
| 6,291,707 B1 | 9/2001 | Lin |
| 6,299,783 B1 | 10/2001 | Gerlich et al. |
| 6,307,099 B1 | 10/2001 | Turner et al. |
| 6,322,761 B1 | 11/2001 | Yamauchi et al. |
| 6,362,367 B2 | 3/2002 | Braithwaite |
| 6,375,921 B1 | 4/2002 | Eickhoff et al. |
| 6,392,091 B2 | 5/2002 | Lin |
| 6,437,176 B2 | 8/2002 | Matsuoka et al. |
| 6,489,527 B1 | 12/2002 | Ou et al. |
| 6,500,347 B2 | 12/2002 | Ohkoshi et al. |
| 6,521,786 B1 | 2/2003 | Codignola et al. |
| 6,541,525 B2 | 4/2003 | Culross |
| 6,562,997 B2 | 5/2003 | Sikkenga et al. |
| 6,620,966 B2 | 9/2003 | Ohkoshi et al. |
| 6,639,104 B2 | 10/2003 | Piras et al. |
| 6,761,860 B2 | 7/2004 | Codignola et al. |
| 6,765,113 B2 | 7/2004 | Graham et al. |
| 6,804,609 B1 | 10/2004 | Brumbaugh |
| 6,805,847 B2 | 10/2004 | Lee |
| 6,838,487 B1 | 1/2005 | Demirel et al. |
| 6,861,494 B2 | 3/2005 | Debruin |
| 7,060,853 B2 | 6/2006 | Housley et al. |
| 7,078,439 B2 | 7/2006 | Odueyungbo et al. |
| 7,273,950 B2 | 9/2007 | Varela-Fuentes et al. |
| 2001/0007910 A1 | 7/2001 | Housley et al. |
| 2001/0041811 A1 | 11/2001 | Sikkenga et al. |
| 2002/0002304 A1 | 1/2002 | Lin |
| 2002/0082462 A1 | 6/2002 | Ferraro et al. |
| 2002/0091285 A1 | 7/2002 | Housley et al. |
| 2002/0137805 A1 | 9/2002 | Huang et al. |
| 2002/0182123 A1 | 12/2002 | Ramachandran et al. |
| 2002/0183546 A1 | 12/2002 | Sheppard et al. |
| 2002/0193269 A1 | 12/2002 | Anderson et al. |
| 2002/0193629 A1 | 12/2002 | Miller, Jr. et al. |
| 2002/0193630 A1 | 12/2002 | Lin et al. |
| 2002/0198405 A1 | 12/2002 | O'Meadhra et al. |
| 2003/0147791 A1 | 8/2003 | Ding et al. |
| 2003/0152507 A1 | 8/2003 | Satchell, Jr. et al. |
| 2003/0229247 A1 | 12/2003 | Housley et al. |
| 2003/0229248 A1 | 12/2003 | Housley et al. |
| 2004/0044246 A1 | 3/2004 | Nubel et al. |
| 2004/0087814 A1 | 5/2004 | Gnagnetti et al. |
| 2004/0110980 A1 | 6/2004 | Sheppard et al. |
| 2004/0110981 A1 | 6/2004 | Sheppard et al. |
| 2004/0133057 A1 | 7/2004 | Jiang et al. |
| 2004/0143065 A1 | 7/2004 | Holub et al. |
| 2004/0215036 A1 | 10/2004 | Lin et al. |
| 2004/0225148 A1 | 11/2004 | Isogai et al. |
| 2004/0234435 A1 | 11/2004 | Bickham et al. |
| 2004/0249208 A1 | 12/2004 | Lin et al. |
| 2005/0038288 A1 | 2/2005 | Lin et al. |
| 2005/0065373 A1 | 3/2005 | Sumner, Jr. et al. |
| 2005/0107630 A1 | 5/2005 | Belmonte et al. |
| 2006/0047147 A1 | 3/2006 | Wonders |
| 2006/0047163 A1 | 3/2006 | De Vreede et al. |
| 2006/0047166 A1 | 3/2006 | Lin et al. |
| 2007/0155986 A1 | 7/2007 | Wonders et al. |
| 2007/0208190 A1 | 9/2007 | Wonders et al. |

FOREIGN PATENT DOCUMENTS

| | | |
|---|---|---|
| BE | 724 040 | 5/1969 |
| CN | 1486968 A | 4/2004 |
| CN | 1528732 A | 9/2004 |
| CN | 1785495 A | 6/2006 |
| DE | 102 11 907 | 10/2003 |
| EP | 0 265 137 | 10/1987 |
| EP | 0 274 020 A1 | 7/1988 |
| EP | 0 704 416 | 4/1996 |
| EP | 0 847 800 | 6/1998 |
| EP | 1 484 306 | 12/2004 |
| FR | 1 394 471 | 4/1965 |
| FR | 2 768 724 | 3/1999 |
| GB | 1 062 482 | 3/1967 |
| GB | 1 237 298 | 6/1971 |
| GB | 1 250 222 | 10/1971 |
| GB | 1 301 291 | 12/1972 |
| GB | 1 309 451 | 3/1973 |
| GB | 1 373 230 | 11/1974 |
| GB | 1 428 831 | 3/1976 |
| GB | 1 555 246 | 11/1979 |
| GB | 1 593 117 | 7/1981 |
| JP | 57-018647 | 1/1982 |
| JP | 58-189134 | 11/1983 |
| JP | 58-189135 | 11/1983 |
| JP | 59-093029 | 5/1984 |
| JP | 59-193101 | 11/1984 |
| JP | 59-196705 | 11/1984 |
| JP | 62 192490 | 8/1987 |
| JP | 63-209702 | 8/1988 |
| JP | 63-237207 | 10/1988 |
| JP | 406055062 | 1/1994 |
| JP | 06 215618 | 8/1994 |
| JP | 08151347 | 6/1996 |
| JP | 036313 | 2/1998 |
| JP | 10226666 | 8/1998 |
| JP | 63-267744 | 11/1998 |
| JP | 2000/191583 | 7/2000 |
| JP | 2001/226315 | 8/2001 |
| JP | 2004-168716 | 6/2004 |
| RU | 2 268 086 C2 | 1/2006 |
| WO | WO 93/24441 A1 | 12/1993 |
| WO | WO 96/03163 A1 | 2/1996 |
| WO | WO 97/27168 | 7/1997 |
| WO | WO 97/30963 | 8/1997 |
| WO | WO 00/23383 | 4/2000 |
| WO | WO 00/31014 | 6/2000 |
| WO | WO 01/51443 A2 | 7/2001 |
| WO | WO 02/055468 | 7/2002 |
| WO | WO 2004/052820 | 6/2004 |
| WO | WO 2004/058377 A1 | 7/2004 |
| WO | WO 2006/096311 A1 | 9/2006 |

OTHER PUBLICATIONS

New Copending U.S. Appl. No. 12/702,725, filed Feb. 9, 2010, Alan George Wonders, et al.

New Copending U.S. Appl. No. 12/703,331, filed Feb. 10, 2010, Alan George Wonders, et al.

USPTO Office Action dated Mar. 15, 2010 for copending U.S. Appl. No. 12/490,441.

USPTO Office Action dated Mar. 25, 2010 for copending U.S. Appl. No. 11/153,994.

Jeanneret, John J., "Handbook of Petroleum Refining Processes," 1997, Chapter 2.6, McGraw-Hill.

Haibo Jin et al., "An experimental study of holdups in large-scale p-xylene oxidation reactors using the y-ray attenuation approach," Feb. 24, 2005, Chemical Engineering Science.

Mathis, Kyle, "Safe Handling and Storage of Paraxylene," 2005, Chevron Phillips Chemical Company.

Lemoine, Romain, et al., "Hydrodynamic and Mass-Transfer Characteristics in Organic Liquid Mixtures in a Large-Scale Bubble Column Reactor for the Toluene Oxidation Process", Ind. Eng. Chem. Res., 2004, pp. 6195-6212, vol. 43, American Chemical Society.

Maretto, C., et al., "Design and optimisation of a multi-stage bubble column slurry reactor for Fischer-Tropsch synthesis," Catalysis Today, 2001, pp. 241-248, vol. 66.

Dziallas, Holger, et al., "Measurement of Local Phase Holdups in a Two- and Three-Phase Bubble Column," Chem. Eng. Technol., 2000, pp. 877-884, vol. 23, No. 10.

Mills, P. L. and Chaudhari, R. V.; "Reaction engineering of emerging oxidation processes," Catalysis Today, 1999, pp. 17-29, vol. 48.

Lam, Margaretha J.; "Vibration Control through Passive Constrained Layer Damping and Active Control," Journal of Intelligent Material Systems and Structures, Aug. 1997, pp. 663-677, vol. 8.

Jin, Haibo et al.; "Bubble Behavior of a Large-Scare Bubble Column with Elevated Pressure", Chemical Engineering and Technology, Sep. 1, 2004; pp. 1007-1013, vol. 27, No. 9.

Saxena S.C., "Bubble Column Reactors and Fischer-Tropsch Synthesis," Catalysis Reviews Science and Engineering, 1995, pp. 237-309, vol. 37, No. 2, New York.

Vitankar, V.S. et al., "A low Reynolds number k-e model for the prediction of flow pattern and pressure drop in bubble column reactors," Chemical Engineering Science, 2002, pp. 3235-3260, vol. 57.

Gerstenberg, H., "Bubble-column Reactors," Chemie Ingenieur Technik, Wiley Vch., 1979, pp. 208-216, vol. 51, No. 3.

Tang, C. et al., "Time-Dependent Gas Holdup Variation in an Air-Water Bubble Column," Chemical Engineering Science, vol. 59, No. 3, Feb. 2004.

Partenheimer, W., "Methodology and scope of metal/bromide autoxidation of hydrocarbons," Catalysis Today, 1995, vol. 23, p. 81.

Rubio, F. Camacho et al., "Mixing in Bubble Columns; a New Approach for Characterizing Dispersion Coefficients," Chemical Engineering Science, Jun. 2004, pp. 4369-4376, vol. 59, No. 20, Oxford, GB.

Urseanu, M.I. et al., "Influence of Operating Pressure on the Gas Hold-Up in Bubble Column for High Viscous Media," Chemical Engineering Science, Feb. 2003, pp. 697-704, vol. 58, No. 3-6, Oxford, GB.

Bando, Yoshijuki et al., "Effects of Equipment Dimensions on Liquid Mixing Time of Bubble Column with Draft Tube," Journal of Chemical Engineering of Japan, Oct. 1998, pp. 765-770, vol. 31, No. 5, Society of Chemical Engineers, Tokyo, Japan.

Andou, Satoshi et al., "Effect of Gas Sparger Type on Operational Characteristics of a Bubble Column under Mechanical Foam Control," Journal of Chemical Technology and Biotechnology, May 1996, pp. 65-71, vol. 66, No. 1, Wiley & Sons, Chichester, GB.

Li, Xi, "From Chemical Reaction Engineering toward Process System Engineering: The Road of Research on Domestic Development of PTA Technology," Chemical Reaction Engineering and Technology, China, Oct. 2005, pp. 385-391, vol. 21, No. 5.

Michele, V. et al.; "Liquid Flow and Phase Holdup-Measurement and CFD Modeling for Two-and Three-Phase Bubble Columns"; Chemical Engineering Science, Oxford, GB, vol. 57, No. 11, Jun. 2002, pp. 1899-1908.

Boyer, C. et al; "Measuring Techniques in Gas-Liquid and Gas-Liquid-Solid Reactors"; Chemical Engineering Science, Oxford, GB, vol. 57, No. 16, Aug. 2002, pp. 3185-3215.

Zehner, P. et al; "Ullmann's Encyclopedia of Industrial Chemistry, Chapter Bubble Columns"; Ullmann's Encyclopedia of Industrial Chemistry. Electronic Release, 1999, pp. 1-63.

Kim, D. et al, "Analysis of Organic Impurities in Terephthalic Acid Manufacturing Process," Kongop Hwahak 1996, 7(6), 1204-1208.

Xie, G. et al., "Concentration Profile of TA in p-Xylene Oxidation Bubble Column Reactors," Polyester Industry, China, vol. 18, No. 2, 2005.

Copending U.S. Appl. No. 11/154,480, filed Jun. 16, 2005.
Copending U.S. Appl. No. 11/154,140, filed Jun. 16, 2005.
Copending U.S. Appl. No. 11/154,220, filed Jun. 16, 2005.
Copending U.S. Appl. No. 11/154,481, filed Jun. 16, 2005.
Copending U.S. Appl. No. 11/154,448, filed Jun. 16, 2005.
Copending U.S. Appl. No. 11/154,478, filed Jun. 16, 2005.
Copending U.S. Appl. No. 11/154,116, filed Jun. 16, 2005.
Copending U.S. Appl. No. 11/154,484, filed Jun. 16, 2005.
Copending U.S. Appl. No. 11/154,479, filed Jun. 16, 2005.
Copending U.S. Appl. No. 11/154,221, filed Jun. 16, 2005.
Copending U.S. Appl. No. 11/154,219, filed Jun. 16, 2005.
Copending U.S. Appl. No. 11/154,482, filed Jun. 16, 2005.
Copending U.S. Appl. No. 11/154,163, filed Jun. 16, 2005.
Copending U.S. Appl. No. 11/154,201, filed Jun. 16, 2005.
Copending U.S. Appl. No. 11/154,504, filed Jun. 16, 2005.
Copending U.S. Appl. No. 11/154,139, filed Jun. 16, 2005.
Copending U.S. Appl. No. 11/154,253, filed Jun. 16, 2005.
Copending U.S. Appl. No. 11/154,396, filed Jun. 16, 2005.
Copending U.S. Appl. No. 11/154,237, filed Jun. 16, 2005.
Copending U.S. Appl. No. 11/154,165, filed Jun. 16, 2005.
Copending U.S. Appl. No. 11/153,994, filed Jun. 16, 2005.
Copending U.S. Appl. No. 11/153,993, filed Jun. 16, 2005.
Copending U.S. Appl. No. 11/154,218, filed Jun. 16, 2005.
Copending U.S. Appl. No. 11/154,202, filed Jun. 16, 2005.
Copending U.S. Appl. No. 11/271,308, filed Jun. 16, 2005.
Copending U.S. Appl. No. 11/365,461, filed Mar. 1, 2006.
Copending U.S. Appl. No. 11/365,350, filed Mar. 1, 2006.
Copending U.S. Appl. No. 11/365,441, filed Mar. 1, 2006.
Copending U.S. Appl. No. 11/846,822, filed Aug. 29, 2007.
Copending U.S. Appl. No. 11/846,817, filed Aug. 29, 2007.
Copending U.S. Appl. No. 11/846,801, filed Aug. 29, 2007.
Copending U.S. Appl. No. 11/846,811, filed Aug. 29, 2007.
Copending U.S. Appl. No. 11/846,851, filed Aug. 29, 2007.
Copending U.S. Appl. No. 12/105,389, filed Apr. 18, 2008.
USPTO office action dated Jan. 30, 2007, for copending U.S. Appl. No. 11/154,478.
USPTO Office Action dated Mar. 23, 2007, for copending U.S. Appl. No. 11/154,484.
USPTO Office Action dated Mar. 20, 2007, for copending U.S. Appl. No. 11/365,461.
USPTO Office Action dated Mar. 19, 2007, for copending U.S. Appl. No. 11/365,350.
USPTO Office Action dated Mar. 21, 2007, for copending U.S. Appl. No. 11/154,220.
USPTO Office Action dated Mar. 28, 2007 for copending U.S. Appl. No. 11/154,165.
Reactor Technology, in Kirk-Othmer Encyclopedia of Chemical Technology, 2001, John Wiley & Sons, Inc.; http://www.interscience.wiley.come/emrw/0471238966/kirk/titles?filter=R.
Neathery, J.K., "A Composition of Fischer-Tropsch Synthesis in a Slurry Bubble Column Reactor and a Continuous Stirred Tank Reactor," Studies in Surface Science and Catalysis, 2001, 139, 407-414.
USPTO Office Action dated Apr. 5, 2007 for copending U.S. Appl. No. 11/153,994.
USPTO Office Action dated Apr. 10, 2007 for copending U.S. Appl. No. 11/154,139.
USPTO Office Action dated Apr. 13, 2007 for copending U.S. Appl. No. 11/154,140.
USPTO Office Action dated Apr. 16, 2007 for copending U.S. Appl. No. 11/154,482.
USPTO Office Action dated Apr. 17, 2007 for copending U.S. Appl. No. 11/154,480.
USPTO Office Action dated Apr. 20, 2007 for copending U.S. Appl. No. 11/154,221.
USPTO Office Action dated May 17, 2007 for copending U.S. Appl. No. 11/154,448.
USPTO Office Action dated Jun. 4, 2007 for copending U.S. Appl. No. 11/154,481.
USPTO Office Action dated Aug. 24, 2007 for copending U.S. Appl. No. 11/154,478.
USPTO Notice of Allowance dated Sep. 20, 2007 for copending U.S. Appl. No. 11/154,481.
USPTO Office Action dated Nov. 2, 2007 for copending U.S. Appl. No. 11/154,448.
USPTO Office Action dated Nov. 2, 2007 for copending U.S. Appl. No. 11/153,994.
USPTO Notice of Allowance dated Nov. 20, 2007 for copending U.S. Appl. No. 11/154,140.
USPTO Notice of Allowance dated Nov. 8, 2007 for copending U.S. Appl. No. 11/365,461.
USPTO Notice of Allowance dated Nov. 13, 2007 for copending U.S. Appl. No. 11/365,350.
USPTO Notice of Allowance dated Nov. 13, 2007 for copending U.S. Appl. No. 11/154,484.
USPTO Notice of Allowance dated Nov. 20, 2007 for copending U.S. Appl. No. 11/154,139.
USPTO Office Action dated Nov. 16, 2007 for copending U.S. Appl. No. 11/154,480.
USPTO Office Action dated Nov. 6, 2007 for copending U.S. Appl. No. 11/154,220.
USPTO Office Action dated Nov. 21, 2007 for copending U.S. Appl. No. 11/154,219.
USPTO Office Action dated Dec. 5, 2007 for copending U.S. Appl. No. 11/154,163.
USPTO Office Action dated Dec. 5, 2007 for copending U.S. Appl. No. 11/846,811.
USPTO Office Action dated Dec. 5, 2007 for copending U.S. Appl. No. 11/154,221.
USPTO Notice of Allowance dated Dec. 10, 2007 for copending U.S. Appl. No. 11/154,165.
USPTO Notice of Allowance dated Dec. 10, 2007 for copending U.S. Appl. No. 11/154,482.
USPTO Office Action dated Dec. 13, 2007 for copending U.S. Appl. No. 11/271,308.
USPTO Office Action dated Jan. 24, 2008 for copending U.S. Appl. No. 11/846,801.

USPTO Office Action dated Feb. 2, 2008 for copending U.S. Appl. No. 11/365,441.
USPTO Office Action dated Feb. 21, 2008 for copending U.S. Appl. No. 11/153,994.
USPTO Office Action dated Apr. 11, 2008 for copending U.S. Appl. No. 11/154,237.
USPTO Office Action dated Apr. 15, 2008 for copending U.S. Appl. No. 11/154,140.
USPTO Notice of Allowance dated Apr. 17, 2008 for copending U.S. Appl. No. 11/154,165.
Copending U.S. Appl. No. 12/116,249, filed May 7, 2008, Wonders.
USPTO Office Action dated May 9, 2008 for copending U.S. Appl. No. 11/154,504.
USPTO Office Action dated May 7, 2008 for copending U.S. Appl. No. 11/154,253.
USPTO Office Action dated May 7, 2008 for copending U.S. Appl. No. 11/154,396.
USPTO Notice of Allowance dated Apr. 30, 2008 for copending U.S. Appl. No. 11/154,220.
USPTO Office Action dated May 7, 2008 for copending U.S. Appl. No. 11/154,116.
USPTO Office Action dated May 7, 2008 for copending U.S. Appl. No. 11/153,993.
USPTO Office Action dated May 8, 2008 for copending U.S. Appl. No. 11/154,479.
USPTO Office Action dated May 8, 2008 for copending U.S. Appl. No. 11/154,218.
USPTO Notice of Allowance dated May 6, 2008 for copending U.S. Appl. No. 11/154,221.
USPTO Office Action dated May 14, 2008 for copending U.S. Appl. No. 11/846,811.
USPTO Office Action dated May 30, 2008 for copending U.S. Appl. No. 11/154,448.
USPTO Office Action dated May 30, 2008 for copending U.S. Appl. No. 11/154,202.
USPTO Office Action dated Jun. 19, 2008 for copending U.S. Appl. No. 11/154,480.
USPTO Office Action dated Jun. 30, 2008 for copending U.S. Appl. No. 11/846,817.
USPTO Office Action dated Jul. 1, 2008 for copending U.S. Appl. No. 11/846,822.
USPTO Office Action dated Jun. 30, 2008 for copending U.S. Appl. No. 11/154,201.
Perry's Chemical Engineers' Handbook ($7^{th}$ Edition), p. 23-49, McGraw-Hill.
Collection of Czechoslovak Chemical Communications (1984), 49(9), 1939-48.
Sisak, Hungarian Journal of Industrial Chemistry (1986), 14(1), 39-48.
USPTO Office action dated Jul. 9, 2008 for copending U.S. Appl. No. 11/153,994.
USPTO Office Action dated Jul. 18, 2008 for copending U.S. Appl. No. 11/154,163.
USPTO Office Action dated Jul. 18, 2008 for copending U.S. Appl. No. 11/154,219.
USPTO Office Action dated Jul. 16, 2008 for copending U.S. Appl. No. 11/846,851.
USPTO Office Action dated Jul. 24, 2008 for copending U.S. Appl. No. 11/154,478.
USPTO Office Action dated Jul. 29, 2008 for copending U.S. Appl. No. 11/365,441.
Letzel, H.M., et al., "Gas Holdup and Mass Transfer in Bubble Column Reactors Operated at Elevated Pressure," 1999, Chemical Engineering Science 54, 2237-2246, Elsevier Science Ltd.
USPTO Office Action dated Oct. 14, 2008 for copending U.S. Appl. No. 11/846,801.
USPTO Office Action dated Oct. 29, 2008 for copending U.S. Appl. No. 11/154,448.
USPTO Notice of Allowance dated Nov. 3, 2008 for copending U.S. Appl. No. 11/154,480.
USPTO Notice of Allowance dated Nov. 10, 2008 for copending U.S. Appl. No. 11/154,218.
USPTO Office Action dated Nov. 13, 2008 for copending U.S. Appl. No. 11/153,994.
USPTO Office Action dated Nov. 13, 2008 for copending U.S. Appl. No. 11/153,993.
USPTO Notice of Allowance dated Nov. 17, 2008 for copending U.S. Appl. No. 11/154,140.
USPTO Notice of Allowance dated Nov. 20, 2008 for copending U.S. Appl. No. 11/846,822.
USPTO Office Action dated Nov. 26, 2008 for copending U.S. Appl. No. 11/154,253.
USPTO Office Action dated Nov. 26, 2008 for copending U.S. Appl. No. 11/154,202.
USPTO Notice of Allowance dated Nov. 25, 2008 for copending U.S. Appl. No. 11/846,851.
USPTO Notice of Allowance dated Dec. 3, 2008 for copending U.S. Appl. No. 11/846,817.
USPTO Notice of Allowance dated Dec. 3, 2008 for copending U.S. Appl. No. 11/154,237.
USPTO Office Action dated Dec. 9, 2008 for copending U.S. Appl. No. 11/154,396.
USPTO Office Action dated Dec. 10, 2008 for copending U.S. Appl. No. 11/856,811.
USPTO Office Action dated Dec. 19, 2008 for copending U.S. Appl. No. 12/116,249.
USPTO Office Action dated Dec. 22, 2008 for copending U.S. Appl. No. 11/154,201.
USPTO Office Action dated Dec. 24, 2008 for copending U.S. Appl. No. 11/154,479.
USPTO Office Action dated Jan. 6, 2009 for copending U.S. Appl. No. 11/154,163.
USPTO Notice of Allowance dated Jan. 9, 2009 for copending U.S. Appl. No. 11/154,116.
USPTO Notice of Allowance dated Jan. 12, 2009 for copending U.S. Appl. No. 11/154,504.
USPTO Office Action dated Jan. 23, 2009 for copending U.S. Appl. No. 11/154,219.
USPTO Office Action dated Jan. 26, 2009 for copending U.S. Appl. No. 11/365,441.
Copending U.S. Appl. No. 12/362,811, filed Jan. 30, 2009, Marcel de Vreede et al.
Copending U.S. Appl. No. 12/362,815, filed Jan. 30, 2009, Alan George Wonders, et al.
Copending U.S. Appl. No. 12/392,119, filed Feb. 25, 2009, Alan George Wonders et al.
USPTO Office Action dated Feb. 20, 2009 for copending U.S. Appl. No. 11/153,994.
USPTO Office Action dated Mar. 5, 2009 for copending U.S. Appl. No. 12/105,389.
USPTO Office Action dated Apr. 15, 2009 for copending U.S. Appl. No. 11/154,253.
USPTO Notice of Allowance dated Jun. 8, 2009 for copending U.S. Appl. No. 11/154,396.
USPTO Notice of Allowance dated Jun. 12, 2009 for copending U.S. Appl. No. 11/154,448.
USPTO Notice of Allowance dated Jun. 26, 2009 for copending U.S. Appl. No. 11/153,993.
USPTO Notice of Allowance dated Jun. 19, 2009 for copending U.S. Appl. No. 11/154,163.
USPTO Office Action dated Jun. 25, 2009 for copending U.S. Appl. No. 11/365,441.
USPTO Office Action dated Jun. 23, 2009 for copending U.S. Appl. No. 11/154,219.
USPTO Office Action dated Jul. 29, 2010 for copending U.S. Appl. No. 12/392,119.
New copending U.S. Appl. No. 12/846,411, filed Jul. 29, 2010, Marcel de Vreede et al.
USPTO Office Action dated Nov. 12, 2009 for copending U.S. Appl. No. 12/105,389.
USPTO Notice of Allowance dated Nov. 18, 2009 for copending U.S. Appl. No. 11/154,202.
USPTO Notice of Allowance dated Oct. 7, 2009 for copending U.S. Appl. No. 11/154,201.

USPTO Office Action dated Oct. 14, 2009 for copending U.S. Appl. No. 11/153,994.
USPTO Office Action dated Oct. 2, 2009 for copending U.S. Appl. No. 12/116,249.
USPTO Notice of Allowance dated Jun. 18, 2009 for copending U.S. Appl. No. 11/154,479.
New Copending U.S. Appl. No. 12/548,475, filed Aug. 27, 2009, Alan George Wonders, et al.
USPTO Office Action dated Jul. 20, 2009 for copending U.S. Appl. No. 11/846,811.
USPTO Office Action dated Jun. 18, 2010 for copending U.S. Appl. No. 12/105,389.
USPTO Notice of Allowance dated Mar. 1, 2010 for copending U.S. Appl. No. 11/365,441.
USPTO Office Action dated May 28, 2010 for copending U.S. Appl. No. 12/362,811.
New Copending U.S. Appl. No. 12/702,725, filed Feb. 22, 2010, Alan George Wonders et al.
USPTO Office Action dated Apr. 15, 2010 for copending U.S. Appl. No. 12/703,331.
USPTO Office Action dated Sep. 16, 2010 for copending U.S. Appl. No. 12/548,475.
USPTO Office Action dated Sep. 20, 2010 for copending U.S. Appl. No. 12/846,411.
USPTO Office Action dated Oct. 20, 2010 for copending U.S. Appl. No. 12/490,441.
USPTO Office Action dated Oct. 20, 2010 for copending U.S. Appl. No. 11/153,994.
USPTO Notice of Allowance dated Dec. 8, 2010 for copending U.S. Appl. No. 12/392,119.
USPTO Notice of Allowance dated Jan. 19, 2011 for copending U.S. Appl. No. 12/548,475.
USPTO Office Action dated Jan. 5, 2011 for copending U.S. Appl. No. 12/702,725.
USPTO Notice of Allowance dated Jan. 11, 2011 for copending U.S. Appl. No. 12/490,441.
USPTO Notice of Allowance dated Jan. 12, 2011 for copending U.S. Appl. No. 12/105,389.
USPTO Notice of Allowance dated Jan. 21, 2011 for copending U.S. Appl. No. 11/153,994.

* cited by examiner

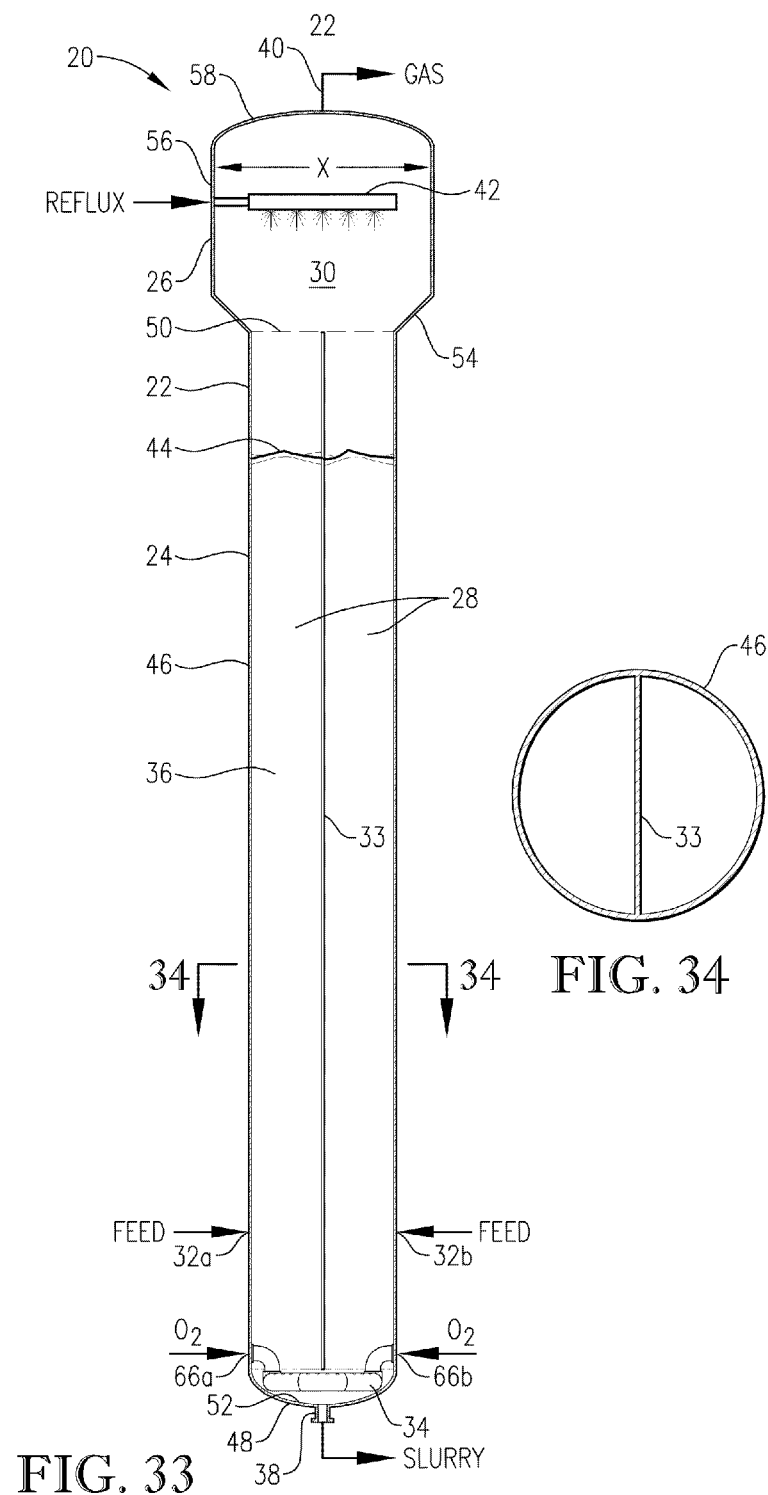

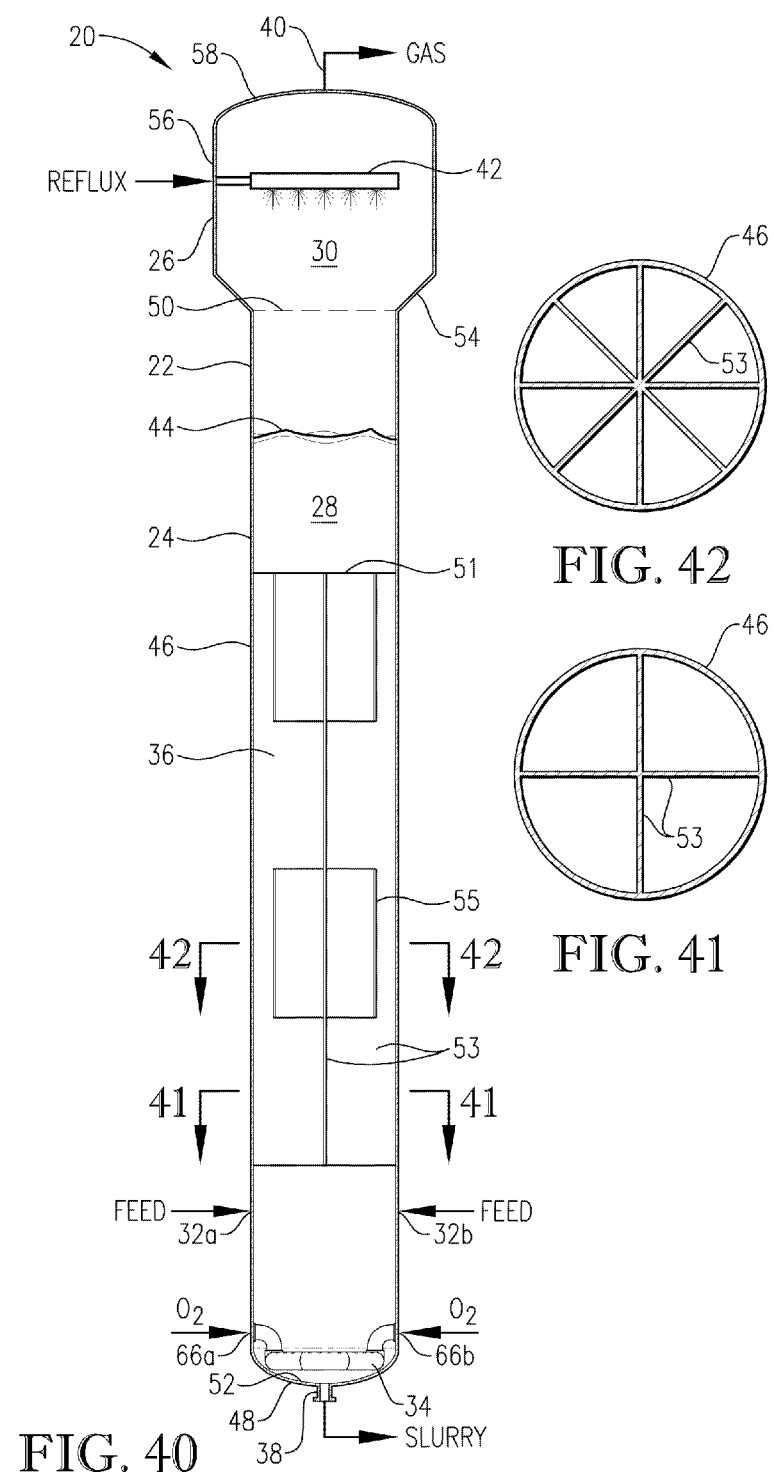

| Example | pX feed, kg/hr | Comment | D, W, m | Ug, indexed to #1 | Overall Height, m | L, m | L/D | H, m | H/W | Medium Volume, m^3 | STR, kg/hr pX per m^3 medium | Slurry Mass, kg | Slurry mass/pX feed rate, hr | Column Pressure Drop, MPa |
|---|---|---|---|---|---|---|---|---|---|---|---|---|---|---|
| 1 | 7,000 | known design | 2.44 | 1.0 | 33.2 | 32.6 | 13.4 | 25.6 | 10.5 | 118 | 59 | 58,000 | 8.3 | 0.12 |
| 2 | 49,000 | prior art, scale #1 by Ug, L/D | 6.46 | 1.0 | 88.0 | 86.3 | 13.4 | 67.8 | 10.5 | 2,200 | 22 | 1,100,000 | 22 | 0.33 |
| 3 | 49,000 | prior art, scale #1 by Ug, STR | 6.46 | 1.0 | 35.2 | 33.6 | 5.2 | 26.1 | 4.0 | 828 | 59 | 410,000 | 8.3 | 0.13 |
| 4 | 49,000 | #3 plus novel upright drag | 6.46 | 1.0 | 35.2 | 33.6 | 5.2 | 26.3 | 4.1 | 828 | 59 | 410,000 | 8.3 | 0.13 |
| 5 | 49,000 | #3 plus novel baffle | 6.46 | 1.0 | 35.2 | 33.6 | 5.2 | 26.1 | 4.0 | 828 | 59 | 410,000 | 8.3 | 0.13 |
| 6 | 49,000 | smaller D; higher, novel Ug | 5.00 | 1.7 | 72.5 | 71.3 | 14.3 | 61.3 | 12.3 | 1,190 | 41 | 420,000 | 8.7 | 0.21 |
| 7 | 49,000 | yet higher Ug | 4.60 | 2.0 | 71.9 | 61.2 | 13.3 | 61.2 | 13.3 | 1,000 | 49 | 320,000 | 6.5 | 0.19 |
| 8 | 49,000 | #7 + higher level | 4.60 | 2.0 | 71.9 | 61.2 | 13.3 | 63.2 | 13.7 | 1,060 | 46 | 330,000 | 6.8 | 0.20 |
| 9 | 49,000 | #7 + dual feeds | 4.60 | 2.0 | 71.9 | 61.2 | 13.3 | 63.7 | 13.8 | 1,070 | 46 | 340,000 | 6.9 | 0.20 |
| 10 | 49,000 | stepped Ug | ----- multiple diameters, see text ----- | | | | | | | 1,080 | 45 | 400,000 | 8.1 | 0.20 |

Ug = superficial velocity of gas phase at mid-height reaction medium

FIG. 58

OPTIMIZED LIQUID-PHASE OXIDATION

CROSS-REFERENCE TO RELATED APPLICATIONS

This application is a divisional of application Ser. No. 11/154,396 entitled "Optimized Liquid-Phase Oxidation," filed on Jun. 16, 2005, which claims priority to U.S. Provisional Application Ser. Nos. 60/606,731, filed Sep. 2, 2004 and 60/631,400, filed Nov. 29, 2004, the disclosures of which are incorporated herein by reference in their entirety.

FIELD OF THE INVENTION

This invention relates generally to a process for the liquid-phase, catalytic oxidation of an aromatic compound. One aspect of the invention concerns the partial oxidation of a dialkyl aromatic compound (e.g., para-xylene) to produce a crude aromatic dicarboxylic acid (e.g., crude terephthalic acid), which can thereafter be subjected to purification and separation. Another aspect of the invention concerns an improved bubble column reactor that provides for a more effective and economical liquid-phase oxidation process.

BACKGROUND OF THE INVENTION

Liquid-phase oxidation reactions are employed in a variety of existing commercial processes. For example, liquid-phase oxidation is currently used for the oxidation of aldehydes to acids (e.g., propionaldehyde to propionic acid), the oxidation of cyclohexane to adipic acid, and the oxidation of alkyl aromatics to alcohols, acids, or diacids. A particularly significant commercial oxidation process in the latter category (oxidation of alkyl aromatics) is the liquid-phase catalytic partial oxidation of para-xylene to terephthalic acid. Terephthalic acid is an important compound with a variety of applications. The primary use of terephthalic acid is as a feedstock in the production of polyethylene terephthalate (PET). PET is a well-known plastic used in great quantities around the world to make products such as bottles, fibers, and packaging.

In a typical liquid-phase oxidation process, including partial oxidation of para-xylene to terephthalic acid, a liquid-phase feed stream and a gas-phase oxidant stream are introduced into a reactor and form a multi-phase reaction medium in the reactor. The liquid-phase feed stream introduced into the reactor contains at least one oxidizable organic compound (e.g., para-xylene), while the gas-phase oxidant stream contains molecular oxygen. At least a portion of the molecular oxygen introduced into the reactor as a gas dissolves into the liquid phase of the reaction medium to provide oxygen availability for the liquid-phase reaction. If the liquid phase of the multi-phase reaction medium contains an insufficient concentration of molecular oxygen (i.e., if certain portions of the reaction medium are "oxygen-starved"), undesirable side-reactions can generate impurities and/or the intended reactions can be retarded in rate. If the liquid phase of the reaction medium contains too little of the oxidizable compound, the rate of reaction may be undesirably slow. Further, if the liquid phase of the reaction medium contains an excess concentration of the oxidizable compound, additional undesirable side-reactions can generate impurities.

Conventional liquid-phase oxidation reactors are equipped with agitation means for mixing the multi-phase reaction medium contained therein. Agitation of the reaction medium is supplied in an effort to promote dissolution of molecular oxygen into the liquid phase of the reaction medium, maintain relatively uniform concentrations of dissolved oxygen in the liquid phase of the reaction medium, and maintain relatively uniform concentrations of the oxidizable organic compound in the liquid phase of the reaction medium.

Agitation of the reaction medium undergoing liquid-phase oxidation is frequently provided by mechanical agitation means in vessels such as, for example, continuous stirred tank reactors (CSTRs). Although CSTRs can provide thorough mixing of the reaction medium, CSTRs have a number of drawbacks. For example, CSTRs have a relatively high capital cost due to their requirement for expensive motors, fluid-sealed bearings and drive shafts, and/or complex stirring mechanisms. Further, the rotating and/or oscillating mechanical components of conventional CSTRs require regular maintenance. The labor and shutdown time associated with such maintenance adds to the operating cost of CSTRs. However, even with regular maintenance, the mechanical agitation systems employed in CSTRs are prone to mechanical failure and may require replacement over relatively short periods of time.

Bubble column reactors provide an attractive alternative to CSTRs and other mechanically agitated oxidation reactors. Bubble column reactors provide agitation of the reaction medium without requiring expensive and unreliable mechanical equipment. Bubble column reactors typically include an elongated upright reaction zone within which the reaction medium is contained. Agitation of the reaction medium in the reaction zone is provided primarily by the natural buoyancy of gas bubbles rising through the liquid phase of the reaction medium. This natural-buoyancy agitation provided in bubble column reactors reduces capital and maintenance costs relative to mechanically agitated reactors. Further, the substantial absence of moving mechanical parts associated with bubble column reactors provides an oxidation system that is less prone to mechanical failure than mechanically agitated reactors.

When liquid-phase partial oxidation of para-xylene is carried out in a conventional oxidation reactor (CSTR or bubble column), the product withdrawn from the reactor is typically a slurry comprising crude terephthalic acid (CTA) and a mother liquor. CTA contains relatively high levels of impurities (e.g., 4-carboxybenzaldehyde, para-toluic acid, fluorenones, and other color bodies) that render it unsuitable as a feedstock for the production of PET. Thus, the CTA produced in conventional oxidation reactors is typically subjected to a purification process that converts the CTA into purified terephthalic acid (PTA) suitable for making PET.

One typical purification process for converting CTA to PTA includes the following steps: (1) replacing the mother liquor of the CTA-containing slurry with water, (2) heating the CTA/water slurry to dissolve the CTA in water, (3) catalytically hydrogenating the CTA/water solution to convert impurities to more desirable and/or easily-separable compounds, (4) precipitating the resulting PTA from the hydrogenated solution via multiple crystallization steps, and (5) separating the crystallized PTA from the remaining liquids. Although effective, this type of conventional purification process can be very expensive. Individual factors contributing to the high cost of conventional CTA purification methods include, for example, the heat energy required to promote dissolution of the CTA in water, the catalyst required for hydrogenation, the hydrogen stream required for hydrogenation, the yield loss caused by hydrogenation of some terephthalic acid, and the multiple vessels required for multi-step crystallization. Thus, it would be desirable to provide a CTA product that could be purified without requiring heat-promoted dissolution in water, hydrogenation, and/or multi-step crystallization.

OBJECTS OF THE INVENTION

It is, therefore, an object of the present invention to provide a more effective and economical liquid-phase oxidation reactor and process.

Another object of the invention is to provide a more effective and economical reactor and process for the liquid-phase catalytic partial oxidation of para-xylene to terephthalic acid.

Still another object of the invention is to provide a bubble column reactor that facilitates improved liquid-phase oxidation reactions with reduced formation of impurities.

Yet another object of the invention is to provide a more effective and economical system for producing pure terephthalic acid (PTA) via liquid-phase oxidation of para-xylene to produce crude terephthalic acid (CTA) and subsequently, purifying the CTA to PTA.

A further object of the invention is to provide a bubble column reactor for oxidizing para-xylene and producing a CTA product capable of being purified without requiring heat-promoted dissolution of the CTA in water, hydrogenation of the dissolved CTA, and/or multi-step crystallization of the hydrogenated PTA.

It should be noted that the scope of the present invention, as defined in the appended claims, is not limited to processes or apparatuses capable of realizing all of the objects listed above. Rather, the scope of the claimed invention may encompass a variety of systems that do not accomplish all or any of the above-listed objects. Additional objects and advantages of the present invention will be readily apparent to one skilled in the art upon reviewing the following detailed description and associated drawings.

SUMMARY OF THE INVENTION

One embodiment of the present invention concerns a process comprising oxidizing an oxidizable compound in a liquid phase of a multi-phase reaction medium contained in a reaction zone of a bubble column reactor, wherein the reaction medium includes a lower portion having a maximum horizontal cross-sectional area and an upper portion having a minimum horizontal cross-sectional area, wherein the maximum cross-sectional area is at least about 10 percent greater than the minimum cross-sectional area.

Another embodiment of the present invention concerns a process comprising the following steps: (a) forming a multi-phase reaction medium in a bubble column reactor; (b) causing a gas phase of the reaction medium to rise though a lower section of the reactor in a manner such that the gas phase of the reaction medium has a first time-averaged superficial velocity at the half height of the lower section; and (c) causing at least a portion of the gas phase to rise through an upper section of the reactor in a manner such that the gas phase of the reaction medium has a second time-averaged superficial velocity at the half height of the upper section, wherein the second superficial velocity is at least about 15 percent greater than the first superficial velocity.

Still another embodiment of the present invention concerns a process for making purified terephthalic acid comprising the following steps: (a) oxidizing para-xylene in a liquid phase of a three-phase reaction medium contained in a reaction zone of a bubble column reactor to thereby form crude terephthalic acid, wherein the reaction medium includes a lower portion having a maximum horizontal cross-sectional area and an upper portion having a minimum horizontal cross-sectional area, wherein the maximum cross-sectional area is at least about 10 percent greater than the minimum cross-sectional area; and (b) oxidizing at least a portion of the crude terephthalic acid in a secondary oxidation reactor to thereby form purer terephthalic acid.

Yet another embodiment of the present invention concerns a bubble column reactor. The bubble column reactor includes a vessel shell. The vessel shell defines a reaction zone. The reaction zone includes a normally-lower section having a first maximum horizontal cross-sectional area and a normally-upper section having a second maximum horizontal cross-sectional area. The first maximum cross-sectional area is at least about 10 percent greater than the second maximum cross-sectional area.

BRIEF DESCRIPTION OF THE DRAWINGS

Preferred embodiments of the invention are described in detail below with reference to the attached drawing figures, wherein;

FIG. 33 is a side view of a bubble column reactor equipped with an upright divider wall for adding upright surface area that contacts the reaction medium;

FIG. 34 is a sectional view taken along line 34-34 in FIG. 33, particularly illustrating that the divider wall is a planar member dividing the reaction zone into two substantially equal sections;

FIG. 40 is a side view of a bubble column reactor equipped with alternating, differently-configured, upright internal members for adding upright surface area that contacts the reaction medium;

FIG. 41 is a sectional view taken along line 41-41 in FIG. 40, particularly illustrating one configuration of the upright members that has an "X" shape and divides a portion of the reaction zone into four substantially equal quadrants;

FIG. 42 is a sectional view taken along line 42-42 in FIG. 40, particularly illustrating the other configuration of the upright members that divides a portion of the reaction zone into eight substantially equal wedge-shaped sections;

FIG. 58 is a table summarizing various operating parameters of a bubble column oxidation reactor, wherein certain of the operating parameters have been adjusted in accordance with the description provide in the Examples section.

DETAILED DESCRIPTION

One embodiment of the present invention concerns the liquid-phase partial oxidation of an oxidizable compound. Such oxidation is preferably carried out in the liquid phase of a multi-phase reaction medium contained in one or more agitated reactors. Suitable agitated reactors include, for example, bubble-agitated reactors (e.g., bubble column reactors), mechanically agitated reactors (e.g., continuous stirred tank reactors), and flow agitated reactors (e.g., jet reactors). In one embodiment of the invention, the liquid-phase oxidation is carried out in a single bubble column reactor.

As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the term "agitation" shall denote work dissipated into the reaction medium causing fluid flow and/or mixing. As used herein, the terms "majority", "primarily", and "predominately" shall mean more than 50 percent. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. As used herein, the term "flow agitation" shall denote agitation of the reaction medium caused by high velocity injection and/or recirculation of one or more fluids in the reaction medium. For example, flow agitation can be provided by nozzles, ejectors, and/or eductors.

In a preferred embodiment of the present invention, less than about 40 percent of the agitation of the reaction medium in the bubble column reactor during oxidation is provided by mechanical and/or flow agitation, more preferably less than about 20 percent of the agitation is provided by mechanical and/or flow agitation, and most preferably less than 5 percent of the agitation is provided by mechanical and/or flow agitation. Preferably, the amount of mechanical and/or flow agitation imparted to the multi-phase reaction medium during oxidation is less than about 3 kilowatts per cubic meter of the reaction medium, more preferably less than about 2 kilowatts per cubic meter, and most preferably less than 1 kilowatt per cubic meter.

Figure 1:
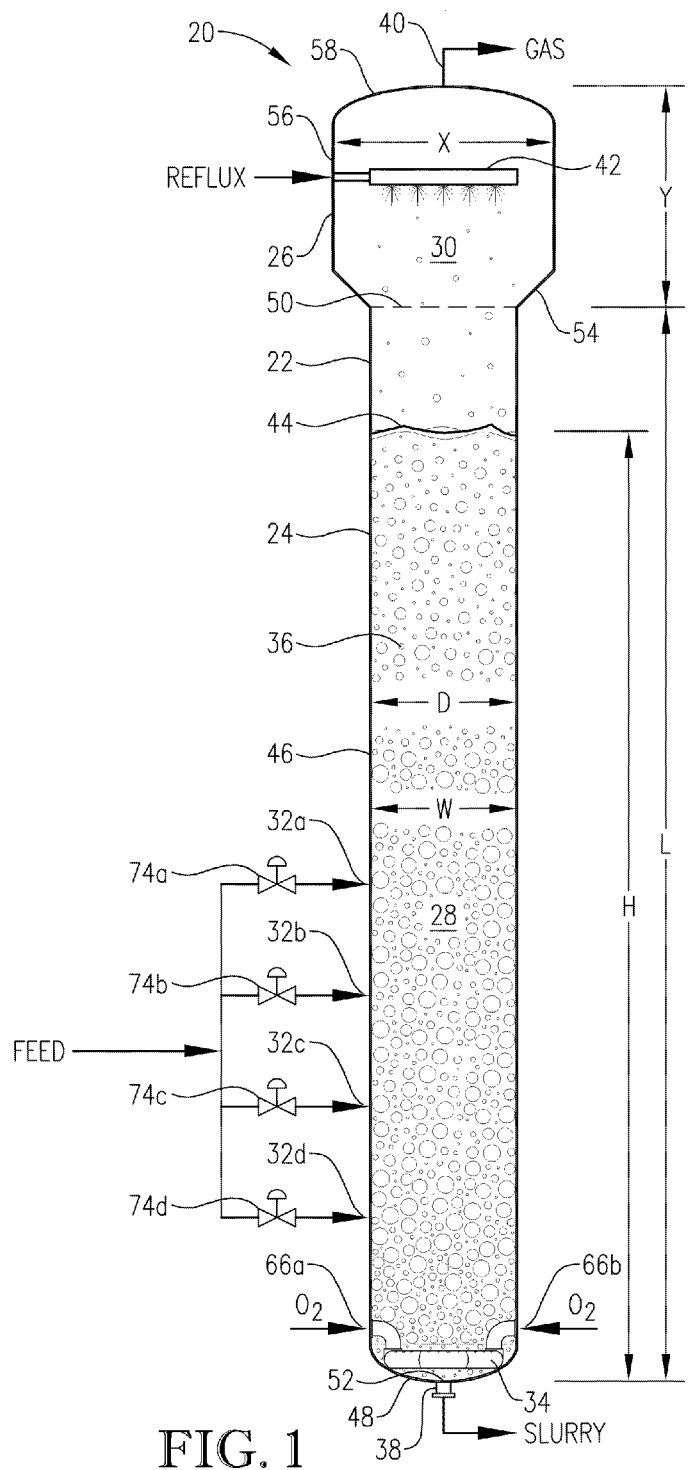
FIG. 1 is a side view of an oxidation reactor constructed in accordance with one embodiment of the present invention, particularly illustrating the introduction of feed, oxidant, and reflux streams into the reactor, the presence of a multi-phase reaction medium in the reactor, and the withdrawal of a gas and a slurry from the top and bottom of the reactor, respectively.

Referring now to FIG. 1, a preferred bubble column reactor 20 is illustrated as comprising a vessel shell 22 having of a reaction section 24 and a disengagement section 26. Reaction section 24 defines an internal reaction zone 28, while disengagement section 26 defines an internal disengagement zone 30. A predominately liquid-phase feed stream is introduced into reaction zone 28 via feed inlets 32a,b,c,d. A predominately gas-phase oxidant stream is introduced into reaction zone 28 via an oxidant sparger 34 located in the lower portion of reaction zone 28. The liquid-phase feed stream and gas-phase oxidant stream cooperatively form a multi-phase reaction medium 36 within reaction zone 28. Multi-phase reaction medium 36 comprises a liquid phase and a gas phase. More preferably, multiphase reaction medium 36 comprises a three-phase medium having solid-phase, liquid-phase, and gas-phase components. The solid-phase component of the reaction medium 36 preferably precipitates within reaction zone 28 as a result of the oxidation reaction carried out in the liquid phase of reaction medium 36. Bubble column reactor 20 includes a slurry outlet 38 located near the bottom of reaction zone 28 and a gas outlet 40 located near the top of disengagement zone 30. A slurry effluent comprising liquid-phase and solid-phase components of reaction medium 36 is withdrawn from reaction zone 28 via slurry outlet 38, while a predominantly gaseous effluent is withdrawn from disengagement zone 30 via gas outlet 40.

The liquid-phase feed stream introduced into bubble column reactor 20 via feed inlets 32a,b,c,d preferably comprises an oxidizable compound, a solvent, and a catalyst system.

The oxidizable compound present in the liquid-phase feed stream preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group", as defined herein, is at least one carbon atom that is bonded only to hydrogen atoms or to other carbon atoms. A "substituted hydrocarbyl group", as defined herein, is at least one carbon atom bonded to at least one heteroatom and to at least one hydrogen atom. "Heteroatoms", as defined herein, are all atoms other than carbon and hydrogen atoms. Aromatic compounds, as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

Suitable examples of the oxidizable compound include aliphatic hydrocarbons (e.g., alkanes, branched alkanes, cyclic alkanes, aliphatic alkenes, branched alkenes, and cyclic alkenes); aliphatic aldehydes (e.g., acetaldehyde, propionaldehyde, isobutyraldehyde, and n-butyraldehyde); aliphatic alcohols (e.g., ethanol, isopropanol, n-propanol, n-butanol, and isobutanol); aliphatic ketones (e.g., dimethyl ketone, ethyl methyl ketone, diethyl ketone, and isopropyl methyl ketone); aliphatic esters (e.g., methyl formate, methyl acetate, ethyl acetate); aliphatic peroxides, peracids, and hydroperoxides (e.g., t-butyl hydroperoxide, peracetic acid, and di-t-butyl hydroperoxide); aliphatic compounds with groups that are combinations of the above aliphatic species plus other heteroatoms (e.g., aliphatic compounds comprising one or more molecular segments of hydrocarbons, aldehydes, alcohols, ketones, esters, peroxides, peracids, and/or hydroperoxides in combination with sodium, bromine, cobalt, manganese, and zirconium); various benzene rings, naphthalene rings, biphenyls, terphenyls, and other aromatic groups with one or more attached hydrocarbyl groups (e.g., toluene, ethylbenzene, isopropylbenzene, n-propylbenzene, neopentylbenzene, para-xylene, meta-xylene, ortho-xylene, all isomers of trimethylbenzenes, all isomers of tetramethylbenzenes, pentamethylbenzene, hexamethylbenzene, all isomers of ethyl-methylbenzenes, all isomers of diethylbenzenes, all isomers of ethyl-dimethylbenzenes, all isomers of dimethylnaphthalenes, all isomers of ethyl-methylnaphthalenes, all isomers of diethylnaphthalenes all isomers of dimethylbiphenyls, all isomers of ethyl-methylbiphenyls, and all isomers of diethylbiphenyls, stilbene and with one or more attached hydrocarbyl groups, fluorene and with one or more attached hydrocarbyl groups, anthracene and with one or more attached hydrocarbyl groups, and diphenylethane and with one or more attached hydrocarbyl groups); various benzene rings, naphthalene rings, biphenyls, terphenyls, and other aromatic groups with one or more attached hydrocarbyl groups and/or one or more attached heteroatoms, which may connect to other atoms or groups of atoms (e.g., phenol, all isomers of methylphenols, all isomers of dimethylphenols, all isomers of naphthols, benzyl methyl ether, all isomers of bromophenols, bromobenzene, all isomers of bromotoluenes including alpha-bromotoluene, dibromobenzene, cobalt naphthenate, and all isomers of bromobiphenyls); various benzene rings, naphthalene rings, biphenyls, terphenyls, and other aromatic groups with one or more attached hydrocarbyl groups and/or one or more attached heteroatoms and/or one or more attached substituted hydrocarbyl groups (e.g., benzaldehyde, all isomers of bromobenzaldehydes, all isomers of brominated tolualdehydes including all isomers of alpha-bromotolualdehydes, all isomers of hydroxybenzaldehydes, all isomers of bromo-hydroxybenzaldehydes, all isomers of benzene dicarboxaldehydes, all isomers of benzene tricarboxaldehydes, para-tolualdehyde, meta-tolualdehyde, ortho-tolualdehyde, all isomers of toluene dicarboxaldehydes, all isomers of toluene tricarboxaldehydes, all isomers of toluene tetracarboxaldehydes, all isomers of dimethylbenzene dicarboxaldehydes, all isomers of dimethylbenzene tricarboxaldehydes, all isomers of dimethylbenzene tetracarboxaldehydes, all isomers of trimethylbenzene tricarboxaldehydes, all isomers of ethyltolualdehydes, all isomers of trimethylbenzene dicarboxaldehydes, tetramethylbenzene dicarboxaldehyde, hydroxymethyl-benzene, all isomers of hydroxymethyl-toluenes, all isomers of hydroxymethyl-bromotoluenes, all isomers of hydroxymethyl-tolualdehydes, all isomers of hydroxymethyl-bromotolualdehydes, benzyl hydroperoxide, benzoyl hydroperoxide, all isomers of tolyl methyl-hydroperoxides, and all isomers of methylphenol methyl-hydroperoxides); various benzene rings, naphthalenes rings, biphenyls, terphenyls, and other aromatic groups with one or more attached selected groups, selected groups meaning hydrocarbyl groups and/or attached heteroatoms and/or substituted hydrocarbyl groups and/or carboxylic acid groups and/or peroxy acid groups (e.g., benzoic acid, para-toluic acid, meta-toluic acid, ortho-toluic acid, all isomers of ethylbenzoic acids, all isomers of propylbenzoic acids, all isomers of butylbenzoic acids, all isomers of pentylbenzoic acids, all isomers of dimethylbenzoic acids, all isomers of ethylmethylbenzoic acids, all isomers of trimethylbenzoic acids, all isomers of tetramethylbenzoic acids, pentamethylbenzoic acid, all isomers of diethylbenzoic acids, all isomers of benzene dicarboxylic acids, all isomers of benzene tricarboxylic acids, all isomers of methylbenzene dicarboxylic acids, all isomers of dimethylbenzene dicarboxylic acids, all isomers of methylbenzene tricarboxylic acids, all isomers of bromobenzoic acids, all isomers of dibromobenzoic acids, all isomers of bromotoluic acids including alpha-bromotoluic acids, tolyl acetic acid, all isomers of hydroxybenzoic acids, all isomers of hydroxymethyl-benzoic acids, all isomers of hydroxytoluic acids, all isomers of hydroxymethyl-toluic acids, all isomers of hydroxymethyl-benzene dicarboxylic acids, all isomers of hydroxybromobenzoic acids, all isomers of hydroxybromotoluic acids, all isomers of hydroxymethyl-bromobenzoic acids, all isomers of carboxy benzaldehydes, all isomers of dicarboxy benzaldehydes, perbenzoic acid, all isomers of hydroperoxymethyl-benzoic acids, all isomers of hydroperoxymethyl-hydroxybenzoic acids, all isomers of hydroperoxycarbonyl-benzoic acids, all isomers of hydroperoxycarbonyl-toluenes, all isomers of methylbiphenyl carboxylic acids, all isomers of dimethylbiphenyl carboxylic acids, all isomers of methylbiphenyl dicarboxylic acids, all isomers of biphenyl tricarboxylic acids, all isomers of stilbene with one or more attached selected groups, all isomers of fluorenone with one or more attached selected groups, all isomers of naphthalene with one or more attached selected groups, benzil, all isomers of benzil with one or more attached selected groups, benzophenone, all isomers of benzophenone with one or more attached selected groups, anthraquinone, all isomers of anthraquinone with one or more attached selected groups, all isomers of diphenylethane with one or more attached selected groups, benzocoumarin, and all isomers of benzocoumarin with one or more attached selected groups).

If the oxidizable compound present in the liquid-phase feed stream is a normally-solid compound (i.e., is a solid at standard temperature and pressure), it is preferred for the oxidizable compound to be substantially dissolved in the solvent when introduced into reaction zone 28. It is preferred for the boiling point of the oxidizable compound at atmospheric pressure to be at least about 50° C. More preferably, the boiling point of the oxidizable compound is in the range of from about 80 to about 400° C., and most preferably in the range of from 125 to 155° C. The amount of oxidizable compound present in the liquid-phase feed is preferably in the range of from about 2 to about 40 weight percent, more preferably in the range of from about 4 to about 20 weight percent, and most preferably in the range of from 6 to 15 weight percent.

It is now noted that the oxidizable compound present in the liquid-phase feed may comprise a combination of two or more different oxidizable chemicals. These two or more different chemical materials can be fed commingled in the liquid-phase feed stream or may be fed separately in multiple feed streams. For example, an oxidizable compound comprising para-xylene, meta-xylene, para-tolualdehyde, para-toluic acid, and acetaldehyde may be fed to the reactor via a single inlet or multiple separate inlets.

The solvent present in the liquid-phase feed stream preferably comprises an acid component and a water component. The solvent is preferably present in the liquid-phase feed stream at a concentration in the range of from about 60 to about 98 weight percent, more preferably in the range of from about 80 to about 96 weight percent, and most preferably in the range of from 85 to 94 weight percent. The acid component of the solvent is preferably primarily an organic low molecular weight monocarboxylic acid having 1-6 carbon atoms, more preferably 2 carbon atoms. Most preferably, the acid component of the solvent is primarily acetic acid. Preferably, the acid component makes up at least about 75 weight percent of the solvent, more preferably at least about 80 weight percent of the solvent, and most preferably 85 to 98 weight percent of the solvent, with the balance being primarily water. The solvent introduced into bubble column reactor 20 can include small quantities of impurities such as, for example, para-tolualdehyde, terephthaldehyde, 4-carboxybenzaldehyde (4-CBA), benzoic acid, para-toluic acid, para-toluic aldehyde, alpha-bromo-para-toluic acid, isophthalic acid, phthalic acid, trimellitic acid, polyaromatics, and/or suspended particulate. It is preferred that the total amount of impurities in the solvent introduced into bubble column reactor 20 is less than about 3 weight percent.

The catalyst system present in the liquid-phase feed stream is preferably a homogeneous, liquid-phase catalyst system capable of promoting oxidation (including partial oxidation) of the oxidizable compound. More preferably, the catalyst system comprises at least one multivalent transition metal. Still more preferably, the multivalent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the liquid-phase feed stream to be such that the concentration of cobalt in the liquid phase of reaction medium 36 is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the liquid-phase feed stream to be such that the concentration of bromine in the liquid phase of reaction medium 36 is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the liquid-phase feed stream to be such that the concentration of manganese in the liquid phase of reaction medium 36 is maintained in the range of from about 20 to about 1,000 ppmw, more preferably in the range of from about 40 to about 500 ppmw, most preferably in the range of from 50 to 200 ppmw.

The concentrations of the cobalt, bromine, and/or manganese in the liquid phase of reaction medium 36, provided above, are expressed on a time-averaged and volume-averaged basis. As used herein, the term "time-averaged" shall denote an average of at least 10 measurements taken equally over a continuous period of at least 100 seconds. As used herein, the term "volume-averaged" shall denote an average of at least 10 measurements taken at uniform 3-dimensional spacing throughout a certain volume.

The weight ratio of cobalt to bromine (Co:Br) in the catalyst system introduced into reaction zone 28 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced into reaction zone 28 is preferably in the range of from about 0.3:1 to about 40:1, more preferably in the range of from about 5:1 to about 30:1, and most preferably in the range of from 10:1 to 25:1.

The liquid-phase feed stream introduced into bubble column reactor 20 can include small quantities of impurities such as, for example, toluene, ethylbenzene, para-tolualdehyde, terephthaldehyde, 4-carboxybenzaldehyde (4-CBA), benzoic acid, para-toluic acid, para-toluic aldehyde, alpha bromo para-toluic acid, isophthalic acid, phthalic acid, trimellitic acid, polyaromatics, and/or suspended particulate. When bubble column reactor 20 is employed for the production of terephthalic acid, meta-xylene and ortho-xylene are also considered impurities. It is preferred that the total amount of impurities in the liquid-phase feed stream introduced into bubble column reactor 20 is less than about 3 weight percent.

Although FIG. 1 illustrates an embodiment where the oxidizable compound, the solvent, and the catalyst system are mixed together and introduced into bubble column reactor 20 as a single feed stream, in an alternative embodiment of the present invention, the oxidizable compound, the solvent, and the catalyst can be separately introduced into bubble column reactor 20. For example, it is possible to feed a pure para-xylene stream into bubble column reactor 20 via an inlet separate from the solvent and catalyst inlet(s).

The predominately gas-phase oxidant stream introduced into bubble column reactor 20 via oxidant sparger 34 comprises molecular oxygen ($O_2$). Preferably, the oxidant stream comprises in the range of from about 5 to about 40 mole percent molecular oxygen, more preferably in the range of from about 15 to about 30 mole percent molecular oxygen, and most preferably in the range of from 18 to 24 mole percent molecular oxygen. It is preferred for the balance of the oxidant stream to be comprised primarily of a gas or gasses, such as nitrogen, that are inert to oxidation. More preferably, the oxidant stream consists essentially of molecular oxygen and nitrogen. Most preferably, the oxidant stream is dry air that comprises about 21 mole percent molecular oxygen and about 78 to about 81 mole percent nitrogen. In an alternative embodiment of the present invention, the oxidant stream can comprise substantially pure oxygen.

Referring again to FIG. 1, bubble column reactor 20 is preferably equipped with a reflux distributor 42 positioned above an upper surface 44 of reaction medium 36. Reflux distributor 42 is operable to introduce droplets of a predominately liquid-phase reflux stream into disengagement zone 30 by any means of droplet formation known in the art. More preferably, reflux distributor 42 produces a spray of droplets directed downwardly towards upper surface 44 of reaction medium 36. Preferably, this downward spray of droplets affects (i.e., engages and influences) at least about 50 percent of the maximum horizontal cross-sectional area of disengagement zone 30. More preferably, the spray of droplets affects at least about 75 percent of the maximum horizontal cross-sectional area of disengagement zone 30. Most preferably, the spray of droplets affects at least 90 percent of the maximum horizontal cross-sectional area of disengagement zone 30. This downward liquid reflux spray can help prevent foaming at or above upper surface 44 of reaction medium 36 and can also aid in the disengagement of any liquid or slurry droplets entrained in the upwardly moving gas that flows towards gas outlet 40. Further, the liquid reflux may serve to reduce the amount of particulates and potentially precipitating compounds (e.g., dissolved benzoic acid, para-toluic acid, 4-CBA, terephthalic acid, and catalyst metal salts) exiting in the gaseous effluent withdrawn from disengagement zone 30 via gas outlet 40. In addition, the introduction of reflux droplets into disengagement zone 30 can, by a distillation action, be used to adjust the composition of the gaseous effluent withdrawn via gas outlet 40.

The liquid reflux stream introduced into bubble column reactor 20 via reflux distributor 42 preferably has about the same composition as the solvent component of the liquid-phase feed stream introduced into bubble column reactor 20 via feed inlets 32a,b,c,d. Thus, it is preferred for the liquid reflux stream to comprise an acid component and water. The acid component of the reflux stream is preferably a low molecular weight organic monocarboxylic acid having 1-6 carbon atoms, more preferably 2 carbon atoms. Most preferably, the acid component of the reflux stream is acetic acid. Preferably, the acid component makes up at least about 75 weight percent of the reflux stream, more preferably at least about 80 weight percent of the reflux stream, and most preferably 85 to 98 weight percent of the reflux stream, with the balance being water. Because the reflux stream typically has substantially the same composition as the solvent in the liquid-phase feed stream, when this description refers to the "total solvent" introduced into the reactor, such "total solvent" shall include both the reflux stream and the solvent portion of the feed stream.

During liquid-phase oxidation in bubble column reactor 20, it is preferred for the feed, oxidant, and reflux streams to be substantially continuously introduced into reaction zone 28, while the gas and slurry effluent streams are substantially continuously withdrawn from reaction zone 28. As used herein, the term "substantially continuously" shall mean for a period of at least 10 hours interrupted by less than 10 minutes. During oxidation, it is preferred for the oxidizable compound (e.g., para-xylene) to be substantially continuously introduced into reaction zone 28 at a rate of at least about 8,000 kilograms per hour, more preferably at a rate in the range of from about 13,000 to about 80,000 kilograms per hour, still more preferably in the range of from about 18,000 to about 50,000 kilograms per hour, and most preferably in the range of from 22,000 to 30,000 kilograms per hour. Although it is generally preferred for the flow rates of the incoming feed, oxidant, and reflux streams to be substantially steady, it is now noted that one embodiment of the presenting invention contemplates pulsing the incoming feed, oxidant, and/or reflux stream in order to improve mixing and mass transfer. When the incoming feed, oxidant, and/or reflux stream are introduced in a pulsed fashion, it is preferred for their flow rates to vary within about 0 to about 500 percent of the steady-state flow rates recited herein, more preferably within about 30 to about 200 percent of the steady-state flow rates recited herein, and most preferably within 80 to 120 percent of the steady-state flow rates recited herein.

The average space-time rate of reaction (STR) in bubble column oxidation reactor 20 is defined as the mass of the oxidizable compound fed per unit volume of reaction medium 36 per unit time (e.g., kilograms of para-xylene fed per cubic meter per hour). In conventional usage, the amount of oxidizable compound not converted to product would typically be subtracted from the amount of oxidizable compound in the feed stream before calculating the STR. However, conversions and yields are typically high for many of the oxidizable compounds preferred herein (e.g., para-xylene), and it is convenient to define the term herein as stated above. For reasons of capital cost and operating inventory, among others, it is generally preferred that the reaction be conducted with a high STR. However, conducting the reaction at increasingly higher STR may affect the quality or yield of the partial oxidation. Bubble column reactor 20 is particularly useful when the STR of the oxidizable compound (e.g., para-xylene) is in the range of from about 25 kilograms per cubic meter per hour to about 400 kilograms per cubic meter per hour, more preferably in the range of from about 30 kilograms per cubic meter per hour to about 250 kilograms per cubic meter per hour, still more preferably from about 35 kilograms per cubic meter per hour to about 150 kilograms per cubic meter per hour, and most preferably in the range of from 40 kilograms per cubic meter per hour to 100 kilograms per cubic meter per hour.

The oxygen-STR in bubble column oxidation reactor 20 is defined as the weight of molecular oxygen consumed per unit volume of reaction medium 36 per unit time (e.g., kilograms of molecular oxygen consumed per cubic meter per hour). For reasons of capital cost and oxidative consumption of solvent, among others, it is generally preferred that the reaction be conducted with a high oxygen-STR. However, conducting the reaction at increasingly higher oxygen-STR eventually reduces the quality or yield of the partial oxidation. Without being bound by theory, it appears that this possibly relates to the transfer rate of molecular oxygen from the gas phase into the liquid at the interfacial surface area and thence into the bulk liquid. Too high an oxygen-STR possibly leads to too low a dissolved oxygen content in the bulk liquid phase of the reaction medium.

The global-average-oxygen-STR is defined herein as the weight of all oxygen consumed in the entire volume of reaction medium 36 per unit time (e.g., kilograms of molecular oxygen consumed per cubic meter per hour). Bubble column reactor 20 is particularly useful when the global-average-oxygen-STR is in the range of from about 25 kilograms per cubic meter per hour to about 400 kilograms per cubic meter per hour, more preferably in the range of from about 30 kilograms per cubic meter per hour to about 250 kilograms per cubic meter per hour, still more preferably from about 35 kilograms per cubic meter per hour to about 150 kilograms per cubic meter per hour, and most preferably in the range of from 40 kilograms per cubic meter per hour to 100 kilograms per cubic meter per hour.

During oxidation in bubble column reactor 20, it is preferred for the ratio of the mass flow rate of the total solvent (from both the feed and reflux streams) to the mass flow rate of the oxidizable compound entering reaction zone 28 to be maintained in the range of from about 2:1 to about 50:1, more preferably in the range of from about 5:1 to about 40:1, and most preferably in the range of from 7.5:1 to 25:1. Preferably, the ratio of the mass flow rate of solvent introduced as part of the feed stream to the mass flow rate of solvent introduced as part of the reflux stream is maintained in the range of from about 0.5:1 to no reflux stream flow whatsoever, more preferably in the range of from about 0.5:1 to about 4:1, still more preferably in the range of from about 1:1 to about 2:1, and most preferably in the range of from 1.25:1 to 1.5:1.

During liquid-phase oxidation in bubble column reactor 20, it is preferred for the oxidant stream to be introduced into bubble column reactor 20 in an amount that provides molecular oxygen somewhat exceeding the stoichiometric oxygen demand. The amount of excess molecular oxygen required for best results with a particular oxidizable compound affects the overall economics of the liquid-phase oxidation. During liquid-phase oxidation in bubble column reactor 20, it is preferred that the ratio of the mass flow rate of the oxidant stream to the mass flow rate of the oxidizable organic compound (e.g., para-xylene) entering reactor 20 is maintained in the range of from about 0.5:1 to about 20:1, more preferably in the range of from about 1:1 to about 10:1, and most preferably in the range of from 2:1 to 6:1.

Referring again to FIG. 1, the feed, oxidant, and reflux streams introduced into bubble column reactor 20 cooperatively form at least a portion of multi-phase reaction medium 36. Reaction medium 36 is preferably a three-phase medium comprising a solid phase, a liquid phase, and a gas phase. As mentioned above, oxidation of the oxidizable compound (e.g., para-xylene) takes place predominately in the liquid phase of reaction medium 36. Thus, the liquid phase of reaction medium 36 comprises dissolved oxygen and the oxidizable compound. The exothermic nature of the oxidation reaction that takes place in bubble column reactor 20 causes a portion of the solvent (e.g., acetic acid and water) introduced via feed inlets 32a,b,c,d to boil/vaporize. Thus, the gas phase of reaction medium 36 in reactor 20 is formed primarily of vaporized solvent and an undissolved, unreacted portion of the oxidant stream. Certain prior art oxidation reactors employ heat exchange tubes/fins to heat or cool the reaction medium. However, such heat exchange structures may be undesirable in the inventive reactor and process described herein. Thus, it is preferred for bubble column reactor 20 to include substantially no surfaces that contact reaction medium 36 and exhibit a time-averaged heat flux greater than 30,000 watts per meter squared.

The concentration of dissolved oxygen in the liquid phase of reaction medium 36 is a dynamic balance between the rate of mass transfer from the gas phase and the rate of reactive consumption within the liquid phase (i.e. it is not set simply by the partial pressure of molecular oxygen in the supplying gas phase, though this is one factor in the supply rate of dissolved oxygen and it does affect the limiting upper concentration of dissolved oxygen). The amount of dissolved oxygen varies locally, being higher near bubble interfaces. Globally, the amount of dissolved oxygen depends on the balance of supply and demand factors in different regions of reaction medium 36. Temporally, the amount of dissolved oxygen depends on the uniformity of gas and liquid mixing relative to chemical consumption rates. In designing to match appropriately the supply of and demand for dissolved oxygen in the liquid phase of reaction medium 36, it is preferred for the time-averaged and volume-averaged oxygen concentration in the liquid phase of reaction medium 36 to be maintained above about 1 ppm molar, more preferably in the range from about 4 to about 1,000 ppm molar, still more preferably in the range from about 8 to about 500 ppm molar, and most preferably in the range from 12 to 120 ppm molar.

The liquid-phase oxidation reaction carried out in bubble column reactor 20 is preferably a precipitating reaction that generates solids. More preferably, the liquid-phase oxidation carried out in bubble column reactor 20 causes at least about 10 weight percent of the oxidizable compound (e.g., para-xylene) introduced into reaction zone 28 to form a solid compound (e.g., crude terephthalic acid particles) in reaction medium 36. Still more preferably, the liquid-phase oxidation causes at least about 50 weight percent of the oxidizable compound to form a solid compound in reaction medium 36. Most preferably, the liquid-phase oxidation causes at least 90 weight percent of the oxidizable compound to form a solid compound in reaction medium 36. It is preferred for the total amount of solids in reaction medium 36 to be greater than about 3 percent by weight on a time-averaged and volume-averaged basis. More preferably, the total amount of solids in reaction medium 36 is maintained in the range of from about 5 to about 40 weight percent, still more preferably in the range of from about 10 to about 35 weight percent, and most preferably in the range of from 15 to 30 weight percent. It is preferred for a substantial portion of the oxidation product (e.g., terephthalic acid) produced in bubble column reactor 20 to be present in reaction medium 36 as solids, as opposed to remaining dissolved in the liquid phase of reaction medium 36. The amount of the solid phase oxidation product present in reaction medium 36 is preferably at least about 25 percent by weight of the total oxidation product (solid and liquid phase) in reaction medium 36, more preferably at least about 75 percent by weight of the total oxidation product in reaction medium 36, and most preferably at least 95 percent by weight of the total oxidation product in reaction medium 36. The numerical ranges provided above for the amount of solids in reaction medium 36 apply to substantially steady-state operation of bubble column 20 over a substantially continuous period of time, not to start-up, shut-down, or sub-optimal operation of bubble column reactor 20. The amount of solids in reaction medium 36 is determined by a gravimetric method. In this gravimetric method, a representative portion of slurry is withdrawn from the reaction medium and weighed. At conditions that effectively maintain the overall solid-liquid partitioning present within the reaction medium, free liquid is removed from the solids portion by sedimentation or filtration, effectively without loss of precipitated solids and with less than about 10 percent of the initial liquid mass remaining with the portion of solids. The remaining liquid on the solids is evaporated to dryness, effectively without sublimation of solids. The remaining portion of solids is weighed. The ratio of the weight of the portion of solids to the weight of the original portion of slurry is the fraction of solids, typically expressed as a percentage.

The precipitating reaction carried out in bubble column reactor 20 can cause fouling (i.e., solids build-up) on the surface of certain rigid structures that contact reaction medium 36. Thus, in one embodiment of the present invention, it is preferred for bubble column reactor 20 to include substantially no internal heat exchange, stirring, or baffling structures in reaction zone 28 because such structures would be prone to fouling. If internal structures are present in reaction zone 28, it is desirable to avoid internal structures having outer surfaces that include a significant amount of upwardly facing planar surface area because such upwardly facing planar surfaces would be highly prone to fouling. Thus, if any internal structures are present in reaction zone 28, it is preferred for less than about 20 percent of the total upwardly facing exposed outer surface area of such internal structures to be formed by substantially planar surfaces inclined less than about 15 degrees from horizontal.

Referring again to FIG. 1, the physical configuration of bubble column reactor 20 helps provide for optimized oxidation of the oxidizable compound (e.g., para-xylene) with minimal impurity generation. It is preferred for elongated reaction section 24 of vessel shell 22 to include a substantially cylindrical main body 46 and a lower head 48. The upper end of reaction zone 28 is defined by a horizontal plane 50 extending across the top of cylindrical main body 46. A lower end 52 of reaction zone 28 is defined by the lowest internal surface of lower head 48. Typically, lower end 52 of reaction zone 28 is located proximate the opening for slurry outlet 38. Thus, elongated reaction zone 28 defined within bubble column reactor 20 has a maximum length "L" measured from the top end 50 to the bottom end 52 of reaction zone 28 along the axis of elongation of cylindrical main body 46. The length "L" of reaction zone 28 is preferably in the range of from about 10 to about 100 meters, more preferably in the range of from about 20 to about 75 meters, and most preferably in the range of from 25 to 50 meters. Reaction zone 28 has a maximum diameter (width) "D" that is typically equal to the maximum internal diameter of cylindrical main body 46. The maximum diameter "D" of reaction zone 28 is preferably in the range of from about 1 to about 12 meters, more preferably in the range of from about 2 to about 10 meters, still more preferably in the range of from about 3.1 to about 9 meters, and most preferably in the range of from 4 to 8 meters. In a preferred embodiment of the present invention, reaction zone 28 has a length-to-diameter "L:D" ratio in the range of from about 6:1 to about 30:1. Still more preferably, reaction zone 28 has an L:D ratio in the range of from about 8:1 to about 20:1. Most preferably, reaction zone 28 has an L:D ratio in the range of from 9:1 to 15:1.

As discussed above, reaction zone 28 of bubble column reactor 20 receives multi-phase reaction medium 36. Reaction medium 36 has a bottom end coincident with lower end 52 of reaction zone 28 and a top end located at upper surface 44. Upper surface 44 of reaction medium 36 is defined along a horizontal plane that cuts through reaction zone 28 at a vertical location where the contents of reaction zone 28 transitions from a gas-phase-continuous state to a liquid-phase-continuous state. Upper surface 44 is preferably positioned at the vertical location where the local time-averaged gas hold-up of a thin horizontal slice of the contents of reaction zone 28 is 0.9.

Reaction medium 36 has a maximum height "H" measured between its upper and lower ends. The maximum width "W" of reaction medium 36 is typically equal to the maximum diameter "D" of cylindrical main body 46. During liquid-phase oxidation in bubble column reactor 20, it is preferred that H is maintained at about 60 to about 120 percent of L, more preferably about 80 to about 110 percent of L, and most preferably 85 to 100 percent of L. In a preferred embodiment of the present invention, reaction medium 36 has a height-to-width "H:W" ratio greater than about 3:1. More preferably, reaction medium 36 has an H:W ratio in the range of from about 7:1 to about 25:1. Still more preferably, reaction medium 36 has an H:W ratio in the range of from about 8:1 to about 20:1. Most preferably, reaction medium 36 has an H:W ratio in the range of from 9:1 to 15:1. In one embodiment of the invention, L=H and D=W so that various dimensions or ratios provide herein for L and D also apply to H and W, and vice-versa.

The relatively high L:D and H:W ratios provided in accordance with an embodiment of the invention can contribute to several important advantages of the inventive system. As discussed in further detail below, it has been discovered that higher L:D and H:W ratios, as well as certain other features discussed below, can promote beneficial vertical gradients in the concentrations of molecular oxygen and/or the oxidizable compound (e.g., para-xylene) in reaction medium 36. Contrary to conventional wisdom, which would favor a well-mixed reaction medium with relatively uniform concentrations throughout, it has been discovered that the vertical staging of the oxygen and/or the oxidizable compound concentrations facilitates a more effective and economical oxidation reaction. Minimizing the oxygen and oxidizable compound concentrations near the top of reaction medium 36 can help avoid loss of unreacted oxygen and unreacted oxidizable compound through upper gas outlet 40. However, if the concentrations of oxidizable compound and unreacted oxygen are low throughout reaction medium 36, then the rate and/or selectivity of oxidation are reduced. Thus, it is preferred for the concentrations of molecular oxygen and/or the oxidizable compound to be significantly higher near the bottom of reaction medium 36 than near the top of reaction medium 36.

In addition, high L:D and H:W ratios cause the pressure at the bottom of reaction medium 36 to be substantially greater than the pressure at the top of reaction medium 36. This vertical pressure gradient is a result of the height and density of reaction medium 36. One advantage of this vertical pressure gradient is that the elevated pressure at the bottom of the vessel drives more oxygen solubility and mass transfer than would otherwise be achievable at comparable temperatures and overhead pressures in shallow reactors. Thus, the oxidation reaction can be carried out at lower temperatures than would be required in a shallower vessel. When bubble column reactor 20 is used for the partial oxidation of para-xylene to crude terephthalic acid (CTA), the ability to operate at lower reaction temperatures with the same or better oxygen mass transfer rates has a number of advantages. For example, low temperature oxidation of para-xylene reduces the amount of solvent burned during the reaction. As discussed in further detail below, low temperature oxidation also favors the formation of small, high surface area, loosely bound, easily dissolved CTA particles, which can be subjected to more economical purification techniques than the large, low surface area, dense CTA particles produced by conventional high temperature oxidation processes.

During oxidation in reactor 20, it is preferred for the time-averaged and volume-averaged temperature of reaction medium 36 to be maintained in the range of from about 125 to about 200° C., more preferably in the range of from about 140 to about 180° C., and most preferably in the range of from 150 to 170° C. The overhead pressure above reaction medium 36 is preferably maintained in the range of from about 1 to about 20 bar gauge (barg), more preferably in the range of from about 2 to about 12 barg, and most preferably in the range of from 4 to 8 barg. Preferably, the pressure difference between the top of reaction medium 36 and the bottom of reaction medium 36 is in the range of from about 0.4 to about 5 bar, more preferably the pressure difference is in the range of from about 0.7 to about 3 bars, and most preferably the pressure difference is 1 to 2 bar. Although it is generally preferred for the overhead pressure above reaction medium 36 to be maintained at a relatively constant value, one embodiment of the present invention contemplates pulsing the overhead pressure to facilitate improved mixing and/or mass transfer in reaction medium 36. When the overhead pressure is pulsed, it is preferred for the pulsed pressures to range between about 60 to about 140 percent of the steady-state overhead pressure recited herein, more preferably between about 85 and about 115 percent of the steady-state overhead pressure recited herein, and most preferably between 95 and 105 percent of the steady-state overhead pressure recited herein.

A further advantage of the high L:D ratio of reaction zone 28 is that it can contribute to an increase in the average superficial velocity of reaction medium 36. The term "superficial velocity" and "superficial gas velocity", as used herein with reference to reaction medium 36, shall denote the volumetric flow rate of the gas phase of reaction medium 36 at an elevation in the reactor divided by the horizontal cross-sectional area of the reactor at that elevation. The increased superficial velocity provided by the high L:D ratio of reaction zone 28 can promote local mixing and increase the gas hold-up of reaction medium 36. The time-averaged superficial velocities of reaction medium 36 at one-quarter height, half height, and/or three-quarter height of reaction medium 36 are preferably greater than about 0.3 meters per second, more preferably in the range of from about 0.8 to about 5 meters per second, still more preferably in the range of from about 0.9 to about 4 meters per second, and most preferably in the range of from 1 to 3 meters per second.

Referring again to FIG. 1, disengagement section 26 of bubble column reactor 20 is simply a widened portion of vessel shell 22 located immediately above reaction section 24. Disengagement section 26 reduces the velocity of the upwardly-flowing gas phase in bubble column reactor 20 as the gas phase rises above the upper surface 44 of reaction medium 36 and approaches gas outlet 40. This reduction in the upward velocity of the gas phase helps facilitate removal of entrained liquids and/or solids in the upwardly flowing gas phase and thereby reduces undesirable loss of certain components present in the liquid phase of reaction medium 36.

Disengagement section 26 preferably includes a generally frustoconical transition wall 54, a generally cylindrical broad sidewall 56, and an upper head 58. The narrow lower end of transition wall 54 is coupled to the top of cylindrical main body 46 of reaction section 24. The wide upper end of transition wall 54 is coupled to the bottom of broad sidewall 56. It is preferred for transition wall 54 to extend upwardly and outwardly from its narrow lower end at an angle in the range of from about 10 to about 70 degrees from vertical, more preferably in the range of about 15 to about 50 degrees from vertical, and most preferably in the range of from 15 to 45 degrees from vertical. Broad sidewall 56 has a maximum diameter "X" that is generally greater than the maximum diameter "D" of reaction section 24, though when the upper portion of reaction section 24 has a smaller diameter than the overall maximum diameter of reaction section 24, then X may actually be smaller than D. In a preferred embodiment of the present invention, the ratio of the diameter of broad sidewall 56 to the maximum diameter of reaction section 24 "X:D" is in the range of from about 0.8:1 to about 4:1, most preferably in the range of from 1.1:1 to 2:1. Upper head 58 is coupled to the top of broad sidewall 56. Upper head 58 is preferably a generally elliptical head member defining a central opening that permits gas to escape disengagement zone 30 via gas outlet 40. Alternatively, upper head 58 may be of any shape, including conical. Disengagement zone 30 has a maximum height "Y" measured from the top 50 of reaction zone 28 to the uppermost portion of disengagement zone 30. The ratio of the length of reaction zone 28 to the height of disengagement zone 30 "L:Y" is preferably in the range of from about 2:1 to about 24:1, more preferably in the range of from about 3:1 to about 20:1, and most preferably in the range of from 4:1 to 16:1.

Figure 2:
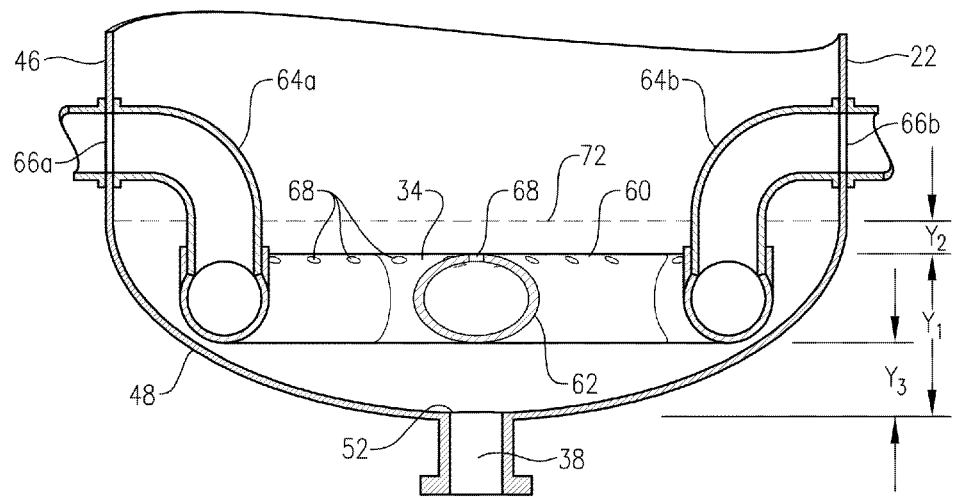
FIG. 2 is an enlarged sectional side view of the bottom of the bubble column reactor taken along line 2-2 in FIG. 3, particularly illustrating the location and configuration of a oxidant sparger used to introduce the oxidant stream into the reactor.
Figure 3:
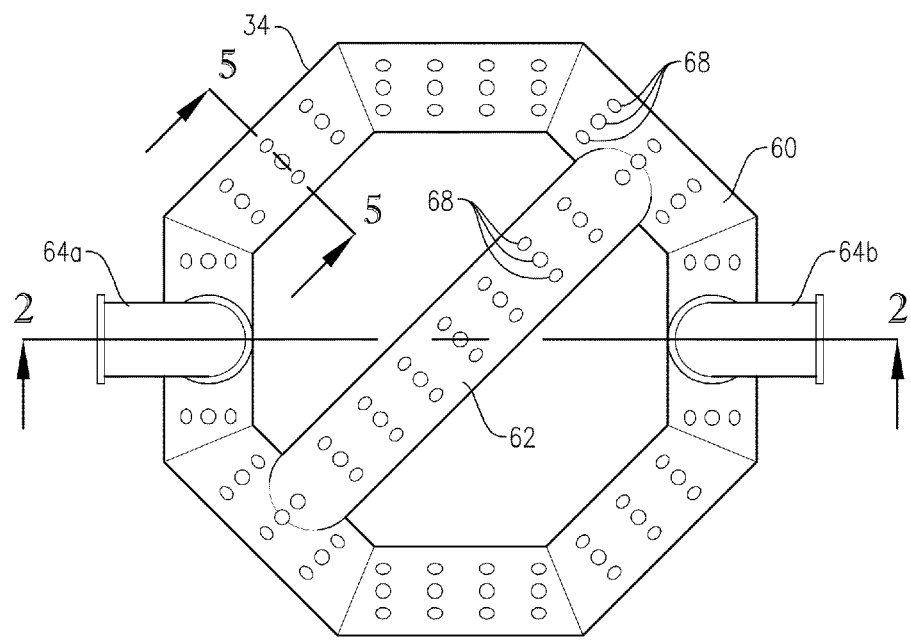
FIG. 3 is a top view of the oxidant sparger of FIG. 2, particularly illustrating the oxidant openings in the top of the oxidant sparger.
Figure 4:
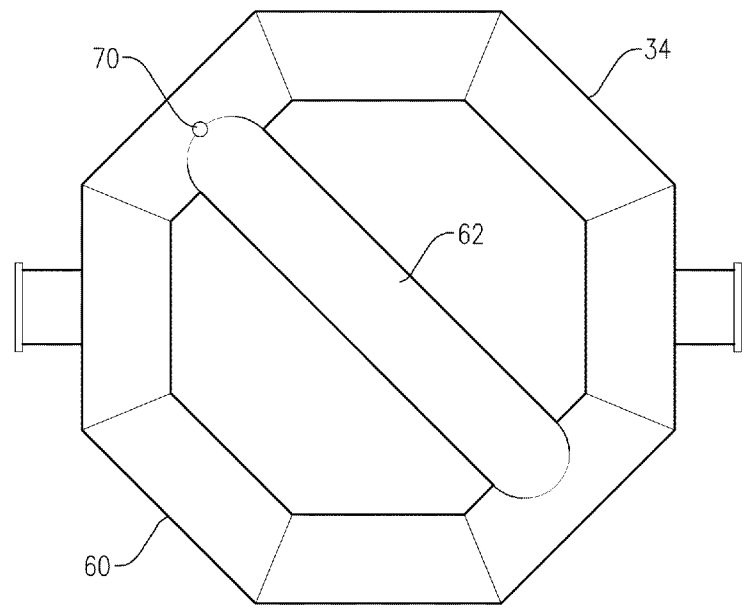
FIG. 4 is a bottom view of the oxidant sparger of FIG. 2, particularly illustrating the oxidant openings in the bottom of the oxidant sparger.

Referring now to FIGS. 1-5, the location and configuration of oxidant sparger 34 will now be discussed in greater detail. FIGS. 2 and 3 show that oxidant sparger 34 can include a ring member 60, a cross-member 62, and a pair of oxidant entry conduits 64a,b. Conveniently, these oxidant entry conduits 64a,b can enter the vessel at an elevation above the ring member 60 and then turn downwards as shown in FIGS. 2 and 3. Alternatively, an oxidant entry conduit 64a,b may enter the vessel below the ring member 60 or on about the same horizontal plane as ring member 60. Each oxidant entry conduit 64a,b includes a first end coupled to a respective oxidant inlet 66a,b formed in the vessel shell 22 and a second end fluidly coupled to ring member 60. Ring member 60 is preferably formed of conduits, more preferably of a plurality of straight conduit sections, and most preferably a plurality of straight pipe sections, rigidly coupled to one another to form a tubular polygonal ring. Preferably, ring member 60 is formed of at least 3 straight pipe sections, more preferably 6 to 10 pipe sections, and most preferably 8 pipe sections. Accordingly, when ring member 60 is formed of 8 pipe sections, it has a generally octagonal configuration. Cross-member 62 is preferably formed of a substantially straight pipe section that is fluidly coupled to and extends diagonally between opposite pipe sections of ring member 60. The pipe section used for cross-member 62 preferably has substantially the same diameter as the pipe sections used to form ring member 60. It is preferred for the pipe sections that make up oxidant entry conduits 64a,b, ring member 60, and cross-member 62 to have a nominal diameter greater than about 0.1 meter, more preferable in the range of from about 0.2 to about 2 meters, and most preferably in the range of from 0.25 to 1 meters. As perhaps best illustrated in FIG. 3, ring member 60 and cross-member 62 each present a plurality of upper oxidant openings 68 for discharging the oxidant stream upwardly into reaction zone 28. As perhaps best illustrated in FIG. 4, ring member 60 and/or cross-member 62 can present one or more lower oxidant openings 70 for discharging the oxidant stream downwardly into reaction zone 28. Lower oxidant openings 70 can also be used to discharge liquids and/or solids that might intrude within ring member 60 and/or cross-member 62. In order to prevent solids from building up inside oxidant sparger 34, a liquid stream can be continuously or periodically passed through sparger 34 to flush out any accumulated solids.

Referring again to FIGS. 1-4, during oxidation in bubble column reactor 20, oxidant streams are forced through oxidant inlets 66a,b and into oxidant entry conduits 64a,b, respectively. The oxidant streams are then transported via oxidant entry conduits 64a,b to ring member 60. Once the oxidant stream has entered ring member 60, the oxidant stream is distributed throughout the internal volumes of ring member 60 and cross-member 62. The oxidant stream is then forced out of oxidant sparger 34 and into reaction zone 28 via upper and lower oxidant openings 68,70 of ring member 60 and cross-member 62.

The outlets of upper oxidant openings 68 are laterally spaced from one another and are positioned at substantially the same elevation in reaction zone 28. Thus, the outlets of upper oxidant openings 68 are generally located along a substantially horizontal plane defined by the top of oxidant sparger 34. The outlets of lower oxidant openings 70 are laterally spaced from one another and are positioned at substantially the same elevation in reaction zone 28. Thus, the outlets of lower oxidant openings 70 are generally located along a substantially horizontal plane defined by the bottom of oxidant sparger 34.

In one embodiment of the present invention, oxidant sparger 34 has at least about 20 upper oxidant openings 68 formed therein. More preferably, oxidant sparger 34 has in the range of from about 40 to about 800 upper oxidant openings formed therein. Most preferably, oxidant sparger 34 has in the range of from 60 to 400 upper oxidant openings 68 formed therein. Oxidant sparger 34 preferably has at least about 1 lower oxidant opening 70 formed therein. More preferably, oxidant sparger 34 has in the range of from about 2 to about 40 lower oxidant openings 70 formed therein. Most preferably, oxidant sparger 34 has in the range of from 8 to 20 lower oxidant openings 70 formed therein. The ratio of the number of upper oxidant openings 68 to lower oxidant openings 70 in oxidant sparger 34 is preferably in the range of from about 2:1 to about 100:1, more preferably in the range of from about 5:1 to about 25:1, and most preferably in the range of from 8:1 to 15:1. The diameters of substantially all upper and lower oxidant openings 68,70 are preferably substantially the same, so that the ratio of the volumetric flow rate of the oxidant stream out of upper and lower openings 68,70 is substantially the same as the ratios, given above, for the relative number of upper and lower oxidant openings 68,70.

Figure 5:
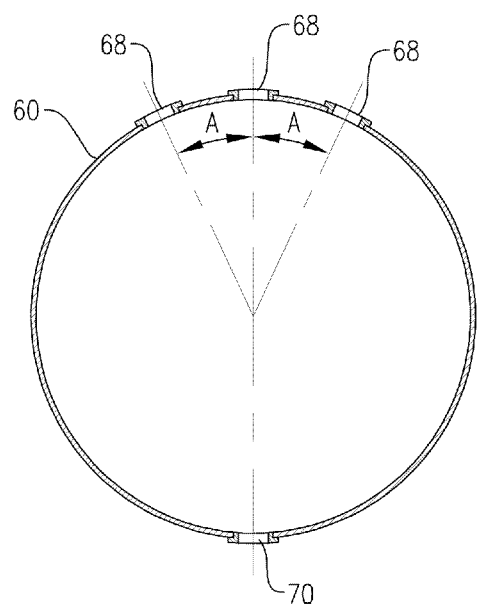
FIG. 5 is a sectional side view of the oxidant sparger taken along line 5-5 in FIG. 3, particularly illustrating the orientation of the oxidant openings in the top and bottom of the oxidant sparger.

FIG. 5 illustrates the direction of oxidant discharge from upper and lower oxidant openings 68,70. With reference to upper oxidant openings 68, it is preferred for at least a portion of upper oxidant openings 68 to discharge the oxidant stream in at an angle "A" that is skewed from vertical. It is preferred for the percentage of upper oxidant openings 68 that are skewed from vertical by angle "A" to be in the range of from about 30 to about 90 percent, more preferably in the range of from about 50 to about 80 percent, still more preferably in the range of from 60 to 75 percent, and most preferably about 67 percent. The angle "A" is preferably in the range of from about 5 to about 60 degrees, more preferably in the range of from about 10 to about 45 degrees, and most preferably in the range of from 15 to 30 degrees. As for lower oxidant openings 70, it is preferred that substantially all of lower oxidant openings 70 are located near the bottom-most portion of the ring member 60 and/or cross-member 62. Thus, any liquids and/or solids that may have unintentionally entered oxidant sparger 34 can be readily discharged from oxidant sparger 34 via lower oxidant openings 70. Preferably, lower oxidant openings 70 discharge the oxidant stream downwardly at a substantially vertical angle. For purposes of this description, an upper oxidant opening can be any opening that discharges an oxidant stream in a generally upward direction (i.e., at an angle above horizontal), and a lower oxidant opening can be any opening that discharges an oxidant stream in a generally downward direction (i.e., at an angle below horizontal).

In many conventional bubble column reactors containing a multi-phase reaction medium, substantially all of the reaction medium located below the oxidant sparger (or other mechanism for introducing the oxidant stream into the reaction zone) has a very low gas hold-up value. As known in the art, "gas hold-up" is simply the volume fraction of a multi-phase medium that is in the gaseous state. Zones of low gas hold-up in a medium can also be referred to as "unaerated" zones. In many conventional slurry bubble column reactors, a significant portion of the total volume of the reaction medium is located below the oxidant sparger (or other mechanism for introducing the oxidant stream into the reaction zone). Thus, a significant portion of the reaction medium present at the bottom of conventional bubble column reactors is unaerated.

It has been discovered that minimizing the amount of unaerated zones in a reaction medium subjected to oxidization in a bubble column reactor can minimize the generation of certain types of undesirable impurities. Unaerated zones of a reaction medium contain relatively few oxidant bubbles. This low volume of oxidant bubbles reduces the amount of molecular oxygen available for dissolution into the liquid phase of the reaction medium. Thus, the liquid phase in an unaerated zone of the reaction medium has a relatively low concentration of molecular oxygen. These oxygen-starved, unaerated zones of the reaction medium have a tendency to promote undesirable side reactions, rather than the desired oxidation reaction. For example, when para-xylene is partially oxidized to form terephthalic acid, insufficient oxygen availability in the liquid phase of the reaction medium can cause the formation of undesirably high quantities of benzoic acid and coupled aromatic rings, notably including highly undesirable colored molecules known as fluorenones and anthraquinones.

In accordance with one embodiment of the present invention, liquid-phase oxidation is carried out in a bubble column reactor configured and operated in a manner such that the volume fraction of the reaction medium with low gas hold-up values is minimized. This minimization of unaerated zones can be quantified by theoretically partitioning the entire volume of the reaction medium into 2,000 discrete horizontal slices of uniform volume. With the exception of the highest and lowest horizontal slices, each horizontal slice is a discrete volume bounded on its sides by the sidewall of the reactor and bounded on its top and bottom by imaginary horizontal planes. The highest horizontal slice is bounded on its bottom by an imaginary horizontal plane and on its top by the upper surface of the reaction medium. The lowest horizontal slice is bounded on its top by an imaginary horizontal plane and on its bottom by the lower end of the vessel. Once the reaction medium has been theoretically partitioned into 2,000 discrete horizontal slices of equal volume, the time-averaged and volume-averaged gas hold-up of each horizontal slice can be determined. When this method of quantifying the amount of unaerated zones is employed, it is preferred for the number of horizontal slices having a time-averaged and volume-averaged gas hold-up less than 0.1 to be less than 30, more preferably less than 15, still more preferably less than 6, even more preferably less than 4, and most preferably less than 2. It is preferred for the number of horizontal slices having a gas hold-up less than 0.2 to be less than 80, more preferably less than 40, still more preferably less than 20, even more preferably less than 12, and most preferably less than 5. It is preferred for the number of horizontal slices having a gas hold-up less than 0.3 to be less than 120, more preferably less than 80, still more preferably less than 40, even more preferably less than 20, and most preferably less than 15.

Referring again to FIGS. 1 and 2, it has been discovered that positioning oxidant sparger 34 lower in reaction zone 28 provides several advantages, including reduction of the amount of unaerated zones in reaction medium 36. Given a height "H" of reaction medium 36, a length "L" of reaction zone 28, and a maximum diameter "D" of reaction zone 28, it is preferred for a majority (i.e., >50 percent by weight) of the oxidant stream to be introduced into reaction zone 28 within about 0.025H, 0.022L, and/or 0.25D of lower end 52 of reaction zone 28. More preferably, a majority of the oxidant stream is introduced into reaction zone 28 within about 0.02H, 0.018L, and/or 0.2D of lower end 52 of reaction zone 28. Most preferably, a majority of the oxidant stream is introduced into reaction zone 28 within 0.015H, 0.013L, and/or 0.15D of lower end 52 of reaction zone 28.

In the embodiment illustrated in FIG. 2, the vertical distance "$Y_1$" between lower end 52 of reaction zone 28 and the outlet of upper oxidant openings 68 of oxidant sparger 34 is less than about 0.25H, 0.022L, and/or 0.25D, so that substantially all of the oxidant stream enters reaction zone 28 within about 0.25H, 0.022L, and/or 0.25D of lower end 52 of reaction zone 28. More preferably, $Y_1$ is less than about 0.02H, 0.018L, and/or 0.2D. Most preferably, $Y_1$ is less than 0.015H, 0.013L, and/or 0.15D, but more than 0.005H, 0.004L, and/or 0.06D. FIG. 2 illustrates a tangent line 72 at the location where the bottom edge of cylindrical main body 46 of vessel shell 22 joins with the top edge of elliptical lower head 48 of vessel shell 22. Alternatively, lower head 48 can be of any shape, including conical, and the tangent line is still defined as the bottom edge of cylindrical main body 46. The vertical distance "$Y_2$" between tangent line 72 and the top of oxidant sparger 34 is preferably at least about 0.0012H, 0.001L, and/or 0.01D; more preferably at least about 0.005H, 0.004L, and/or 0.05D; and most preferably at least 0.01H, 0.008L, and/or 0.1D. The vertical distance "$Y_3$" between lower end 52 of reaction zone 28 and the outlet of lower oxidant openings 70 of oxidant sparger 34 is preferably less than about 0.015H, 0.013L, and/or 0.15D; more preferably less than about 0.012H, 0.01L, and/or 0.1D; and most preferably less than 0.01H, 0.008L, and/or 0.075D, but more than 0.003H, 0.002L, and/or 0.025D.

In a preferred embodiment of the present invention, the openings that discharge the oxidant stream and the feed stream into the reaction zone are configured so that the amount (by weight) of the oxidant or feed stream discharged from an opening is directly proportional to the open area of the opening. Thus, for example, if 50 percent of the cumulative open area defined by all oxidants openings is located within 0.15D of the bottom of the reaction zone, then 50 weight percent of the oxidant stream enters the reaction zone within 0.15D of the bottom of the reaction zone and vice-versa.

In addition to the advantages provided by minimizing unaerated zones (i.e., zones with low gas hold-up) in reaction medium 36, it has been discovered that oxidation can be enhanced by maximizing the gas hold-up of the entire reaction medium 36. Reaction medium 36 preferably has time-averaged and volume-averaged gas hold-up of at least about 0.4, more preferably in the range of from about 0.6 to about 0.9, and most preferably in the range of from 0.65 to 0.85. Several physical and operational attributes of bubble column reactor 20 contribute to the high gas hold-up discussed above. For example, for a given reactor size and flow of oxidant stream, the high L:D ratio of reaction zone 28 yields a lower diameter which increases the superficial velocity in reaction medium 36 which in turn increases gas hold-up. Additionally, the actual diameter of a bubble column and the L:D ratio are known to influence the average gas hold-up even for a given constant superficial velocity. In addition, the minimization of unaerated zones, particularly in the bottom of reaction zone 28, contributes to an increased gas hold-up value. Further, the overhead pressure and mechanical configuration of the bubble column reactor can affect operating stability at the high superficial velocities and gas hold-up values disclosed herein.

Furthermore, the inventors have discovered the importance of operating with an optimized overhead pressure to obtain increased gas hold-up and increased mass transfer. It might seem that operating with a lower overhead pressure, which reduces the solubility of molecular oxygen according to a Henry's Law effect, would reduce the mass transfer rate of molecular oxygen from gas to liquid. In a mechanically agitated vessel, such is typically the case because aeration levels and mass transfer rates are dominated by agitator design and overhead pressure. However, in a bubble column reactor according to a preferred embodiment of the present invention, it has been discovered how to use a lower overhead pressure to cause a given mass of gas-phase oxidant stream to occupy more volume, increasing the superficial velocity in reaction medium 36 and in turn increasing the gas hold-up and transfer rate of molecular oxygen.

The balance between bubble coalescence and breakup is an extremely complicated phenomenon, leading on the one hand to a tendency to foam, which reduces internal circulation rates of the liquid phase and which may require very, very large disengaging zones, and on the other hand to a tendency to fewer, very large bubbles that give a lower gas hold-up and lower mass transfer rate from the oxidant stream to the liquid phase. Concerning the liquid phase, its composition, density, viscosity and surface tension, among other factors, are known to interact in a very complicated manner to produce very complicated results even in the absence of a solid-phase. For example, laboratory investigators have found it useful to qualify whether "water" is tap water, distilled water, or de-ionized water, when reporting and evaluating observations for even simple water-air bubble columns. For complex mixtures in the liquid phase and for the addition of a solid phase, the degree of complexity rises further. The surface irregularities of individual particles of solids, the average size of solids, the particle size distribution, the amount of solids relative to the liquid phase, and the ability of the liquid to wet the surface of the solid, among other things, are all important in their interaction with the liquid phase and the oxidant stream in establishing what bubbling behavior and natural convection flow patterns will result.

Thus, the ability of the bubble column reactor to function usefully with the high superficial velocities and high gas hold-up disclosed herein depends, for example, on an appropriate selection of: (1) the composition of the liquid phase of the reaction medium; (2) the amount and type of precipitated solids, both of which can be adjusted by reaction conditions; (3) the amount of oxidant stream fed to the reactor; (4) the overhead pressure, which affects the volumetric flow of oxidant stream, the stability of bubbles, and, via the energy balance, the reaction temperature; (5) the reaction temperature itself, which affects the fluid properties, the properties of precipitated solids, and the specific volume of the oxidant stream; and (6) the geometry and mechanical details of the reaction vessel, including the L:D ratio.

Referring again to FIG. 1, it has been discovered that improved distribution of the oxidizable compound (e.g., para-xylene) in reaction medium 36 can be provided by introducing the liquid-phase feed stream into reaction zone 28 at multiple vertically-spaced locations. Preferably, the liquid-phase feed stream is introduced into reaction zone 28 via at least 3 feed openings, more preferably at least 4 feed openings. As used herein, the term "feed openings" shall denote openings where the liquid-phase feed stream is discharged into reaction zone 28 for mixing with reaction medium 36. It is preferred for at least 2 of the feed openings to be vertically-spaced from one another by at least about 0.5D, more preferably at least about 1.5D, and most preferably at least 3D. However, it is preferred for the highest feed opening to be vertically-spaced from the lowest oxidant opening by not more than about 0.75H, 0.65L, and/or 8D; more preferably not more than about 0.5H, 0.4L, and/or 5D; and most preferably not more than 0.4H, 0.35L, and/or 4D.

Although it is desirable to introduce the liquid-phase feed stream at multiple vertical locations, it has also been discovered that improved distribution of the oxidizable compound in reaction medium 36 is provided if the majority of the liquid-phase feed stream is introduced into the bottom half of reaction medium 36 and/or reaction zone 28. Preferably, at least about 75 weight percent of the liquid-phase feed stream is introduced into the bottom half of reaction medium 36 and/or reaction zone 28. Most preferably, at least 90 weight percent of the liquid-phase feed stream is introduced into the bottom half of reaction medium 36 and/or reaction zone 28. In addition, it is preferred for at least about 30 weight percent of the liquid-phase feed stream to be introduced into reaction zone 28 within about 1.5D of the lowest vertical location where the oxidant stream is introduced into reaction zone 28. This lowest vertical location where the oxidant stream is introduced into reaction zone 28 is typically at the bottom of oxidant sparger; however, a variety of alternative configurations for introducing the oxidant stream into reaction zone 28 are contemplated by a preferred embodiment of the present invention. Preferably, at least about 50 weight percent of the liquid-phase feed is introduced within about 2.5D of the lowest vertical location where the oxidant stream is introduced into reaction zone 28. Preferably, at least about 75 weight percent of the liquid-phase feed stream is introduced within about 5D of the lowest vertical location where the oxidant stream is introduced into reaction zone 28.

Each feed opening defines an open area through which the feed is discharged. It is preferred that at least about 30 percent of the cumulative open area of all the feed inlets is located within about 1.5D of the lowest vertical location where the oxidant stream is introduced into reaction zone 28. Preferably, at least about 50 percent of the cumulative open area of all the feed inlets is located within about 2.5D of the lowest vertical location where the oxidant stream is introduced into reaction zone 28. Preferably, at least about 75 percent of the cumulative open area of all the feed inlets is located within about 5D of the lowest vertical location where the oxidant stream is introduced into reaction zone 28.

Referring again to FIG. 1, in one embodiment of the present invention, feed inlets 32a,b,c,d are simply a series of vertically-aligned openings along one side of vessel shell 22. These feed openings preferably have substantially similar diameters of less than about 7 centimeters, more preferably in the range of from about 0.25 to about 5 centimeters, and most preferably in the range of from 0.4 to 2 centimeters. Bubble column reactor 20 is preferably equipped with a system for controlling the flow rate of the liquid-phase feed stream out of each feed opening. Such flow control system preferably includes an individual flow control valve 74a,b,c,d for each respective feed inlet 32a,b,c,d. In addition, it is preferred for bubble column reactor 20 to be equipped with a flow control system that allows at least a portion of the liquid-phase feed stream to be introduced into reaction zone 28 at an elevated inlet superficial velocity of at least about 2 meters per second, more preferably at least about 5 meters per second, still more preferably at least about 6 meters per second, and most preferably in the range of from 8 to 20 meters per second. As used herein, the term "inlet superficial velocity" denotes the time-averaged volumetric flow rate of the feed stream out of the feed opening divided by the area of the feed opening. Preferably, at least about 50 weight percent of the feed stream is introduced into reaction zone 28 at an elevated inlet superficial velocity. Most preferably, substantially all the feed stream is introduced into reaction zone 28 at an elevated inlet superficial velocity.

Figure 6:
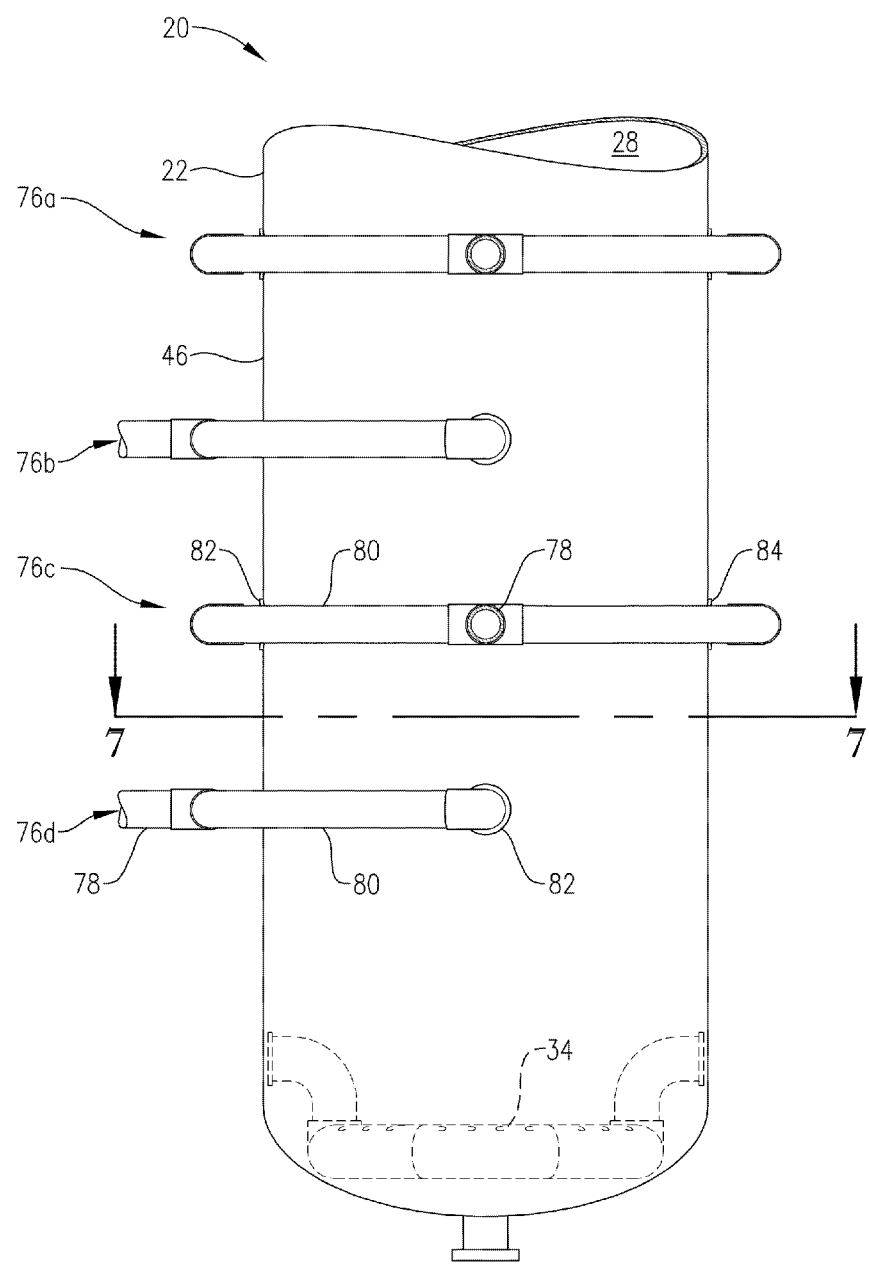
FIG. 6 is an enlarged side view of the bottom portion of the bubble column reactor, particular illustrating a system for introducing the feed stream into the reactor at multiple, vertically-space locations.
Figure 7:
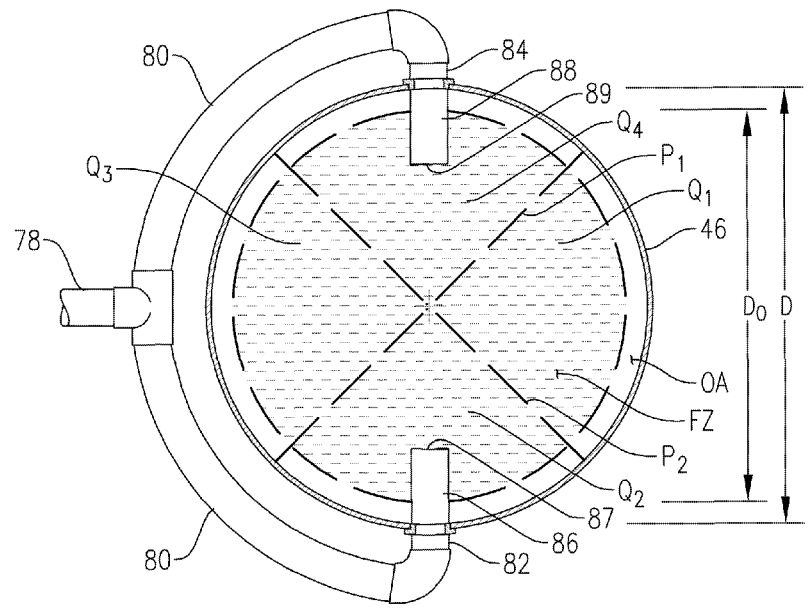
FIG. 7 is a sectional top view taken along line 7-7 in FIG. 6, particularly illustrating how the feed introduction system shown in FIG. 6 distributes the feed stream into in a preferred radial feed zone (FZ) and more than one azimuthal quadrant ($Q_1$, $Q_2$, $Q_3$, $Q_4$)

Referring now to FIGS. 6-7, an alternative system for introducing the liquid-phase feed stream into reaction zone 28 is illustrated. In this embodiment, the feed stream is introduced into reaction zone 28 at four different elevations. Each elevation is equipped with a respective feed distribution system 76a,b,c,d. Each feed distribution system 76 includes a main feed conduit 78 and a manifold 80. Each manifold 80 is provided with at least two outlets 82,84 coupled to respective insert conduits 86,88, which extend into reaction zone 28 of vessel shell 22. Each insert conduit 86,88 presents a respective feed opening 87,89 for discharging the feed stream into reaction zone 28. Feed openings 87,89 preferably have substantially similar diameters of less than about 7 centimeters, more preferably in the range of from about 0.25 to about 5 centimeters, and most preferably in the range of from 0.4 to 2 centimeters. It is preferred for feed openings 87,89 of each feed distribution system 76a,b,c,d to be diametrically opposed so as to introduce the feed stream into reaction zone 28 in opposite directions. Further, it is preferred for the diametrically opposed feed openings 86,88 of adjacent feed distribution systems 76 to be oriented at 90 degrees of rotation relative to one another. In operation, the liquid-phase feed stream is charged to main feed conduit 78 and subsequently enters manifold 80. Manifold 80 distributes the feed stream evenly for simultaneous introduction on opposite sides of reactor 20 via feed openings 87,89.

Figure 8:
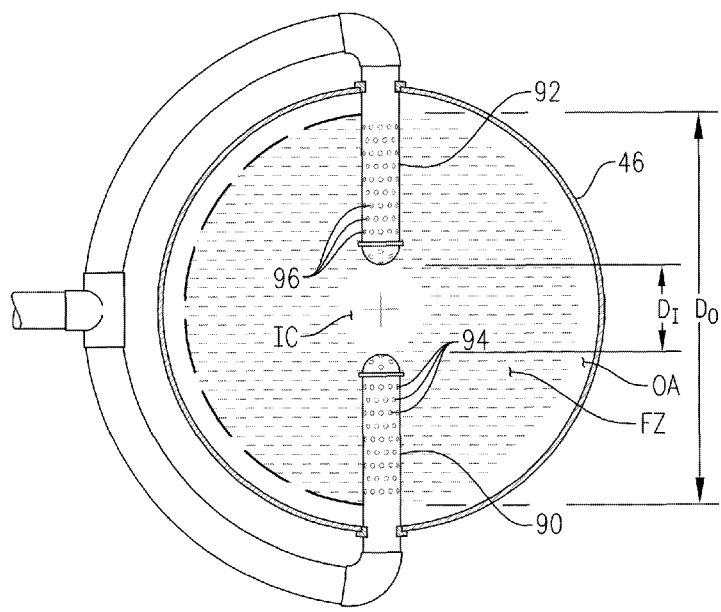
FIG. 8 is a sectional top view similar to FIG. 7, but illustrating an alternative means for discharging the feed stream into the reactor using bayonet tubes each having a plurality of small feed openings.

FIG. 8 illustrates an alternative configuration wherein each feed distribution system 76 is equipped with bayonet tubes 90,92 rather than insert conduits 86,88 (shown in FIG. 7). Bayonet tubes 90,92 project into reaction zone 28 and include a plurality of small feed openings 94,96 for discharging the liquid-phase feed into reaction zone 28. It is preferred for the small feed openings 94,96 of bayonet tubes 90,92 to have substantially the same diameters of less than about 50 millimeters, more preferably about 2 to about 25 millimeters, and most preferably 4 to 15 millimeters.

Figure 9:
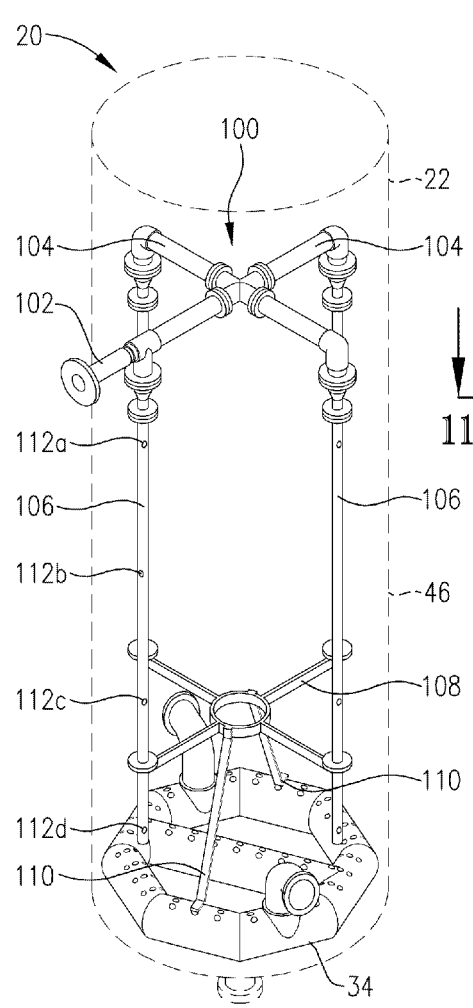
FIG. 9 is an isometric view of an alternative system for introducing the feed stream into the reaction zone at multiple vertically-space locations without requiring multiple vessel penetrations, particularly illustrating that the feed distribution system can be at least partly supported on the oxidant sparger.
Figure 11:
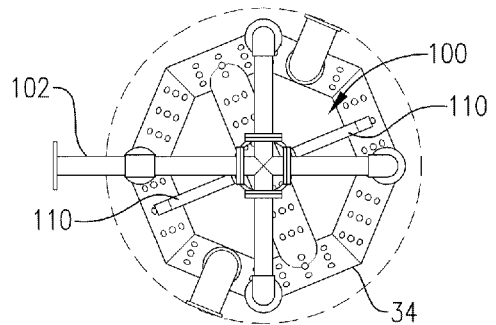
FIG. 11 is a sectional top view taken along line 11-11 in FIG. 10 and further illustrating the single-penetration feed distribution system supported on the oxidant sparger.
Figure 10:
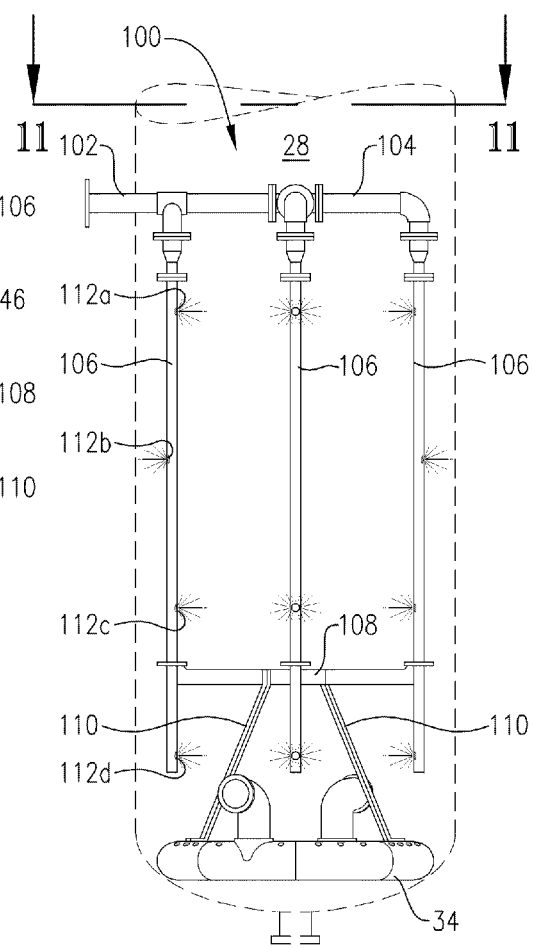
FIG. 10 is a side view of the single-penetration feed distribution system and oxidant sparger illustrated in FIG. 9.
Figure 12:
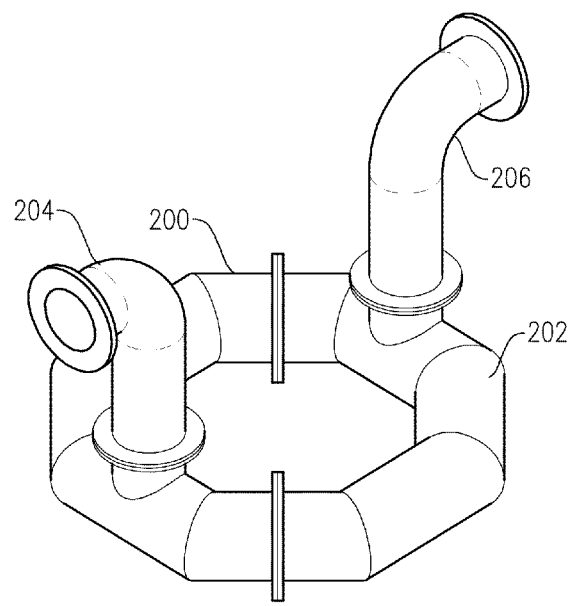
FIG. 12 is an isometric view of an alternative oxidant sparger having all of the oxidant openings located in the bottom of the ring member.
Figure 13:
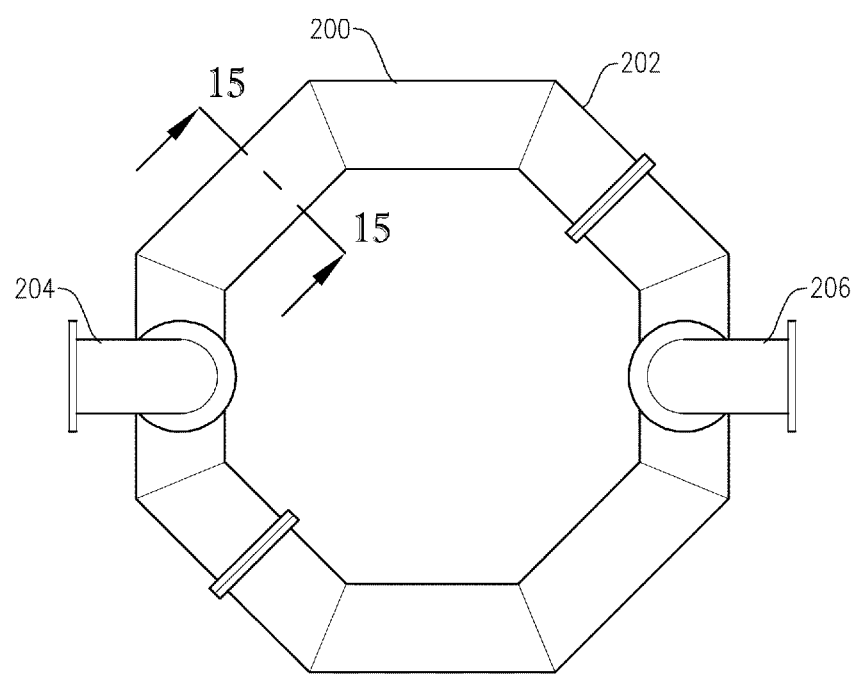
FIG. 13 is a top view of the alternative oxidant sparger of FIG. 12.

FIGS. 9-11 illustrate an alternative feed distribution system 100. Feed distribution system 100 introduces the liquid-phase feed stream at a plurality of vertically-spaced and laterally-spaced locations without requiring multiple penetrations of the sidewall of bubble column reactor 20. Feed introduction system 100 generally includes a single inlet conduit 102, a header 104, a plurality of upright distribution tubes 106, a lateral support mechanism 108, and a vertical support mechanism 110. Inlet conduit 102 penetrates the sidewall of main body 46 of vessel shell 22. Inlet conduit 102 is fluidly coupled to header 104. Header 104 distributes the feed stream received from inlet conduit 102 evenly among upright distribution tubes 106. Each distribution tube 106 has a plurality of vertically-spaced feed openings 112a,b,c,d for discharging the feed stream into reaction zone 28. Lateral support mechanism 108 is coupled to each distribution tube 106 and inhibits relative lateral movement of distribution tubes 106. Vertical support mechanism 110 is preferably coupled to lateral support mechanism 108 and to the top of oxidant sparger 34. Vertical support mechanism 110 substantially inhibits vertical movement of distribution tubes 106 in reaction zone 28. It is preferred for feed openings 112 to have substantially the same diameters of less than about 50 millimeters, more preferably about 2 to about 25 millimeters, and most preferably 4 to 15 millimeters. The vertical spacing of feed openings 112 of feed distribution system 100 illustrated in FIGS. 9-11 can be substantially the same as described above with reference to the feed distribution system of FIG. 1.

It has been discovered that the flow patterns of the reaction medium in many bubble column reactors can permit uneven azimuthal distribution of the oxidizable compound in the reaction medium, especially when the oxidizable compound is primarily introduced along one side of the reaction medium. As used herein, the term "azimuthal" shall denote an angle or spacing around the upright axis of elongation of the reaction zone. As used herein, "upright" shall mean within 45° of vertical. In one embodiment of the present invention, the feed stream containing the oxidizable compound (e.g., para-xylene) is introduced into the reaction zone via a plurality of azimuthally-spaced feed openings. These azimuthally-spaced feed openings can help prevent regions of excessively high and excessively low oxidizable compound concentrations in the reaction medium. The various feed introduction systems illustrated in FIGS. 6-11 are examples of systems that provide proper azimuthal spacing of feed openings.

Referring again to FIG. 7, in order to quantify the azimuthally-spaced introduction of the liquid-phase feed stream into the reaction medium, the reaction medium can be theoretically partitioned into four upright azimuthal quadrants "$Q_1, Q_2, Q_3, Q_4$" of approximately equal volume. These azimuthal quadrants "$Q_1, Q_2, Q_3, Q_4$" are defined by a pair of imaginary intersecting perpendicular vertical planes "$P_1, P_2$" extending beyond the maximum vertical dimension and maximum radial dimension of the reaction medium. When the reaction medium is contained in a cylindrical vessel, the line of intersection of the imaginary intersecting vertical planes $P_1, P_2$ will be approximately coincident with the vertical centerline of the cylinder, and each azimuthal quadrant $Q_1, Q_2, Q_3, Q_4$ will be a generally wedge-shaped vertical volume having a height equal to the height of the reaction medium. It is preferred for a substantial portion of the oxidizable compound to be discharged into the reaction medium via feed openings located in at least two different azimuthal quadrants.

In a preferred embodiment of the present invention, not more than about 80 weight percent of the oxidizable compound is discharged into the reaction medium through feed openings that can be located in a single azimuthal quadrant. More preferably, not more than about 60 weight percent of the oxidizable compound is discharged into the reaction medium through feed openings that can be located in a single azimuthal quadrant. Most preferably, not more than 40 weight percent of the oxidizable compound is discharged into the reaction medium through feed openings that can be located in a single azimuthal quadrant. These parameters for azimuthal distribution of the oxidizable compound are measured when the azimuthal quadrants are azimuthally oriented such that the maximum possible amount of oxidizable compound is being discharged into one of the azimuthal quadrants. For example, if the entire feed stream is discharged into the reaction medium via two feed openings that are azimuthally spaced from one another by 89 degrees, for purposes of determining azimuthal distribution in four azimuthal quadrants, 100 weight percent of the feed stream is discharged into the reaction medium in a single azimuthal quadrant because the azimuthal quadrants can be azimuthally oriented in such a manner that both of the feed openings are located in a single azimuthal quadrant.

In addition to the advantages associated with the proper azimuthal-spacing of the feed openings, it has also been discovered that proper radial spacing of the feed openings in a bubble column reactor can also be important. It is preferred for a substantial portion of the oxidizable compound introduced into the reaction medium to be discharged via feed openings that are radially spaced inwardly from the sidewall of the vessel. Thus, in one embodiment of the present invention, a substantial portion of the oxidizable compound enters the reaction zone via feed openings located in a "preferred radial feed zone" that is spaced inwardly from the upright sidewalls defining the reaction zone.

Referring again to FIG. 7, the preferred radial feed zone "FZ" can take the shape of a theoretical upright cylinder centered in reaction zone 28 and having an outer diameter "$D_O$" of 0.9D, where "D" is the diameter of reaction zone 28. Thus, an outer annulus "OA" having a thickness of 0.05D is defined between the preferred radial feed zone FZ and the inside of the sidewall defining reaction zone 28. It is preferred for little or none of the oxidizable compound to be introduced into reaction zone 28 via feed openings located in this outer annulus OA.

In another embodiment, it is preferred for little or none of the oxidizable compound to be introduced into the center of reaction zone 28. Thus, as illustrated in FIG. 8, the preferred radial feed zone FZ can take the shape of a theoretical upright annulus centered in reaction zone 28, having an outer diameter $D_O$ of 0.9D, and having an inner diameter $D_I$ of 0.2D. Thus, in this embodiment, an inner cylinder IC having a diameter of 0.2D is "cut out" of the center of the preferred radial feed zone FZ. It is preferred for little or none of the oxidizable compound to be introduced into reaction zone 28 via feed openings located in this inner cylinder IC.

In a preferred embodiment of the present invention, a substantial portion of the oxidizable compound is introduced into reaction medium 36 via feed openings located in the preferred radial feed zone, regardless of whether the preferred radial feed zone has the cylindrical or annular shape described above. More preferably, at least about 25 weight percent of the oxidizable compound is discharged into reaction medium 36 via feed openings located in the preferred radial feed zone. Still more preferably, at least about 50 weight percent of the oxidizable compound is discharged into reaction medium 36 via feed openings located in the preferred radial feed zone. Most preferably, at least 75 weight percent of the oxidizable compound is discharged into reaction medium 36 via feed openings located in the preferred radial feed zone.

Although the theoretical azimuthal quadrants and theoretical preferred radial feed zone illustrated in FIGS. 7 and 8 are described with reference to the distribution of the liquid-phase feed stream, it has been discovered that proper azimuthal and radial distribution of the gas-phase oxidant stream can also provide certain advantages. Thus, in one embodiment of the present invention, the description of the azimuthal and radial distribution of the liquid-phase feed stream, provided above, also applies to the manner in which the gas-phase oxidant stream is introduced into the reaction medium 36.

Referring now to FIGS. 12-15, an alternative oxidant sparger 200 is illustrated as generally comprising a ring member 202 and a pair of oxidant entry conduits 204,206. Oxidant sparger 200 of FIGS. 12-15 is similar to oxidant sparger 34 of FIGS. 1-11 with the following three primary differences: (1) oxidant sparger 200 does not include a diagonal cross-member; (2) the upper portion of ring member 202 has no openings for discharging the oxidant in an upward direction; and (3) oxidant sparger 200 has many more openings in the lower portion of ring member 202.

Figure 14:
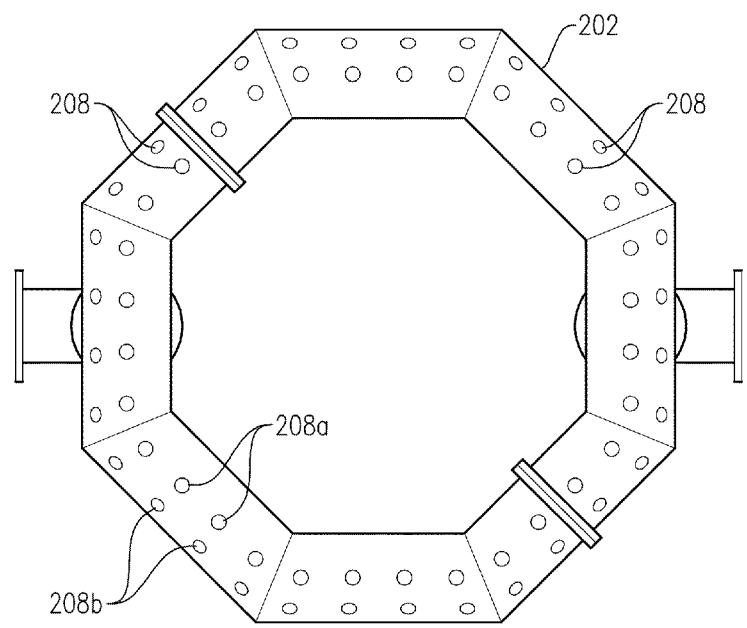
FIG. 14 is a bottom view of the alternative oxidant sparger of FIG. 12, particularly illustrating the location of the bottom openings for introducing the oxidant stream into the reaction zone.
Figure 15:
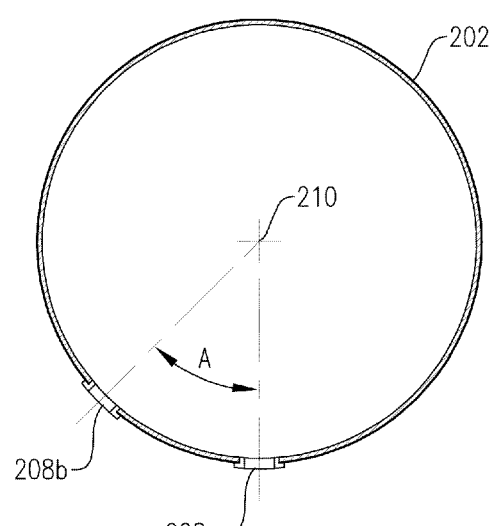
FIG. 15 is a sectional side view of the oxidant sparger taken along line 15-15 in FIG. 13, particularly illustrating the orientation of the lower oxidant openings.

As perhaps best illustrated in FIGS. 14 and 15, the bottom portion of oxidant sparger ring 202 presents a plurality of oxidant openings 208. Oxidant openings 208 are preferably configured such that at least about 1 percent of the total open area defined by oxidant openings 208 is located below the centerline 210 (FIG. 15) of ring member 202, where centerline 210 is located at the elevation of the volumetric centroid of ring member 202. More preferably, at least about 5 percent of the total open area defined by all oxidant openings 208 is located below centerline 210, with at least about 2 percent of the total open area being defined by openings 208 that discharge the oxidant stream in a generally downward direction within about 30 degrees of vertical. Still more preferably, at least about 20 percent of the total open area defined by all oxidant openings 208 is located below centerline 210, with at least about 10 percent of the total open area being defined by openings 208 that discharge the oxidant stream in a generally downward direction within 30 degrees of vertical. Most preferably, at least about 75 percent of the total open area defined by all oxidant openings 208 is located below centerline 210, with at least about 40 percent of the total open area being defined by openings 208 that discharge the oxidant stream in a generally downward direction within 30 degrees of vertical. The fraction of the total open area defined by all oxidant openings 208 that are located above centerline 210 is preferably less than about 75 percent, more preferably less than about 50 percent, still more preferably less than about 25 percent, and most preferably less than 5 percent.

As illustrated in FIGS. 14 and 15, oxidant openings 208 include downward openings 208a and skewed openings 208b. Downward openings 208a are configured to discharge the oxidant stream generally downwardly at an angle within about 30 degrees of vertical, more preferably within about 15 degrees of vertical, and most preferably within 5 degrees of vertical. Skewed openings 208b are configured to discharge the oxidant stream generally outwardly and downwardly at an angle "A" that is in the range of from about 15 to about 75 degrees from vertical, more preferably angle A is in the range of from about 30 to about 60 degrees from vertical, and most preferably angle A is in the range of from 40 to 50 degrees from vertical.

It is preferred for substantially all oxidant openings 208 to have approximately the same diameter. The diameter of oxidant openings 208 is preferably in the range of from about 2 to about 300 millimeters, more preferably in the range of from about 4 to about 120 millimeters, and most preferably in the range of from 8 to 60 millimeters. The total number of oxidant openings 208 in ring member 202 is selected to meet the low pressure drop criteria detailed below. Preferably, the total number of oxidant openings 208 formed in ring member 202 is at least about 10, more preferably the total number of oxidant openings 208 is in the range of from about 20 to about 200, and most preferably the total number of oxidant openings 208 is in the range of from 40 to 100.

Although FIGS. 12-15 illustrate a very specific configuration for oxidant sparger 200, it is now noted that a variety of oxidant sparger configurations can be employed to achieve the advantages described herein. For example, the oxidant sparger does not necessarily need to have the octagonal ring member configuration illustrated in FIGS. 12-13. Rather, it is possible for the oxidant sparger to be formed of any configuration of flow conduit(s) that employs a plurality of spaced-apart openings for discharging the oxidant stream. The size, number, and discharge direction of the oxidant openings in the flow conduit are preferably within the ranges stated above. Further, the oxidant sparger is preferably configured to provide the azimuthal and radial distribution of molecular oxygen described above.

Regardless of the specific configuration of the oxidant sparger, it is preferred for the oxidant sparger to be physically configured and operated in a manner that minimizes the pressure drop associated with discharging the oxidant stream out of the flow conduit(s), through the oxidant openings, and into the reaction zone. Such pressure drop is calculated as the time-averaged static pressure of the oxidant stream inside the flow conduit at oxidant inlets 66a,b of the oxidant sparger minus the time-averaged static pressure in the reaction zone at the elevation where one-half of the oxidant stream is introduced above that vertical location and one-half of the oxidant stream is introduced below that vertical location. In a preferred embodiment of the present invention, the time-averaged pressure drop associated with discharging the oxidant stream from the oxidant sparger is less than about 0.3 megapascal (MPa), more preferably less than about 0.2 MPa, still more preferably less than about 0.1 MPa, and most preferably less than 0.05 MPa. Under the preferred operating conditions of the bubble column reactor described herein, the pressure of the oxidant stream inside the flow conduit(s) of the oxidant sparger is preferably in the range of from about 0.35 to about 1 MPa, more preferably in the range of from about 0.45 to about 0.85 MPa, and most preferably in the range of from 0.5 to 0.7 MPa.

As alluded to earlier with reference to the oxidant sparger configuration illustrated in FIGS. 2-5, it may be desirable to continuously or periodically flush the oxidant sparger with a liquid (e.g., acetic acid, water, and/or para-xylene) to prevent fouling of the oxidant sparger with solids. When such a liquid flush is employed, it is preferred for an effective amount of the liquid (i.e., not just the minor amount of liquid droplets that might naturally be present in the oxidant stream) to be passed through the oxidant sparger and out of the oxidant openings for at least one period of more than one minute each day. When a liquid is continuously or periodically discharged from the oxidant sparger, it is preferred for the time-averaged ratio of the mass flow rate of the liquid through the oxidant sparger to the mass flow rate of the molecular oxygen through the oxidant sparger to be in the range of from about 0.05:1 to about 30:1, or in the range of from about 0.1:1 to about 2:1, or even in the range of from 0.2:1 to 1:1.

In one embodiment of the present invention, a significant portion of the oxidizable compound (e.g., para-xylene) can be introduced into the reaction zone through the oxidant sparger. In such a configuration, it is preferred for the oxidizable compound and the molecular oxygen to be discharged from the oxidant sparger through the same openings in the oxidant sparger. As noted above, the oxidizable compound is typically a liquid at STP. Therefore, in this embodiment, a two-phase stream may be discharged from the oxidant sparger, with the liquid phase comprising the oxidizable compound and the gas phase comprising the molecular oxygen. It should be recognized, however, that at least a portion of the oxidizable compound may be in a gaseous state when discharged from the oxidant sparger. In one embodiment, the liquid phase discharged from the oxidant sparger is formed predominately of the oxidizable compound. In another embodiment, the liquid phase discharged from the oxidant sparger has substantially the same composition as the feed stream, described above. When the liquid phase discharged from the oxidant sparger has substantially the same composition as the feed stream, such liquid phase may comprise a solvent and/or a catalyst system in the amounts and ratios described above with reference to the composition of the feed stream.

In one embodiment of the present invention, it is preferred for at least about 10 weight percent of all the oxidizable compound introduced into the reaction zone to be introduced via the oxidant sparger, more preferably at least about 40 weight percent of the oxidizable compound is introduced into the reaction zone via the oxidant sparger, and most preferably at least 80 weight percent of the oxidizable compound is introduced into the reaction zone via the oxidant sparger. When all or part of the oxidizable compound is introduced into the reaction zone via the oxidant sparger, it is preferred for at least about 10 weight percent of all the molecular oxygen introduced into the reaction zone to be introduced via the same oxidant sparger, more preferably at least about 40 weight percent of the oxidizable compound is introduced into the reaction zone via the same oxidant sparger, and most preferably at least 80 weight percent of the oxidizable compound is introduced into the reaction zone via the same oxidant sparger. When a significant portion of the oxidizable compound is introduced into the reaction zone via the oxidant sparger, it is preferred for one or more temperature sensing devices (e.g., thermocouples) to be disposed in the oxidant sparger. These temperature sensors can be employed to help to make sure the temperature in the oxidant sparger does not become dangerously high.

Figure 16:
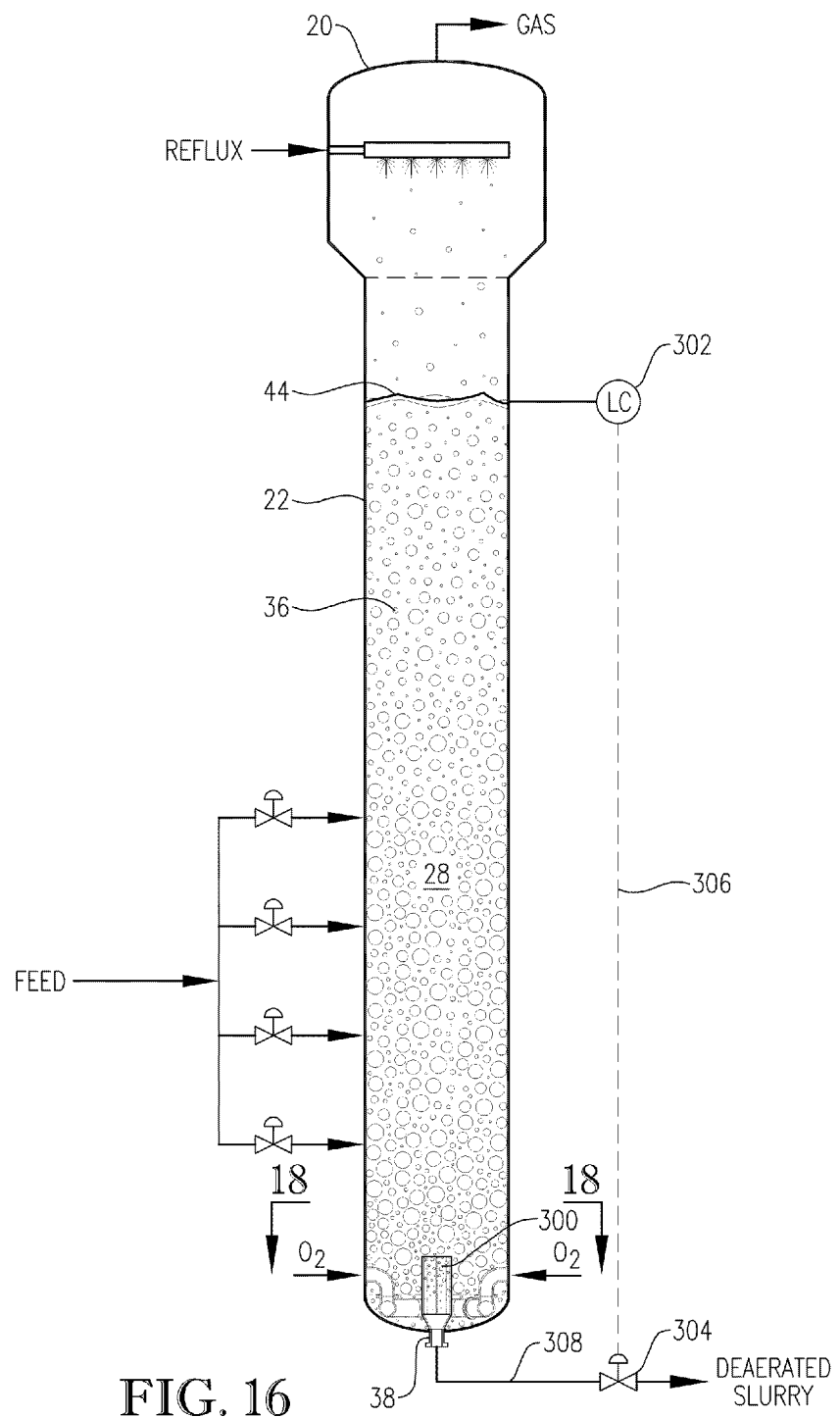
FIG. 16 is a side view of a bubble column reactor equipped with an internal deaeration vessel near the bottom outlet of the reactor.
Figure 17:
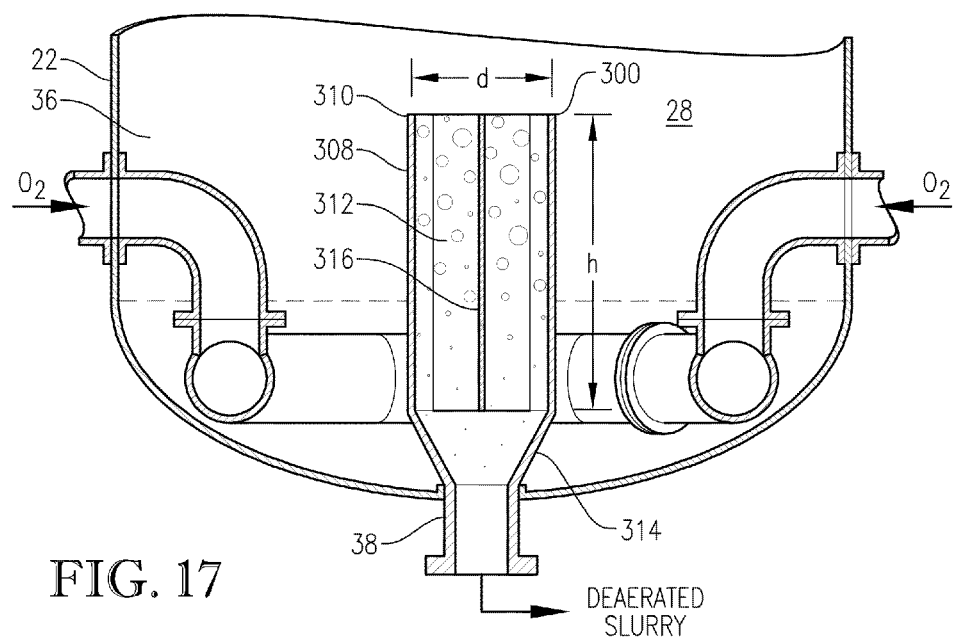
FIG. 17 is an enlarged sectional side view of the lower portion of the bubble column reactor of FIG. 16 taken along line 17-17 in FIG. 18, particularly illustrating the configuration of the internal deaeration vessel positioned at the bottom outlet of the bubble column reactor.
Figure 18:
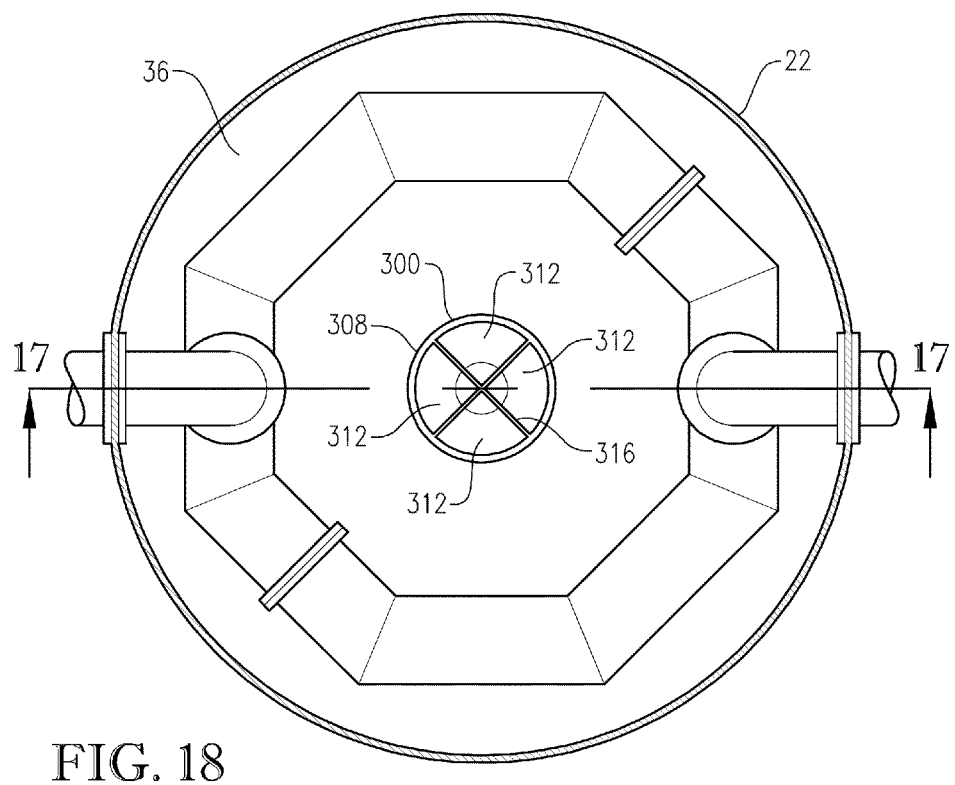
FIG. 18 is a sectional top view taken along line 18-18 in FIG. 16, particularly illustrating a vortex breaker disposed in the deaeration vessel.

Referring now to FIGS. 16-18, bubble column reactor 20 is illustrated as including an internal deaeration vessel 300 disposed in the bottom of reaction zone 28 near slurry outlet 38. It has been discovered that impurity-forming side reactions occur at a relatively high rate during deaeration of reaction medium 36. As used herein, "deaeration" shall denote the disengagement of a gas phase from multi-phase reaction medium. When reaction medium 36 is highly aerated (>0.3 gas hold-up), impurity formation is minimal. When reaction medium 36 is highly unaerated (<0.01 gas hold-up), impurity formation is also minimal. However, when reaction medium is partially-aerated (0.01-0.3 gas hold-up), undesirable side reactions are promoted and increased impurities are generated. Deaeration vessel 300 addresses this and other problems by minimizing the volume of reaction medium 36 in a partially-aerated stated, and by minimizing the time it takes to deaerate reaction medium 36. A substantially deaerated slurry is produced from the bottom of deaeration vessel 300 and exits reactor 20 via slurry outlet 38. The substantially deaerated slurry preferably contains less than about 5 volume percent gas phase, more preferably less than about 2 volume percent gas phase, and most preferably less than 1 volume percent gas phase.

In FIG. 16, bubble column reactor 20 is illustrated as including a level controller 302 and a flow control valve 304. Level controller 302 and flow control valve 304 cooperate to maintain reaction medium 36 at a substantially constant elevation in reaction zone 28. Level controller 302 is operable to sense (e.g., by differential pressure level sensing or by nuclear level sensing) the elevation of upper surface 44 of reaction medium 36 and generate a control signal 306 responsive to the elevation of reaction medium 36. Flow control valve 304 receives control signal 306 and adjusts the flow rate of a slurry through a slurry outlet conduit 308. Thus, the flow rate of the slurry out of slurry outlet 38 can vary between a maximum slurry volumetric flow rate ($F_{max}$) when the elevation of reaction medium 36 is too high and a minimum slurry volumetric flow rate ($F_{min}$) when the elevation of reaction medium 36 is too low.

In order to remove solid-phase oxidation product from reaction zone 28, a portion must first pass through deaeration vessel 300. Deaeration vessel 300 provides a low-turbulence internal volume that permits the gas phase of reaction medium 36 to naturally rise out of the liquid and solid phases of reaction medium 36 as the liquid and solids flow downwardly toward slurry outlet 38. The rising of the gas phase out of the liquid and solid phases is caused by the natural upward buoyancy of the gas phase in the liquid and solid phases. When deaeration vessel 300 is employed, the transitioning of reaction medium 36 from a fully-aerated, three-phase medium to a fully-deaerated, two-phase slurry is quick and efficient.

Referring now to FIGS. 17 and 18, deaeration vessel 300 includes a generally upright sidewall 308 defining a deaeration zone 312 therebetween. Preferably, sidewall 308 extends upwardly within about 30 degrees of vertical, more preferably within about 10 degrees of vertical. Most preferably, sidewall 308 is substantially vertical. Deaeration zone 312 is separate from reaction zone 28 and has height "h" and a diameter "d." An upper end 310 of sidewall 308 is open so as to receive reaction medium from reaction zone 28 into internal volume 312. The lower end of sidewall 308 is fluidly coupled to slurry outlet 38 via a transition section 314. In certain instances, such as when the opening of slurry outlet 38 is large or when the diameter "d" of sidewall 308 is small, transition section 314 can be eliminated. As perhaps best illustrated in FIG. 18, deaeration vessel 300 can also include a vortex breaker 316 disposed in deaeration zone 312. Vortex breaker 316 can be any structure operable to inhibit the formation of vortices as the solid and liquid phases flow downwardly towards slurry outlet 38.

In order to permit proper disengagement of the gas phase from the solid and liquid phases in deaeration vessel 300, the height "h" and horizontal cross-sectional area of internal deaeration zone 312 are carefully selected. The height "h" and horizontal cross-sectional area of internal deaeration zone 312 should provide sufficient distance and time so that even when the maximum amount of slurry is being withdrawn (i.e., when slurry is being withdrawn at $F_{max}$), substantially all of the gas bubble volume can rise out of the solid and liquid phases before the gas bubbles reach the bottom outlet of deaeration vessel 300. Thus, it is preferred for the cross-sectional area of deaeration zone 312 to be such that the maximum downward velocity ($V_{dmax}$) of the liquid and solid phases through deaeration zone 312 is substantially less than the natural rise velocity ($V_u$) of the gas phase bubbles through the liquid and solid phases. The maximum downward velocity ($V_{dmax}$) of the liquid and solid phases through deaeration zone 312 occurs at the maximum slurry volumetric flow rate ($F_{max}$), discussed above. The natural rise velocity ($V_u$) of the gas bubbles through the liquid and solid phases varies depending on the size of the bubbles; however, the natural rise velocity ($V_{u0.5}$) of 0.5 centimeter diameter value because substantially all of the bubble volume initially in reaction medium 36 will be greater than 0.5 centimeters. Preferably, the cross-sectional area of deaeration zone 312 is such that $V_{dmax}$ is less than about 75 percent of $V_{u0.5}$, more preferably $V_{dmax}$ is less than about 40 percent of $V_{u0.5}$, most preferably $V_{dmax}$ is less than 20 percent of $V_{u0.5}$.

The downward velocity of the liquid and solid phases in deaeration zone 312 of deaeration vessel 300 is calculated as the volumetric flow rate of the deaerated slurry through slurry outlet 38 divided by the minimum cross-sectional area of deaeration zone 312. The downward velocity of the liquid and solid phases in deaeration zone 312 of deaeration vessel 300 is preferably less than about 50 centimeters per second, more preferably less than about 30 centimeters per second, and most preferably less than 10 centimeters per second.

It is now noted that although upright sidewall 308 of deaeration vessel 300 is illustrated as having a cylindrical configuration, sidewall 308 could comprise a plurality of sidewalls that form a variety of configurations (e.g., triangular, square, or oval), so long as the walls defines an internal volume having an appropriate volume, cross-sectional area, width "d", and height "h". In a preferred embodiment of the present invention, "d" is in the range of from about 0.2 to about 2 meters, more preferably in the range of from about 0.3 to about 1.5 meters, and most preferably in the range of from 0.4 to 1.2 meters. In a preferred embodiment of the present invention, "h" is in the range of from about 0.3 meters to about 5 meters, more preferably in the range of from about 0.5 to about 3 meters, and most preferably in the range of from 0.75 to 2 meters.

In a preferred embodiment of the present invention, sidewall 308 is substantially vertical so that the horizontal cross-sectional area of deaeration zone 312 is substantially constant along the entire height "h" of deaeration zone 312. Preferably, the maximum horizontal cross-sectional area of deaeration zone 312 is less than about 25 percent of the maximum horizontal cross-sectional area of reaction zone 28. More preferably, the maximum horizontal cross-sectional area of deaeration zone 312 is in the range of from about 0.1 to about 10 percent of the maximum horizontal cross-sectional area of reaction zone 28. Most preferably, the maximum horizontal cross-sectional area of deaeration zone 312 is in the range of from 0.25 to 4 percent of the maximum horizontal cross-sectional area of reaction zone 28. Preferably, the maximum horizontal cross-sectional area of deaeration zone 312 is in the range of from about 0.02 to about 3 square meters, more preferably in the range of from about 0.05 to about 2 square meters, and most preferably in the range of from 0.1 to 1.2 square meters. The volume of deaeration zone 312 is preferably less than about 5 percent of the total volume of reaction medium 36 or reaction zone 28. More preferably, the volume of deaeration zone 312 is in the range of from about 0.01 to about 2 percent of the total volume of reaction medium 36 or reaction zone 28. Most preferably, the volume of deaeration zone 312 is in the range of from 0.05 to about 1 percent of the total volume of reaction medium 36 or reaction zone 28. The volume of deaeration zone 312 is preferably less than about 2 cubic meters, more preferably in the range of from about 0.01 to about 1 cubic meters, and most preferably in the range of from 0.05 to 0.5 cubic meters.

Figure 19:
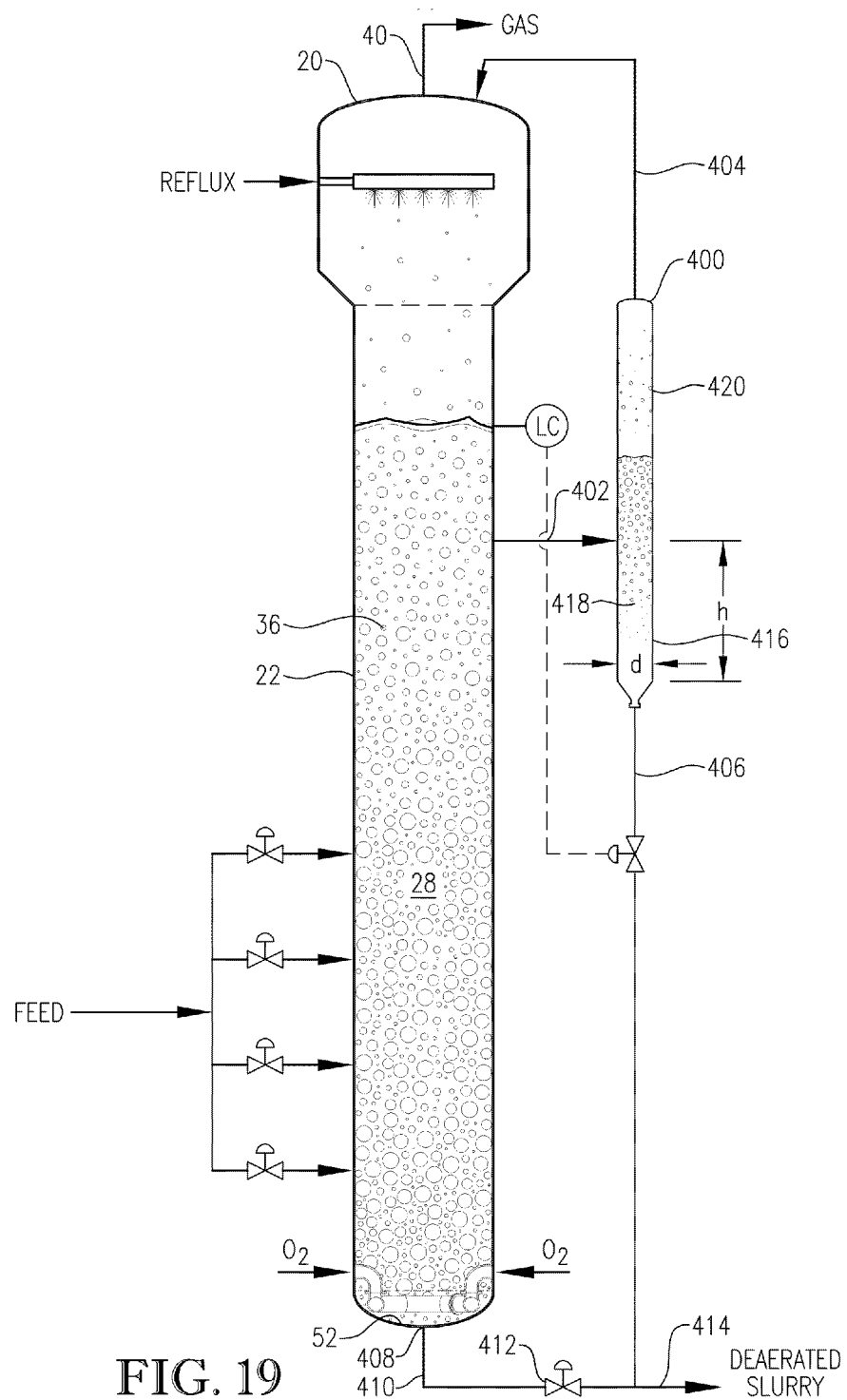
FIG. 19 is a side view of a bubble column reactor equipped with an external deaeration vessel and illustrating the manner in which a portion of the deaerated slurry exiting the bottom of the deaeration vessel can be used to flush out a de-inventorying line coupled to the bottom of the reactor.

Turning now to FIG. 19, bubble column reactor 20 is illustrated as including an external deaeration vessel 400. In this configuration, aerated reaction medium 36 is withdrawn from reaction zone 28 via an elevated opening in the side of vessel shell 22. The withdrawn aerated medium is transported to external deaeration vessel 400 via an outlet conduit 402 for disengagement of the gas phase from the solid and liquid phases. The disengaged gas phase exits deaeration vessel 400 via conduit 404, while the substantially deaerated slurry exits deaeration vessel 400 via conduit 406.

In FIG. 19, outlet conduit 402 is shown as being approximately straight, horizontal, and orthogonal to vessel shell 22. This is merely one convenient configuration; and outlet conduit 402 may be otherwise in any respect, providing that it usefully connects bubble column reactor 20 with external deaeration vessel 400. Turning to conduit 404, it is useful for this conduit to connect at or near the top deaeration vessel 400 in order to control safety issues relating to a stagnant gas pocket containing oxidizable compound and oxidant. Furthermore, conduits 402 and 404 may usefully comprise means of flow isolation, such as valves.

When reaction medium 36 is withdrawn from reactor 20 via an elevated outlet, as shown in FIG. 19, it is preferred for bubble column reactor 20 to be equipped with a lower outlet 408 near the bottom 52 of reaction zone 28. Lower outlet 408 and a lower conduit 410, coupled thereto, can be used to de-inventory (i.e., empty) reactor 20 during shutdowns. Preferably, one or more lower outlet 408 is provided in the bottom one-third of the height of reaction medium 36, more preferably in the bottom one-fourth of reaction medium 36, and most preferably at the lowest point of reaction zone 28.

With the elevated slurry withdrawal and deaeration system shown in FIG. 19, lower conduit 410 and outlet 408 are not used to withdraw slurry from reaction zone 28 during oxidation. It is known in the art that solids tend to settle by gravity forces in unaerated and otherwise unagitated portions of the slurry, including in stagnant flow conduits. Furthermore, the settled solids (e.g., terephthalic acid) can tend to solidify into large agglomerates by continuing precipitation and/or crystalline reorganization. Thus, in order to avoid plugging of lower flow conduit 410, a fraction of the deaerated slurry from the bottom of deaeration vessel 400 can be used to continuously or intermittently flush lower conduit 410 during normal operation of reactor 20. A preferred means of providing such a slurry flush to conduit 410 is to periodically open a valve 412 in conduit 410 and allow a fraction of the deaerated slurry to flow through conduit 410 and into reaction zone 28 via lower opening 408. Even when valve 412 is fully or partially open, only a fraction of the deaerated slurry flows through lower conduit 410 and back into reaction zone 28. The remaining fraction of the deaerated slurry not used to flush lower conduit 410 is carried via conduit 414 away from reactor 20 for further downstream processing (e.g., purification).

During normal operation of bubble column reactor 20 over a substantial length of time (e.g., >100 hours), it is preferred for the amount of deaerated slurry used to flush lower conduit 410 to be less than 50 percent by weight of the total deaerated slurry produced from the bottom of deaeration vessel 400, more preferably less than about 20 percent by weight, and most preferably less than 5 percent by weight. Further, it is preferred that over a substantial length of time the average mass flow rate of deaerated slurry used to flush lower conduit 410 is less than about 4 times the average mass flow rate of the oxidizable compound into reaction zone 28, more preferably less than about 2 times the average mass flow rate of the oxidizable compound into reaction zone 28, still more preferably less than the average mass flow rate of the oxidizable compound into reaction zone 28, and most preferably less than 0.5 times the average mass flow rate of the oxidizable compound into reaction zone 28.

Referring again to FIG. 19, deaeration vessel 400 includes a substantially upright, preferably cylindrical sidewall 416 defining a deaeration zone 418. Deaeration zone 418 has a diameter "d" and height "h." Height "h" is measured as the vertical distance between the location where the aerated reaction medium enters deaeration vessel 400 and the bottom of sidewall 416. The height "h", diameter "d", area, and volume of deaeration zone 418 is preferably substantially the same as described above with reference to deaeration zone 312 of deaeration vessel 300 illustrated in FIGS. 16-18. In addition, deaeration vessel 400 includes an upper section 420 formed by extending sidewall 416 above deaeration zone 418. Upper section 420 of deaeration vessel 400 may be of any height, though it preferably extends upwardly to or above the level of reaction medium 36 in reaction zone 28. Upper section 420 ensures that the gas phase has room to properly disengage from the liquid and solid phases before exiting deaeration vessel 400 via conduit 404. It is now noted that although conduit 404 is illustrated as returning the disengaged gas phase to the disengagement zone of reactor 20, conduit 404 could alternatively be coupled to vessel shell 22 at any elevation above outlet conduit 402. Optionally, conduit 404 could be coupled to gas outlet conduit 40 so that the disengaged gas phase from deaeration vessel 400 is combined with the removed overhead vapor stream in conduit 40 and sent downstream for further processing.

Figure 20:
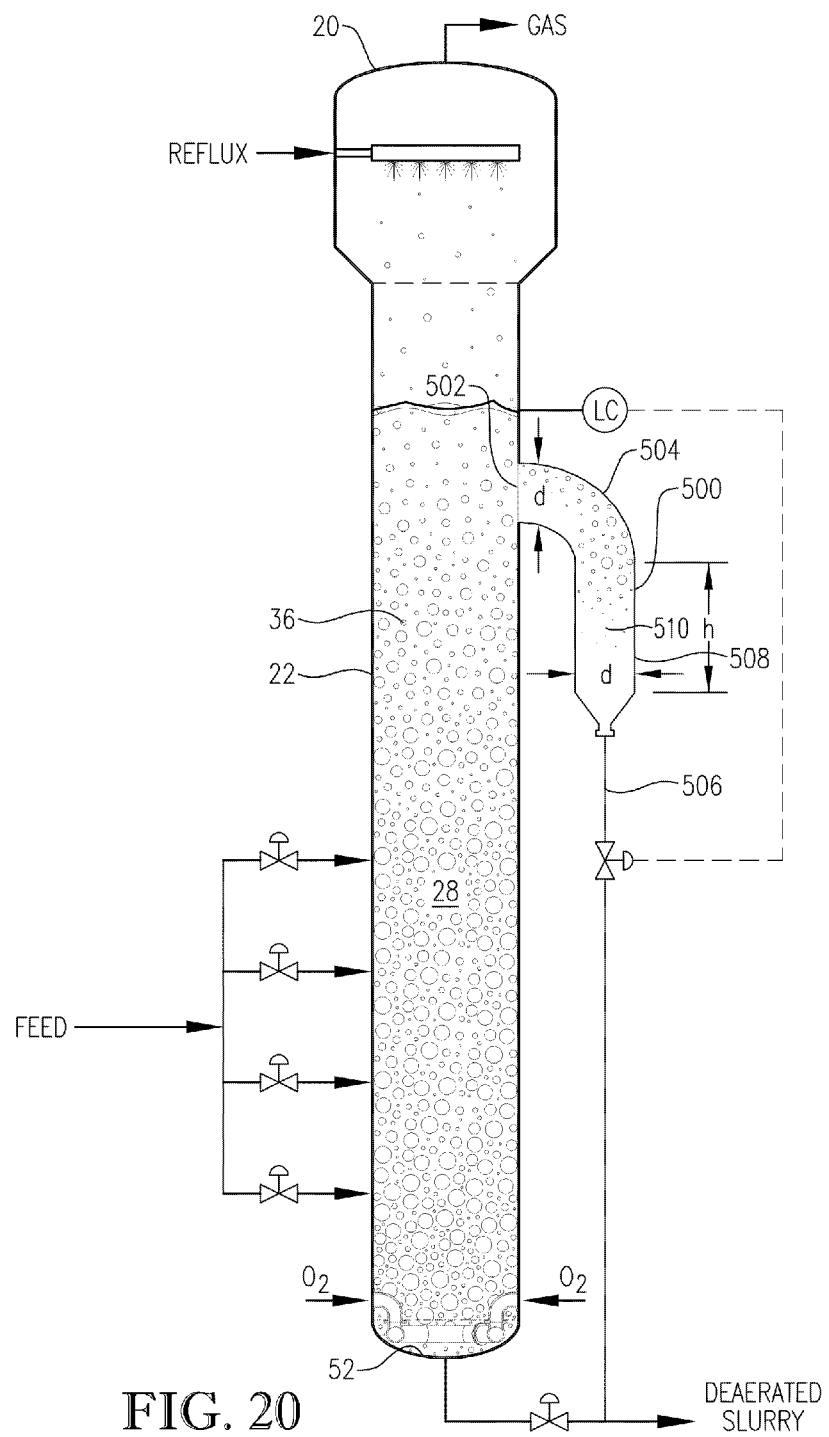
FIG. 20 is a side view of a bubble column reactor equipped with a hybrid internal/external deaeration vessel for disengaging the gas phase of a reaction medium withdrawn from an elevated side location in the reactor.

Turning now to FIG. 20, bubble column reactor 20 is illustrated as including a hybrid internal-external deaeration vessel 500. In this configuration, a portion of reaction medium 36 is withdrawn from reaction zone 28 through a relatively large elevated opening 502 in the sidewall of vessel shell 22. The withdrawn reaction medium 36 is then transported through an elbow conduit 504 of relatively large diameter and enters the top of deaeration vessel 500. In FIG. 20, elbow conduit 504 is shown as connecting orthogonally to the sidewall of vessel shell 22 and as comprising a smooth turn through an angle of about 90 degrees. This is merely one convenient configuration; and elbow conduit 504 may be otherwise in any respect, providing that it usefully connects bubble column reactor 20 with external deaeration vessel 500, as described. Furthermore, elbow conduit 504 may usefully comprise means of flow isolation, such as valves.

In deaeration vessel 500, the gas phase moves upwardly, while the solid and liquid phases move downwardly. The upwardly moving gas phase can re-enter elbow conduit 504 and then escape through opening 502 back into reaction zone 28. Thus, a counter-current flow of the entering reaction medium 36 and the exiting disengaged gas can occur at opening 502. The deaerated slurry exits deaeration vessel 500 via conduit 506. Deaeration vessel 500 includes a substantially upright, preferably cylindrical sidewall 508 defining a deaeration zone 510. Deaeration zone 510 has a height "h" and a diameter "d." It is preferred for elevated opening 502 and elbow conduit 504 to have a diameter the same as, or greater than, the diameter "d" of deaeration zone 510. The height "h", diameter "d", area, and volume of deaeration zone 510 are preferably substantially the same as described above with reference to deaeration zone 312 of deaeration vessel 300 illustrated in FIGS. 16-18.

FIGS. 19 and 20 illustrate an embodiment of bubble column reactor 20 where the solid product (e.g., crude terephthalic acid) produced in reaction zone 28 is withdrawn from reaction zone 28 via an elevated outlet. Withdrawing aerated reaction medium 36 from an elevated location above the bottom of bubble column reactor 20 can help avoid accumulation and stagnation of poorly aerated reaction medium 36 at the bottom 52 of reaction zone 28. According to other aspects of the present invention, the concentrations of oxygen and the oxidizable compound (e.g., para-xylene) in the reaction medium 36 near the top of reaction medium 36 are preferably lower than near the bottom. Thus, withdrawing reaction medium 36 at an elevated location can increase yield by lowering the amount of unreacted reactants withdrawn from reactor 20. Also, the temperature of reaction medium 36 varies significantly in the vertical direction when bubble column reactor 20 is operated with the high STR and the gradients of chemical composition as disclosed herein. Under such conditions, the temperature of reaction medium 36 will typically have local minima near the lower end and the upper end of reaction zone 28. Near the lower end, the minimum relates to the evaporation of solvent near where all or part of the oxidant is admitted. Near the upper end, the minimum is again due to evaporation of solvent, though here due to declining pressure within the reaction medium. In addition, other local minima may occur in between the upper and lower ends wherever additional feed or oxidant is admitted to the reaction medium. Thus, there exist one or more temperature maxima, driven by the exothermic heat of oxidation reactions, between the lower end and upper end of reaction zone 28. Withdrawing reaction medium 36 at an elevated location of higher temperature can be particularly advantageous when downstream processing occurs at higher temperatures, because energy costs associated with heating the withdrawn medium for downstream processing are reduced.

Thus, in a preferred embodiment of the present invention and especially when downstream processing occurs at higher temperatures, reaction medium 36 is withdrawn from bubble column reactor 20 via an elevated outlet(s) positioned above the location(s) where at least 50 weight percent of the liquid-phase feed stream and/or the gas-phase oxidant stream enter reaction zone 28. More preferably, reaction medium 36 is withdrawn from bubble column reactor 20 via an elevated outlet(s) positioned above the location(s) where substantially all of the liquid-phase feed stream and/or the gas-phase oxidant stream enter reaction zone 28. Preferably, at least 50 weight percent of the solid-phase and liquid-phase components withdrawn from bubble column reactor 20 are withdrawn via an elevated outlet(s). More preferably, substantially all of the solid-phase and liquid-phase components withdrawn from bubble column reactor 20 are withdrawn via an elevated outlet(s). Preferably, the elevated outlet(s) is located at least about 1D above lower end 52 of reaction zone 28. More preferably, the elevated outlet(s) is located at least about 2D above lower end 52 of reaction zone 28. Most preferably, the elevated outlet(s) is located at least 3D above lower end 52 of reaction zone 28. Given a height "H" of reaction medium 36, it is preferred for the elevated outlet(s) to be vertically located between about 0.2H and about 0.8H, more preferably between about 0.3H and about 0.7H, and most preferably between 0.4H and 0.6H. Furthermore, it is preferred that the temperature of reaction medium 36 at an elevated outlet from reaction zone 28 is at least 1° C. greater than the temperature of reaction medium 36 at lower end 52 of reaction zone 28. More preferably, the temperature of reaction medium 36 at the elevated outlet of reaction zone 28 is in the range of from about 1.5 to about 16° C. hotter than the temperature of reaction medium 36 at lower end 52 of reaction zone 28. Most preferably, the temperature of reaction medium 36 at the elevated outlet of reaction zone 28 is in the range of from 2 to 12° C. hotter than the temperature of reaction medium 36 at lower end 52 of reaction zone 28.

Figure 21:
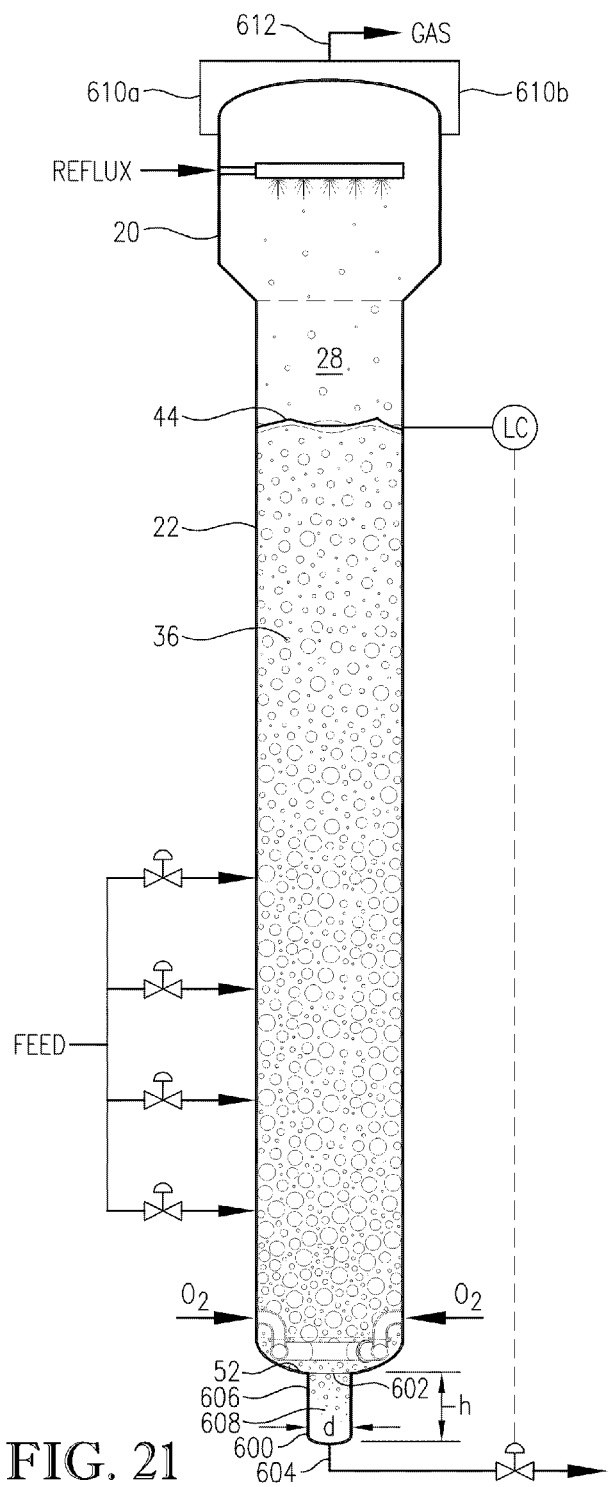
FIG. 21 is a side view of a bubble column reactor equipped with an alternative hybrid deaeration vessel near the bottom of the reactor.

Referring now to FIG. 21, bubble column reactor 20 is illustrated as including an alternative hybrid deaeration vessel 600 positioned at the bottom of reactor 20. In this configuration, aerated reaction medium 36 is withdrawn from reaction zone 28 through a relatively large opening 602 in the lower end 52 of vessel shell 22. Opening 602 defines the open upper end of deaeration vessel 600. In deaeration vessel 600, the gas phase moves upwardly, while the solid and liquid phases move downwardly. The upwardly moving gas phase can re-enter reaction zone 28 through opening 602. Thus, a counter-current flow of the entering reaction medium 36 and the exiting disengaged gas can occur at opening 602. The deaerated slurry exits deaeration vessel 600 via conduit 604. Deaeration vessel 600 includes a substantially upright, preferably cylindrical sidewall 606 defining a deaeration zone 608. Deaeration zone 608 has a height "h" and a diameter "d." It is preferred for opening 602 to have a diameter the same as, or greater than, the diameter "d" of deaeration zone 608. The height "h", diameter "d", area, and volume of deaeration zone 608 are preferably substantially the same as described above with reference to deaeration zone 312 of deaeration vessel 300 illustrated in FIGS. 16-18.

Figure 22:
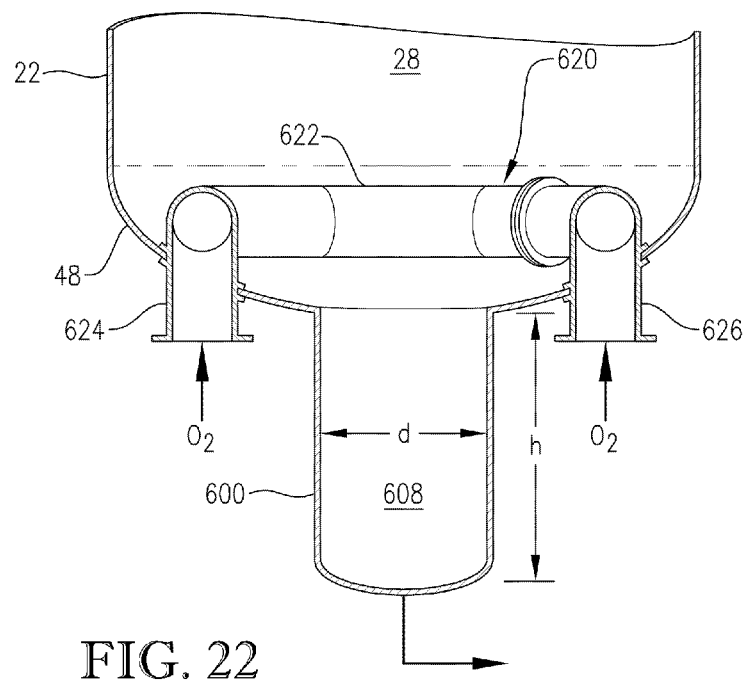
FIG. 22 is an enlarged sectional side view of the lower portion of the bubble column reactor of FIG. 21, particularly illustrating the use of an alternative oxidant sparger employing inlet conduits that receive the oxidant stream through the bottom head of the reactor.

Referring now to FIG. 22, bubble column reactor 20 of FIG. 21 is illustrated as including an alternative oxidant sparger 620. Oxidant sparger 620 includes a ring member 622 and a pair of inlet conduits 624,626. Ring member 622 preferably has substantially the same configuration as ring member 202, described above with reference to FIGS. 12-15. Inlet conduits 624,626 extend upwardly through openings in lower head 48 of vessel shell 22 and provide the oxidant stream to ring member 622.

Figure 23:
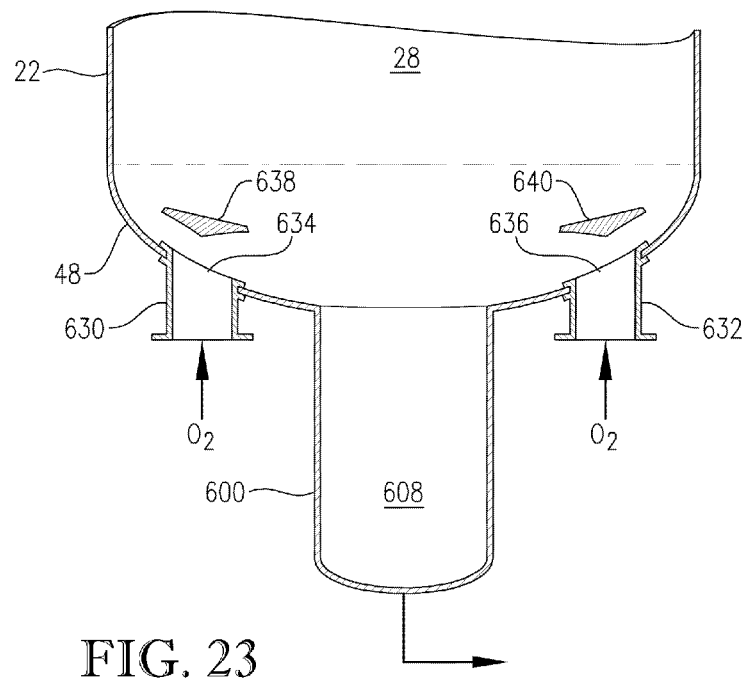
FIG. 23 is an enlarged sectional side view similar to FIG. 22, particularly illustrating an alternative means for introducing the oxidant stream into the reactor via a plurality of openings in the lower head of the reactor and, optionally, employing impingement plates to more evenly distribute the oxidant stream in the reactor.

Referring now to FIG. 23, bubble column reactor 20 of FIG. 21 is illustrated as including a spargerless means for introducing the oxidant stream into reaction zone 28. In the configuration of FIG. 23, the oxidant stream is provided to reactor 20 via oxidant conduits 630,632. Oxidant conduits 630,632 are coupled to respective oxidant openings 634,636 in lower head 48 of vessel shell 22. The oxidant stream is introduced directly into reaction zone 28 via oxidant openings 634,636. Optional impingement plates 638,640 can be provided to deflect the flow of the oxidant stream once it has initially entered reaction zone 28.

As mentioned above, it is preferred for the oxidation reactor to be configured and operated in a manner that avoids zones of high concentration of oxidizable compound in the reaction medium because such zones can lead to the formation of impurities. One way to improve initial dispersion of the oxidizable compound (e.g., para-xylene) in the reaction medium is by diluting the oxidizable compound with a liquid. The liquid used to dilute the oxidizable compound can originate from a portion of the reaction medium located a substantial distance from the location(s) where the oxidizable compound is fed to the reaction zone. This liquid from a distant portion of the reaction medium can be circulated to a location proximate the location of entry of the oxidizable compound via a flow conduit that is disposed internally and/or externally to the main reaction vessel.

Figure 24:
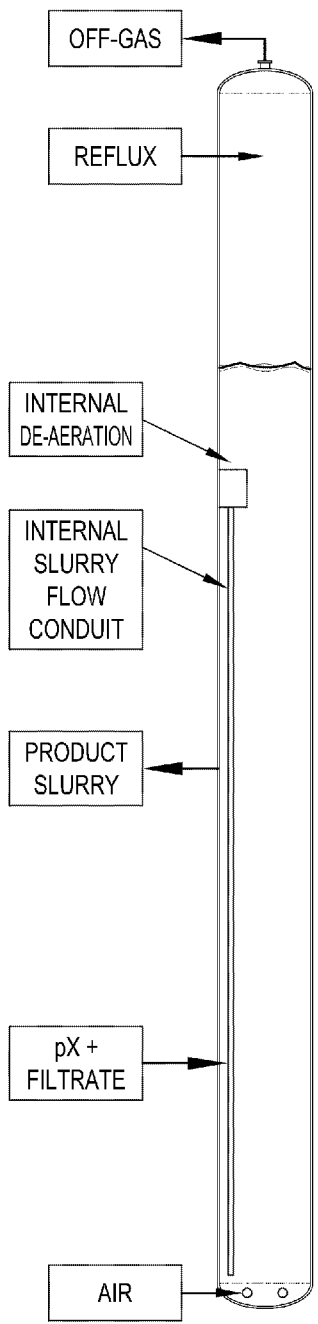
FIG. 24 is a side view of a bubble column reactor employing an internal flow conduit to help improve dispersion of an oxidizable compound by recirculating a portion of the reaction medium from an upper portion of the reactor to a lower portion of the reactor.
Figure 25:
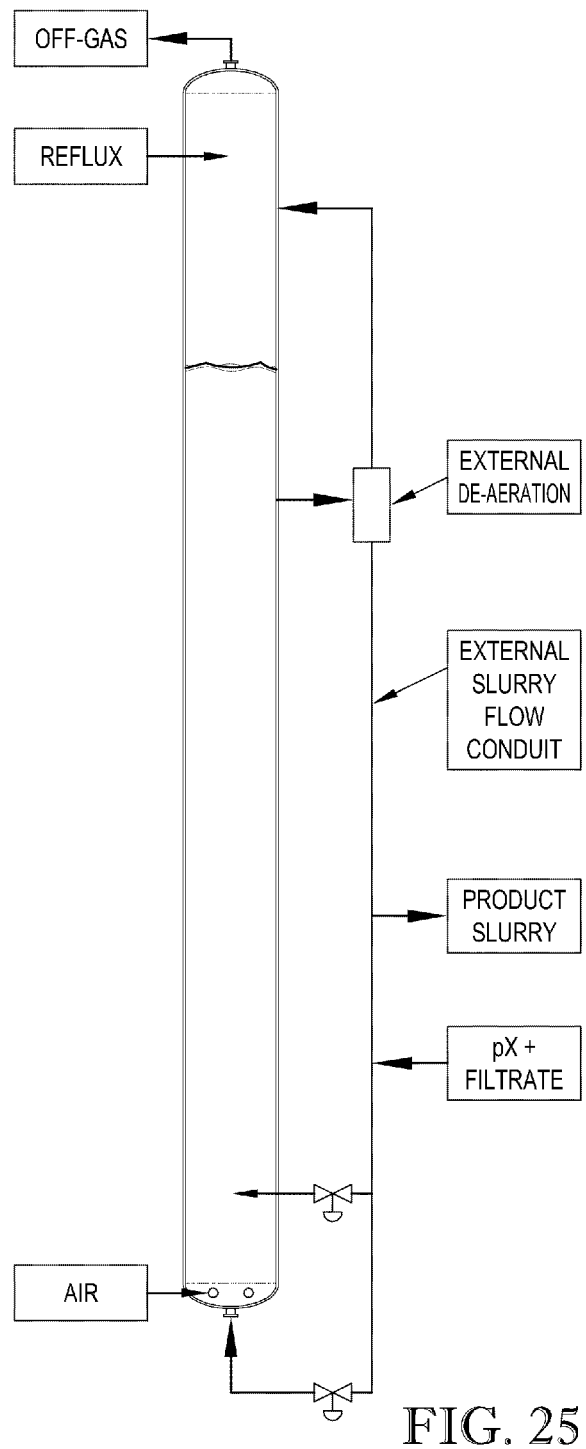
FIG. 25 is a side view of a bubble column reactor employing an external flow conduit to help improve dispersion of the oxidizable compound by recirculating a portion of the reaction medium from an upper portion of the reactor to a lower portion of the reactor.

FIGS. 24 and 25 illustrate two preferred methods of circulating liquid from a distant portion of the reaction medium to a location near the inlet of the oxidizable compound using an internal (FIG. 24) or external (FIG. 25) conduit. Preferably, the length of the flow conduit from its inlet (i.e., opening(s) where the liquid enters the conduit) to its outlet (i.e., opening(s) where the liquid is discharge from the conduit) is greater than about 1 meter, more preferably greater than about 3 meters, still more preferably greater than about 6 meters, and most preferably greater than 9 meters. However, the actual length of the conduit becomes less relevant if the liquid is obtained from a separate vessel, perhaps located immediately above or beside the vessel into which the oxidizable compound feed is initially released. Liquid from any separate vessel containing at least some of the reaction medium is a preferred source for initial dilution of the oxidizable compound.

It is preferred that the liquid flowing through the conduit, whatever the source, has a lower standing concentration of oxidizable compound than the reaction medium immediately adjacent to at least one outlet of the conduit. Furthermore, it is preferred that the liquid flowing through the conduit has a concentration of oxidizable compound in the liquid phase below about 100,000 ppmw, more preferably below about 10,000 ppmw, still more preferably below about 1,000 ppmw and most preferably below 100 ppmw, where the concentrations are measured before addition to the conduit of the increment of oxidizable compound feed and of any optional, separate solvent feed. When measured after adding the increment of oxidizable compound feed and optional solvent feed, it is preferable that the combined liquid stream entering the reaction medium has a concentration of oxidizable compound in the liquid phase below about 300,000 ppmw, more preferably below about 50,000 ppmw, and most preferably below 10,000 ppmw.

It is desirable to maintain the flow through the conduit at a low enough rate so that the circulated liquid does suppress the desirable overall gradient of oxidizable compound within the reaction medium. In this regard, it is preferable that the ratio of the mass of the liquid phase in the reaction zone to which the increment of oxidizable compound is initially released to the mass flow rate of liquid flowing through the conduit be greater than about 0.3 minutes, more preferably greater than about 1 minute, still more preferably between about 2 minutes and about 120 minutes, and most preferably between 3 minutes and 60 minutes.

There are many means for compelling the liquid to flow through the conduit. Preferred means include gravity, eductors of all types employing either gas or liquid or both as the motive fluid, and mechanical pumps of all types. When using an eductor, one embodiment of the invention uses as a motive fluid at least one fluid selected from the group consisting of: feed of oxidizable compound (liquid or gas), feed of oxidant (gas), feed of solvent (liquid), and a pumped source of reaction medium (slurry). Another embodiment uses as a motive fluid at least two fluids selected from the group consisting of: feed of oxidizable compound, feed of oxidant, and feed of solvent. Still another embodiment uses as a motive fluid a combination feed of oxidizable compound, feed of oxidant, and feed of solvent.

The appropriate diameter or diameters of the circulation conduit may vary according to the amount and properties of material being conveyed, the energy available for compelling the flow movement, and consideration of capital cost. It is preferable that the minimum diameter for such conduit is greater than about 0.02 meters, more preferably between about 0.06 meters and about 2 meters, and most preferably between 0.12 and 0.8 meters As noted above, it is desirable to control flow through the conduit in certain preferred ranges. There are many means known in the art to affect this control by setting an appropriate fixed geometry during construction of the flow conduit. Another preferred embodiment is to use geometries that are variable during operation, notably including valves of all sorts and descriptions, including both manual operation and powered operation by any means, including feed back control loops from a sensing element or without. Another preferred means of controlling the flow of the dilution liquid is to vary the energy input between inlet and outlet of the conduit. Preferred means include changing the flow rate of one or more motive fluids to an eductor, changing the energy input to a pump driver, and changing the density difference or elevation difference when using gravitational force. These preferred means may be used in all combinations as well.

The conduit used for circulation of liquid from the reaction medium may be of any type known in the art. One embodiment employs a conduit constructed in whole or part using conventional piping materials. Another embodiment employs a conduit constructed in whole or part using the reaction vessel wall as one part of the conduit. A conduit may be constructed entirely enclosed within the boundaries of the reaction vessel (FIG. 24), or it may be constructed entirely outside the reaction vessel (FIG. 25), or it may comprise sections both within and without the reaction vessel.

The inventors contemplate that, particularly in larger reactors, it may be desirable to have multiple conduits and of various designs for movement of the liquid through the conduit. Further, it may be desirable to provide multiple outlets at multiple positions on one or all of the conduits. The particulars of the design will balance the desirable overall gradient in standing concentrations of oxidizable compound with the desirable initial dilution of oxidizable compound feed, according to other aspects of the current invention.

FIGS. 24 and 25 both illustrate designs that employ a deaeration vessel coupled to the conduit. This deaeration vessel ensures that the portion of the reaction medium used to dilute the incoming oxidizable compound is substantially de-aerated slurry. It is now noted, however, that the liquid or slurry used to dilute the incoming oxidizable compound may be in an aerated form as well as a de-aerated form.

The use of a liquid flowing through a conduit to provide dilution of the oxidizable compound feed is particularly useful in bubble column reactors. Furthermore, in bubble column reactors, a good benefit for the initial dilution of the oxidizable compound feed can be achieved even without adding the oxidizable compound feed directly into the conduit, providing that the outlet of the conduit lies sufficiently close to the position of addition of the oxidizable compound. In such an embodiment, it is preferable that the outlet of the conduit be located within about 27 conduit outlet diameters of the nearest addition location for the oxidizable compound, more preferably within about 9 conduit outlet diameters, still more preferably within about 3 conduit outlet diameters, and most preferably within 1 conduit outlet diameter.

Figure 26:
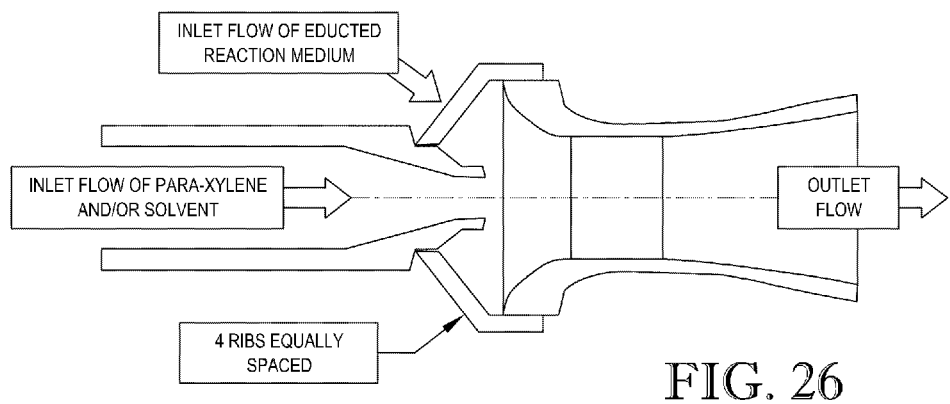
FIG. 26 is a sectional side view of a horizontal eductor that can be used to improve dispersion of the oxidizable compound in an oxidation reactor, particularly illustrating an eductor that uses incoming liquid feed to draw reaction medium into the eductor and discharges the mixture of feed and reaction medium into a reaction zone at high velocity.
Figure 27:
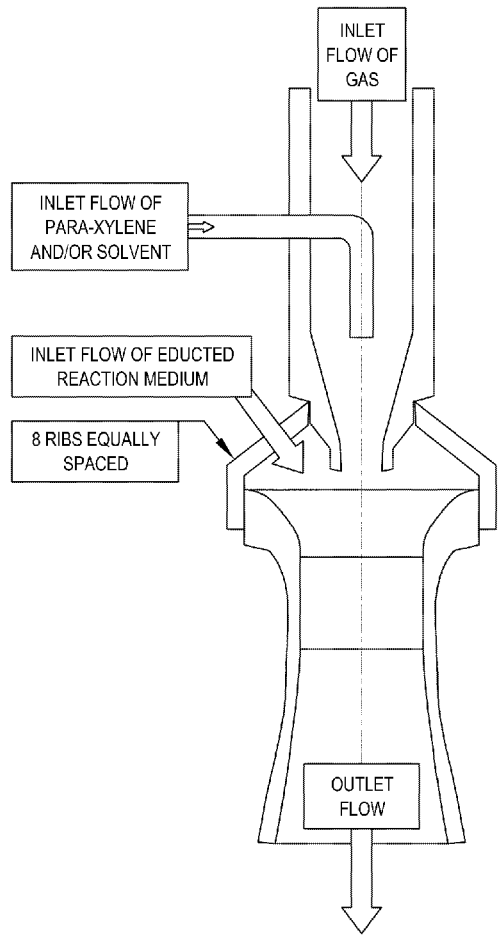
FIG. 27 is a sectional side view of a vertical eductor that can be used improve dispersion of the oxidizable compound in an oxidation reactor, particularly illustrating an eductor that combines the liquid feed and inlet gas and uses the combined two-phase fluid to draw reaction medium into the eductor and discharge the mixture of liquid feed, inlet gas, and reaction medium into a reaction zone at high velocity.

It has also been discovered that flow eductors can be useful for initial dilution of oxidizable compound feed in oxidation bubble columns according to on embodiment of the present invention, even without the use of conduits for obtaining dilution liquid from a distant portion of the reaction medium. In such cases, the eductor is located within the reaction medium and has an open pathway from the reaction medium into the throat of the eductor, where low pressure draws in adjacent reaction medium. Examples of two possible eductor configurations are illustrated in FIGS. 26 and 27. In a preferred embodiment of these eductors, the nearest location of feeding oxidizable compound is within about 4 meters, more preferably within about 1 meter and most preferably 0.3 meters of the throat of the eductor. In another embodiment, the oxidizable compound is fed under pressure as a motive fluid. In still another embodiment, either the solvent or the oxidant is fed under pressure as additional motive fluid along with the oxidizable compound. In yet another embodiment, both the solvent and ant oxidant are fed under pressure as additional motive fluid along with the oxidizable compound.

The inventors contemplate that, particularly in larger reactors, it may be desirable to have multiple eductors and of various designs situated at various positions within the reaction medium. The particulars of the design will balance the desirable overall gradient in standing concentrations of the oxidizable compound with the desirable initial dilution of the oxidizable compound feed, according to other aspects of the current invention. In addition, the inventors contemplate that the outlet flow plumes from an eductor may be oriented in any direction. When multiple eductors are used, each eductor may be oriented separately, again in any direction.

As mentioned above, certain physical and operational features of bubble column reactor 20, described above with reference to FIGS. 1-27, provide for vertical gradients in the pressure, temperature, and reactant (i.e., oxygen and oxidizable compound) concentrations of reaction medium 36. As discussed above, these vertical gradients can provide for a more effective and economical oxidation process as compared to conventional oxidations processes, which favor a well-mixed reaction medium of relatively uniform pressure, temperature, and reactant concentration throughout. The vertical gradients for oxygen, oxidizable compound (e.g., paraxylene), and temperature made possible by employing an oxidation system in accordance with an embodiment of the present invention will now be discussed in greater detail.

Figure 28:
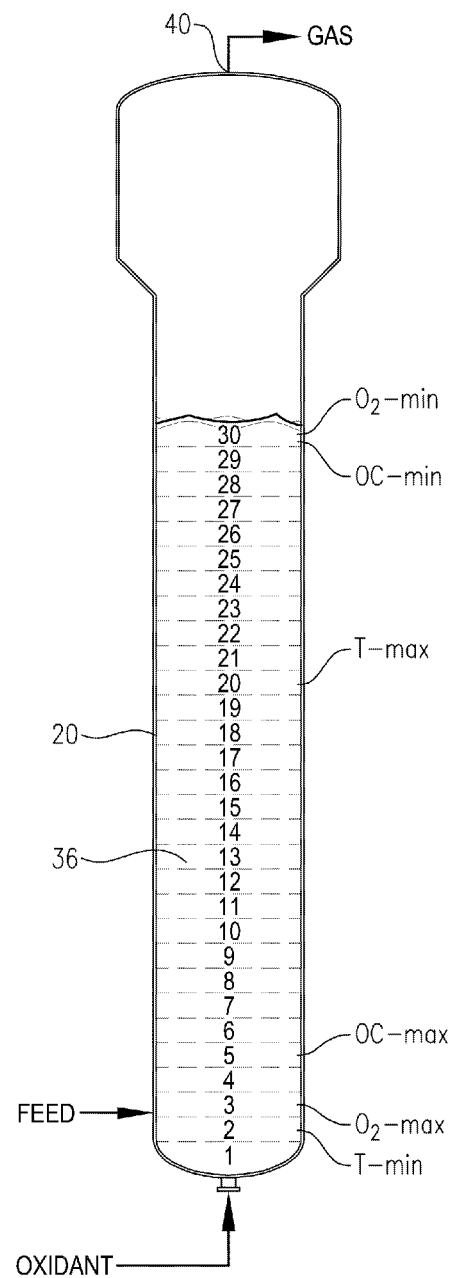
FIG. 28 is a side view of a bubble column reactor containing a multi-phase reaction medium, particularly illustrating the reaction medium being theoretically partitioned into 30 horizontal slices of equal volume in order to quantify certain gradients in the reaction medium.

Referring now to FIG. 28, in order to quantify the reactant concentration gradients existing in reaction medium 36 during oxidation in bubble column reactor 20, the entire volume of reaction medium 36 can be theoretically partitioned into 30 discrete horizontal slices of equal volume. FIG. 28 illustrates the concept of dividing reaction medium 36 into 30 discrete horizontal slices of equal volume. With the exception of the highest and lowest horizontal slices, each horizontal slice is a discrete volume bounded on its top and bottom by imaginary horizontal planes and bounded on its sides by the wall of reactor 20. The highest horizontal slice is bounded on its bottom by an imaginary horizontal plane and on its top by the upper surface of reaction medium 36. The lowest horizontal slice is bounded on its top by an imaginary horizontal plane and on its bottom by the bottom of the vessel shell. Once reaction medium 36 has been theoretically partitioned into 30 discrete horizontal slices of equal volume, the time-averaged and volume-averaged concentration of each horizontal slice can then be determined. The individual horizontal slice having the maximum concentration of all 30 horizontal slices can be identified as the "C-max horizontal slice." The individual horizontal slice located above the C-max horizontal slice and having the minimum concentration of all horizontal slices located above the C-max horizontal slice can be identified as the "C-min horizontal slice." The vertical concentration gradient can then be calculated as the ratio of the concentration in the C-max horizontal slice to the concentration in the C-min horizontal slice.

With respect to quantifying the oxygen concentration gradient, when reaction medium 36 is theoretically partitioned into 30 discrete horizontal slices of equal volume, an $O_2$-max horizontal slice is identified as having the maximum oxygen concentration of all the 30 horizontal slices and an $O_2$-min horizontal slice is identified as having the minimum oxygen concentration of the horizontal slices located above the $O_2$-max horizontal slice. The oxygen concentrations of the horizontal slices are measured in the gas phase of reaction medium 36 on a time-averaged and volume-averaged molar wet basis. It is preferred for the ratio of the oxygen concentration of the $O_2$-max horizontal slice to the oxygen concentration of the $O_2$-min horizontal slice to be in the range of from about 2:1 to about 25:1, more preferably in the range of from about 3:1 to about 15:1, and most preferably in the range of 4:1 to 10:1.

Typically, the $O_2$-max horizontal slice will be located near the bottom of reaction medium 36, while the $O_2$-min horizontal slice will be located near the top of reaction medium 36. Preferably, the $O_2$-min horizontal slice is one of the 5 uppermost horizontal slices of the 30 discrete horizontal slices. Most preferably, the $O_2$-min horizontal slice is the uppermost one of the 30 discrete horizontal slices, as illustrated in FIG. 28. Preferably, the $O_2$-max horizontal slice is one of the 10 lower-most horizontal slices of the 30 discrete horizontal slices. Most preferably, the $O_2$-max horizontal slice is one of the 5 lower-most horizontal slices of the 30 discrete horizontal slices. For example, FIG. 28 illustrates the $O_2$-max horizontal slice as the third horizontal slice from the bottom of reactor 20. It is preferred for the vertical spacing between the $O_2$-min and $O_2$-max horizontal slices to be at least about 2W, more preferably at least about 4W, and most preferably at least 6W. It is preferred for the vertical spacing between the $O_2$-min and $O_2$-max horizontal slices to be at least about 0.2H, more preferably at least about 0.4H, and most preferably at least 0.6H The time-averaged and volume-averaged oxygen concentration, on a wet basis, of the $O_2$-min horizontal slice is preferably in the range of from about 0.1 to about 3 mole percent, more preferably in the range of from about 0.3 to about 2 mole percent, and most preferably in the range of from 0.5 to 1.5 mole percent. The time-averaged and volume-averaged oxygen concentration of the $O_2$-max horizontal slice is preferably in the range of from about 4 to about 20 mole percent, more preferably in the range of from about 5 to about 15 mole percent, and most preferably in the range of from 6 to 12 mole percent. The time-averaged concentration of oxygen, on a dry basis, in the gaseous effluent discharged from reactor 20 via gas outlet 40 is preferably in the range of from about 0.5 to about 9 mole percent, more preferably in the range of from about 1 to about 7 mole percent, and most preferably in the range of from 1.5 to 5 mole percent.

Because the oxygen concentration decays so markedly toward the top of reaction medium 36, it is desirable that the demand for oxygen be reduced in the top of reaction medium 36. This reduced demand for oxygen near the top of reaction medium 36 can be accomplished by creating a vertical gradient in the concentration of the oxidizable compound (e.g., para-xylene), where the minimum concentration of oxidizable compound is located near the top of reaction medium 36.

With respect to quantifying the oxidizable compound (e.g., para-xylene) concentration gradient, when reaction medium 36 is theoretically partitioned into 30 discrete horizontal slices of equal volume, an OC-max horizontal slice is identified as having the maximum oxidizable compound concentration of all the 30 horizontal slices and an OC-min horizontal slice is identified as having the minimum oxidizable compound concentration of the horizontal slices located above the OC-max horizontal slice. The oxidizable compound concentrations of the horizontal slices are measured in the liquid phase on a time-averaged and volume-averaged mass fraction basis. It is preferred for the ratio of the oxidizable compound concentration of the OC-max horizontal slice to the oxidizable compound concentration of the OC-min horizontal slice to be greater than about 5:1, more preferably greater than about 10:1, still more preferably greater than about 20:1, and most preferably in the range of from 40:1 to 1000:1.

Typically, the OC-max horizontal slice will be located near the bottom of reaction medium 36, while the OC-min horizontal slice will be located near the top of reaction medium 36. Preferably, the OC-min horizontal slice is one of the 5 upper-most horizontal slices of the 30 discrete horizontal slices. Most preferably, the OC-min horizontal slice is the upper-most one of the 30 discrete horizontal slices, as illustrated in FIG. 28. Preferably, the OC-max horizontal slice is one of the 10 lower-most horizontal slices of the 30 discrete horizontal slices. Most preferably, the OC-max horizontal slice is one of the 5 lower-most horizontal slices of the 30 discrete horizontal slices. For example, FIG. 28 illustrates the OC-max horizontal slice as the fifth horizontal slice from the bottom of reactor 20. It is preferred for the vertical spacing between the OC-min and OC-max horizontal slices to be at least about 2W, where "W" is the maximum width of reaction medium 36. More preferably, the vertical spacing between the OC-min and OC-max horizontal slices is at least about 4W, and most preferably at least 6W. Given a height "H" of reaction medium 36, it is preferred for the vertical spacing between the OC-min and OC-max horizontal slices to be at least about 0.2H, more preferably at least about 0.4H, and most preferably at least 0.6H.

The time-averaged and volume-averaged oxidizable compound (e.g., para-xylene) concentration in the liquid phase of the OC-min horizontal slice is preferably less than about 5,000 ppmw, more preferably less than about 2,000 ppmw, still more preferably less than about 400 ppmw, and most preferably in the range of from 1 ppmw to 100 ppmw. The time-averaged and volume-averaged oxidizable compound concentration in the liquid phase of the OC-max horizontal slice is preferably in the range of from about 100 ppmw to about 10,000 ppmw, more preferably in the range of from about 200 ppmw to about 5,000 ppmw, and most preferably in the range of from 500 ppmw to 3,000 ppmw.

Although it is preferred for bubble column reactor 20 to provide vertical gradients in the concentration of the oxidizable compound, it is also preferred that the volume percent of reaction medium 36 having an oxidizable compound concentration in the liquid phase above 1,000 ppmw be minimized. Preferably, the time-averaged volume percent of reaction medium 36 having an oxidizable compound concentration in the liquid phase above 1,000 ppmw is less than about 9 percent, more preferably less than about 6 percent, and most preferably less than 3 percent. Preferably, the time-averaged volume percent of reaction medium 36 having an oxidizable compound concentration in the liquid phase above 2,500 ppmw is less than about 1.5 percent, more preferably less than about 1 percent, and most preferably less than 0.5 percent. Preferably, the time-averaged volume percent of reaction medium 36 having an oxidizable compound concentration in the liquid phase above 10,000 ppmw is less than about 0.3 percent, more preferably less than about 0.1 percent, and most preferably less than 0.03 percent. Preferably, the time-averaged volume percent of reaction medium 36 having an oxidizable compound concentration in the liquid phase above 25,000 ppmw is less than about 0.03 percent, more preferably less than about 0.015 percent, and most preferably less than 0.007 percent. The inventors note that the volume of reaction medium 36 having the elevated levels of oxidizable compound need not lie in a single contiguous volume. At many times, the chaotic flow patterns in a bubble column reaction vessel produce simultaneously two or more continuous but segregated portions of reaction medium 36 having the elevated levels of oxidizable compound. At each time used in the time averaging, all such continuous but segregated volumes larger than 0.0001 volume percent of the total reaction medium are added together to determine the total volume having the elevated levels of oxidizable compound concentration in the liquid phase.

In addition to the concentration gradients of oxygen and oxidizable compound, discussed above, it is preferred for a temperature gradient to exist in reaction medium 36. Referring again to FIG. 28, this temperature gradient can be quantified in a manner similar to the concentration gradients by theoretically partitioning reaction medium 36 into 30 discrete horizontal slices of equal volume and measuring the time-averaged and volume-averaged temperature of each slice. The horizontal slice with the lowest temperature out of the lowest 15 horizontal slices can then be identified as the T-min horizontal slice, and the horizontal slice located above the T-min horizontal slice and having the maximum temperature of all the slices above the T-min horizontal slice can then be identified as the "T-max horizontal slice." It is preferred for the temperature of the T-max horizontal slice be at least about 1° C. higher than the temperature of the T-min horizontal slice. More preferably the temperature of the T-max horizontal slice is in the range of from about 1.25 to about 12° C. higher than the temperature of the T-min horizontal slice. Most preferably the temperature of the T-max horizontal slice is in the range of from 2 to 8° C. higher than the temperature of the T-min horizontal slice. The temperature of the T-max horizontal slice is preferably in the range of from about 125 to about 200° C., more preferably in the range of from about 140 to about 180° C., and most preferably in the range of from 150 to 170° C.

Typically, the T-max horizontal slice will be located near the center of reaction medium 36, while the T-min horizontal slice will be located near the bottom of reaction medium 36. Preferably, the T-min horizontal slice is one of the lower-most horizontal slices of the 15 lowest horizontal slices. Most preferably, the T-min horizontal slice is one of the 5 lower-most horizontal slices of the 15 lowest horizontal slices. For example, FIG. 28 illustrates the T-min horizontal slice as the second horizontal slice from the bottom of reactor 20. Preferably, the T-max horizontal slice is one of the 20 middle horizontal slices of the 30 discrete horizontal slices. Most preferably, the T-min horizontal slice is one of the 14 middle horizontal slices of the 30 discrete horizontal slices. For example, FIG. 28 illustrates the T-max horizontal slice as the twentieth horizontal slice from the bottom of reactor 20 (i.e., one of the middle 10 horizontal slices). It is preferred for the vertical spacing between the T-min and T-max horizontal slices to be at least about 2W, more preferably at least about 4W, and most preferably at least 6W. It is preferred for the vertical spacing between the T-min and T-max horizontal slices to be at least about 0.2H, more preferably at least about 0.4H, and most preferably at least 0.6H.

As discussed above, when a vertical temperature gradient exists in reaction medium 36, it can be advantageous to withdraw reaction medium 36 at an elevated location where the temperature of reaction medium is highest, especially when the withdrawn product is subjected to further downstream processing at higher temperatures. Thus, when reaction medium 36 is withdrawn from reaction zone 28 via one or more elevated outlets, as illustrated in FIGS. 19 and 20, it is preferred for the elevated outlet(s) to be located near the T-max horizontal slice. Preferably, the elevated outlet is located within 10 horizontal slices of the T-max horizontal slice, more preferably within 5 horizontal slices of the T-max horizontal slice, and most preferably within 2 horizontal slices of the T-max horizontal slice.

It is now noted that many of the inventive features described herein can be employed in multiple oxidation reactor systems—not just systems employing a single oxidation reactor. In addition, certain inventive features described herein can be employed in mechanically-agitated and/or flow-agitated oxidation reactors—not just bubble-agitated reactors (i.e., bubble column reactors). For example, the inventors have discovered certain advantages associated with staging/varying oxygen concentration and/or oxygen consumption rate throughout the reaction medium. The advantages realized by the staging of oxygen concentration/consumption in the reaction medium can be realized whether the total volume of the reaction medium is contained in a single vessel or in multiple vessels. Further, the advantages realized by the staging of oxygen concentration/consumption in the reaction medium can be realized whether the reaction vessel(s) is mechanically-agitated, flow-agitated, and/or bubble-agitated.

Figure 29:
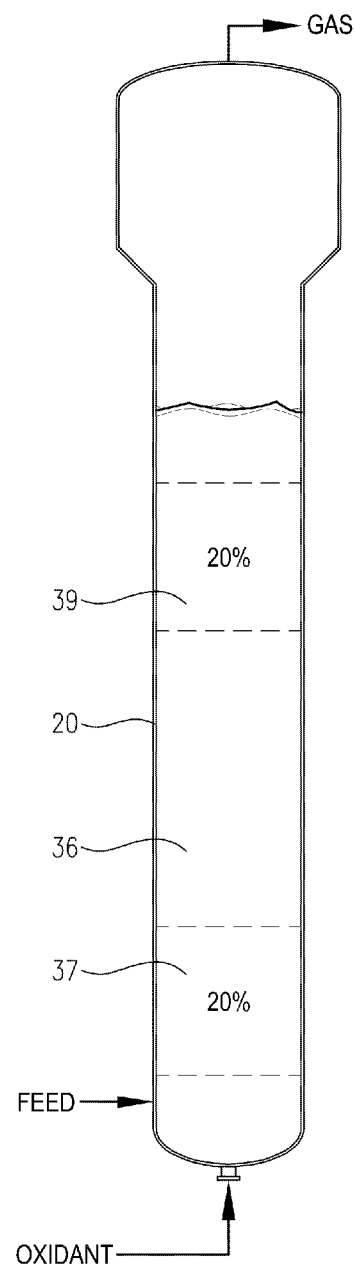
FIG. 29 is a side view of a bubble column reactor containing a multi-phase reaction medium, particularly illustrating first and second discrete 20-percent continuous volumes of the reaction medium that have substantially different oxygen concentrations and/or oxygen consumption rates.
Figure 30:
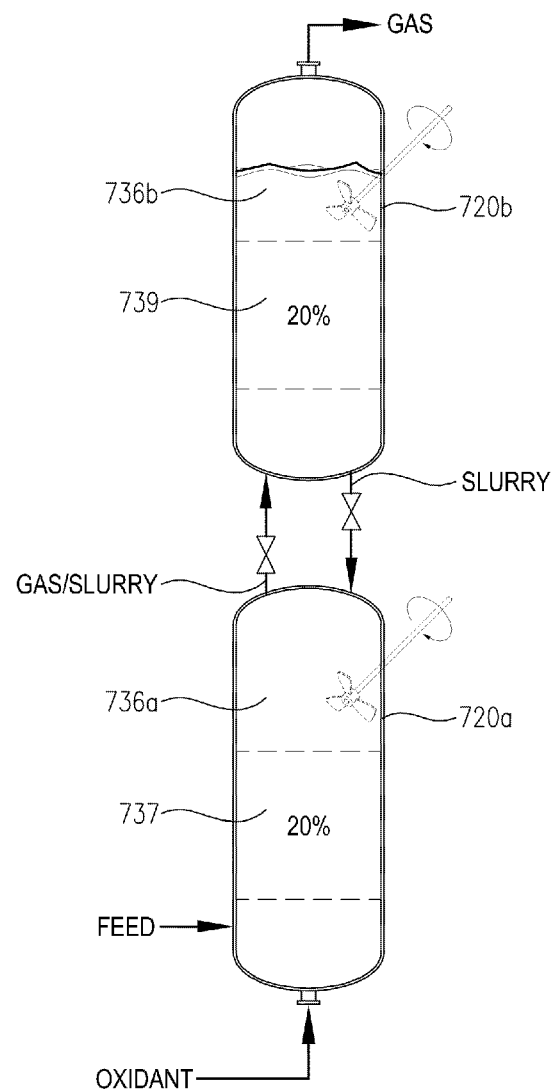
FIG. 30 is a side view of two stacked reaction vessels, with or without optional mechanical agitation, containing a multi-phase reaction medium, particularly illustrating that the vessels contain discrete 20-percent continuous volumes of the reaction medium having substantially different oxygen concentrations and/or oxygen consumption rates.
Figure 31:
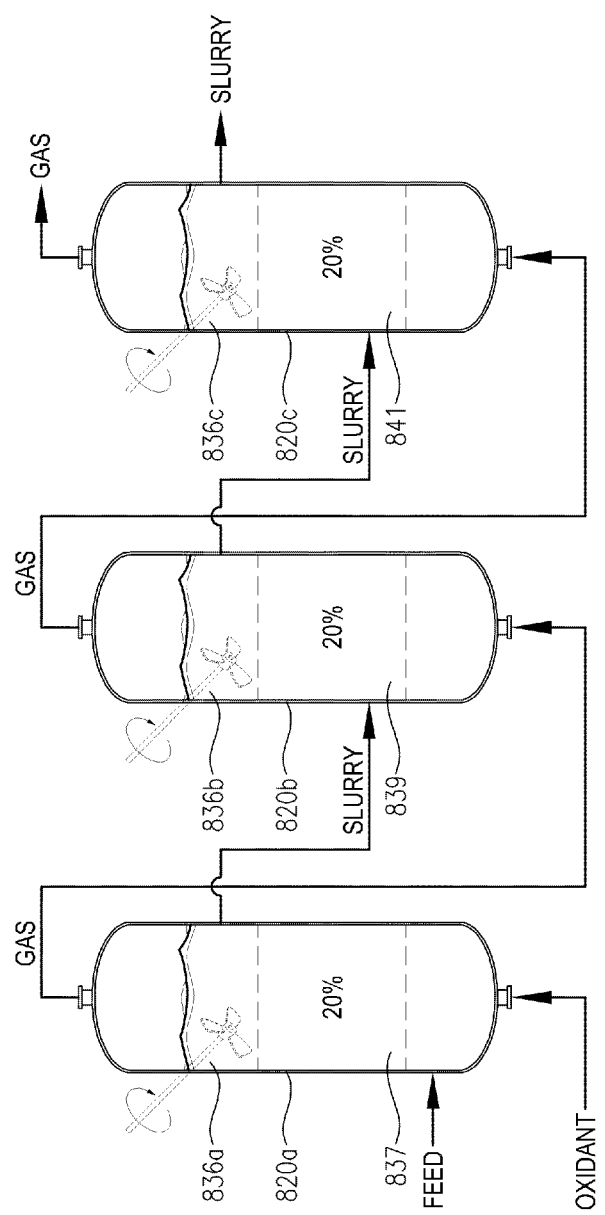
FIG. 31 is a side view of three side-by-side reaction vessels, with or without optional mechanical agitation, containing a multi-phase reaction medium, particularly illustrating that the vessels contain discrete 20-percent continuous volumes of the reaction medium having substantially different oxygen concentrations and/or oxygen consumption rates.

One way of quantifying the degree of staging of oxygen concentration and/or consumption rate in a reaction medium is to compare two or more distinct 20-percent continuous volumes of the reaction medium. These 20-percent continuous volumes need not be defined by any particular shape. However, each 20-percent continuous volume must be formed of a contiguous volume of the reaction medium (i.e., each volume is "continuous"), and the 20-percent continuous volumes must not overlap one another (i.e., the volumes are "distinct"). FIGS. 29-31 illustrate that these distinct 20-percent continuous volumes can be located in the same reactor (FIG. 29) or in multiple reactors (FIGS. 30 and 31). It is noted that the reactors illustrated in FIGS. 29-31 can be mechanically-agitated, flow-agitated, and/or bubble-agitated reactors. In one embodiment, it is preferred for the reactors illustrated in FIGS. 29-31 to be bubble-agitated reactors (i.e., bubble column reactors).

Referring now to FIG. 29, reactor 20 is illustrated as containing a reaction medium 36. Reaction medium 36 includes a first distinct 20-percent continuous volume 37 and a second distinct 20-percent continuous volume 39.

Referring now to FIG. 30, a multiple reactor system is illustrated as including a first reactor 720a and a second reactor 720b. Reactors 720a,b cooperatively contain a total volume of a reaction medium 736. First reactor 720a contains a first reaction medium portion 736a, while second reactor 720b contains a second reaction medium portion 736b. A first distinct 20-percent continuous volume 737 of reaction medium 736 is shown as being defined within first reactor 720a, while a second distinct 20-percent continuous volume 739 of reaction medium 736 is shown as being defined within second reactor 720b.

Referring now to FIG. 31, a multiple reactor system is illustrated as including a first reactor 820a, a second reactor 820b, and a third reactor 820c. Reactors 820a,b,c cooperatively contain a total volume of a reaction medium 836. First reactor 820a contains a first reaction medium portion 836a; second reactor 820b contains a second reaction medium portion 836b; and third reactor 820c contains a third reaction medium portion 836c. A first distinct 20-percent continuous volume 837 of reaction medium 836 is shown as being defined within first reactor 820a; a second distinct 20-percent continuous volume 839 of reaction medium 836 is shown as being defined within second reactor 820b; and a third distinct 20-percent continuous volume 841 of reaction medium 836 is show as being defined within third reactor 820c.

The staging of oxygen availability in the reaction medium can be quantified by referring to the 20-percent continuous volume of reaction medium having the most abundant mole fraction of oxygen in the gas phase and by referring to the 20-percent continuous volume of reaction medium having the most depleted mole fraction of oxygen in the gas phase. In the gas phase of the distinct 20-percent continuous volume of the reaction medium containing the highest concentration of oxygen in the gas phase, the time-averaged and volume-averaged oxygen concentration, on a wet basis, is preferably in the range of from about 3 to about 18 mole percent, more preferably in the range of from about 3.5 to about 14 mole percent, and most preferably in the range of from 4 to 10 mole percent. In the gas phase of the distinct 20-percent continuous volume of the reaction medium containing the lowest concentration of oxygen in the gas phase, the time-averaged and volume-averaged oxygen concentration, on a wet basis, is preferably in the range of from about 0.3 to about 5 mole percent, more preferably in the range of from about 0.6 to about 4 mole percent, and most preferably in the range of from 0.9 to 3 mole percent. Furthermore, the ratio of the time-averaged and volume-averaged oxygen concentration, on a wet basis, in the most abundant 20-percent continuous volume of reaction medium compared to the most depleted 20-percent continuous volume of reaction medium is preferably in the range of from about 1.5:1 to about 20:1, more preferably in the range of from about 2:1 to about 12:1, and most preferably in the range of from 3:1 to 9:1.

The staging of oxygen consumption rate in the reaction medium can be quantified in terms of an oxygen-STR, initially described above. Oxygen-STR was previously describe in a global sense (i.e., from the perspective of the average oxygen-STR of the entire reaction medium); however, oxygen-STR may also be considered in a local sense (i.e., a portion of the reaction medium) in order to quantify staging of the oxygen consumption rate throughout the reaction medium.

The inventors have discovered that it is very useful to cause the oxygen-STR to vary throughout the reaction medium in general harmony with the desirable gradients disclosed herein relating to pressure in the reaction medium and to the mole fraction of molecular oxygen in the gas phase of the reaction medium. Thus, it is preferable that the ratio of the oxygen-STR of a first distinct 20-percent continuous volume of the reaction medium compared to the oxygen-STR of a second distinct 20-percent continuous volume of the reaction medium be in the range of from about 1.5:1 to about 20:1, more preferably in the range of from about 2:1 to about 12:1, and most preferably in the range of from 3:1 to 9:1. In one embodiment the "first distinct 20-percent continuous volume" is located closer than the "second distinct 20-percent continuous volume" to the location where molecular oxygen is initially introduced into the reaction medium. These large gradients in oxygen-STR are desirable whether the partial oxidation reaction medium is contained in a bubble column oxidation reactor or in any other type of reaction vessel in which gradients are created in pressure and/or mole fraction of molecular oxygen in the gas phase of the reaction medium (e.g., in a mechanically agitated vessel having multiple, vertically disposed stirring zones achieved by using multiple impellers having strong radial flow, possibly augmented by generally horizontal baffle assemblies, with oxidant flow rising generally upwards from a feed near the lower portion of the reaction vessel, notwithstanding that considerable back-mixing of oxidant flow may occur within each vertically disposed stirring zone and that some back-mixing of oxidant flow may occur between adjacent vertically disposed stirring zones). That is, when a gradient exists in the pressure and/or mole fraction of molecular oxygen in the gas phase of the reaction medium, the inventors have discovered that it is desirable to create a similar gradient in the chemical demand for dissolved oxygen by the means disclosed herein.

A preferred means of causing the local oxygen-STR to vary is by controlling the locations of feeding the oxidizable compound and by controlling the mixing of the liquid phase of the reaction medium to control gradients in concentration of oxidizable compound according to other disclosures of the present invention. Other useful means of causing the local oxygen-STR to vary include causing variation in reaction activity by causing local temperature variation and by changing the local mixture of catalyst and solvent components (e.g., by introducing an additional gas to cause evaporative cooling in a particular portion of the reaction medium and by adding a solvent stream containing a higher amount of water to decrease activity in a particular portion of the reaction medium).

As discussed above with reference to FIGS. 30 and 31, the partial oxidation reaction can be usefully conducted in multiple reaction vessels wherein at least a portion, preferably at least 25 percent, more preferably at least 50 percent, and most preferable at least 75 percent, of the molecular oxygen exiting from a first reaction vessel is conducted to one or more subsequent reaction vessels for consumption of an additional increment, preferably more than 10 percent, more preferably more than 20 percent, and most preferably more than 40 percent, of the molecular oxygen exiting the first/upstream reaction vessel. When using such a series flow of molecular oxygen from one reactor to others, it is desirable that the first reaction vessel is operated with a higher reaction intensity than at least one of the subsequent reaction vessels, preferably with the ratio of the vessel-average-oxygen-STR within the first reaction vessel to the vessel-average-oxygen-STR within the subsequent reaction vessel in the range of from about 1.5:1 to about 20:1, more preferably in the range of from about 2:1 to about 12:1, and most preferably in the range of from 3:1 to 9:1.

As discussed above, all types of first reaction vessel (e.g.; bubble column, mechanically-agitated, back-mixed, internally staged, plug flow, and so on) and all types of subsequent reaction vessels, which may or not be of different type than the first reaction vessel, are useful for series flow of molecular oxygen to subsequent reaction vessels with according to the present invention. The means of causing the vessel-average-oxygen-STR to decline within subsequent reaction vessels usefully include reduced temperature, reduced concentrations of oxidizable compound, and reduced reaction activity of the particular mixture of catalytic components and solvent (e.g., reduced concentration of cobalt, increased concentration of water, and addition of a catalytic retardant such as small quantities of ionic copper).

In flowing from the first reaction vessel to a subsequent reaction vessel, the oxidant stream may be treated by any means known in the art such as compression or pressure reduction, cooling or heating, and removing mass or adding mass of any amount or any type. However, the use of declining vessel-average-oxygen-STR in subsequent reaction vessels is particularly useful when the absolute pressure in the upper portion of the first reaction vessel is less than about 2.0 megapascal, more preferably less than about 1.6 megapascal, and most preferably less than 1.2 megapascal. Furthermore, the use of declining vessel-average-oxygen-STR in subsequent reaction vessels is particularly useful when the ratio of the absolute pressure in the upper portion of the first reaction vessel compared to the absolute pressure in the upper portion of at least one subsequent reaction vessel is in the range from about 0.5:1 to 6:1, more preferably in a range from about 0.6:1 to about 4:1, and most preferably in a range from 0.7:1 to 2:1. Pressure reductions in subsequent vessels below these lower bounds overly reduce the availability of molecular oxygen, and pressure increases above these upper bounds are increasingly costly compared to using a fresh supply of oxidant.

When using series flow of molecular oxygen to subsequent reaction vessels having declining vessel-average-oxygen-STR, fresh feed streams of oxidizable compound, solvent and oxidant may flow into subsequent reaction vessels and/or into the first reaction vessel. Flows of the liquid phase and the solid phase, if present, of the reaction medium may flow in any direction between reaction vessels. All or part of the gas phase leaving the first reaction vessel and entering a subsequent reaction vessel may flow separated from or commingled with portions of the liquid phase or the solid phase, if present, of the reaction medium from the first reaction vessel. A flow of product stream comprising liquid phase and solid phase, if present, may be withdrawn from the reaction medium in any reaction vessel in the system.

Referring again to FIGS. 1-29, in one embodiment of the present invention, oxidation bubble column reactor 20 has a significantly higher production rate than conventional oxidation bubble column reactors, particularly conventional bubble column reactors used to produce terephthalic acid. In order to provide increased production rates, the size of bubble column reactor 20 must be increased. However, the naturally-convected, multi-phase fluid flow dynamics of the reaction medium in such a scaled-up bubble column reactor are significantly, troublesomely different than the flow dynamics in smaller conventional reactors. It has been discovered that certain design and operating parameters are important for the proper functionality of high production rate scaled-up oxidation bubble column reactors.

When bubble column 20 is a high production rate scaled-up oxidation bubble column reactor in accordance with one embodiment of the present invention, the height "H" of reaction medium 36 is preferably at least about 30 meters, more preferable in the range of from about 35 to about 70 meters, and most preferably in the range of from 40 to 60 meters. The density and height of reaction medium 36 in scaled-up bubble column reactor 20 cause a significant pressure differential between the top of reaction medium 36 and the bottom of reaction medium 36. Preferably the pressure differential between the top and bottom of reaction medium 36 is at least about 1 bar, more preferably at least about 1.4 bar, and most preferably in the range of from 1.6 to 3 bar. The maximum width "W" of reaction medium 36 is preferably at least about 2.5 meters, more preferable in the range of from about 3 to about 20 meters, still more preferably in the range of from about 3.25 to about 12 meters, and most preferably in the range of from 4 to 10 meters. The H:W ratio of reaction medium 36 is preferably at least about 6:1, more preferably in the range of from about 8:1 to about 20:1, and most preferably in the range of from 9:1 to 15:1. The total volume of reaction medium 36 and/or reaction zone 28 is preferably at least about 250 cubic meters, more preferably at least about 500 cubic meters, and most preferably at least 1,000 cubic meters.

During operation of scaled-up oxidation bubble column reactor 20, it is preferred for the time-averaged superficial velocity of the gas phase of reaction medium 36 at one-quarter height, half height, and/or three-quarter height to be in the range of from about 0.8 to about 5 meters per second, more preferably in the range of from about 0.9 to about 3 meters per second, and most preferably in the range of from 1 to 2 meters per second. When scaled-up oxidation bubble column reactor 20 is employed to produce terephthalic acid via partial oxidation of para-xylene, it is preferred for para-xylene to be fed to reaction zone 28 at a rate of at least about 11,000 kilograms per hour, more preferably at a rate in the range of from about 20,000 to about 100,000 kilograms per hour, and most preferably in the range of from 30,000 to 80,000 kilograms per hour. The terephthalic acid production rate of scaled-up bubble column 20 is preferably at least about 400 tons per day, more preferably at least about 700 tons per day, and most preferably in the range of from 750 to 3,000 tons per day. Other design and operating parameters of scaled-up oxidation bubble column reactor 20 can be substantially the same as initially described above with reference to FIGS. 1-29.

Figure 32:
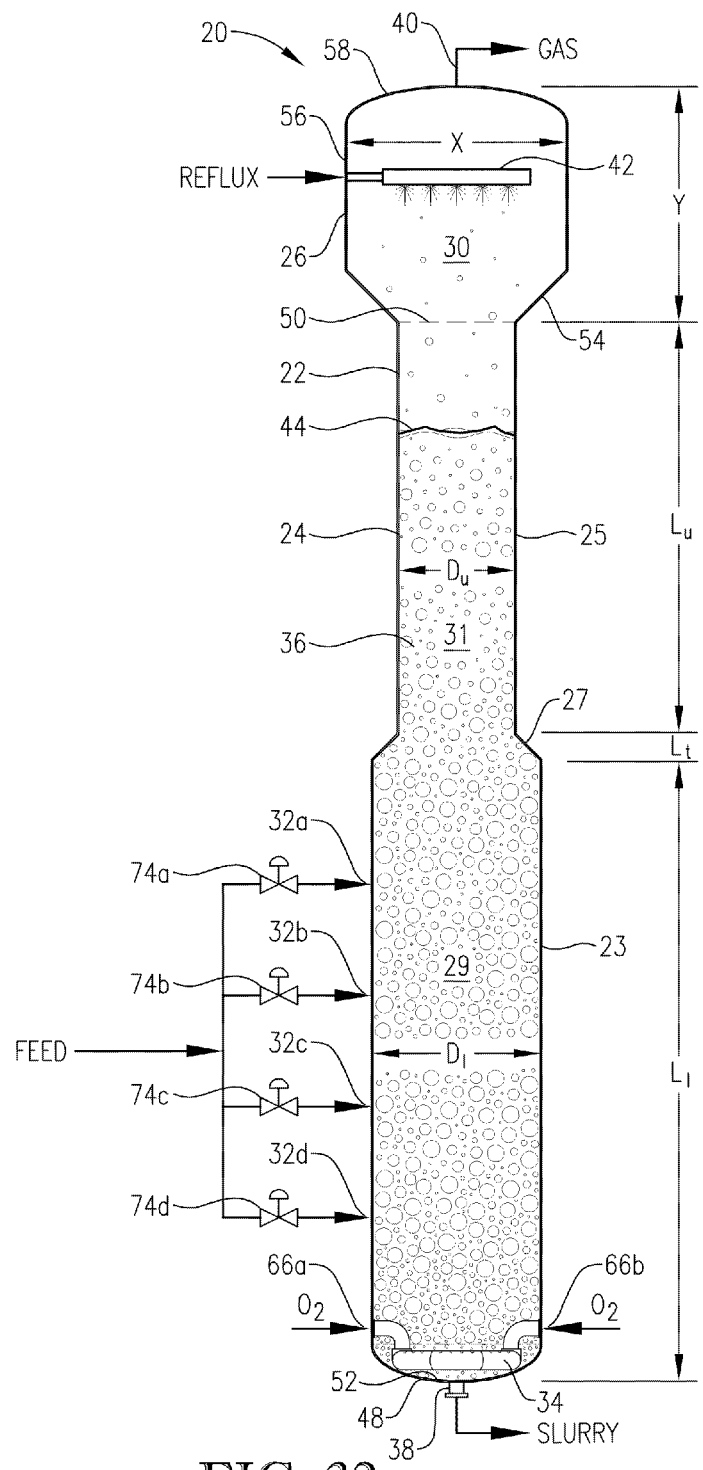
FIG. 32 is a side view of a staged-velocity bubble column reactor having a broad lower reaction zone and a narrow upper reaction zone.

It has been discovered that varying the horizontal cross-sectional area of the reaction zone of a bubble column reactor along the height of the reactor can help improve the fluid flow dynamics of the reaction medium, especially in the scaled-up oxidation bubble column reactor designs discussed above. Referring now to FIG. 32, in one embodiment of the present invention, vessel shell 22 of oxidation bubble column reactor 20 includes a broad lower section 23, a narrow upper section 25, and a transition section 27. Preferably, lower and upper sections 23,25 are substantially cylindrical in shape and are aligned along a common central upright axis. Transition section 27 may have many suitable shapes (e.g., a horizontal planar shape, a 2:1 elliptical shape, a hemispherical shape, and so on). Preferably, transition section 27 is a generally frustoconical member that transitions vessel shell 22 from broad lower section 23 to narrow upper section 25. Lower section 23 of vessel shell 22 defines a broad lower reaction zone 29. Upper section 25 of vessel shell 22 defines a narrow upper reaction zone 31. Transition section 27 defines a transition zone located between lower and upper reaction zones 29,31. Lower reaction zone 29, upper reaction zone 31, and the transition zone cooperatively form the total reaction zone of oxidation bubble column reactor 20 that receives multi-phase reaction medium 36.

In a preferred embodiment of the present invention, the maximum horizontal cross-sectional area of reaction medium 36 in lower reaction zone 29 is at least about 10 percent greater than the minimum cross-sectional area of reaction medium 36 in upper reaction zone 31. More preferably, the maximum horizontal cross-sectional area of reaction medium 36 in lower reaction zone 29 is in the range of from about 25 to about 210 percent greater than the minimum horizontal cross-sectional area of reaction medium 36 in upper reaction zone 31. Most preferably, the maximum horizontal cross-sectional area of reaction medium 36 in lower reaction zone 29 is in the range of from 35 to 160 percent greater than the minimum horizontal cross-sectional area of reaction medium 36 in upper reaction zone 31.

As illustrated in FIG. 32, lower reaction zone 29 has a maximum diameter "$D_l$" that is greater than the minimum diameter "$D_u$" of upper reaction zone 31. Preferably, $D_l$ is at least about 5 percent greater than $D_u$. More preferably, $D_l$ is in the range of from about 10 to about 100 percent greater than about $D_u$. Most preferably, $D_l$ is in the range of from 15 to 50 percent greater than $D_u$. FIG. 32 also illustrates that lower reaction zone 29 has a maximum height "$L_l$", upper reaction zone 31 has a maximum height "$L_u$", and the transition zone has a maximum height "$L_t$". It should be noted that the height of the portion of reaction medium 36 contained in lower reaction zone 29 is $L_l$ and the height of the portion of reaction medium 36 contained in the transition zone is $L_t$. In one embodiment, the height of the portion of reaction medium 36 located in upper reaction zone 31 is $L_u$. However, in certain instances the height of reaction medium 36 in upper reaction zone 31 may be less than $L_u$. In other instances, the total height of reaction medium 36 may extend above the top end 50 of upper reaction zone 31 (i.e. the total height of reaction medium 36 is more than the sum of $L_l$ plus $L_t$ plus $L_u$. Preferably, the total height of the reaction medium 36 is within 50, 25, or 10 percent of $L_u$ measured either up or down from the top end 50 of upper reaction zone 31. Preferably, oxidation bubble column reactor 20 has an $L_l$:$L_u$ ratio in the range of from about 0.05:1 to about 5:1, more preferably in the range of from about 0.1:1 to about 2.5:1, and most preferably in the range of from 0.15:1 to 1.5:1. Preferably, oxidation bubble column reactor 20 has an $L_l$:$D_l$ ratio greater than about 0.5:1, more preferably in the range of from about 1:1 to about 10:1, and most preferably in the range of from 1.5:1 to 8:1. Oxidation bubble column reactor 20 preferably has an $L_u$:$D_u$ ratio greater than about 2:1, more preferably in the range of from about 2.5:1 to about 20:1, and most preferably in the range of from 3:1 to 15:1. In a preferred embodiment of the present invention $L_l$ is at least about 2 meters, more preferably $L_l$ is in the range of from about 4 to about 50 meters, and most preferably in the range of from 6 to 40 meters. Preferably, $L_u$ is at least about 4 meters, more preferably in the range of from about 5 to about 80 meters, and most preferably in the range of from 10 to 60 meters. Preferably, $D_l$ is in the range of from about 2 to about 12 meters, more preferably in the range of from about 3.1 to about 10 meters, and most preferably in the range of from 4 to 9 meters.

FIG. 32 also illustrates that oxidation bubble column reactor 20 has a disengagement section 26 located above upper reaction section 31. Disengagement section 26 defines disengagement zone 30. As shown in FIG. 32, disengagement zone 30 has a maximum height "Y" and a maximum width "X". It is preferred for oxidation bubble column reactor 20 to have an X:$D_l$ ratio in the range of from about 0.8:1 to about 4:1, most preferably in the range of from 1.1:1 to 2:1. Oxidation bubble column reactor 20 preferably has an $L_u$:Y ratio in the range of from about 1:1 to about 10:1, most preferably in the range from 2:1 to 5:1. Oxidation bubble column reactor 20 preferably has an $L_l$:Y ratio in the range of from about 0.4:1 to about 8:1, most preferably in the range from 0.6:1 to 4:1. Transition section 27 of vessel shell 22 has a maximum diameter "$D_t$" adjacent lower section 23 and minimum diameter "$D_u$" adjacent upper section 25. Oxidation bubble column reactor 20 preferably has an $L_t$:$D_l$ ratio in the range of from about 0.05:1 to about 5:1, most preferably in the range of from 0.1:1 to 2:1.

The vertically-varying horizontal cross-sectional area of oxidation bubble column reactor 20 illustrated in FIG. 32 provides the portion of reaction medium 36 contained in upper reaction zone 31 with a higher superficial gas velocity and higher gas hold-up than the portion of reaction medium 36 contained in lower reaction zone 29. Preferably, the time-averaged superficial gas velocity of the portion of reaction medium 36 contained in upper reaction zone 31 at half height of the reaction medium in upper reaction zone 31 is at least about 15 percent greater than the time-averaged superficial gas velocity of the portion of reaction medium 36 contained in lower reaction zone 29 at half height of the reaction medium in lower reaction zone 29. More preferably, the portion of reaction medium 36 contained in upper reaction zone 31 has a time-averaged superficial gas velocity at half-height of the reaction medium in upper reaction zone 31 that is in the range of from about 25 to about 210 percent greater than the time-averaged superficial gas velocity of the portion of reaction medium 36 contained in lower reaction zone 29 at half height of the reaction medium in lower reaction zone 29. Most preferably, the time-averaged superficial gas velocity of the portion of reaction medium 36 contained in upper reaction zone 31 at half height of the reaction medium in upper reaction zone 31 is in the range of from 35 to 160 percent greater than the time-averaged superficial gas velocity of the portion of reaction medium 36 contained in lower reaction zone 29 at half height of the reaction medium in lower reaction zone 29. Preferably, the time-averaged and volume-averaged gas hold-up of the portion of reaction medium 36 contained in upper reaction zone 31 is at least about 4 percent greater than the time-averaged and volume-average gas hold-up of the portion of reaction medium 36 contained in a lower reaction zone 29. More preferably, the time-averaged and volume-averaged gas hold-up of the portion of reaction medium 36 contained in upper reaction zone 31 is in the range of from about 6 to about 80 percent greater than the time-averaged and volume-averaged gas hold-up of the portion of reaction medium 36 contained in lower reaction zone 29. Most preferably, the time-averaged and volume-averaged gas hold-up of the portion of reaction medium 36 contained in upper reaction zone 31 is in the range of from 8 to 70 percent greater than the time-averaged and volume-averaged gas hold-up of the portion of reaction medium 36 contained in lower reaction zone 29.

Although FIG. 32 illustrates a very specific two-stage, cylindrical sidewall bubble column design, it should be understood that many other designs may fall within the ambit of this embodiment of the invention. For example, the narrow upper and broad lower sections of the reactor may be formed of one or more sloped sidewalls and/or a plurality of stepped-diameter sidewall segments. In any case, the claims, not the drawing, capture the essence of this embodiment.

As mentioned above, in certain instances, it may be desirable to employ larger bubble column reactors in order to permit higher production rates for a single reactor. However, as the size of bubble column reactors increases, the fluid flow behavior of the multi-phase reaction medium contained therein changes significantly from the flow behavior of smaller reactors. It has been discovered that the changing fluid flow behavior of larger bubble column reactors can be counteracted by contacting the multi-phase reaction medium contained in the bubble column reactor with additional upright surfaces. Accordingly, FIGS. 33-44 illustrate various ways of providing additional upright surface area in the reaction zone of a scaled-up bubble column reactor. Each of the bubble column reactors illustrated in FIGS. 33-44 include one or more upright internal members contained in the reaction zone of the bubble column reactor. These upright internal members are provided in addition to the upright pressure-containing sidewalls of the reactor. As previously discussed, the reaction medium contained in the bubble column reactor has a maximum height "H" and a maximum width "W". The minimum width of the reaction medium occurring above a height of H/5 is referred to herein as "Wmin". In a preferred embodiment of the present invention the total upright surface area of the bubble column reactor that contacts the reaction medium is preferably greater than about 3.25WminH, more preferably in the range of from about 3.5WminH to about 20WminH, still more preferably in the range of from about 4WminH to about 15WminH, and most preferably in the range of from 5WminH to 10WminH. This total upright surface area that contacts the reaction medium includes all area of upright surfaces, including upright surfaces of the pressure-containing reactor sidewall and upright surfaces of any internal members present within the reaction zone. As used herein the term "upright" denotes less than 45° from vertical. Preferably, the upright surfaces contacting the reaction medium in the bubble column reactor extend at an angle within 30° of vertical, more preferably within 15° of vertical, still more preferable within 5° of vertical, and most preferably substantially vertical.

It is further preferred that the total amount of upright surface area contacting the reaction medium that is attributable to the non-pressure-containing internal members is at least about 10 percent of the total amount of upright surface area contacting the reaction medium that is attributable to the pressure-containing sidewalls of the vessel. More preferably, the total exposed upright surface area presented by the internal members and contacting the reaction medium is in the range of from about 15 to about 600 percent of the total exposed upright surface area presented by the pressure-containing sidewalls and contacting the reaction medium, still more preferably in the range of from about 25 to about 400 percent, and most preferably in the range of from 35 to 200 percent. The presence of added upright surface area in bubble column oxidation can permit lower H:W ratios than would be possible in conventional bubble column reactors having little or no added upright surface area. Thus, it is preferred for the H:W ratio of a bubble column reactor employing added upright surface area to be in the range of from about 3:1 to about 20:1, more preferably in the range of from about 3.5:1 to about 15:1, and most preferably in the range of from 4:1 to 12:1.

Referring now to the embodiment illustrated in FIGS. 33 and 34, oxidation bubble column reactor 20 can include a single divider wall 33 extending diametrically from one side of sidewall 46 to the opposite side of sidewall 46. Divider wall 33 is disposed above sparger 34 so that substantially all of the oxidant stream is introduced below the bottom of divider wall 33. Thus, approximately one-half of the gas phase of reaction medium 36, which includes an undissolved portion of the oxidant stream, flows upwardly on each side of divider wall 33. Preferably, approximately one-half of the feed stream is introduced via feed inlet 32a on one side of divider wall 33, and the other half of the feed stream is introduced via feed inlet 32b on the other side of divider wall 33. The height of divider wall 33 is substantially equal to the height of cylindrical sidewall 46.

Divider wall 33 divides reaction zone 28 into approximately two halves with reaction medium 36 being disposed on each side of divider wall 33. Substantially all of the upright surface area of reactor 20 that contacts reaction medium 36 is attributable to the inner exposed surfaces of sidewall 46 and the outer exposed surfaces of divider wall 33. If divider wall 33 were not present in reaction zone 28, then substantially all of the upright surface area in contact with reaction medium 36 would be attributable to sidewalls 46 of the pressure-containing vessel shell 22. Divider wall 33 provides additional surface area that affects the fluid flow dynamics of reaction medium 36 and permits oxidation bubble column reactor 20 to be scaled-up without significant negative effects on reactor performance.

Figure 35:
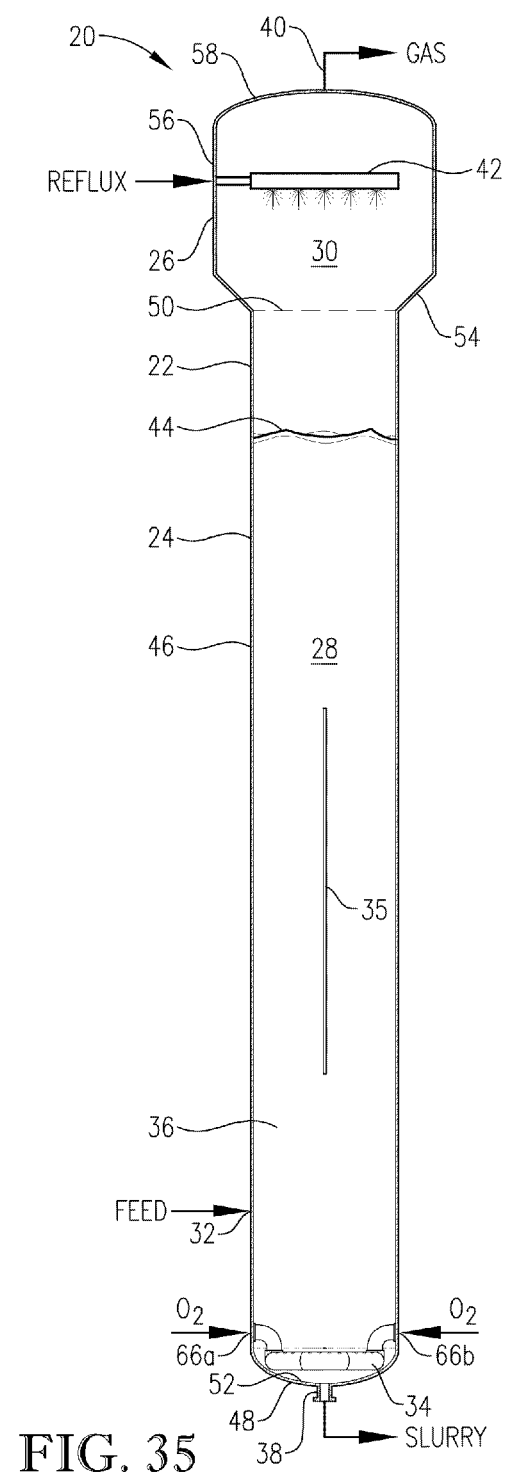
FIG. 35 is a side view a bubble column reactor equipped with a shortened upright divider wall for adding upright surface area that contacts the reaction medium.

Referring now to the embodiment illustrated in FIG. 35, oxidation bubble column reactor 20 is illustrated as including a truncated divider wall 35. Divider wall 35 of FIG. 35 is similar to divider wall 33 of FIGS. 33 and 34; however, divider wall 35 of FIG. 35 has a height that is significantly less than the overall height of reaction medium 36. In the configuration illustrated in FIG. 35, is preferred for substantially all of the feed stream and the oxidant stream to be introduced into reaction zone 28 below the bottom of divider wall 35. The top of divider wall 35 is preferably spaced a substantial distance from the upper surface 44 of reaction medium 36. In this configuration the two halves of reaction medium 36 disposed on either side of divider wall 35 can mix with one another above and below divider wall 35.

Figures 36, 37:
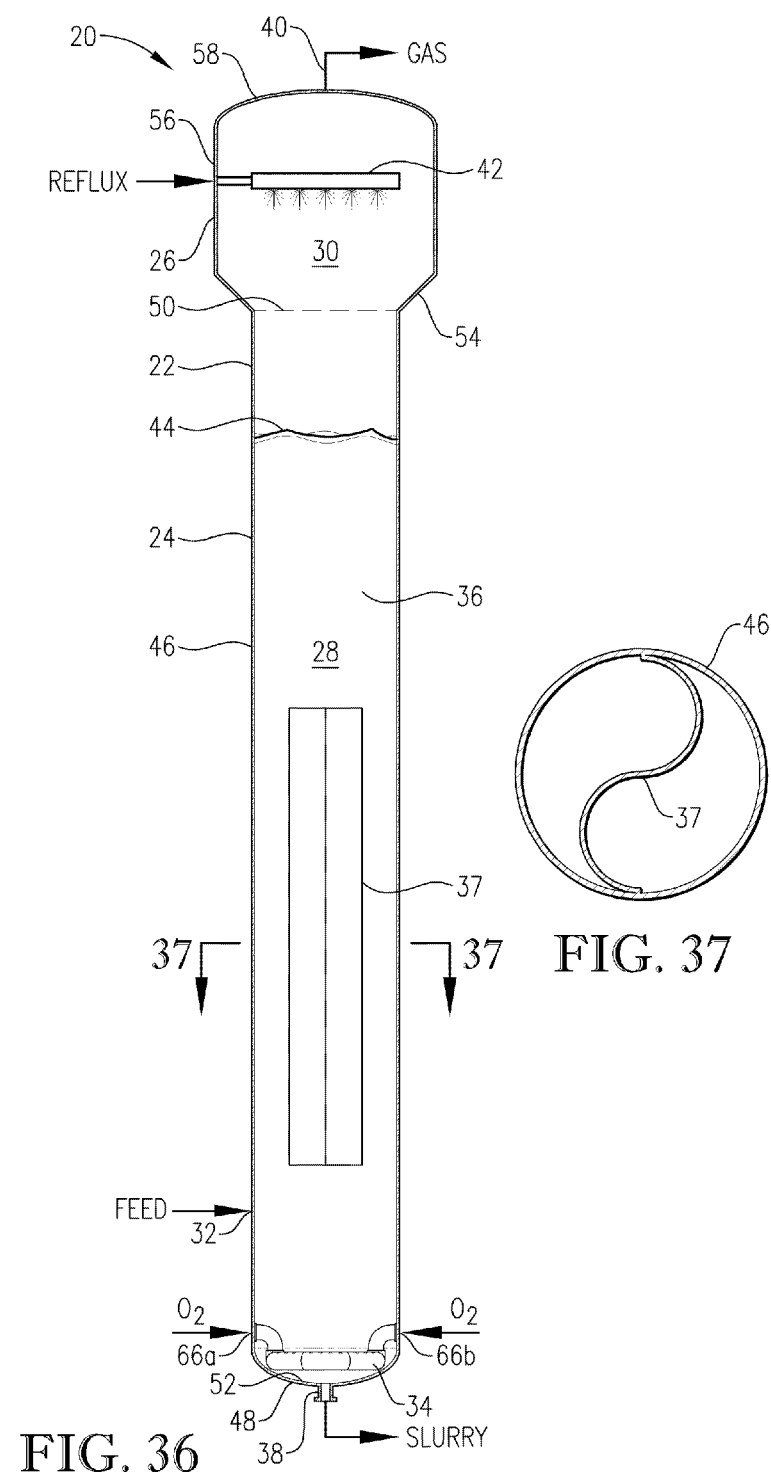
FIG. 36 is a side view of a bubble column reactor equipped with a shortened and curved upright divider wall for adding upright surface area that contacts the reaction medium.
FIG. 37 is a sectional view taken along line 37-37 in FIG. 36, particularly illustrating that the curved upright divider wall is a generally S-shaped member dividing a portion of the reaction zone into two substantially equal sections.

Referring now to the embodiment illustrated in FIGS. 36 and 37, oxidation bubble column reactor 20 can include a non-planer divider wall 37 which permits a substantial amount of upright surface area to be added to reactor 20, without requiring a plurality of additional internal members in reaction zone 28. Like divider walls 33,35 of FIGS. 33-35, divider wall 37 of FIGS. 36 and 37 is coupled to and extends between diametrically opposed inner sidewall surfaces of sidewall 46.

Figures 38, 39:
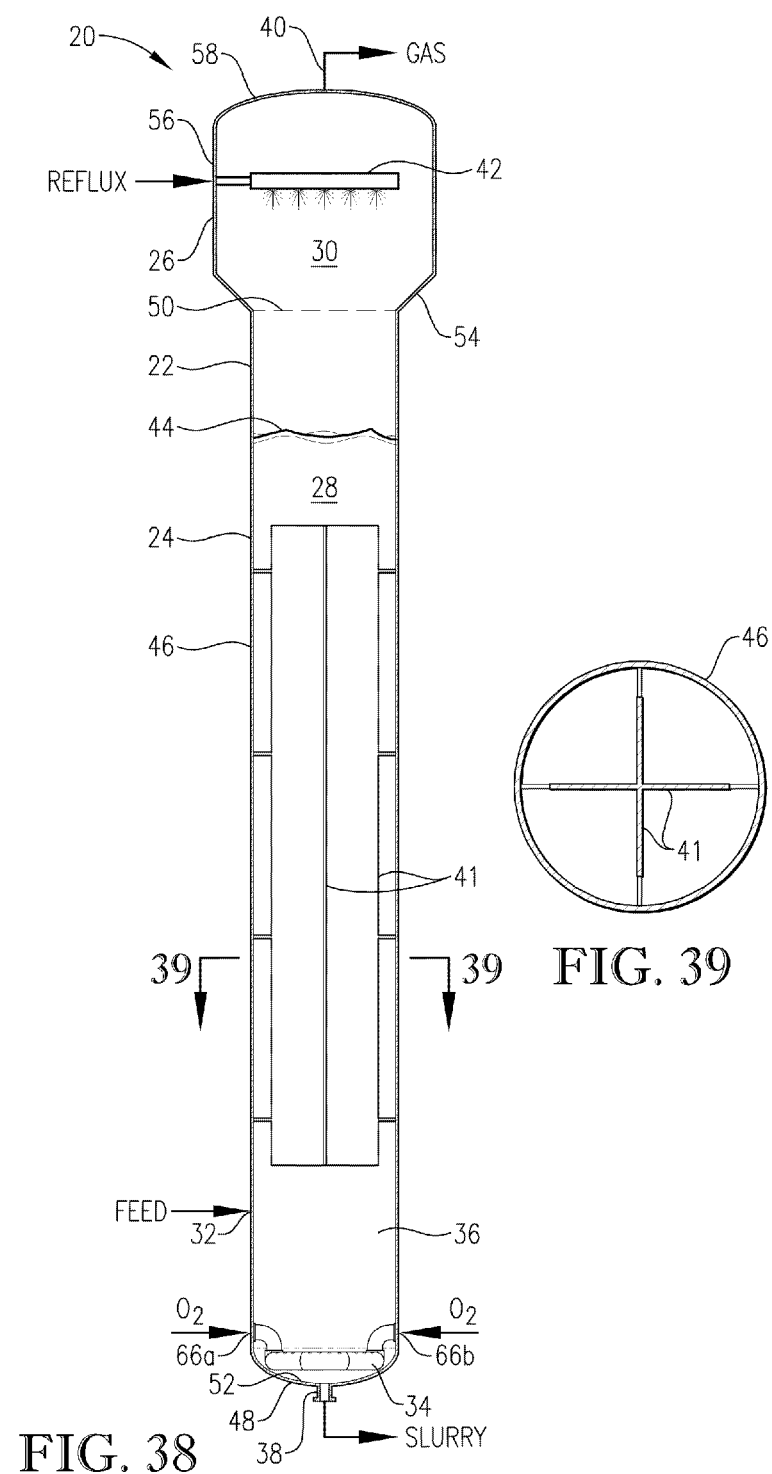
FIG. 38 is a side view of a bubble column reactor equipped with a shortened upright internal member for adding upright surface area that contacts the reaction medium.
FIG. 39 is a sectional view taken along line 39-39 in FIG. 38, particularly illustrating that the upright internal member has an "X" shape and the edges of the internal member do not extend all the way to the reactor side wall.

In the embodiment illustrated in FIGS. 38 and 39, oxidation bubble column reactor 20 includes an upright internal member 41 having a generally X-shaped configuration. The outer vertical edges of internal member 41 are spaced inwardly from the inner surfaces of sidewall 46 so that reaction medium 36 can flow between the partial quadrants defined by X-shaped internal member 41. The various exposed outer upright surfaces of internal member 71 add a significant amount of surface area that contacts reaction medium 36.

FIGS. 40-42 illustrate an embodiment where a portion of reaction zone 28 is divided into 4 vertical quadrants via internal member 53, while another portion of reaction zone 28 is divided into 8 vertical wedge-shaped sections via internal member 55. As illustrated in FIG. 40, reaction zone 28 alternates vertically between division into 4 vertical quadrants with internal member 53 and 8 vertical wedge-shaped sections via internal member 55.

Figures 43, 44:
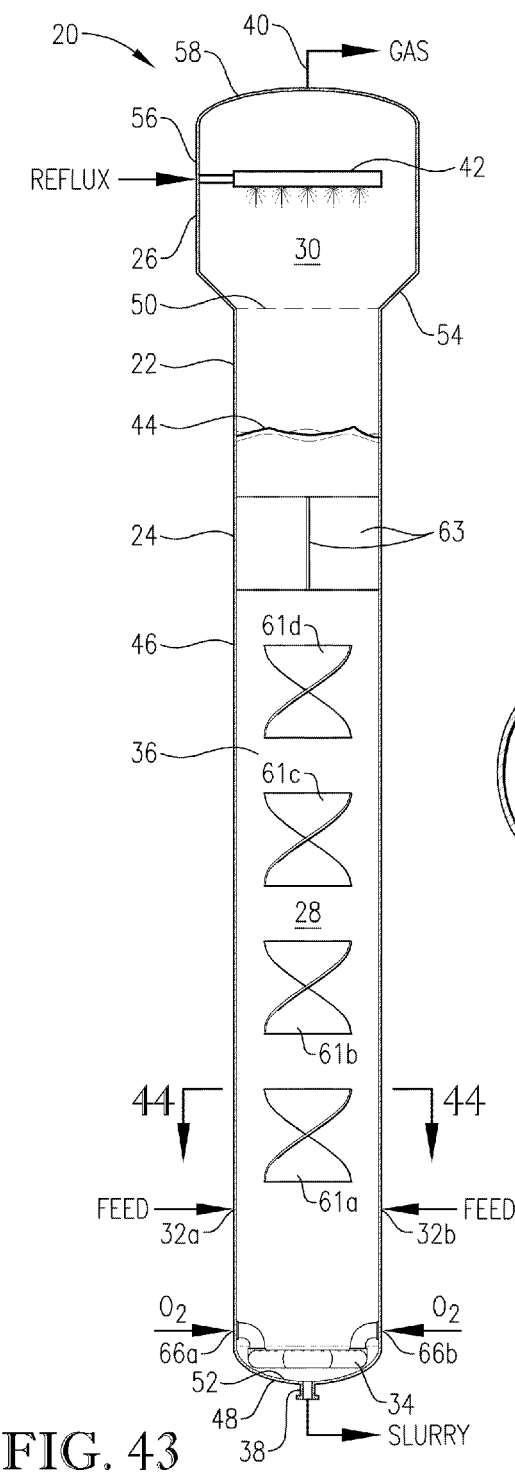
FIG. 43 is a side view of a bubble column reactor equipped with a plurality of helicoid-shaped internal members for adding upright surface area that contacts the reaction medium.
FIG. 44 is a sectional view taken along line 44-44 in FIG. 43, particularly illustrating the shape of one of the helicoid-shaped internal members.

Referring now to FIGS. 43 and 44, oxidation bubble column reactor 20 is illustrated as including a plurality of generally helicoid-shaped internal members 61a,b,c,d and a vertical X-shaped divider member 63 disposed above helical members 61. Helicoid members 61 present sloped outer surfaces that induce a swirling flow pattern in the upwardly flowing portion of reaction medium 36. It is preferred for the direction of slope of helicoid members 61 to be such that adjacent helical members 61 cause swirling of reaction medium 36 in generally opposite directions. Thus, if helicoid member 61a causes reaction medium to rotate clockwise as reaction medium 36 rises in reaction zone 28, helicoid member 61b (disposed immediately above helical member 61a) causes the upwardly moving reaction medium 36 to swirl in a counter-clockwise fashion. Vertical internal divider member 93 adds additional upright surface area to oxidation bubble column reactor 20, and can also function to minimize swirling/turbulence of reaction medium 36 as the gas-phase rises towards upper surface 44 of reaction medium 36.

Regardless of which configuration illustrated in FIGS. 33-44 is employed in oxidation bubble column reactor 20, it is preferred for the oxidant stream and the feed stream to be introduced into reaction zone 28 in a manner such that a substantial portion of the molecular oxygen and oxidizable compound are introduced into reaction zone 28 below a significant portion of the upright internal member or members. Preferably, at least about 50 weight percent of all the molecular oxygen and oxidizable compound introduced into reaction zone 28 enters reaction zone 28 below at least 50 percent of the upright exposed outer surface area of the internal member or members, more preferably at least about 75 weight percent of the molecular oxygen and oxidizable compound enter reaction zone below at least 50 percent of the upright exposed outer surface area of the internal member(s), still more preferably at least about 90 weight percent of the molecular oxygen and oxidizable compound enter reaction zone below at least 50 percent of the upright exposed outer surface area of the internal member(s), and most preferably substantially all of the molecular oxygen and oxidizable compound enter reaction zone below at least 50 percent of the upright exposed outer surface area of the internal member(s). In addition, it is preferred for the oxidant stream and the feed stream to be introduced in a manner such that a substantial portion of the gas phase of reaction medium 36 flows upwardly on all sides of the additional exposed outer surface area provided by the internal member or members. It is further preferred for the oxidant and feed streams to be introduced into reaction zone 28 in accordance with the radial and azimuthal distribution schemes described above.

Although certain prior art oxidation reactors may employ heat exchange surfaces that contact the reaction medium in a manner similar to that of the internal member(s) described herein, it should be noted that it is undesirable for the internal member(s) of the present invention to provide any significant degree of heating or cooling to the reaction medium. Thus, it is preferred for the heat flux of the exposed (i.e., contacting the reaction medium) upright surfaces of the internal member(s) described herein to be less than about 30,000 watts per square meter.

FIGS. 45-53 illustrate embodiments of the present invention where oxidation bubble column reactor 20 is equipped with one or more baffles that contact multi-phase reaction medium 36 in order to facilitate improved oxidation with minimal impurities formation. Baffles are especially useful in the scaled-up bubble column reactor designs described above. In each of the baffled bubble column reactors 20 illustrated in FIGS. 45-53, it is preferred for the baffle or baffles to have an open area in the range of from about 10 to about 90 percent. As used herein, percent open area of a baffle means the minimum percent of the horizontal cross-sectional area of a reaction zone that is open (i.e., not filled by the structure of the baffle) at the vertical location of the baffle. More preferably, the open area of the baffle or baffles illustrated in FIGS. 45-53 is in the range of from about 25 to about 75 percent, most preferably in the range of from 35 to 65 percent.

A significant feature of the baffles illustrated in FIGS. 45-53 is the ability of the baffles to resist fouling. As mentioned previously, oxidation bubble column reactor 20 is preferably employed in precipitating oxidation service, where solids are formed in reaction medium 36 during oxidation. Baffles having a significant amount of near-horizontal upwardly-facing planar surface area are prone to fouling in a reactor operating under precipitating conditions. When baffles foul, solids build up on the upwardly-facing surfaces of the baffles, and as the amount of solids deposited on the baffles increases, chunks of the precipitated solids may dislodge from the baffles and fall towards the bottom of the reactor. These chunks of dislodged solids can build up in the bottom of the reactor and can cause a number of problems including, for example, inhibition of slurry discharge out of the bottom of the reactor.

In view of the foregoing, it is preferred in one embodiment for the baffle or baffles employed in oxidation bubble column reactor 20 to present no upwardly-facing planar outer surfaces (e.g., the baffle can be constructed from piping materials having a circular cross section). Unless otherwise defined herein, an upwardly-facing surface is a surface having a normal vector projecting above horizontal. In another embodiment, a small amount of substantially planar surfaces can be utilized so long as less than about 50 percent of the total upwardly-facing exposed (i.e., contacting reaction medium 36) outer surface area of the baffle or baffles is attributable to substantially planar surfaces inclined less than 30°, or 20°, or even 10° from horizontal. More preferably, less than about 35 percent of the total upwardly-facing exposed outer surface area of the baffle or baffles is attributable to planar surfaces inclined less than 30°, or 20°, or even 10° from horizontal. Most preferably, less than 25 percent of the total upwardly-facing exposed outer surface area of the baffle or baffles is attributable to substantially planar surfaces inclined less than 30°, or 20°, or even 10° from horizontal. It is further preferred for the upwardly-facing exposed outer surfaces of the baffle or baffles to have a substantially smooth finish so as to further resist fouling. Preferably, at least a substantial portion of the upwardly-facing exposed outer surfaces of the baffle or baffles have a surface roughness less than about 125 micron RMS, more preferably less than about 64 micron RMS, and most preferably less than 32 micron RMS. Electro-polished finishes and smooth "2B" mill rolled finishes are particularly useful.

In addition to the non-fouling design of the baffle or baffles illustrated in FIGS. 45-53, is preferred for the baffle(s) to be properly spaced from the upper and lower ends of reaction medium 36 so as to provide optimized effectiveness. In a preferred embodiment of the present invention the baffle or baffles are spaced at least 0.5W and/or 0.05H from both the upper and lower ends of reaction medium 36, where "W" is the maximum width of reaction medium 36 and "H" is the maximum height of reaction medium 36. More preferably, the baffle or baffles are spaced at least 1W and/or 0.1H from both the upper and lower ends of reaction medium 36. Most preferably, the baffle or baffles are spaced at least 1.5W and/or 0.15H from both the upper and lower ends of reaction medium 36. The presence of a baffle or baffles in oxidation bubble column reactor 20 can permit lower H:W ratios than would be possible in similar non-baffled reactors. Thus, it is preferred for the H:W ratio of baffled bubble column reactors to be in the range of from about 3:1 to about 20:1, more preferably in the range of from about 3.5:1 to about 15:1, and most preferably in the range of from 4:1 to 12:1.

Figures 45, 46, 47:
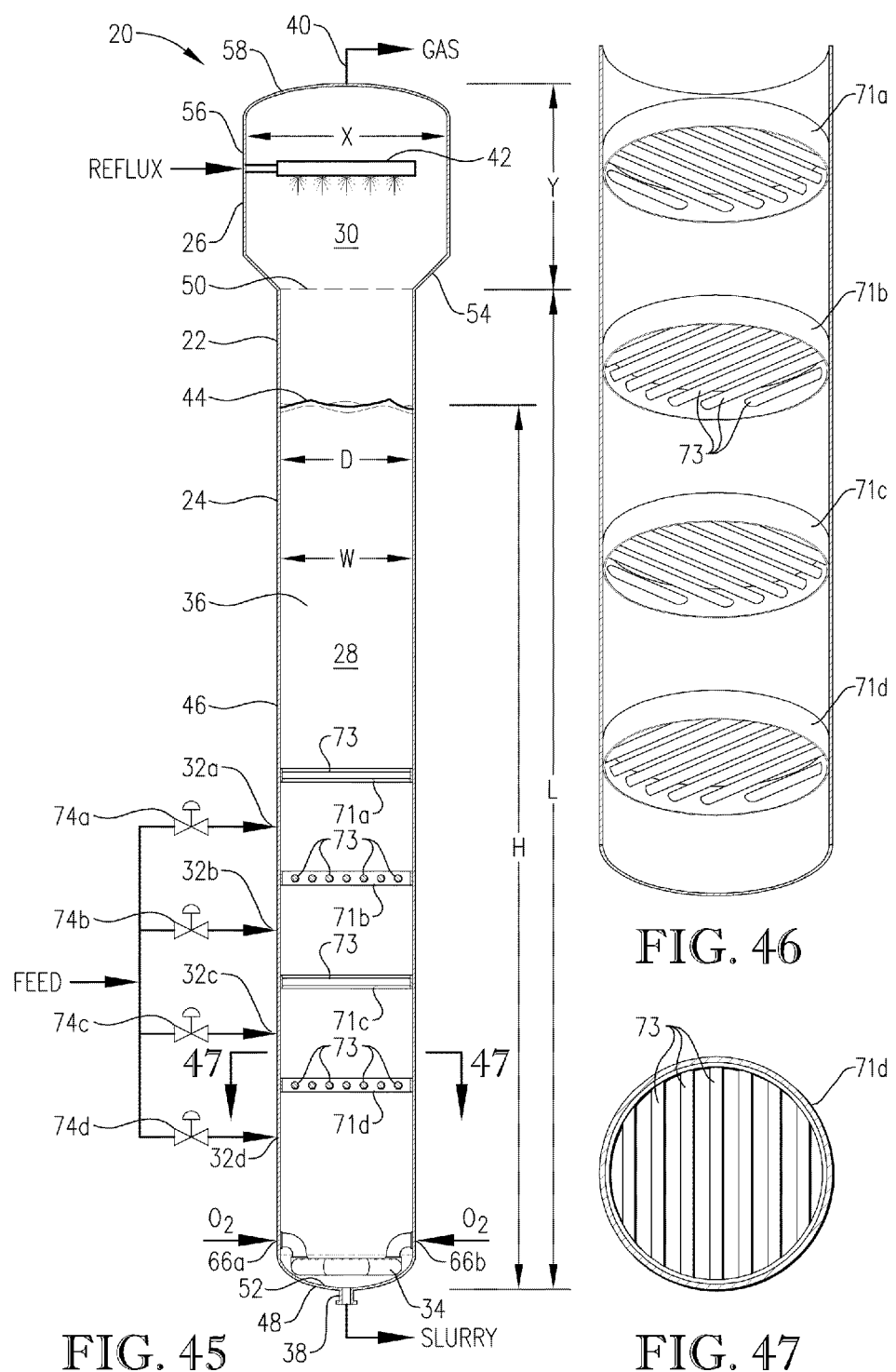
FIG. 45 is a side view of a bubble column reactor equipped a plurality of baffles, each comprising a plurality of cylindrical bars for contacting the reaction medium.
FIG. 46 is an enlarged isometric view of the baffles of FIG. 45, particularly illustrating the manner in which the cylindrical bars of adjacent baffles are rotated 90 degrees relative to one another.
FIG. 47 is a sectional view taken along line 47-47 in FIG. 45, particularly illustrating a single one of the baffles.

Referring now to FIGS. 45-47 in detail, oxidation bubble column reactor 20 is illustrated as including a plurality of vertically-spaced baffles 71a,b,c,d. Preferably, oxidation bubble column reactor 20 includes in the range of from 2 to 20 vertically-spaced baffles, most preferably 3 to 8 vertically-spaced baffles. Preferably, each baffle 71 comprises a plurality of elongated individual baffle members 73. In this embodiment, each individual baffle member 73 presents a substantially cylindrical exposed outer surface that contacts reaction medium 36. In the embodiment illustrated in FIGS. 45-47, baffles 71a,b,c,d are rotated relative to one another so that individual baffle members 73 of adjacent baffles 71 extend substantially perpendicular to one another.

Figures 48, 49, 50:
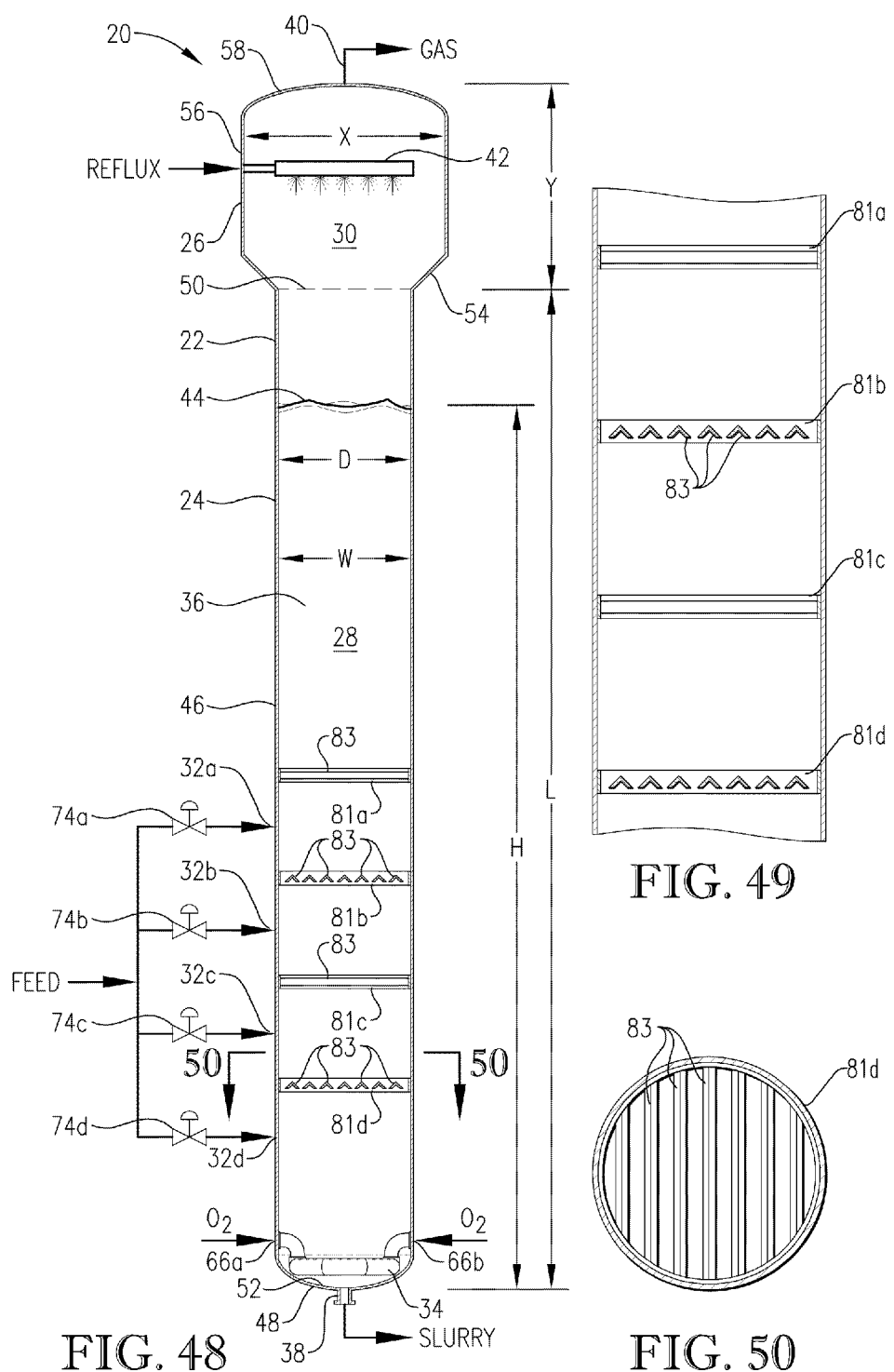
FIG. 48 is a side view of a bubble column reactor equipped with a plurality of baffles, each comprising a plurality of L-section members for contacting the reaction medium.
FIG. 49 is an enlarged side view of the baffles of FIG. 48, particularly illustrating the manner in which the L-section members of adjacent baffles are rotated 90 degrees relative to one another.
FIG. 50 is a sectional view taken along line 50-50 in FIG. 48, particularly illustrating a single one of the baffles.

Referring now to FIGS. 48-50 in detail, alternative baffles 81a,b,c,d are illustrated as comprising a plurality of elongated individual baffle members 83. In this embodiment, each baffle member 83 is formed of an L-section member and presents a generally inverted V-shaped upwardly-facing exposed outer surface. The configuration of the exposed outer surfaces of individual baffle members 83 helps prevent fouling with the precipitating solids in reaction medium 36. The number, spacing, and orientation of angle iron baffle members 83 can be substantially the same as described above for cylindrical baffle members 73 of FIGS. 45-47.

Figures 51, 52, 53:
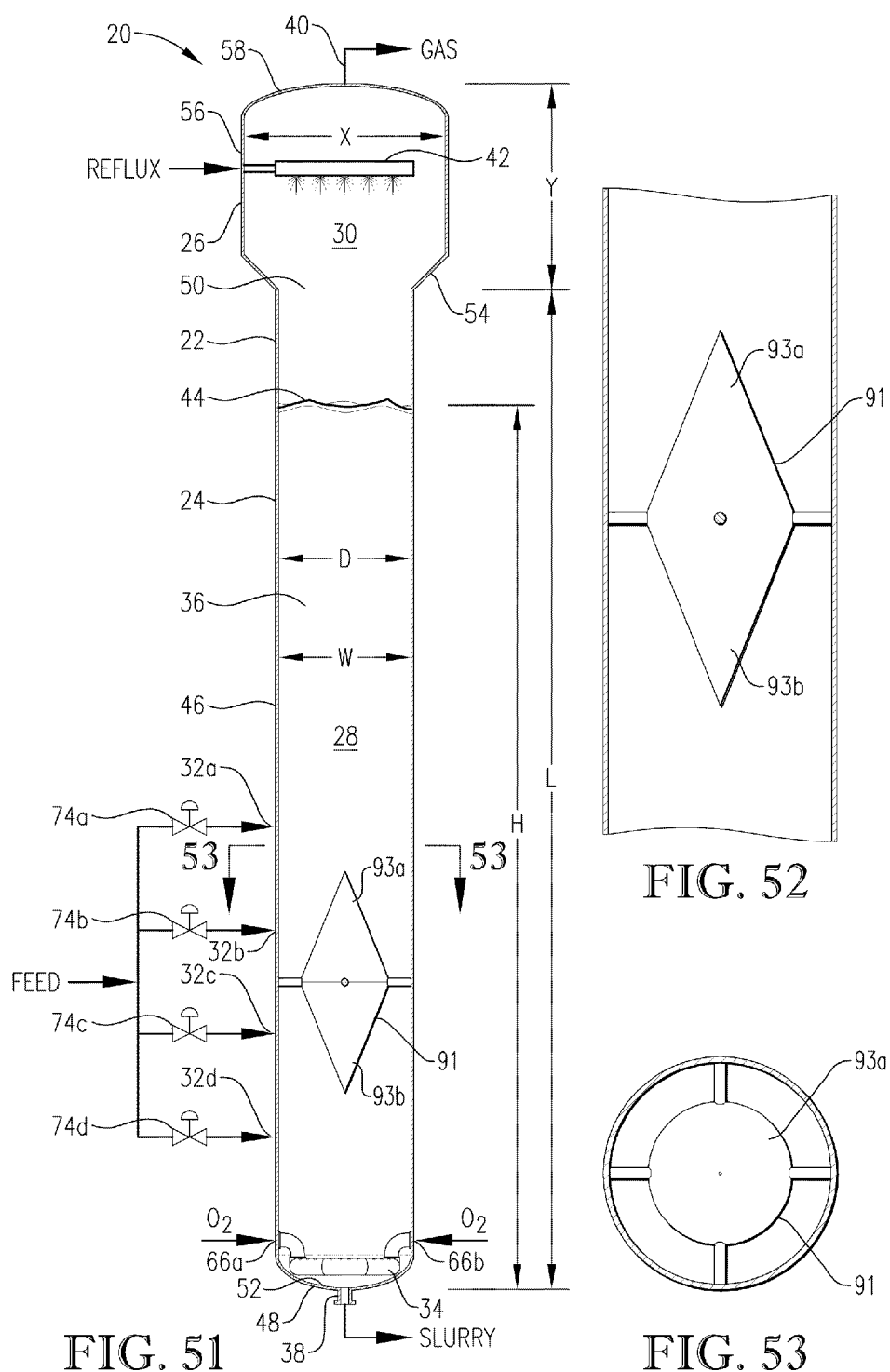
FIG. 51 is a side view of a bubble column reactor equipped with a single monolithic, cylindrical, diamond-shaped baffle for contacting the reaction medium.
FIG. 52 is an enlarged side view of the monolithic baffle of FIG. 51.
FIG. 53 is a sectional view taken along line 53-53 in FIG. 51 and illustrating the cylindrical nature of the monolithic baffle.

Referring now to FIGS. 51-53 in detail, oxidation bubble column reactor 20 is illustrated as including a single monolithic baffle 91 having generally the shape of two oppositely-extending vertical cones 93a,b joined at their base. The slope of the exposed upwardly-facing outer surface of monolithic baffle 91 helps prevent fouling of baffle 91 with the solids precipitating in reaction medium 36.

The various baffle configurations illustrated in FIGS. 45-53 are only exemplary, and many other baffle configurations may fall within the ambit of the present invention. It should also be noted that the baffle configurations illustrated in FIGS. 45-53 can be used in combination.

Although certain prior art oxidation reactors may employ heat exchange tubes that contact the reaction medium in a manner similar to that of the baffle(s) described herein, it should be noted that it is undesirable for the baffles of the present invention to provide any significant degree of heating or cooling of the reaction medium. Thus, it is preferred for the heat flux of the exposed (i.e., contacting the reaction medium) outer surfaces of the baffles described herein to be less than about 30,000 watts per square meter.

Referring again to FIGS. 1-53, oxidation is preferably carried out in bubble column reactor 20 under conditions that are markedly different, according to preferred embodiments disclosed herein, than conventional oxidation reactors. When bubble column reactor 20 is used to carry out the liquid-phase partial oxidation of para-xylene to crude terephthalic acid (CTA) according to preferred embodiments disclosed herein, the spatial profiles of local reaction intensity, of local evaporation intensity, and of local temperature combined with the liquid flow patterns within the reaction medium and the preferred, relatively low oxidation temperatures contribute to the formation of CTA particles having unique and advantageous properties.

Figure 54A:
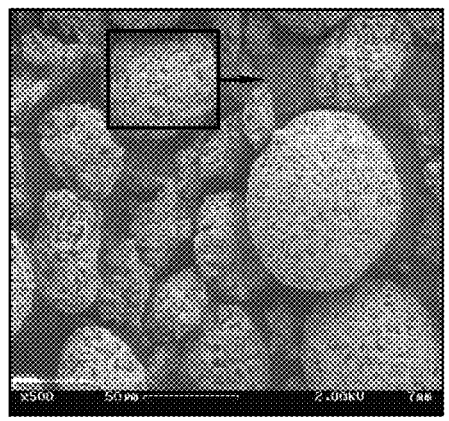
FIGS. 54A and 54B are magnified views of crude terephthalic acid (CTA) particles produced in accordance with one embodiment of the present invention, particularly illustrating that each CTA particle is a low density, high surface area particle composed of a plurality of loosely-bound CTA subparticles.
Figure 54B:
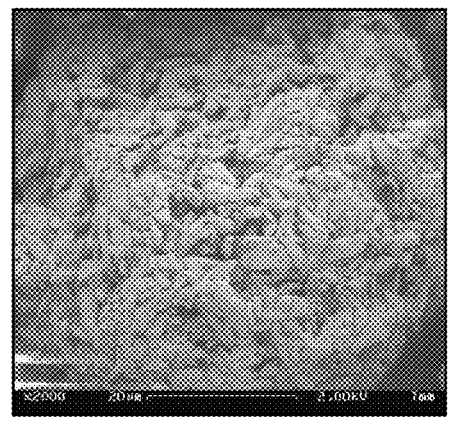

FIGS. 54A and 54B illustrate base CTA particles produced in accordance with one embodiment of the present invention. FIG. 54A shows the base CTA particles at 500 times magnification, while FIG. 54B zooms in on one of the base CTA particles and shows that particle at 2,000 times magnification. As perhaps best illustrated in FIG. 54B, each base CTA particle is typically formed of a large number of small, agglomerated CTA subparticles, thereby giving the base CTA particle a relatively high surface area, high porosity, low density, and good dissolvability. The base CTA particles typically have a mean particle size in the range of from about 20 to about 150 microns, more preferably in the range of from about 30 to about 120 microns, and most preferably in the range of from 40 to 90 microns. The CTA subparticles typically have a mean particle size in the range of from about 0.5 to about 30 microns, more preferably from about 1 to about 15 microns, and most preferably in the range of from 2 to 5 microns. The relatively high surface area of the base CTA particles illustrated in FIGS. 54A and 54B, can be quantified using a Braunauer-Emmett-Teller (BET) surface area measurement method. Preferably, the base CTA particles have an average BET surface of at least about 0.6 meters squared per gram ($m^2/g$). More preferably, the base CTA particles have an average BET surface area in the range of from about 0.8 to about 4 m²/g. Most preferably, the base CTA particles have an average BET surface area in the range of from 0.9 to 2 m²/g. The physical properties (e.g., particle size, BET surface area, porosity, and dissolvability) of the base CTA particles formed by optimized oxidation process of a preferred embodiment of the present invention permit purification of the CTA particles by more effective and/or economical methods, as described in further detail below with respect to FIG. 57.

The mean particle size values provided above were determined using polarized light microscopy and image analysis. The equipment employed in the particle size analysis included a Nikon E800 optical microscope with a 4× Plan Flour N.A. 0.13 objective, a Spot RT™ digital camera, and a personal computer running Image Pro Plus™ V4.5.0.19 image analysis software. The particle size analysis method included the following main steps: (1) dispersing the CTA powders in mineral oil; (2) preparing a microscope slide/cover slip of the dispersion; (3) examining the slide using polarized light microscopy (crossed polars condition—particles appear as bright objects on black background); (4) capturing different images for each sample preparation (field size=3×2.25 mm; pixel size=1.84 microns/pixel); (5) performing image analysis with Image Pro Plus™ software; (6) exporting the particle measures to a spreadsheet; and (7) performing statistical characterization in the spreadsheet. Step (5) of "performing image analysis with Image Pro Plus™ software" included the substeps of: (a) setting the image threshold to detect white particles on dark background; (b) creating a binary image; (c) running a single-pass open filter to filter out pixel noise; (d) measuring all particles in the image; and (e) reporting the mean diameter measured for each particle. The Image Pro Plus™ software defines mean diameter of individual particles as the number average length of diameters of a particle measured at 2 degree intervals and passing through the particle's centroid. Step 7 of "performing statistical characterization in the spreadsheet" comprises calculating the volume-weighted mean particle size as follows. The volume of each of the n particles in a sample is calculated as if it were spherical using pi/6*$d_i$^3; multiplying the volume of each particle times its diameter to find pi/6*$d_i$^4; summing for all particles in the sample of the values of pi/6*$d_i$^4; summing the volumes of all particles in the sample; and calculating the volume-weighted particle diameter as sum for all n particles in the sample of (pi/6*$d_i$^4) divided by sum for all n particles in the sample of (pi/6*$d_i$^3). As used herein, "mean particle size" refers to the volume-weighted mean particle size determined according to the above-described test method; and it is also referred to as D(4,3).

$$D(4,3) = \frac{\sum_{i=1}^{n} \frac{\pi}{6} d_i^4}{\sum_{i=1}^{n} \frac{\pi}{6} d_i^3}$$

In addition, step 7 comprises finding the particle sizes for which various fractions of the total sample volume are smaller. For example, D(v,0.1) is the particle size for which 10 percent of the total sample volume is smaller and 90 percent is larger; D(v,0.5) is the particle size for which one-half of the sample volume is larger and one-half is smaller; D(v,0.9) is the particle size for which 90 percent of the total sample volume is smaller; and so on. In addition, step 7 comprises calculating the value of D(v,0.9) minus D(v,0.1), which is herein defined as the "particle size spread"; and step 7 comprises calculating the value of the particle size spread divided by D(4,3), which is herein defined as the "particle size relative spread."

Furthermore, it is preferable that the D(v,0.1) of the CTA particles as measured above be in the range from about 5 to about 65 microns, more preferably in the range from about 15 to about 55 microns and most preferably in the range from 25 to 45 microns. It is preferable that the D(v,0.5) of the CTA particles as measured above be in the range from about 10 to about 90 microns, more preferably in the range from about 20 to about 80 microns, and most preferably in the range from 30 to 70 microns. It is preferable that the D(v,0.9) of the CTA particles as measured above be in the range from about 30 to about 150 microns, more preferably in the range from about 40 to about 130 microns, and most preferably in the range from 50 to 110 microns. It is preferable that the particle size relative spread be in the range from about 0.5 to about 2.0, more preferably in the range from about 0.6 to about 1.5, and most preferably in the range from 0.7 to 1.3.

The BET surface area values provided above were measured on a Micromeritics ASAP2000 (available from Micromeritics Instrument Corporation of Norcross, Ga.). In the first step of the measurement process, a 2 to 4 gram of sample of the particles was weighed and dried under vacuum at 50° C. The sample was then placed on the analysis gas manifold and cooled to 77° K. A nitrogen adsorption isotherm was measured at a minimum of 5 equilibrium pressures by exposing the sample to known volumes of nitrogen gas and measuring the pressure decline. The equilibrium pressures were appropriately in the range of $P/P_0$=0.01-0.20, where P is equilibrium pressure and $P_0$ is vapor pressure of liquid nitrogen at 77° K. The resulting isotherm was then plotted according to the following BET equation:

$$\frac{P}{V_a(P_o - P)} = \frac{1}{V_m C} + \frac{C-1}{V_m C}\left(\frac{P}{P_o}\right)$$

where $V_a$ is volume of gas adsorbed by sample at P, $V_m$ is volume of gas required to cover the entire surface of the sample with a monolayer of gas, and C is a constant. From this plot, $V_m$ and C were determined. $V_m$ was then converted to a surface area using the cross sectional area of nitrogen at 77° K by:

$$A = \sigma \frac{V_m}{RT}$$

where σ is cross sectional area of nitrogen at 77° K, T is 77° K, and R is the gas constant.

As alluded to above, CTA formed in accordance with one embodiment of the present invention exhibits superior dissolution properties verses conventional CTA made by other processes. This enhanced dissolution rate allows the inventive CTA to be purified by more efficient and/or more effective purification processes. The following description addresses the manner in which the rate of dissolution of CTA can quantified.

The rate of dissolution of a known amount of solids into a known amount of solvent in an agitated mixture can be measured by various protocols. As used herein, a measurement method called the "timed dissolution test" is defined as follows. An ambient pressure of about 0.1 megapascal is used throughout the timed dissolution test. The ambient temperature used throughout the timed dissolution test is about 22° C.

Furthermore, the solids, solvent and all dissolution apparatus are fully equilibrated thermally at this temperature before beginning testing, and there is no appreciable heating or cooling of the beaker or its contents during the dissolution time period. A solvent portion of fresh, HPLC analytical grade of tetrahydrofuran (>99.9 percent purity), hereafter THF, measuring 250 grams is placed into a cleaned KIMAX tall form 400 milliliter glass beaker (Kimble® part number 14020, Kimble/Kontes, Vineland, N.J.), which is uninsulated, smooth-sided, and generally cylindrical in form. A Teflon-coated magnetic stirring bar (VWR part number 58948-230, about 1-inch long with 3/8-inch diameter, octagonal cross section, VWR International, West Chester, Pa. 19380) is placed in the beaker, where it naturally settles to the bottom. The sample is stirred using a Variomag® multipoint 15 magnetic stirrer (H&P Labortechnik AG, Oberschleissheim, Germany) magnetic stirrer at a setting of 800 revolutions per minute. This stirring begins no more than 5 minutes before the addition of solids and continues steadily for at least 30 minutes after adding the solids. A solid sample of crude or purified TPA particulates amounting to 250 milligrams is weighed into a non-sticking sample weighing pan. At a starting time designated as t=0, the weighed solids are poured all at once into the stirred THF, and a timer is started simultaneously. Properly done, the THF very rapidly wets the solids and forms a dilute, well-agitated slurry within 5 seconds. Subsequently, samples of this mixture are obtained at the following times, measured in minutes from t=0:0.08, 0.25, 0.50, 0.75, 1.00, 1.50, 2.00, 2.50, 3.00, 4.00, 5.00, 6.00, 8.00, 10.00, 15.00, and 30.00. Each small sample is withdrawn from the dilute, well-agitated mixture using a new, disposable syringe (Becton, Dickinson and Co, 5 milliliter, REF 30163, Franklin Lakes, N.J. 07417). Immediately upon withdrawal from the beaker, approximately 2 milliliters of clear liquid sample is rapidly discharged through a new, unused syringe filter (25 mm diameter, 0.45 micron, Gelman GHP Acrodisc GF®, Pall Corporation, East Hills, N.Y. 11548) into a new, labeled glass sample vial. The duration of each syringe filling, filter placement, and discharging into a sample vial is correctly less than about 5 seconds, and this interval is appropriately started and ended within about 3 seconds either side of each target sampling time. Within about five minutes of each filling, the sample vials are capped shut and maintained at approximately constant temperature until performing the following chemical analysis. After the final sample is taken at a time of 30 minutes past t=0, all sixteen samples are analyzed for the amount of dissolved TPA using a HPLC-DAD method generally as described elsewhere within this disclosure. However, in the present test, the calibration standards and the results reported are both based upon milligrams of dissolved TPA per gram of THF solvent (hereafter "ppm in THF"). For example, if all of the 250 milligrams of solids were very pure TPA and if this entire amount fully dissolved in the 250 grams of THF solvent before a particular sample were taken, the correctly measured concentration would be about 1,000 ppm in THF.

When CTA according to the present invention is subjected to the timed dissolution test described above, it is preferred that a sample taken at one minute past t=0 dissolves to a concentration of at least about 500 ppm in THF, more preferably to at least 600 ppm in THF. For a sample taken at two minutes past t=0, it is preferred that CTA according to the current invention will dissolve to a concentration of at least about 700 ppm in THF, more preferably to at least 750 ppm in THF. For a sample taken at four minutes past t=0, it is preferred that CTA according to the current invention will dissolve to a concentration of at least about 840 ppm in THF, more preferably to at least 880 ppm in THF.

The inventors have found that a relatively simple negative exponential growth model is useful to describe the time dependence of the entire data set from a complete timed dissolution test, notwithstanding the complexity of the particulate samples and of the dissolution process. The form of the equation, hereinafter the "timed dissolution model", is as follows:

$$S = A + B^*(1-\exp(-C^*t)), \text{ where}$$

t time in units of minutes;
S=solubility, in units of ppm in THF, at time t;
exp=exponential function in the base of the natural logarithm of 2;
A, B=regressed constants in units of ppm in THF, where A relates mostly to the rapid dissolution of the smaller particles at very short times, and where the sum of A+B relates mostly to the total amount of dissolution near the end of the specified testing period; and
C=a regressed time constant in units of reciprocal minutes.

The regressed constants are adjusted to minimize the sum of the squares of the errors between the actual data points and the corresponding model values, which method is commonly called a "least squares" fit. A preferred software package for executing this data regression is JMP Release 5.1.2 (SAS Institute Inc., JMP Software, SAS Campus Drive, Cary, N.C. 27513).

When CTA according to the present invention is tested with the timed dissolution test and fitted to the timed dissolution model described above, it is preferred for the CTA to have a time constant "C" greater than about 0.5 reciprocal minutes, more preferably greater than about 0.6 reciprocal minutes, and most preferably greater than 0.7 reciprocal minutes.

Figure 55A:
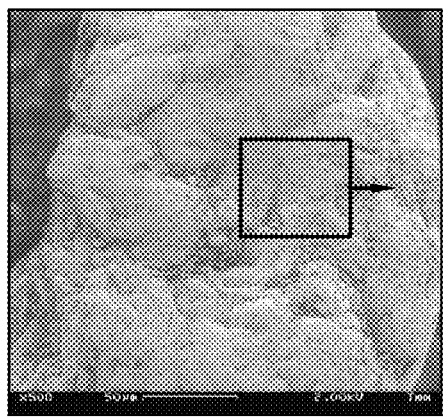
FIGS. 55A and 55B are magnified views of a conventionally-produced CTA, particularly illustrating that the conventional CTA particle has a larger particle size, lower density, and lower surface area than the inventive CTA particle of FIGS. 54A and 54B.
Figure 55B:
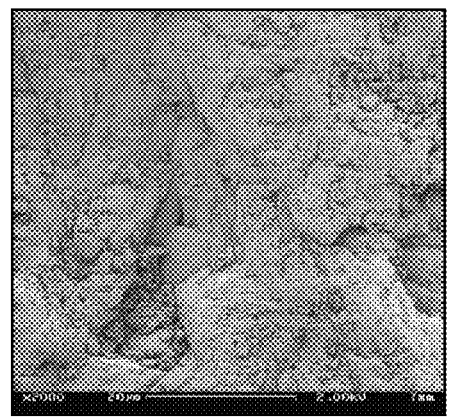

FIGS. 55A and 55B illustrate a conventional CTA particle made by a conventional high-temperature oxidation process in a continuous stirred tank reactor (CSTR). FIG. 55A shows the conventional CTA particle at 500 times magnification, while FIG. 55B zooms in and shows the CTA particle at 2,000 times magnification. A visual comparison of the inventive CTA particles illustrated in FIGS. 54A and 54B and the conventional CTA particle illustrated in FIGS. 55A and 55B shows that the conventional CTA particle has a higher density, lower surface area, lower porosity, and larger particle size than the inventive CTA particles. In fact, the conventional CTA represented in FIGS. 55A and 55B has a mean particle size of about 205 microns and a BET surface area of about 0.57 $m^2/g$.

Figure 56:
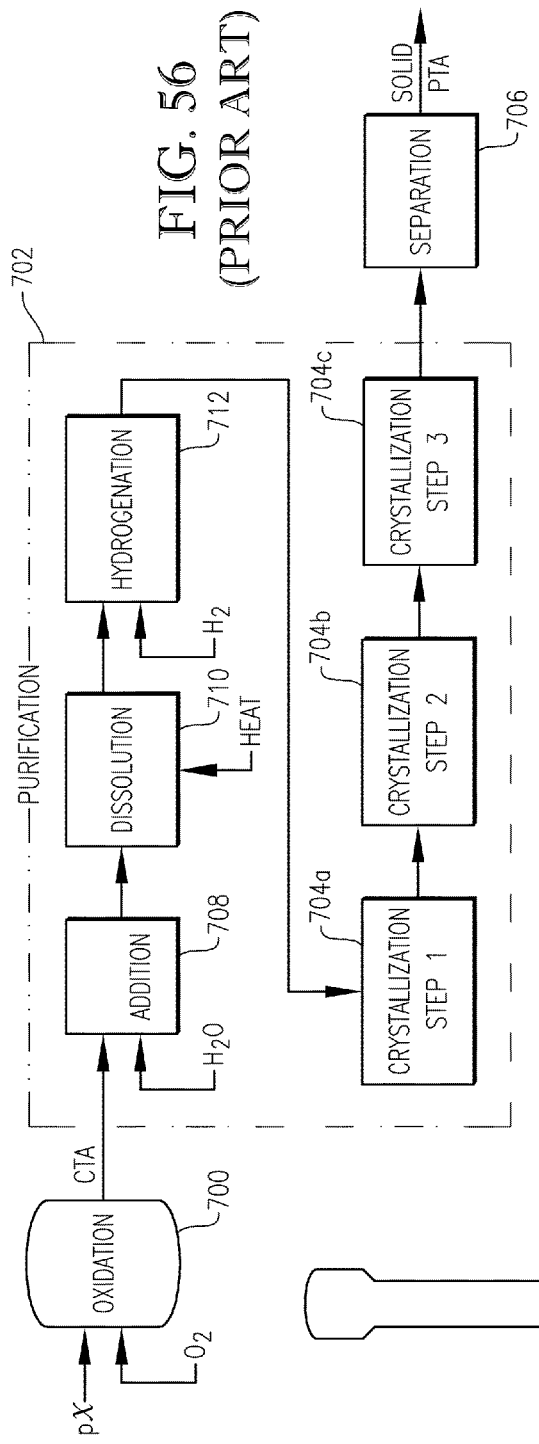
FIG. 56 is a simplified process flow diagram of a prior art process for making purified terephthalic acid (PTA)

FIG. 56 illustrates a conventional process for making purified terephthalic acid (PTA). In the conventional PTA process, para-xylene is partially oxidized in a mechanically agitated high temperature oxidation reactor 700. A slurry comprising CTA is withdrawn from reactor 700 and then purified in a purification system 702. The PTA product of purification system 702 is introduced into a separation system 706 for separation and drying of the PTA particles. Purification system 702 represents a large portion of the costs associated with producing PTA particles by conventional methods. Purification system 702 generally includes a water addition/exchange system 708, a dissolution system 710, a hydrogenation system 712, and three separate crystallization vessels 704a,b,c. In water addition/exchange system 708, a substantial portion of the mother liquor is displaced with water. After water addition, the water/CTA slurry is introduced into the dissolution system 710 where the water/CTA mixture is heated until the CTA particles fully dissolve in the water. After CTA dissolution, the CTA-in-water solution is subjected to hydrogenation in hydrogenation system 712. The hydrogenated effluent from hydrogenation system 712 is then subjected to three crystallization steps in crystallization vessels 704a,b,c, followed by PTA separation in separation system 706.

Figure 57:
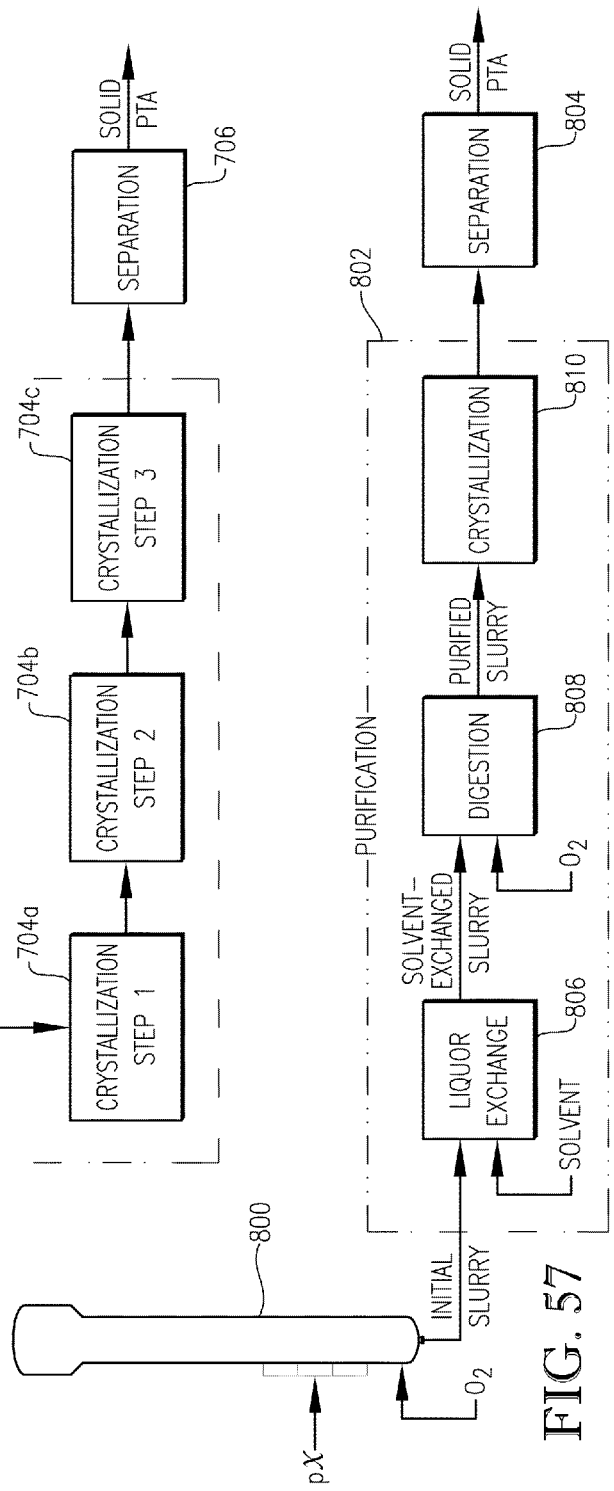
FIG. 57 is a simplified process flow diagram of a process for making PTA in accordance with one embodiment of the present invention.

FIG. 57 illustrates an improved process for producing PTA employing a bubble column oxidation reactor 800 configured in accordance with an embodiment of the present invention. An initial slurry comprising solid CTA particles and a liquid mother liquor is withdrawn from reactor 800. Typically, the initial slurry may contain in the range of from about 10 to about 50 weight percent solid CTA particles, with the balance being liquid mother liquor. The solid CTA particles present in the initial slurry typically contain at least about 400 ppmw of 4-carboxybenzaldehyde (4-CBA), more typically at least about 800 ppmw of 4-CBA, and most typically in the range of from 1,000 to 15,000 ppmw of 4-CBA. The initial slurry withdrawn from reactor 800 is introduced into a purification system 802 to reduce the concentration of 4-CBA and other impurities present in the CTA. A purer/purified slurry is produced from purification system 802 and is subjected to separation and drying in a separation system 804 to thereby produce purer solid terephthalic acid particles comprising less than about 400 ppmw of 4-CBA, more preferably less than about 250 ppmw of 4-CBA, and most preferably in the range of from 10 to 200 ppmw of 4-CBA.

Purification system 802 of the PTA production system illustrated in FIG. 57 provides a number of advantages over purification system 802 of the prior art system illustrated in FIG. 56. Preferably, purification system 802 generally includes a liquor exchange system 806, a digester 808, and a single crystallizer 810. In liquor exchange system 806, at least about 50 weight percent of the mother liquor present in the initial slurry is replaced with a fresh replacement solvent to thereby provide a solvent-exchanged slurry comprising CTA particles and the replacement solvent. The solvent-exchanged slurry exiting liquor exchange system 806 is introduced into digester (or secondary oxidation reactor) 808. In digester 808, a secondary oxidation reaction is preformed at slightly higher temperatures than were used in the initial/primary oxidation reaction carried out in bubble column reactor 800. As discussed above, the high surface area, small particle size, and low density of the CTA particles produced in reactor 800 cause certain impurities trapped in the CTA particles to become available for oxidation in digester 808 without requiring complete dissolution of the CTA particles in digester 808. Thus, the temperature in digester 808 can be lower than many similar prior art processes. The secondary oxidation carried out in digester 808 preferably reduces the concentration of 4-CBA in the CTA by at least 200 ppmw, more preferably at least about 400 ppmw, and most preferably in the range of from 600 to 6,000 ppmw. Preferably, the secondary oxidation temperature in digester 808 is at least about 10° C. higher than the primary oxidation temperature in bubble column reactor 800, more preferably about 20 to about 80° C. higher than the primary oxidation temperature in reactor 800, and most preferably 30 to 50° C. higher than the primary oxidation temperature in reactor 800. The secondary oxidation temperature is preferably in the range of from about 160 to about 240° C., more preferably in the range of from about 180 to about 220° C. and most preferably in the range of from 190 to 210° C. The purified product from digester 808 requires only a single crystallization step in crystallizer 810 prior to separation in separation system 804. Suitable secondary oxidation/digestion techniques are discussed in further detail in U.S. Pat. App. Pub. No. 2005/0065373, the entire disclosure of which is expressly incorporated herein by reference.

Terephthalic acid (e.g., PTA) produced by the system illustrated in FIG. 57 is preferably formed of PTA particles having a mean particle size of at least about 40 microns, more preferably in the range of from about 50 to about 2,000 microns, and most preferably in the range of from 60 to 200 microns. The PTA particles preferably have an average BET surface area less than about 0.25 $m^2$/g, more preferably in the range of from about 0.005 to about 0.2 $m^2$/g, and most preferably in the range of from 0.01 to 0.18 $m^2$/g. PTA produced by the system illustrated in FIG. 57 is suitable for use as a feedstock in the making of PET. Typically, PET is made via esterification of terephthalic with ethylene glycol, followed by polycondensation. Preferably, terephthalic acid produced by an embodiment of the present invention is employed as a feed to the pipe reactor PET process described in U.S. patent application Ser. No. 10/013,318, filed Dec. 7, 2001, the entire disclosure of which is incorporated herein by reference.

CTA particles with the preferred morphology disclosed herein are particularly useful in the above-described oxidative digestion process for reduction of 4-CBA content. In addition, these preferred CTA particles provide advantages in a wide range of other post-processes involving dissolution and/or chemical reaction of the particles. These additional post-processes include, but are not limited too, reaction with at least one hydroxyl-containing compound to form ester compounds, especially the reaction of CTA with methanol to form dimethyl terephthalate and impurity esters; reaction with at least one diol to form ester monomer and/or polymer compounds, especially the reaction of CTA with ethylene glycol to form polyethylene terephthalate (PET); and full or partial dissolution in solvents, including, but not limited too, water, acetic acid, and N-methyl-2-pyrrolidone, which may include further processing, including, but not limited too, reprecipitation of a more pure terephthalic acid and/or selective chemical reduction of carbonyl groups other than carboxylic acid groups. Notably included is the substantial dissolution of CTA in a solvent comprising water coupled with partial hydrogenation that reduces the amount of aldehydes, especially 4-CBA, fluorenones, phenones, and/or anthraquinones.

The inventors also contemplate that CTA particles having the preferred properties disclosed herein can be produced from CTA particles not conforming to the preferred properties disclosed herein (non-conforming CTA particles) by means including, but not limited too, mechanical comminution of non-conforming CTA particles and full or partial dissolution of non-conforming CTA particles followed by full or partial re-precipitation.

In accordance with one embodiment of the present invention, there is provided a process for partially oxidizing an oxidizable aromatic compound to one or more types of aromatic carboxylic acid wherein the purity of the solvent portion of the feed (i.e., the "solvent feed") and the purity of the oxidizable compound portion of the feed (i.e., the "oxidizable compound feed") are controlled within certain ranges specified below. Along with other embodiments of the present invention, this enables the purity of the liquid phase and, if present, the solid phase and the combined slurry (i.e., solid plus liquid) phase of the reaction medium to be controlled in certain preferred ranges, outlined below.

With respect to the solvent feed, it is known to oxidize an oxidizable aromatic compound(s) to produce an aromatic carboxylic acid wherein the solvent feed introduced into the reaction medium is a mixture of analytical-purity acetic acid and water, as is often employed at laboratory scale and pilot scale. Likewise, it is known to conduct the oxidation of oxidizable aromatic compound to aromatic carboxylic acid wherein the solvent leaving the reaction medium is separated from the produced aromatic carboxylic acid and then recycled back to the reaction medium as feed solvent, primarily for reasons of manufacturing cost. This solvent recycling causes certain feed impurities and process by-products to accumulate over time in the recycled solvent. Various means are known in the art to help purify recycled solvent before re-introduction into the reaction medium. Generally, a higher degree of purification of the recycled solvent leads to significantly higher manufacturing cost than does a lower degree of purification by similar means. One embodiment of the present invention relates to understanding and defining the preferred ranges of a large number of impurities within the solvent feed, many of which were heretofore thought largely benign, in order to find an optimal balance between overall manufacturing cost and overall product purity.

"Recycled solvent feed" is defined herein as solvent feed comprising at least about 5 weight percent mass that has previously passed through a reaction medium containing one or more oxidizable aromatic compounds undergoing partial oxidation. For reasons of solvent inventory and of on-stream time in a manufacturing unit, it is preferable that portions of recycled solvent pass through reaction medium at least once per day of operation, more preferably at least once per day for at least seven consecutive days of operation, and most preferably at least once per day for at least 30 consecutive days of operation. For economic reasons, it is preferable that at least about 20 weight percent of the solvent feed to the reaction medium of the present invention is recycled solvent, more preferably at least about 40 weight percent, still more preferably at least about 80 weight percent, and most preferably at least 90 weight percent.

The inventors have discovered that, for reasons of reaction activity and for consideration of metallic impurities left in the oxidation product, the concentrations of selected multivalent metals within the recycled solvent feed are preferably in ranges specified immediately below. The concentration of iron in recycled solvent is preferably below about 150 ppmw, more preferably below about 40 ppmw, and most preferably between 0 and 8 ppmw. The concentration of nickel in recycled solvent is preferably below about 150 ppmw, more preferably below about 40 ppmw, and most preferably between 0 and 8 ppmw. The concentration of chromium in recycled solvent is preferably below about 150 ppmw, more preferably below about 40 ppmw, and most preferably between 0 and 8 ppmw. The concentration of molybdenum in recycled solvent is preferably below about 75 ppmw, more preferably below about 20 ppmw, and most preferably between 0 and 4 ppmw. The concentration of titanium in recycled solvent is preferably below about 75 ppmw, more preferably below about 20 ppmw, and most preferably between 0 and 4 ppmw. The concentration of copper in recycled solvent is preferably below about 20 ppmw, more preferably below about 4 ppmw, and most preferably between 0 and 1 ppmw. Other metallic impurities are also typically present in recycled solvent, generally varying at lower levels in proportion to one or more of the above listed metals. Controlling the above listed metals in the preferred ranges will keep other metallic impurities at suitable levels.

These metals can arise as impurities in any of the incoming process feeds (e.g., in incoming oxidizable compound, solvent, oxidant, and catalyst compounds). Alternatively, the metals can arise as corrosion products from any of the process units contacting reaction medium and/or contacting recycled solvent. The means for controlling the metals in the disclosed concentration ranges include the appropriate specification and monitoring of the purity of various feeds and the appropriate usage of materials of construction, including, but not limited to, many commercial grades of titanium and of stainless steels including those grades known as duplex stainless steels and high molybdenum stainless steels.

The inventors have also discovered preferred ranges for selected aromatic compounds in the recycled solvent. These include both precipitated and dissolved aromatic compounds within the recycled solvent.

Surprisingly, even precipitated product (e.g., TPA) from a partial oxidation of para-xylene, is a contaminant to be managed in recycled solvent. Because there are surprisingly preferred ranges for the levels of solids within the reaction medium, any precipitated product in the solvent feed directly subtracts from the amount of oxidizable compound that can be fed in concert. Furthermore, feeding precipitated TPA solids in the recycled solvent at elevated levels has been discovered to affect adversely the character of the particles formed within a precipitating oxidation medium, leading to undesirable character in downstream operations (e.g., product filtration, solvent washing, oxidative digestion of crude product, dissolution of crude product for further processing, and so on). Another undesirable characteristic of precipitated solids in the recycle solvent feed is that these often contain very high levels of precipitated impurities, as compared to impurity concentrations in the bulk of the solids within the TPA slurries from which much of the recycled solvent is obtained. Possibly, the elevated levels of impurities observed in solids suspended in recycled filtrate may relate to nucleation times for precipitation of certain impurities from the recycled solvent and/or to cooling of the recycled solvent, whether intentional or due to ambient losses. For example, concentrations of highly-colored and undesirable 2,6-dicarboxyfluorenone have been observed at far higher levels in solids present in recycled solvent at 80° C. than are observed in TPA solids separated from recycled solvent at 160° C. Similarly, concentrations of isophthalic acid have been observed at much higher levels in solids present in recycled solvent compared to levels observed in TPA solids from the reaction medium. Exactly how specific precipitated impurities entrained within recycled solvent behave when re-introduced to the reaction medium appears to vary. This depends perhaps upon the relative solubility of the impurity within the liquid phase of the reaction medium, perhaps upon how the precipitated impurity is layered within the precipitated solids, and perhaps upon the local rate of TPA precipitation where the solid first re-enters the reaction medium. Thus, the inventors have found it useful to control the level of certain impurities in the recycled solvent, as disclosed below, without respect to whether these impurities are present in the recycled solvent in dissolved form or are entrained particulates therein.

The amount of precipitated solids present in recycled filtrate is determined by a gravimetric method as follows. A representative sample is withdrawn from the solvent supply to the reaction medium while the solvent is flowing in a conduit toward the reaction medium. A useful sample size is about 100 grams captured in a glass container having about 250 milliliters of internal volume. Before being released to atmospheric pressure, but while continuously flowing toward the sample container, the recycled filtrate is cooled to less than 100° C.; this cooling is in order to limit solvent evaporation during the short interval before being sealed closed in the glass container. After the sample is captured at atmospheric pressure, the glass container is sealed closed immediately. Then the sample is allowed to cool to about 20° C.

while surrounded by air at about 20° C. and without forced convection. After reaching about 20° C., the sample is held at this condition for at least about 2 hours. Then, the sealed container is shaken vigorously until a visibly uniform distribution of solids is obtained. Immediately thereafter, a magnetic stirrer bar is added to the sample container and rotated at sufficient speed to maintain effectively uniform distribution of solids. A 10 milliliter aliquot of the mixed liquid with suspended solids is withdrawn by pipette and weighed. Then the bulk of the liquid phase from this aliquot is separated by vacuum filtration, still at about 20° C. and effectively without loss of solids. The moist solids filtered from this aliquot are then dried, effectively without sublimation of solids, and these dried solids are weighed. The ratio of the weight of the dried solids to the weight of the original aliquot of slurry is the fraction of solids, typically expressed as a percentage and referred to herein as the recycled filtrate content of precipitated solids at 20° C.

The inventors have discovered that aromatic compounds dissolved in the liquid phase of the reaction medium and comprising aromatic carboxylic acids lacking non-aromatic hydrocarbyl groups (e.g., isophthalic acid, benzoic acid, phthalic acid, 2,5,4'-tricarboxybiphenyl) are surprisingly pernicious components. Although these compounds are much reduced in chemical activity in the subject reaction medium compared to oxidizable compounds having non-aromatic hydrocarbyl groups, the inventors have discovered that these compounds nonetheless undergo numerous detrimental reactions. Thus, it is advantageous to control the content of these compounds in preferred ranges in the liquid phase of the reaction medium. This leads to preferred ranges of select compounds in recycled solvent feed and also to preferred ranges of select precursors in the oxidizable aromatic compound feed.

For example, in the liquid-phase partial oxidation of para-xylene to terephthalic acid (TPA), the inventors have discovered that the highly-colored and undesirable impurity 2,7-dicarboxyfluorenone (2,7-DCF) is virtually undetectable in the reaction medium and product off-take when meta-substituted aromatic compounds are at very low levels in the reaction medium. The inventors have discovered that when isophthalic acid impurity is present at increasing levels in the solvent feed, the formation of 2,7-DCF rises in almost direct proportion. The inventors have also discovered that when meta-xylene impurity is present in the feed of para-xylene, the formation of 2,7-DCF again rises almost in direct proportion. Furthermore, even if the solvent feed and oxidizable compound feed are devoid of meta-substituted aromatic compounds, the inventors have discovered that some isophthalic acid is formed during a typical partial oxidation of very pure para-xylene, particularly when benzoic acid is present in the liquid phase of the reaction medium. This self-generated isophthalic acid may, owing to its greater solubility than TPA in solvent comprising acetic acid and water, build up over time in commercial units employing recycled solvent. Thus, the amount of isophthalic acid within solvent feed, the amount of meta-xylene within oxidizable aromatic compound feed, and the rate of self-creation of isophthalic acid within the reaction medium are all appropriately considered in balance with each other and in balance with any reactions that consume isophthalic acid. Isophthalic acid has been discovered to undergo additional consumptive reactions besides the formation of 2,7-DCF, as are disclosed below. In addition, the inventors have discovered that there are other issues to consider when setting appropriate ranges for the meta-substituted aromatic species in the partial oxidation of para-xylene to TPA. Other highly-colored and undesirable impurities, such as 2,6-dicarboxyfluorenone (2,6-DCF), appear to relate greatly to dissolved, para-substituted aromatic species, which are always present with para-xylene feed to a liquid-phase oxidation. Thus, the suppression of 2,7-DCF is best considered in perspective with the level of other colored impurities being produced.

For example, in the liquid-phase partial oxidation of para-xylene to TPA, the inventors have discovered that the formation of trimellitic acid rises as the levels isophthalic acid and phthalic acid rise within the reaction medium. Trimellitic acid is a tri-functional carboxylic acid leading to branching of polymer chains during production of PET from TPA. In many PET applications, branching levels must be controlled to low levels and hence trimellitic acid must be controlled to low levels in purified TPA. Besides leading to trimellitic acid, the presence of meta-substituted and ortho-substituted species in the reaction medium also give rise to other tricarboxylic acids (e.g., 1,3,5-tricarboxybenzene). Furthermore, the increased presence of tricarboxylic acids in the reaction medium increases the amount of tetracarboxylic acid formation (e.g., 1,2,4,5-tetracarboxybenzene). Controlling the summed production of all aromatic carboxylic acids having more than two carboxylic acid groups is one factor in setting the preferred levels of meta-substituted and ortho-substituted species in the recycled solvent feed, in the oxidizable compound feed, and in the reaction medium according to the present invention.

For example, in the liquid-phase partial oxidation of para-xylene to TPA, the inventors have discovered that increased levels in the liquid phase of the reaction medium of several dissolved aromatic carboxylic acids lacking non-aromatic hydrocarbyl groups leads directly to the increased production of carbon monoxide and carbon dioxide. This increased production of carbon oxides represents a yield loss on both oxidant and on oxidizable compound, the later since many of the co-produced aromatic carboxylic acids, which on the one hand may be viewed as impurities, on the other hand also have commercial value. Thus, appropriate removal of relatively soluble carboxylic acids lacking non-aromatic hydrocarbyl groups from recycle solvent has an economic value in preventing yield loss of oxidizable aromatic compound and of oxidant, in addition to suppressing the generation of highly undesirable impurities such as various fluorenones and trimellitic acid.

For example, in the liquid-phase partial oxidation of para-xylene to TPA, the inventors have discovered that formation of 2,5,4'-tricarboxybiphenyl is seemingly unavoidable. The 2,5,4'-tricarboxybiphenyl is an aromatic tricarboxylic acid formed by the coupling of two aromatic rings, perhaps by the coupling of a dissolved para-substituted aromatic species with an aryl radical, perhaps an aryl radical formed by decarboxylation or decarbonylation of a para-substituted aromatic species. Fortunately, the 2,5,4'-tricarboxybiphenyl is typically produced at lower levels than trimellitic acid and does not usually lead to significantly increased difficulties with branching of polymer molecules during production of PET. However, the inventors have discovered that elevated levels of 2,5,4'-tricarboxybiphenyl in a reaction medium comprising oxidation of alkyl aromatics according to preferred embodiments of the present invention lead to increased levels of highly-colored and undesirable 2,6-DCF. The increased 2,6-DCF is possibly created from the 2,5,4'-tricarboxybiphenyl by ring closure with loss of a water molecule, though the exact reaction mechanism is not known with certainty. If 2,5,4'-tricarboxybiphenyl, which is more soluble in solvent comprising acetic acid and water than is TPA, is allowed to build up too high within recycled solvent, conversion rates to 2,6-DCF can become unacceptably large.

For example, in the liquid-phase partial oxidation of para-xylene to TPA, the inventors have discovered that aromatic carboxylic acids lacking non-aromatic hydrocarbyl groups (e.g., isophthalic acid) generally lead to mild suppression of the chemical activity of the reaction medium when present in the liquid phase at sufficient concentration.

For example, in the liquid-phase partial oxidation of para-xylene to TPA, the inventors have discovered that precipitation is very often non-ideal (i.e. non-equilibrium) with respect to the relative concentrations of different chemical species in the solid phase and in the liquid phase. Perhaps, this is because the precipitation rate is very fast at the space-time reaction rates preferred herein, leading to non-ideal co-precipitation of impurities, or even occlusion. Thus, when it is desired to limit the concentration of certain impurities (e.g., trimellitic acid and 2,6-DCF) within crude TPA, owing to the configuration of downstream unit operations, it is preferable to control their concentration in solvent feed as well as their generation rate within the reaction medium.

For example, the inventors have discovered that benzophenone compounds (e.g., 4,4'-dicarboxybenzophenone and 2,5,4'-tricarboxybenzophenone) made during partial oxidation of para-xylene, have undesirable effects in a PET reaction medium even though benzophenone compounds are not as highly colored in TPA per se as are fluorenones and anthraquinones. Accordingly, it is desirable to limit the presence of benzophenones and select precursors in recycled solvent and in oxidizable compound feed. Furthermore, the inventors have discovered that the presence of elevated levels of benzoic acid, whether admitted in recycled solvent or formed within the reaction medium, leads to elevated rates of production of 4,4'-dicarboxybenzophenone.

In review, the inventors have discovered and sufficiently quantified a surprising array of reactions for aromatic compounds lacking non-aromatic hydrocarbyl groups that are present in the liquid-phase partial oxidation of para-xylene to TPA. Recapping just the single case of benzoic acid, the inventors have discovered that increased levels of benzoic acid in the reaction medium of certain embodiments of the present invention lead to greatly increased production of the highly colored and undesirable 9-fluorenone-2-carboxylic acid, to greatly increased levels of 4,4'-dicarboxybiphenyl, to increased levels of 4,4'-dicarboxybenzophenone, to a mild suppression of chemical activity of the intended oxidation of para-xylene, and to increased levels of carbon oxides and attendant yield losses. The inventors have discovered that increased levels of benzoic acid in the reaction medium also lead to increased production of isophthalic acid and phthalic acid, the levels of which are desirably controlled in low ranges according to similar aspects of the current invention. The number and importance of reactions involving benzoic acid are perhaps even more surprising since some recent inventors contemplate using benzoic acid in place of acetic acid as a primary component of solvent (See, e.g., U.S. Pat. No. 6,562,997). Additionally, the present inventors have observed that benzoic acid is self-generated during oxidation of para-xylene at rates that are quite important relative to its formation from impurities, such as toluene and ethylbenzene, commonly found in oxidizable compound feed comprising commercial-purity para-xylene.

On the other hand, the inventors have discovered little value from additional regulation of recycled solvent composition in regard to the presence of oxidizable aromatic compound and in regard to aromatic reaction intermediates that both retain non-aromatic hydrocarbyl groups and are also relatively soluble in the recycled solvent. In general, these compounds are either fed to or created within the reaction medium at rates substantially greater than their presence in recycled solvent; and the consumption rate of these compounds within the reaction medium is great enough, retaining one or more non-aromatic hydrocarbyl groups, to limit appropriately their build-up within recycled solvent. For example, during partial oxidation of para-xylene in a multi-phase reaction medium, para-xylene evaporates to a limited extent along with large quantities of solvent. When this evaporated solvent exits the reactor as part of the off-gas and is condensed for recovery as recycled solvent, a substantial portion of the evaporated para-xylene condenses therein as well. It is not necessary to limit the concentration of this para-xylene in recycled solvent. For example, if solvent is separated from solids upon slurry exiting a para-xylene oxidation reaction medium, this recovered solvent will contain a similar concentration of dissolved para-toluic acid to that present at the point of removal from the reaction medium. Although it may be important to limit the standing concentration of para-toluic acid within the liquid phase of the reaction medium, see below, it is not necessary to regulate separately the para-toluic acid in this portion of recycled solvent owing to its relatively good solubility and to its low mass flow rate relative to the creation of para-toluic acid within the reaction medium. Similarly, the inventors have discovered little reason to limit the concentrations in recycled solvent of aromatic compounds with methyl substituents (e.g. toluic acids), aromatic aldehydes (e.g., terephthaldehyde), of aromatic compounds with hydroxy-methyl substituents (e.g., 4-hydroxymethylbenzoic acid), and of brominated aromatic compounds retaining at least one non-aromatic hydrocarbyl group (e.g., alpha-bromo-para-toluic acid) below those inherently found in the liquid phase exiting from the reaction medium occurring in the partial oxidation of xylene according to preferred embodiments of the present invention. Surprisingly, the inventors have also discovered that it is also not necessary to regulate in recycled solvent the concentration of selected phenols intrinsically produced during partial oxidation of xylene, for these compounds are created and destroyed within the reaction medium at rates much greater than their presence in recycled solvent. For example, the inventors have discovered that 4-hydroxybenzoic acid has relatively small effects on chemical activity in the preferred embodiments of the present invention when co-fed at rates of over 2 grams of 4-hydroxybenzoic acid per 1 kilogram of para-xylene, far higher than the natural presence in recycled solvent, despite being reported by others as a significant poison in similar reaction medium (See, e.g., W. Partenheimer, *Catalysis Today* 23 (1995) p. 81).

Thus, there are numerous reactions and numerous considerations in setting the preferred ranges of various aromatic impurities in the solvent feed as now disclosed. These discoveries are stated in terms of the aggregated weight average composition of all solvent streams being fed to the reaction medium during the course of a set time period, preferably one day, more preferably one hour, and most preferably one minute. For example, if one solvent feed flows substantially continuously with a composition of 40 ppmw of isophthalic acid at a flow rate of 7 kilograms per minute, a second solvent feed flows substantially continuously with a composition of 2,000 ppmw of isophthalic acid at a flow rate of 10 kilograms per minute, and there are no other solvent feed streams entering the reaction medium, then the aggregated weight average composition of the solvent feed is calculated as $(40*7+2,000*10)/(7+10)=1,193$ ppmw of isophthalic acid. It is notable that the weight of any oxidizable compound feed or of any oxidant feed that are perhaps commingled with the solvent feed before entering the reaction medium are not considered in calculating the aggregated weight average composition of the solvent feed.

Table 1, below, lists preferred values for certain components in the solvent feed introduced into the reaction medium. The solvent feed components listed in Table 1 are as follows: 4-carboxybenzaldehyde (4-CBA), 4,4'-dicarboxystilbene (4,4'-DCS), 2,6-dicarboxyanthraquinone (2,6-DCA), 2,6-dicarboxyfluorenone (2,6-DCF), 2,7-dicarboxyfluorenone (2,7-DCF), 3,5-dicarboxyfluorenone (3,5-DCF), 9-fluorenone-2-carboxylic acid (9F-2CA), 9-fluorenone-4-carboxylic acid (9F-4CA), total fluorenones including other fluorenones not individually listed (total fluorenones), 4,4'-dicarboxybiphenyl (4,4'-DCB), 2,5,4'-tricarboxybiphenyl (2,5,4'-TCB), phthalic acid (PA), isophthalic acid (IPA), benzoic acid (BA), trimellitic acid (TMA), 2,6-dicarboxybenzocoumarin (2,6-DCBC), 4,4'-dicarboxybenzil (4,4'-DCBZ), 4,4'-dicarboxybenzophenone (4,4'-DCBP), 2,5,4'-tricarboxybenzophenone (2,5,4'-TCBP), terephthalic acid (TPA), precipitated solids at 20° C., and total aromatic carboxylic acids lacking non-aromatic hydrocarbyl groups. Table 1, below provides the preferred amounts of these impurities in CTA produced according to an embodiment of the present invention.

TABLE 1

Components of Solvent Feed Introduced into Reaction Medium

| Component Identification | Preferred Amt. (ppmw) | More Preferred Amt. (ppmw) | Most Preferred Amt. (ppmw) |
| --- | --- | --- | --- |
| 4-CBA | <1,200 | 30-600 | 60-300 |
| 4,4'-DCS | <3 | <2 | <1 |
| 2,6-DCA | <6 | 0.1-3 | 0.2-1 |
| 2,6-DCF | <20 | 0.1-10 | 0.5-5 |
| 2,7-DCF | <10 | 0.1-5 | 0.5-2 |
| 3,5-DCF | <10 | <5 | <2 |
| 9F-2CA | <10 | 0.1-5 | 0.5-2 |
| 9F-4CA | <5 | <3 | <1 |
| Total fluorenones | <40 | <20 | 1-8 |
| 4,4'-DCB | <45 | <15 | 0.5-5 |
| 2,5,4'-TCB | <45 | 0.1-15 | 0.5-5 |
| PA | <1,000 | 15-400 | 40-150 |
| IPA | 2,500 | 40-1,200 | 120-400 |
| BA | <4,500 | 50-1,500 | 150-500 |
| TMA | <1,000 | 15-400 | 40-150 |
| 2,6-DCBC | <40 | <20 | <5 |
| 4,4'-DCBZ | <40 | <20 | <5 |
| 4,4'-DCBP | <40 | <20 | <5 |
| 2,5,4'-TCBP | <40 | <20 | 0.5-5 |
| TPA | <9,000 | 200-6,000 | 400-2,000 |
| Precipitated Solids at 20° C. | <9,000 | 200-6,000 | 600-2,000 |
| Total Aromatic Carboxylic Acids Lacking Non-Aromatic Hydrocarbyl Groups | <18,000 | 300-9,000 | 450-3,000 |

Many other aromatic impurities are also typically present in recycled solvent, generally varying at even lower levels and/or in proportion to one or more of the disclosed aromatic compounds. Methods for controlling the disclosed aromatic compounds in the preferred ranges will typically keep other aromatic impurities at suitable levels.

When bromine is used within the reaction medium, a large number of ionic and organic forms of bromine are known to exist in a dynamic equilibrium. These various forms of bromine have different stability characteristics once leaving the reaction medium and passing through various unit operations pertaining to recycled solvent. For example, alpha-bromo-para-toluic acid may persist as such at some conditions or may rapidly hydrolyze at other conditions to form 4-hydroxymethylbenzoic acid and hydrogen bromide. In the present invention, it is preferable that at least about 40 weight percent, more preferable that at least about 60 weight percent, and most preferable that at least about 80 weight percent of the total mass of bromine present in the aggregated solvent feed to the reaction medium is in one or more of the following chemical forms: ionic bromine, alpha-bromo-para-toluic acid, and bromoacetic acid.

Although the importance and value of controlling the aggregated weight average purity of solvent feed within the disclosed, desired ranges of the present invention has not heretofore been discovered and/or disclosed, suitable means for controlling the solvent feed purity may be assembled from various methods already known in the art. First, any solvent evaporated from the reaction medium is typically of suitable purity providing that liquid or solids from the reaction medium are not entrained with the evaporated solvent. The feeding of reflux solvent droplets into the off-gas disengaging space above the reaction medium, as disclosed herein, appropriately limits such entrainment; and recycled solvent of suitable purity with respect to aromatic compound can be condensed from such off-gas. Second, the more difficult and costly purification of recycled solvent feed typically relates to solvent taken from the reaction medium in liquid form and to solvent that subsequently contacts the liquid and/or solid phases of the reaction medium withdrawn from the reaction vessel (e.g., recycled solvent obtained from a filter in which solids are concentrated and/or washed, recycled solvent obtained from a centrifuge in which solids are concentrated and/or washed, recycled solvent taken from a crystallization operation, and so on). However, means are also known in the art for effecting the necessary purification of these recycled solvent streams using one or more prior disclosures. With respect to controlling precipitated solids in recycled solvent to be within the ranges specified, suitable control means include, but are not limited to, gravimetric sedimentation, mechanical filtration using filter cloth on rotary belt filters and rotary drum filters, mechanical filtration using stationary filter medium within pressure vessels, hydro-cyclones, and centrifuges. With respect to controlling dissolved aromatic species in recycled solvent to be within the ranges specified, the control means include, but are not limited to, those disclosed in U.S. Pat. No. 4,939,297 and U.S. Pat. App. Pub. No. 2005-0038288, incorporated herein by reference. However, none of these prior inventions discovered and disclosed the preferred levels of purity in the aggregated solvent feed as disclosed herein. Rather, these prior inventions merely provided means to purify selected and partial streams of recycled solvent without deducing the present inventive, optimal values of the composition of the aggregated weight average solvent feed to the reaction medium.

Turning now to the purity of the feed of oxidizable compound, it is known that certain levels of isophthalic acid, phthalic acid, and benzoic acid are present and tolerable at low levels in purified TPA used for polymer production. Moreover, it is known these species are relatively more soluble in many solvents and may be advantageously removed from purified TPA by crystallization processes. However, from an embodiment of the invention disclosed herein, it is now known that controlling the level of several relatively soluble aromatic species, notably including isophthalic acid, phthalic acid, and benzoic acid, in the liquid phase of the reaction medium is surprisingly important for controlling the level of polycyclic and colored aromatic compounds created in the reaction medium, for controlling compounds with more than 2 carboxylic acid functions per molecule, for controlling reaction activity within the partial oxidation reaction medium, and for controlling yield losses of oxidant and of aromatic compound.

It is known within the art that isophthalic acid, phthalic acid, and benzoic acid are formed in the reaction medium as follows. Meta-Xylene feed impurity oxidizes in good conversion and yield to IPA. Ortho-Xylene feed impurity oxidizes in good conversion and yield to phthalic acid. Ethylbenzene and toluene feed impurities oxidize in good conversion and yield to benzoic acid. However, the inventors have observed that significant amounts of isophthalic acid, phthalic acid, and benzoic acid are also formed within a reaction medium comprising para-xylene by means other than oxidation of meta-xylene, ortho-xylene, ethylbenzene, and toluene. These other intrinsic chemical routes possibly include decarbonylation, decarboxylation, the re-organization of transition states, and addition of methyl and carbonyl radicals to aromatic rings.

In determining preferred ranges of impurities in the feed of oxidizable compound, many factors are relevant. Any impurity in the feed is likely to be a direct yield loss and a product purification cost if the purity requirements of the oxidized product are sufficiently strict (e.g., in a reaction medium for partial oxidation of para-xylene, toluene and ethylbenzene typically found in commercial-purity para-xylene lead to benzoic acid, and this benzoic acid is largely removed from most commercial TPA). When the partial oxidation product of a feed impurity participates in additional reactions, factors other than simple yield loss and removal become appropriate when considering how much feed purification cost to incur (e.g., in a reaction medium for partial oxidation of para-xylene, ethylbenzene leads to benzoic acid, and benzoic acid subsequently leads to highly colored 9-fluorenone-2-carboxylic acid, to isophthalic acid, to phthalic acid, and to increased carbon oxides, among others). When the reaction medium self-generates additional amounts of an impurity by chemical mechanisms not directly related to feed impurities, the analysis becomes still more complex (e.g., in a reaction medium for partial oxidation of para-xylene, benzoic acid is also self-generated from para-xylene itself). In addition, the downstream processing of the crude oxidation product may affect the considerations for preferred feed purity. For example, the cost of removing to suitable levels a direct impurity (benzoic acid) and subsequent impurities (isophthalic acid, phthalic acid, 9-fluorenone-2-carboxylic acid, et al.) may be one and the same, may be different from each other, and may be different from the requirements of removing a largely unrelated impurity (e.g., incomplete oxidation product 4-CBA in the oxidation of para-xylene to TPA).

The following disclosed feed purity ranges for para-xylene are preferred where para-xylene is fed with solvent and oxidant to a reaction medium for partial oxidation to produce TPA. These ranges are more preferred in TPA production process having post-oxidation steps to remove from reaction medium impurities other than oxidant and solvent (e.g., catalyst metals). These ranges are still more preferred in TPA production processes that remove additional 4-CBA from CTA (e.g., by conversion of CTA to dimethyl terephthalate plus impurity esters and subsequent separation of the methyl ester of 4-CBA by distillation, by oxidative digestion methods for converting 4-CBA to TPA, by hydrogenation methods for converting 4-CBA to para-toluic acid, which is then separated by partial-crystallization methods). These ranges are most preferred in TPA production processes that remove additional 4-CBA from CTA by oxidative digestion methods for converting 4-CBA to TPA.

Using new knowledge of preferred ranges of recycling aromatic compounds and of the relative amounts of the aromatic compounds formed directly from oxidation of feed impurities as compared to other intrinsic chemical routes, improved ranges for impurities have been discovered for impure para-xylene being fed to a partial oxidation process for TPA production. Table 2, below provides preferred values for the amount of meta-xylene, ortho-xylene, and ethylbenzene+toluene in the para-xylene feed.

TABLE 2

Components of Impure para-xylene Feed

| Component Identification | Preferred Amt. (ppmw) | More Preferred Amt. (ppmw) | Most Preferred Amt. (ppmw) |
|---|---|---|---|
| meta-xylene | 20-800 | 50-600 | 100-400 |
| ortho-xylene | 10-300 | 20-200 | 30-100 |
| ethylbenzene + toluene* | 20-700 | 50-500 | 100-300 |
| total | 50-900 | 100-800 | 200-700 |

*Specification for ethylbenzene + toluene is each separately and in sum

Those skilled in the art will now recognize the above impurities within impure para-xylene may have their greatest effect on the reaction medium after their partial oxidation products have accumulated in recycled solvent. For example, feeding the upper amount of the most preferred range of meta-xylene, 400 ppmw, will immediately produce about 200 ppmw of isophthalic acid within the liquid phase of the reaction medium when operating with about 33 weight percent solids in the reaction medium. This compares with an input from the upper amount of the most preferred range for isophthalic acid in recycled solvent of 400 ppmw which, after allowing for a typical solvent evaporation to cool the reaction medium, amounts to about 1,200 ppmw of isophthalic acid within the liquid phase of the reaction medium. Thus, it is the accumulation of partial oxidation products over time within recycled solvent that represents the greatest probable impact of the meta-xylene, ortho-xylene, ethylbenzene, and toluene impurities in the feed of impure para-xylene. Accordingly, the above ranges for impurities in impure para-xylene feed are preferred to be maintained for at least one-half of each day of operation of any partial oxidation reaction medium in a particular manufacturing unit, more preferably for at least three-quarters of each day for at least seven consecutive days of operation, and most preferably when the mass-weighted averages of the impure para-xylene feed composition are within the preferred ranges for at least 30 consecutive days of operation.

Means for obtaining impure para-xylene of preferred purity are already known in the art and include, but are not limited to, distillation, partial crystallization methods at sub-ambient temperatures, and molecular sieve methods using selective pore-size adsorption. However, the preferred ranges of purity specified herein are, at their high end, more demanding and expensive than characteristically practiced by commercial suppliers of para-xylene; and yet at the low end, the preferred ranges avoid overly costly purification of para-xylene for feeding to a partial oxidation reaction medium by discovering and disclosing where the combined effects of impurity self-generation from para-xylene itself and of impurity consumptive reactions within the reaction medium become more important than the feed rates of impurities within impure para-xylene.

When the xylene-containing feed stream contains selected impurities, such as ethyl-benzene and/or toluene, oxidation of these impurities can generate benzoic acid. As used herein, the term "impurity-generated benzoic acid" shall denote benzoic acid derived from any source other than xylene during xylene oxidation.

As disclosed herein, a portion of the benzoic acid produced during xylene oxidation is derived from the xylene itself. This production of benzoic acid from xylene is distinctly in addition to any portion of benzoic acid production that may be impurity-generated benzoic acid. Without being bound by theory, it is believed that benzoic acid is derived from xylene within the reaction medium when various intermediate oxidation products of xylene spontaneously decarbonylate (carbon monoxide loss) or decarboxylate (carbon dioxide loss) to thereby produce aryl radicals. These aryl radicals can then abstract a hydrogen atom from one of many available sources in the reaction medium and produce self-generated benzoic acid. Whatever the chemical mechanism, the term "self-generated benzoic acid", as used herein, shall denote benzoic acid derived from xylene during xylene oxidation.

As also disclosed herein, when para-xylene is oxidized to produce terephthalic acid (TPA), the production of self-generated benzoic acid causes para-xylene yield loss and oxidant yield loss. In addition, the presence of self-generated benzoic acid in the liquid phase of the reaction medium correlates with increases for many undesirable side reactions, notably including generation of highly colored compounds called monocarboxy-fluorenones. Self-generated benzoic acid also contributes to the undesirable accumulation of benzoic acid in recycled filtrate which further elevates the concentration of benzoic acid in the liquid phase of the reaction medium. Thus, formation of self-generated benzoic acid is desirably minimized, but this is also appropriately considered simultaneously with impurity-generated benzoic acid, with factors affecting consumption of benzoic acid, with factors pertaining to other issues of reaction selectivity, and with overall economics.

The inventors have discovered that the self-generation of benzoic acid can be controlled to low levels by appropriate selection of, for example, temperature, xylene distribution, and oxygen availability within the reaction medium during oxidation. Not wishing to be bound by theory, lower temperatures and improved oxygen availability appear to suppress the decarbonylation and/or decarboxylation rates, thus avoiding the yield loss aspect of self-generated benzoic acid. Sufficient oxygen availability appears to direct aryl radicals toward other more benign products, in particular hydroxybenzoic acids. Distribution of xylene in the reaction medium may also affect the balance between aryl radical conversion to benzoic acid or to hydroxybenzoic acids. Whatever the chemical mechanisms, the inventors have discovered reaction conditions that, although mild enough to reduce benzoic acid production, are severe enough to oxidize a high fraction of the hydroxybenzoic acid production to carbon monoxide and/or carbon dioxide, which are easily removed from the oxidation product.

In a preferred embodiment of the present invention, the oxidation reactor is configured and operated in a manner such that the formation of self-generated benzoic acid is minimized and the oxidation of hydroxybenzoic acids to carbon monoxide and/or carbon dioxide is maximized. When the oxidation reactor is employed to oxidize para-xylene to terephthalic acid, it is preferred that para-xylene makes up at least about 50 weight percent of the total xylene in the feed stream introduced into the reactor. More preferably, para-xylene makes up at least about 75 weight percent of the total xylene in the feed stream. Still more preferably, para-xylene makes up at least 95 weight percent of the total xylene in the feed stream. Most preferably, para-xylene makes up substantially all of the total xylene in the feed stream.

When the reactor is employed to oxidize para-xylene to terephthalic acid, it is preferred for the rate of production of terephthalic acid to be maximized, while the rate of production of self-generated benzoic acid is minimized. Preferably, the ratio of the rate of production (by weight) of terephthalic acid to the rate of production (by weight) of self-generated benzoic acid is at least about 500:1, more preferably at least about 1,000:1, and most preferably at least 1,500:1. As will be seen below, the rate of production of self-generated benzoic acid is preferably measured when the concentration of benzoic acid in the liquid phase of the reaction medium is below 2,000 ppmw, more preferably below 1,000 ppmw, and most preferably below 500 ppmw, because these low concentrations suppress to suitably low rates reactions that convert benzoic acid to other compounds.

Combining the self-generated benzoic acid and the impurity-generated benzoic acid, the ratio of the rate of production (by weight) of terephthalic acid to the rate of production (by weight) of total benzoic acid is preferably at least about 400:1, more preferably at least about 700:1, and most preferably at least 1,100:1. As will be seen below, the summed rate of production of self-generated benzoic acid plus impurity-generated benzoic acid is preferably measured when the concentration of benzoic acid in the liquid phase of the reaction medium is below 2,000 ppmw, more preferably below 1,000 ppmw, and most preferably below 500 ppmw, because these low concentrations suppress to suitably low rates reactions that convert benzoic acid to other compounds.

As disclosed herein, elevated concentrations of benzoic acid in the liquid phase of the reaction medium lead to increased formation of many other aromatic compounds, several of which are noxious impurities in TPA; and, as disclosed herein, elevated concentrations of benzoic acid in the liquid phase of the reaction medium lead to increased formation of carbon oxide gases, the formation of which represents yield loss on oxidant and on aromatic compounds and/or solvent. Furthermore, it is now disclosed that the inventors have discovered a considerable portion of this increased formation of other aromatic compounds and of carbon oxides derives from reactions that convert some of the benzoic acid molecules themselves, as contrasted to benzoic acid catalyzing other reactions without itself being consumed. Accordingly, the "net generation of benzoic acid" is defined herein as the time-averaged weight of all benzoic acid exiting the reaction medium minus the time-averaged weight of all benzoic acid entering the reaction medium during the same period of time. This net generation of benzoic acid is often positive, driven by the formation rates of impurity-generated benzoic acid and of self-generated benzoic acid. However, the inventors have discovered that the conversion rate of benzoic acid to carbon oxides, and to several other compounds, appears to increase approximately linearly as the concentration of benzoic acid is increased in the liquid phase of the reaction medium, measured when other reaction conditions comprising temperature, oxygen availability, STR, and reaction activity are maintained appropriately constant. Thus, when the concentration of benzoic acid in the liquid-phase of the reaction medium is great enough, perhaps due to an elevated concentration of benzoic acid in recycled solvent, then the conversion of benzoic acid molecules to other compounds, including carbon oxides, can become equal to or greater than the chemical generation of new benzoic acid molecules. In this case, the net generation of benzoic acid can become balanced near zero or even negative. The inventors have discovered that when the net generation of benzoic acid is positive, then the ratio of the rate of production (by weight) of terephthalic acid in the reaction medium compared to the rate of net generation of benzoic acid in the reaction medium is preferably above about 700:1, more preferably above about 1,100:1, and most preferably above 4,000:1. The inventors have discovered that when the net generation of benzoic acid is negative, the ratio of the rate of production (by weight) of terephthalic acid in the reaction medium compared to the rate of net generation of benzoic acid in the reaction medium is preferably above about 200:(−1), more preferably above about 1,000:(−1), and most preferably above 5,000:(−1).

The inventors have also discovered preferred ranges for the composition of the slurry (liquid+solid) withdrawn from the reaction medium and for the solid CTA portion of the slurry. The preferred slurry and the preferred CTA compositions are surprisingly superior and useful. For example, purified TPA produced from this preferred CTA by oxidative digestion has a sufficiently low level of total impurities and of colored impurities such that the purified TPA is suitable, without hydrogenation of additional 4-CBA and/or colored impurities, for a wide range of applications in PET fibers and PET packaging applications. For example, the preferred slurry composition provides a liquid phase of the reaction medium that is relatively low in concentration of important impurities and this importantly reduces the creation of other even more undesirable impurities as disclosed herein. In addition, the preferred slurry composition importantly aids the subsequent processing of liquid from the slurry to become suitably pure recycled solvent, according to other embodiments of the present invention.

CTA produced according to one embodiment of the present invention contains less impurities of selected types than CTA produce by conventional processes and apparatuses, notably those employing recycled solvent. Impurities that may be present in CTA include the following: 4-carboxybenzaldehyde (4-CBA), 4,4'-dicarboxystilbene (4,4'-DCS), 2,6-dicarboxyanthraquinone (2,6-DCA), 2,6-dicarboxyfluorenone (2,6-DCF), 2,7-dicarboxyfluorenone (2,7-DCF), 3,5-dicarboxyfluorenone (3,5-DCF), 9-fluorenone-2-carboxylic acid (9F-2CA), 9-fluorenone-4-carboxylic acid (9F-4CA), 4,4'-dicarboxybiphenyl (4,4'-DCB), 2,5,4'-tricarboxybiphenyl (2,5,4'-TCB), phthalic acid (PA), isophthalic acid (IPA), benzoic acid (BA), trimellitic acid (TMA), para-toluic acid (PTAC), 2,6-dicarboxybenzocoumarin (2,6-DCBC), 4,4'-dicarboxybenzil (4,4'-DCBZ), 4,4'-dicarboxybenzophenone (4,4'-DCBP), 2,5,4'-tricarboxybenzophenone (2,5,4'-TCBP). Table 3, below provides the preferred amounts of these impurities in CTA produced according to an embodiment of the present invention.

TABLE 3

| CTA Impurities | | | |
|---|---|---|---|
| Impurity Identification | Preferred Amt. (ppmw) | More Preferred Amt. (ppmw) | Most Preferred Amt. (ppmw) |
| 4-CBA | <15,000 | 100-8,000 | 400-2,000 |
| 4,4'-DCS | <12 | <6 | <3 |
| 2,6-DCA | <9 | <6 | <2 |
| 2,6-DCF | <100 | 2-50 | 5-25 |
| 2,7-DCF | <30 | <15 | <5 |
| 3,5-DCF | <16 | <8 | <2 |
| 9F-2CA | <16 | <8 | <4 |
| 9F-4CA | <8 | <4 | <2 |
| Total fluorenones | <100 | 2-60 | 4-35 |
| 4,4'-DCB | <64 | 1-32 | 2-8 |
| 2,5,4'-TCB | <24 | <12 | <8 |
| PA | <200 | 3-100 | 5-50 |

TABLE 3-continued

| CTA Impurities | | | |
|---|---|---|---|
| Impurity Identification | Preferred Amt. (ppmw) | More Preferred Amt. (ppmw) | Most Preferred Amt. (ppmw) |
| IPA | <800 | 10-400 | 20-200 |
| BA | <600 | 5-300 | 15-100 |
| TMA | <800 | 10-400 | 20-200 |
| PTAC | <2,000 | 10-1,000 | 50-500 |
| 2,6-DCBC | <64 | <32 | <8 |
| 4,4'-DCBZ | <12 | <8 | <4 |
| 4,4'-DCBP | <40 | <30 | <20 |
| 2,5,4'-TCBP | <32 | <16 | <4 |

In addition, it is preferred for CTA produced according to an embodiment of the present invention to have reduced color content relative to CTA produce by conventional processes and apparatuses, notably those employing recycled solvent. Thus, it is preferred for CTA produced in accordance to one embodiment of the present invention have a percent transmittance percent at 340 nanometers (nm) of at least about 25 percent, more preferably of at least about 50 percent, and most preferably of at least 60 percent. It is further preferred for CTA produced in accordance to one embodiment of the present invention to have a percent transmittance percent at 400 nanometers (nm) of at least about 88 percent, more preferably of at least about 90 percent, and most preferably of at least 92 percent.

The test for percent transmittance provides a measure of the colored, light-absorbing impurities present within TPA or CTA. As used herein, the test refers to measurements done on a portion of a solution prepared by dissolving 2.00 grams of dry solid TPA or CTA in 20.0 milliliters of dimethyl sulfoxide (DMSO), analytical grade or better. A portion of this solution is then placed in a Hellma semi-micro flow cell, PN 176.700, which is made of quartz and has a light path of 1.0 cm and a volume of 0.39 milliliters. (Hellma USA, 80 Skyline Drive, Plainview, N.Y. 11803). An Agilent 8453 Diode Array Spectrophotometer is used to measure the transmittance of different wavelengths of light through this filled flow cell. (Agilent Technologies, 395 Page Mill Road, Palo Alto, Calif. 94303). After appropriate correction for absorbance from the background, including but not limited to the cell and the solvent used, the percent transmittance results, characterizing the fraction of incident light that is transmitted through the solution, are reported directly by the machine. Percent transmittance values at light wavelengths of 340 nanometers and 400 nanometers are particularly useful for discriminating pure TPA from many of the impurities typically found therein.

The preferred ranges of various aromatic impurities in the slurry (solid+liquid) phase of the reaction medium are provided below in Table 4.

TABLE 4

| Slurry Impurities | | | |
|---|---|---|---|
| Impurity Identification | Preferred Amt. (ppmw) | More Preferred Amt. (ppmw) | Most Preferred Amt. (ppmw) |
| 4-CBA | <8,000 | <5,000 | <2,500 |
| 4,4'-DCS | <4 | <2 | <1 |
| 2,6-DCA | <6 | <3 | <1 |
| 2,6-DCF | <70 | 2-40 | 4-20 |
| 2,7-DCF | <12 | <8 | <4 |
| 3,5-DCF | <12 | <8 | <4 |
| 9F-2CA | <12 | <8 | <4 |
| 9F-4CA | <8 | <4 | <2 |
| Total fluorenones | <90 | 2-60 | 5-30 |

TABLE 4-continued

Slurry Impurities

| Impurity Identification | Preferred Amt. (ppmw) | More Preferred Amt. (ppmw) | Most Preferred Amt. (ppmw) |
|---|---|---|---|
| 4,4'-DCB | <64 | 1-16 | 2-4 |
| 2,5,4'-TCB | <60 | 2-40 | 4-20 |
| PA | <3,000 | 25-1,500 | 75-500 |
| IPA | 9,000 | 75-4,500 | 225-1,500 |
| BA | <15,000 | 100-6,000 | 300-2,000 |
| TMA | <3,000 | 25-1,500 | 75-500 |
| PTAC | <8,000 | 100-4,000 | 200-2,000 |
| 4,4'-DCBZ | <5 | <4 | <3 |
| 4,4'-DCBP | <240 | <160 | <80 |
| 2,5,4'-TCBP | <120 | <80 | <40 |

These preferred compositions for the slurry embody the preferred composition of the liquid phase of the reaction medium while usefully avoiding experimental difficulties pertaining to precipitation of additional liquid phase components from the reaction medium into solid phase components during sampling from the reaction medium, separation of liquids and solids, and shifting to analytical conditions.

Many other aromatic impurities are also typically present in the slurry phase of the reaction medium and in CTA of the reaction medium, generally varying at even lower levels and/or in proportion to one or more of the disclosed aromatic compounds. Controlling the disclosed aromatic compounds in the preferred ranges will keep other aromatic impurities at suitable levels. These advantaged compositions for the slurry phase in the reaction medium and for the solid CTA taken directly from the slurry are enabled by operating with embodiments of the invention disclosed herein for partial oxidation of para-xylene to TPA.

Measurement of the concentration of low level components in the solvent, recycled solvent, CTA, slurry from the reaction medium, and PTA are performed using liquid chromatography methods. Two interchangeable embodiments are now described.

The method referred to herein as HPLC-DAD comprises high pressure liquid chromatography (HPLC) coupled with a diode array detector (DAD) to provide separation and quantitation of various molecular species within a given sample. The instrument used in this measurement is a model 1100 HPLC equipped with a DAD, provided by Agilent Technologies (Palo Alto, Calif.), though other suitable instruments are also commercially available and from other suppliers As is known in the art, both the elution time and the detector response are calibrated using known compounds present in known amounts, compounds and amounts that are appropriate to those occurring in actual unknown samples.

The method referred to herein as HPLC-MS comprises high pressure liquid chromatography (HPLC) coupled with mass spectrometry (MS) to provide separation, identification, and quantitation of various molecular species within a given sample. The instruments used in this measurement is an Alliance HPLC and ZQ MS provided by Waters Corp. (Milford, Mass.), though other suitable instruments are also commercially available and from other suppliers. As is known in the art, both the elution time and the mass spectrometric response are calibrated using known compounds present in known amounts, compounds and amounts that are appropriate to those occurring in actual unknown samples.

Another embodiment of the current invention relates to partial oxidation of aromatic oxidizable compound with appropriate balancing of the suppression of noxious aromatic impurities on the one hand against the production of carbon dioxide and carbon monoxide, collectively carbon oxides (COx), on the other. These carbon oxides typically exit the reaction vessel in the off-gas, and they correspond to a destructive loss of solvent and of oxidizable compound, including the ultimately preferred oxidized derivatives (e.g., acetic acid, para-xylene, and TPA). The inventors have discovered lower bounds for the production of carbon oxides below which it seems the high creation of noxious aromatic impurities, as described below, and the low overall conversion level are inevitably too poor to be of economic utility. The inventors have also discovered upper bounds of carbon oxides above which the generation of carbon oxides continues to increase with little further value provided by reduction in generation of noxious aromatic impurities.

The inventors have discovered that reducing the liquid-phase concentrations of aromatic oxidizable compound feed and of aromatic intermediate species within a reaction medium leads to lower generation rates for noxious impurities during the partial oxidation of aromatic oxidizable compound. These noxious impurities include coupled aromatic rings and/or aromatic molecules containing more than the desired number of carboxylic acid groups (e.g., in the oxidation of para-xylene the noxious impurities include 2,6-dicarboxyanthraquinone, 2,6-dicarboxyfluorenone, trimellitic acid, 2,5,4'-tricarboxybiphenyl, and 2,5,4'-benzophenone). The aromatic intermediate species include aromatic compounds descended from the feed of oxidizable aromatic compound and still retaining non-aromatic hydrocarbyl groups (e.g., in the oxidation of para-xylene the aromatic intermediate species comprise para-tolualdehyde, terephthaldehyde, para-toluic acid, 4-CBA, 4-hydroxymethylbenzoic acid, and alpha-bromo-para-toluic acid). The aromatic oxidizable compound feed and the aromatic intermediate species retaining non-aromatic hydrocarbyl groups, when present in the liquid phase of the reaction medium, appear to lead to noxious impurities in a manner similar to that already disclosed herein for dissolved aromatic species lacking non-aromatic hydrocarbyl groups (e.g., isophthalic acid).

Set against this need for higher reaction activity to suppress formation of noxious aromatic impurities during partial oxidation of oxidizable aromatic compound, the inventors have discovered that the undesirable attendant result is increased production of carbon oxides. It is important to appreciate that these carbon oxides represent a yield loss of oxidizable compound and oxidant, not just solvent. Explicitly, a substantial and sometimes principal fraction of the carbon oxides comes from the oxidizable compound, and its derivatives, rather than from solvent; and often the oxidizable compound costs more per carbon unit than does solvent. Furthermore, it is important to appreciate that the desired product carboxylic acid (e.g., TPA) is also subject to over-oxidation to carbon oxides when present in the liquid phase of the reaction medium.

It is also important to appreciate that the present invention relates to reactions in the liquid phase of the reaction medium and to reactant concentrations therein. This is in contrast to some prior inventions which relate directly to the creation in precipitated solid form of aromatic compound retaining non-aromatic hydrocarbyl groups. Specifically, for the partial oxidation of para-xylene to TPA, certain prior inventions pertain to the amount of 4-CBA precipitated in the solid phase of CTA. However, the present inventors have discovered a variance of greater than two to one for the ratio of 4-CBA in the solid phase to 4-CBA in the liquid phase, using the same specifications of temperature, pressure, catalysis, solvent composition and space-time reaction rate of para-xylene, depending upon whether the partial oxidation is conducted in a well-mixed autoclave or in a reaction medium with oxygen and para-xylene staging according to the present invention.

Further, the inventors have observed that the ratio of 4-CBA in the solid phase to 4-CBA in the liquid phase can also vary by over two to one in either well-mixed or staged reaction medium depending upon the space-time reaction rate of para-xylene at otherwise similar specifications of temperature, pressure, catalysis, and solvent composition. Additionally, 4-CBA in the solid phase CTA does not appear to contribute to the formation of noxious impurities, and 4-CBA in the solid phase can be recovered and oxidized on to TPA simply and at high yield (e.g., by oxidative digestion of the CTA slurry as is described herein); whereas the removal of noxious impurities is far more difficult and costly than removal of solid phase 4-CBA, and the production of carbon oxides represents a permanent yield loss. Thus, it is important to distinguish that this aspect of the present invention relates to liquid-phase compositions in the reaction medium.

Whether sourced from solvent or oxidizable compound, the inventors have discovered that at conversions of commercial utility the production of carbon oxides relates strongly to the level of overall reaction activity despite wide variation in the specific combination of temperature, metals, halogens, temperature, acidity of the reaction medium as measured by pH, water concentration employed to obtain the level of overall reaction activity. The inventors have found it useful for the partial oxidation of xylene to evaluate the level of overall reaction activity using the liquid-phase concentration of toluic acids at the mid-height of the reaction medium, the bottom of the reaction medium, and the top of the reaction medium.

Thus, there arises an important simultaneous balancing to minimize the creation of noxious impurities by increasing reaction activity and yet to minimize the creation of carbon oxides by lowering reaction activity. That is, if the overall production of carbon oxides is suppressed too low, then excessive levels of noxious impurities are formed, and vice versa.

Furthermore, the inventors have discovered that the solubility and the relative reactivity of the desired carboxylic acid (e.g., TPA) and the presence of other dissolved aromatic species lacking non-aromatic hydrocarbyl groups introduce a very important fulcrum in this balancing of carbon oxides versus noxious impurities. The desired product carboxylic acid is typically dissolved in the liquid phase of the reaction medium, even when also present in solid form. For example, at temperatures in the preferred ranges, TPA is soluble in a reaction medium comprising acetic acid and water at levels ranging from about one thousand ppmw to in excess of 1 weight percent, with solubility increasing as temperature increases. Notwithstanding that there are differences in the reaction rates toward forming various noxious impurities from oxidizable aromatic compound feed (e.g., para-xylene), from aromatic reaction intermediates (e.g., para-toluic acid), from the desired product aromatic carboxylic acid (e.g., TPA), and from aromatic species lacking non-aromatic hydrocarbyl groups (e.g., isophthalic acid), the presence and reactivity of the latter two groups establishes a region of diminishing returns with regards to further suppression of the former two groups, oxidizable aromatic compound feed and aromatic reaction intermediates. For example, in a partial oxidation of para-xylene to TPA, if dissolved TPA amounts to 7,000 ppmw in the liquid phase of the reaction medium at given conditions, dissolved benzoic acid amounts to 8,000 ppmw, dissolved isophthalic acid amounts to 6,000 ppmw, and dissolved phthalic acid amounts to 2,000 ppmw, then the value toward further lowering of total noxious compounds begins to diminish as reaction activity is increased to suppress the liquid-phase concentration para-toluic acid and 4-CBA below similar levels. That is, the presence and concentration in the liquid phase of the reaction medium of aromatic species lacking non-aromatic hydrocarbyl groups is very little altered by increasing reaction activity, and their presence serves to expand upwards the region of diminishing returns for reducing the concentration of reaction intermediates in order to suppress formation of noxious impurities.

Thus, one embodiment of the present invention provides preferred ranges of carbon oxides, bounded on the lower end by low reaction activity and excessive formation of noxious impurities and on upper end by excessive carbon losses, but at levels lower than previously discovered and disclosed as commercially useful. Accordingly, the formation of carbon oxides is preferably controlled as follows. The ratio of moles of total carbon oxides produced to moles of oxidizable aromatic compound fed is preferably greater than about 0.02:1, more preferably greater than about 0.04:1, still more preferably greater than about 0.05:1, and most preferably greater than 0.06:1. At the same time, the ratio of moles of total carbon oxides produced to moles of oxidizable aromatic compound fed is preferably less than about 0.24:1, more preferably less than about 0.22:1, still more preferably less than about 0.19:1, and most preferably less than 0.15:1. The ratio of moles of carbon dioxide produced to moles of oxidizable aromatic compound fed is preferably greater than about 0.01:1, more preferably greater than about 0.03:1, still more preferably greater than about 0.04:1, and most preferably greater than 0.05:1. At the same time, the ratio of moles of carbon dioxide produced to moles of oxidizable aromatic compound fed is preferably less than about 0.21:1, more preferably less than about 0.19:1, still more preferably less than about 0.16:1, and most preferably less than 0.11. The ratio of moles of carbon monoxide produced to moles of oxidizable aromatic compound fed is preferably greater than about 0.005:1, more preferably greater than about 0.010:1, still more preferably greater than about 0.015:1, and most preferably greater than 0.020:1. At the same time, the ratio of moles of carbon monoxide produced to moles of oxidizable aromatic compound fed is preferably less than about 0.09:1, more preferably less than about 0.07:1, still more preferably less than about 0.05:1, and most preferably less than 0.04:1

The content of carbon dioxide in dry off-gas from the oxidation reactor is preferably greater than about 0.10 mole percent, more preferably greater than about 0.20 mole percent, still more preferably greater than about 0.25 mole percent, and most preferably greater than 0.30 mole percent. At the same time, the content of carbon dioxide in dry off-gas from the oxidation reactor is preferably less than about 1.5 mole percent, more preferably less than about 1.2 mole percent, still more preferably less than about 0.9 mole percent, and most preferably less than 0.8 mole percent. The content of carbon monoxide in dry off-gas from the oxidation reactor is preferably greater than about 0.05 mole percent, more preferably greater than about 0.10 mole percent, still more preferably greater than 0.15, and most preferably greater than 0.18 mole percent. At the same time, the content of carbon monoxide in dry off-gas from the oxidation reactor is preferably less than about 0.60 mole percent, more preferably less than about 0.50 mole percent, still more preferably less than about 0.35 mole percent, and most preferably less than 0.28 mole percent The inventors have discovered that an important factor for reducing the production of carbon oxides to these preferred ranges is improving the purity of the recycled filtrate and of the feed of oxidizable compound to reduce the concentration of aromatic compounds lacking non-aromatic hydrocarbyl groups according to disclosures of the present invention—this simultaneously reduces the formation of carbon oxides and of noxious impurities. Another factor is improving distribution of para-xylene and oxidant within the reaction vessel according to disclosures of the present invention. Other factors enabling the above preferred levels of carbon oxides are to operate with the gradients in the reaction medium as disclosed herein for pressure, for temperature, for concentration of oxidizable compound in the liquid phase, and for oxidant in the gas phase. Other factors enabling the above preferred levels of carbon oxides are to operate within the disclosures herein preferred for space-time reaction rate, pressure, temperature, solvent composition, catalyst composition, and mechanical geometry of the reaction vessel.

An important benefit from operating within the preferred ranges of carbon oxide formation is that the usage of molecular oxygen can be reduced, though not to stoichiometric values. Notwithstanding the good staging of oxidant and oxidizable compound according to the present invention, an excess of oxygen must be retained above the stoichiometric value, as calculated for feed of oxidizable compound alone, to allow for some losses to carbon oxides and to provide excess molecular oxygen to control the formation of noxious impurities. Specifically for the case where xylene is the feed of oxidizable compound, the feed ratio of weight of molecular oxygen to weight of xylene is preferably greater than about 0.91:1.00, more preferably greater than about 0.95:1.00, and most preferably greater than 0.99:1.00. At the same time, the feed ratio of weight of molecular oxygen to weight of xylene is preferably less than about 1.20:1.00, more preferably less than about 1.12:1.00, and most preferably less than 1.06:1.00. Specifically for xylene feed, the time-averaged content of molecular oxygen in the dry off-gas from the oxidation reactor is preferably greater than about 0.1 mole percent, more preferably greater than about 1 mole percent, and most preferably greater than 1.5 mole percent. At the same time, the time-averaged content of molecular oxygen in the dry off-gas from the oxidation reactor is preferably less than about 6 mole percent, more preferably less than about 4 mole percent, and most preferably less than 3 mole percent.

Another important benefit from operating within the preferred ranges of carbon oxide formation is that less aromatic compound is converted to carbon oxides and other less valuable forms. This benefit is evaluated using the sum of the moles of all aromatic compounds exiting the reaction medium divided by the sum of the moles of all aromatic compounds entering the reaction medium over a continuous period of time, preferably one hour, more preferably one day, and most preferably 30 consecutive days. This ratio is hereinafter referred to as the "molar survival ratio" for aromatic compounds through the reaction medium and is expressed as a numerical percentage. If all entering aromatic compounds exit the reaction medium as aromatic compounds, albeit mostly in oxidized forms of the entering aromatic compounds, then the molar survival ratio has its maximum value of 100 percent. If exactly 1 of every 100 entering aromatic molecules is converted to carbon oxides and/or other non-aromatic molecules (e.g., acetic acid) while passing through reaction medium, then the molar survival ratio is 99 percent. Specifically for the case where xylene is the principal feed of oxidizable aromatic compound, the molar survival ratio for aromatic compounds through the reaction medium is preferably greater than about 98 percent, more preferably greater than about 98.5 percent, and most preferably less than 99.0 percent. At the same time and in order that sufficient overall reaction activity is present, the molar survival ratio for aromatic compounds through the reaction medium is preferably less than about 99.9 percent, more preferably less than about 99.8 percent, and most preferably less than 99.7 percent when xylene is the principal feed of oxidizable aromatic compound.

Another aspect of the current invention involves the production of methyl acetate in a reaction medium comprising acetic acid and one or more oxidizable aromatic compounds. This methyl acetate is relatively volatile compared to water and acetic acid and thus tends to follow the off-gas unless additional cooling or other unit operations are employed to recover it and/or to destroy it prior to releasing the off-gas back to the environment. The formation of methyl acetate thus represents an operating cost and also a capital cost. Perhaps the methyl acetate is formed by first combining a methyl radical, perhaps from decomposition of acetic acid, with oxygen to produce methyl hydroperoxide, by subsequently decomposing to form methanol, and by finally reacting the produced methanol with remaining acetic acid to form methyl acetate. Whatever the chemical path, the inventors have discovered that whenever methyl acetate production is at too low a rate, then the production of carbon oxides are also too low and the production of noxious aromatic impurities are too high. If methyl acetate production is at too high a rate, then the production of carbon oxides are also unnecessarily high leading to yield losses of solvent, oxidizable compound and oxidant. When employing the preferred embodiments disclosed herein, the production ratio of moles of methyl acetate produced to moles of oxidizable aromatic compound fed is preferably greater than about 0.005:1, more preferably greater than about 0.010:1, and most preferably greater than 0.020:1. At the same time, the production ratio of moles of methyl acetate produced to moles of oxidizable aromatic compound fed is preferably less than about 0.09:1, more preferably less than about 0.07:1, still more preferably less than about 0.05:1, and most preferably less than 0.04:1.

Certain embodiments of this invention can be further illustrated by the following examples, although it should be understood that these examples are included merely for purposes of illustration and are not intended to limit the scope of the invention unless otherwise specifically indicated.

EXAMPLES 1-10

Example 1 is a calculated example of a bubble column oxidation reactor for oxidizing para-xylene in a liquid phase of a three-phase reaction medium. The bubble column reactor of Example 1 represents a proven industrial design with a para-xylene feed rate of 7,000 kilograms per hour. Examples 2 through 10 are calculated examples for bubble column oxidation reactors having operating capacities 7 times greater than the reactor of Example 1. FIG. 58 provides a table outlining the different parameters of the bubble column oxidation reactor that are varied in Examples 1-10.

Example 1

This example employs a bubble column reaction vessel having a vertical, cylindrical section with an inside diameter equaling 2.44 meters. The height of the cylindrical section is 32 meters from the lower tangent line (TL) to the upper TL of the cylindrical section. The vessel is fitted with 2:1 elliptical heads at the top and bottom of the cylindrical section. The height from the bottom of the reaction medium to the top of the cylindrical section is about 32.6 meters, and the overall height of the reaction vessel is about 33.2 meters. The operating level is about 25.6 meters above the bottom of the reaction medium.

Para-xylene is fed to the reactor at a steady rate of 7,000 kilograms per hour. A filtrate solvent comprising primarily acetic acid is fed intimately commingled with the para-xylene at a steady rate of 70,000 kilograms per hour. The feed is distributed within the reaction vessel near an elevation of 2 meters above the bottom of the reaction medium using a horizontal distributor assembly designed to provide a substantially uniform release of the feed over the area of cross section lying inside of a radius of 0.45*(inside diameter). The concentration of catalyst components in the filtrate solvent is such that the composition within the liquid phase of the reaction medium is 1,800 ppmw of cobalt, 1,800 ppmw of bromine, and 100 ppmw of manganese. A separate stream of reflux solvent is fed as droplets into the gas-disengaging zone above the operating level of the reaction medium at a steady rate of 49,000 kilograms per hour, and it is distributed over essentially all of the cross sectional area of the disengaging zone. This reflux solvent is without significant levels of catalyst components. The combined water content of the filtrate solvent feed and of the reflux solvent feed is such that the concentration of water within the liquid phase of the reaction medium is 6 weight percent. The feed rate of air is steady at a rate of 35,000 kilograms per hour through an oxidant inlet distributor similar to the one shown in FIGS. 12-15, and all of the oxidant admission holes are located below the lower TL of the cylindrical section. The operating pressure of the reaction vessel overhead gas is steadily 0.52 megapascal gauge. The reaction vessel is operated in a substantially adiabatic manner so that the heat of reaction elevates the temperature of the incoming feeds and evaporates much of the incoming solvent. Measured near the mid-elevation of the reaction medium, the operating temperature is about 160° C. Reaction medium comprising crude terephthalic acid (CTA) is removed from the side of the reaction vessel at an elevation of 15 meters at a steady rate using an external de-aeration vessel.

The L:D ratio is 13.4 and the H:W ratio is 10.5. The volume occupied by the reaction medium is about 118 cubic meters, and the reaction vessel contains about 58,000 kilograms of slurry. The ratio of slurry mass to para-xylene feed rate is about 8.3 hours. The space time reaction intensity is about 59 kilograms of para-xylene fed per cubic meter of reaction medium per hour. The pressure differential from the bottom of the reaction medium to the overhead off-gas exiting the reaction vessel is about 0.12 megapascal. The superficial velocity of the gas phase at the mid-height of the reaction medium is about 0.8 meters per second. The upright surface area in contact with the reaction medium is about 197 square meters, which is about 3.16*Wmin*H. The ratio of the volume of reaction medium to upright surface area in contact with the reaction medium is about 0.60 meters. Under conditions of Example 1, it is estimated that decomposition of acetic acid in the reaction medium amounts to approximately 0.03 kilograms per kilogram of produced CTA. This is a significant cost in overall production economics.

Useful indicators of end-to-end flow rates within the bubble column reaction vessel are the maximum time-averaged upward velocities of the slurry and of the oxidant phase. In a cylindrical bubble column reaction vessel, these maximum upward velocities occur near the vertical axis of symmetry of the cylindrical section. Calculated by a method derived from the Gas-Liquid Recirculation Model of Gupta (reference *Churn-turbulent bubble columns: experiments and modeling*; Gupta, Puneet; Washington Univ.; St. Louis, Mo., USA. Avail. UMI, Order No. DA3065044; (2002), 357 pp. From: Diss. Abstr. Int., B 2003, 63(9), 4269. Dissertation written in English. CAN 140:130325 AN 2003:424187 CAPLUS) and using a proprietary data base, the maximum time-averaged upwards velocity of the gas phase near the mid-elevation of the reaction medium is about 3.1 meters per second. Similarly calculated, the maximum upwards velocity, time-averaged, of the slurry near the mid-elevation of the reaction medium is about 1.4 meters per second.

Another useful indicator of end-to-end flow rates within the bubble column reaction vessel is the maximum time-averaged downward velocity of the slurry in the parts of the reaction vessel located away from the central core. In a cylindrical reaction vessel, this maximum downward velocity typically occurs in the region lying outside a radius of 0.35* (inside diameter) from the vertical axis of symmetry of the cylindrical section. Calculated by a method derived from the Gas-Liquid Recirculation Model of Gupta and using a proprietary data base, the maximum time-averaged downwards velocity of the slurry in the outer annulus near the mid-elevation of the reaction medium is about 1.4 meters per second.

Example 2

In this example, the bubble column reactor is fed para-xylene at an increased rate of 49,000 kilograms per hour—7 times greater than in Example 1. The superficial gas velocity, often considered an important scale-up variable for bubble columns, is kept approximately equal to Example 1 by increasing the cross-sectional area of the reaction vessel to be about 7 times larger than in Example 1. The H:W and L:D ratios, often considered important scale-up variables for bubble columns, are also kept approximately equal to Example 1.

The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 40 meters at a steady rate using an external de-aeration vessel.

The bubble column reaction vessel comprises a vertical, cylindrical section with an inside diameter equal to 6.46 meters. The L:D ratio is maintained the same as Example 1, and the height from the bottom of the reaction medium to the top of the cylindrical section is thus 86.3 meters. The top and bottom of the cylindrical section are fitted with 2:1 elliptical heads, and the overall height of the reaction vessel is very tall, about 88.0 meters. The feed is again distributed within the reaction vessel near an elevation of 2 meters above the bottom of the reaction medium using a horizontal distributor assembly designed for a substantially uniform release of the feed over the area of cross section lying inside of a radius of 0.45*(inside diameter). The feed of air is again through an oxidant inlet distributor similar to the one shown in FIGS. 12-15, and all of the oxidant admission holes are located below the lower TL of the cylindrical section. The reflux solvent is distributed as droplets over essentially all of the cross sectional area of the disengaging zone.

The H:W ratio of the reaction medium is kept approximately equal to Example 1, and thus the operating level is about 67.8 meters of reaction medium. This leaves a disengaging height of about 18.5 meters in the cylindrical section plus about 1.6 meters in the top elliptical head. This disengaging height is excessive by about 10 meters. Thus, scaling the vessel with constant L:D produces a mechanical installation that is overly expensive for capital (e.g., excessive costs for pressure vessel, for foundations due to mass and wind load, for structural steel, for process and utility piping, and/or for instrument and electrical cabling).

The volume occupied by the reaction medium is about 2,200 cubic meters, and the reaction vessel contains about 1,100,000 kilograms of slurry. The ratio of slurry mass to para-xylene feed rate is about 22 hours, greatly increased compared to Example 1. The space time reaction intensity is only about 22 kilograms of para-xylene fed per cubic meter of reaction medium per hour, greatly decreased compared to Example 1. The pressure differential from the bottom of the reaction medium to the overhead off-gas exiting the reaction vessel rises to about 0.33 megapascal, greatly increased compared to Example 1. The upright surface area in contact with the reaction medium is about 1,393 square meters, which is about 3.18*Wmin*H. The ratio of the volume of reaction medium to upright surface area in contact with the reaction medium is about 1.58 meters, greatly increased compared to Example 1.

Thus, scaling the reaction medium dimensions to maintain both superficial velocity and H:W ratio as approximately constant between this example and Example 1 has produced very large changes in the reaction conditions. On balance, these changes are highly unfavorable. There are positive effects in this example (e.g., more dilute concentrations of oxidizable compound, lower demand on mass transfer rate per unit volume for molecular oxygen from gas to liquid phase, and so on) leading to production of fewer undesirable, colored byproducts per unit CTA. However, there are severe economic penalties relating to the decomposition of acetic acid and to the pressure and power required to supply air to the bottom of the bubble column reaction vessel. The decomposition of acetic acid is approximately proportional to the mass of acetic acid in the reaction medium, whenever the operating temperature and the composition of the liquid phase are kept approximately constant and when para-xylene is fed with an excess of molecular oxygen. Owing to the much greater mass of acetic acid in the reaction vessel compared to the amount of CTA produced in this example, it is estimated that decomposition of acetic acid rises to about 0.09 kilograms per kilogram of produced CTA. In addition, the air compressor must deliver air into the reaction medium with a pressure that is 0.85 megapascal gauge in this example, whereas the delivered pressure is 0.64 megapascal gauge in Example 1. For an air delivery rate of 245,000 kilograms per hour and with typical allowance for various compression and delivery efficiencies, the additional power requirement for the higher delivery pressure in this example is about 3,000 kilowatts, continuously. Thus, scaling the reaction medium of this example with approximately constant superficial gas velocity and H:W ratio provides unacceptable economics, despite the good quality of CTA expected.

Example 3

This example scales the process of Example 1 using superficial velocity and space-time reaction intensity. This leads to poor product quality because, in simple terms, the natural convection flow patterns inherently produce a poor reaction profile vertically.

In this example, the feed rate of para-xylene is again 49,000 kilograms per hour—7 times larger than in Example 1. The superficial gas velocity is again kept approximately equal to Example 1, but the L:D and H:W ratios are not kept equal. Instead, the STR is kept approximately equal to Example 1. This provides a column base pressure and a decomposition ratio of acetic acid that are approximately equal to Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 15 meters at a steady rate using an external de-aeration vessel.

The bubble column reaction vessel includes a vertical, cylindrical section, with the inside diameter equal to 6.46 meters, keeping the superficial velocity of the gas phase approximately constant compared to Examples 1 and 2. In order to keep the same STR as Example 1, the operating level is changed slightly to about 26.1 meters of reaction medium. The height from lower TL to upper TL of the cylindrical section is 32 meters, the same as Example 1 and providing about the same freeboard disengaging height between the top of the reaction medium and the overhead gas outlet. The top and bottom of the cylindrical section are fitted with 2:1 elliptical heads. The height from the bottom of the reaction medium to the top of the cylindrical section is about 33.6 meters, and the overall height of the reaction vessel is about 35.2 meters. The feed is again distributed within the reaction vessel near an elevation of 2 meters above the bottom of the reaction medium using a horizontal distributor assembly designed for a substantially uniform release of the feed over the area of cross section lying inside of a radius of 0.45* (inside diameter). The feed of air is again through an oxidant inlet distributor similar to the one shown in FIGS. 12-15, and all of the oxidant admission holes are located below the lower TL of the cylindrical section. The reflux solvent is distributed as droplets over essentially all of the cross sectional area of the disengaging zone.

The H:W ratio of the reaction medium is decreased markedly to 4.0. The L:D ratio of the reaction vessel is decreased markedly to 5.2. The volume occupied by the reaction medium is about 828 cubic meters, and the reaction vessel contains about 410,000 kilograms of slurry. The ratio of slurry mass to para-xylene feed rate is about 8.3 hours. The STR is about 59 kilograms of para-xylene fed per cubic meter of reaction medium per hour. The pressure differential from the bottom of the reaction medium to the overhead off-gas exiting the reaction vessel is about 0.13 megapascal. The upright surface area in contact with the reaction medium is about 546 square meters, which is about 3.24*Wmin*H. The ratio of the volume of reaction medium to upright surface area in contact with the reaction medium is about 1.52 meters. Under conditions of this example, it is estimated that decomposition of acetic acid in the reaction medium is desirably returned to the lower level of Example 1, approximately 0.03 kilograms per kilogram of produced CTA.

However, the larger diameter of the reaction vessel employed in this example coupled with its smaller H:W ratio leads to very undesirable shifts in the flow velocities, mixing and staging within the reaction medium. This leads to a significant increase in the loss of para-xylene in the overhead off-gas and in the formation of undesirable, colored byproducts. Simply stated, the axial flow velocities produced by natural convection forces grow larger in bubble columns of greater diameter even when superficial velocity is kept constant. Calculated by a method derived from Gas-Liquid Recirculation Model of Gupta and using a proprietary data base, the maximum upwards velocity, time-averaged, of the gas phase near the mid-elevation of the reaction medium is about 3.9 meters per second. Similarly calculated, the maximum time-averaged upwards velocity of the slurry near the mid-elevation of the reaction medium is about 2.2 meters per second. Similarly calculated, the maximum time-averaged downwards velocity of the slurry in the outer annulus near the mid-elevation of the reaction medium is about 2.3 meters per second.

Since the height of the reaction medium is little changed between this example and Example 1, these increased time-averaged vertical velocities cause the end-to-end mixing times to be significantly reduced in this example as compared to Example 1. This produces an undesirable increase in the amount of para-xylene migrating toward the top of the vessel before oxidizing. This leads to an undesirable loss in yield of para-xylene exiting the top of the reaction vessel with the off-gas, and it shifts more of the demand for dissolved molecular oxygen to nearer the top of the reactor where the mole fraction of molecular oxygen is relatively depleted within the gas phase. Furthermore, the increased time-averaged downward velocity of slurry in regions toward the vessel wall in this example causes more and larger bubbles of the gas phase to be pulled downwards against their natural buoyancy in a gravitational field. This leads to an undesirable increase in the recirculation of gas phase partly depleted of molecular oxygen, which in turn leads to reduced availability of dissolved oxygen in these regions. Among other effects, this reduced availability of dissolved oxygen in various portions of the reaction medium leads to a significantly increased formation ratio of undesirable, colored byproducts in this example compared to Example 1, and this elevated level of undesirable, colored byproducts renders the product unusable for many applications in PET.

Thus, Examples 2 and 3 demonstrate the inadequacy of the prior art for designing large scale oxidation bubble columns using primarily superficial gas velocity (Ug), L:D ratio, and average space-time rate of reaction (STR).

Example 4

In this example, the pressure containing members of the bubble column reaction vessel are the same as Example 3, but upright surfaces are added within the reaction medium to impart vertical drag in order to establish reaction staging profiles more similar to Example 1, thereby restoring product quality and para-xylene yield, but without increasing the decomposition ratio of acetic acid as in Example 2.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 15 meters at a steady rate using an external de-aeration vessel.

The bubble column reaction vessel includes a vertical, cylindrical section, with the inside diameter equal to 6.46 meters. The height from lower TL to upper TL of the cylindrical section is 32 meters, and the operating level is about 26.3 meters of reaction medium. The top and bottom of the cylindrical section are fitted with 2:1 elliptical heads. The height from the bottom of the reaction medium to the top of the cylindrical section is about 33.6 meters, and the overall height of the reaction vessel is about 35.2 meters. The feed is again distributed within the reaction vessel near an elevation of 2 meters above the bottom of the reaction medium using a horizontal distributor assembly designed for a substantially uniform release of the feed over the area of cross section lying inside of a radius of 0.45*(inside diameter). The feed of air is again through an oxidant inlet distributor similar to the one shown in FIGS. 12-15, and all of the oxidant admission holes are located below the lower TL of the cylindrical section. The reflux solvent is distributed as droplets over essentially all of the cross sectional area of the disengaging zone.

The bubble column reaction vessel further includes two orthogonal planar surfaces located with their line of intersection coincident with the vertical axis of symmetry of the cylindrical section. These planar surfaces conveniently comprise plate metal of the same type and surface finish as is used in the cylindrical section of the reaction vessel. Each planar surface begins at a lower elevation of 3 meters above the lower TL and extends upwards by 20 meters. The two planar surfaces each extend horizontally essentially all the way to the wall of the cylindrical section (i.e., the width of each is equal to inside diameter) and are supported from the cylindrical section. The thickness and support of the planar surfaces are designed to withstand the various forces that may occur in normal and upset operating conditions. Owing to the volume occupied by the plate metal, the operating level is adjusted upwards slightly to 26.3 meters above the bottom of the reaction medium in order to keep the same STR as Example 1.

Thus, in this example, the reaction medium is subdivided into 4 equally sized and shaped sub-volumes for 20 meters out of the total height of the reaction medium. These 4 sub-volumes communicate with each other both below and above the planar surfaces. Owing to the relatively uniform distribution of oxidant and para-xylene feed below the lower extremity of the planar surfaces, each of the 4 sub-volumes has a similar superficial velocity of the gas phase and a similar reaction intensity profile. The 4 sub-volumes may be conceived as akin to 4 smaller-sized bubble column reaction vessels within the shell of one pressure containing vessel.

The H:W ratio of the reaction medium is 4.1. The L:D ratio of the reaction vessel is 5.2. The volume occupied by the reaction medium is about 828 cubic meters, and the reaction vessel contains about 410,000 kilograms of slurry. The ratio of slurry mass to para-xylene feed rate is about 8.3 hours. The STR is about 59 kilograms of para-xylene fed per cubic meter of reaction medium per hour. The pressure differential from the bottom of the reaction medium to the overhead off-gas exiting the reaction vessel is about 0.13 megapascal. The upright surface area in contact with the reaction medium is about 1,066-square meters, which is about 6.29*Wmin*H. The ratio of the volume of reaction medium to upright surface area in contact with the reaction medium is about 0.78 meters. This value is intermediate between Examples 1 and 3, and it lies usefully closer to Example 1. Under conditions of this example, it is estimated that decomposition of acetic acid in the reaction medium is desirably returned to the lower level of Example 1, approximately 0.03 kilograms per kilogram of produced CTA.

The maximum time-averaged upwards and downwards velocities of the gas phase and of the slurry are reduced in this example as compared to Example 3. This provides useful improvements in the vertical profile of para-xylene, and it leads to improved availability of dissolved oxygen in the liquid phase near the upright wall surfaces. Together, these changes improve para-xylene yield and reduce the formation of undesirable, colored byproducts in this example as compared to Example 3.

Example 5

In this example, the pressure containing members of the reaction vessel are the same as Example 3, but non-fouling baffle members are added within the reaction medium to re-establish reaction staging profiles more similar to Example 1, thereby restoring product quality and para-xylene yield, but without increasing the decomposition ratio of acetic acid as in Example 2.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 15 meters at a steady rate using an external de-aeration vessel.

The bubble column reaction vessel includes a vertical, cylindrical section, with the inside diameter equal to 6.46 meters. The height from lower TL to upper TL of the cylindrical section is 32 meters, and the operating level is about 26.1 meters of reaction medium. The top and bottom of the cylindrical section are fitted with 2:1 elliptical heads. The height from the bottom of the reaction medium to the top of the cylindrical section is about 33.6 meters, and the overall height of the reaction vessel is about 35.2 meters. The feed is again distributed within the reaction vessel near an elevation of 2 meters above the bottom of the reaction medium using a horizontal distributor assembly designed for a substantially uniform release of the feed over the area of cross section lying inside of a radius of 0.45*(inside diameter). The feed of air is again through an oxidant inlet distributor similar to the one shown in FIGS. 12-15, and all of the oxidant admission holes are located below the lower TL of the cylindrical section. The reflux solvent is distributed as droplets over essentially all of the cross sectional area of the disengaging zone.

The bubble column reaction vessel further includes a horizontal baffle assembly located in the bubble column at a height of 12 meters above the lower TL of the reaction vessel. This places the baffle assembly about 13.6 meters, or 2.1*D, above the bottom of the reaction medium. This baffle assembly is comprised of 15 individual baffle members. Each baffle member is comprised of an extruded or fabricated L-shape wherein both legs of the L-shape are 0.15 meters wide and the included angle between the two legs is 90-degrees. The L-shapes are all arranged horizontal, parallel to each other, with the corners pointing upwards, and located at the same elevation. The two terminal edges of each L-shape are all at the same elevation, below the upwards pointing corners. When viewed on end, each member appears as an inverted V-shape. Thus, the percentage of the baffle assembly comprising upwardly-facing planar surfaces inclined less than 5 degrees from horizontal is effectively nil. The gap between the lower edges of each member and its near neighbor is always 0.21 meters. The longest of the members has a length effectively equal to the inside diameter of the cylindrical vessel, extending diametrically across the vessel from wall to wall. The other 14 individual baffle members are all necessarily shorter in length. All baffle members are supported on each end by extending all the way to the cylindrical wall and attaching thereto. Thus, the open area at the elevation of the baffle assembly is about 16-square meters, which is about 50-percent of the cross sectional area of the reaction vessel at that elevation. The baffle members are designed to withstand the various forces that may occur in normal and upset operating conditions. The members are constructed of the same metal as the piping components used in the air sparger assembly, which metal is appropriately selected to resist corrosion and erosion. However, the surfaces of the baffle members are polished to a surface finish of 125 RMS or finer. Despite the precipitation of about 76,000 kilograms per hour of CTA within the reaction vessel, the baffle assembly does not excessively foul or slough away chunks of solids.

The H:W ratio of the reaction medium is 4.0. The L:D ratio of the reaction vessel is 5.2. The volume occupied by the reaction medium is about 828 cubic meters, and the reaction vessel contains about 410,000 kilograms of slurry. The ratio of slurry mass to para-xylene feed rate is about 8.3 hours. The STR is about 59 kilograms of para-xylene fed per cubic meter of reaction medium per hour. The pressure differential from the bottom of the reaction medium to the overhead off-gas exiting the reaction vessel is about 0.13 megapascal. The upright surface area in contact with the reaction medium is about 546 square meters, which is about 3.24*Wmin*H. The ratio of the volume of reaction medium to upright surface area in contact with the reaction medium is about 1.52 meters. Under conditions of this example, it is estimated that decomposition of acetic acid in the reaction medium is desirably returned to the lower level of Example 1, approximately 0.03 kilograms per kilogram of produced CTA.

The effect of the horizontal baffle assembly is to disrupt the vertical velocity of the gas phase and of the slurry within the reaction vessel. This retards the progress of para-xylene toward the top surface of the reaction medium, leading to a beneficial reduction in yield loss of para-xylene in the overhead off-gas. Additionally, the staging of molecular oxygen and oxidizable compound are improved providing a reduction in the formation of undesirable, colored byproducts in this example as compared to Example 3.

Example 6

In this example, the reaction vessel is designed for very high gas superficial velocities and gas hold-up values according to the present invention. Using a smaller D enables a higher L:D ratio without resorting to an excessively tall reaction vessel and without incurring excessive decomposition of acetic acid solvent.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 28 meters at a steady rate using an external de-aeration vessel.

The bubble column reaction vessel includes a vertical, cylindrical section, with the inside diameter equal to 5.00 meters. The height from lower TL to upper TL of the cylindrical section is 70 meters. The top and bottom of the cylindrical section are fitted with 2:1 elliptical heads. The height from the bottom of the reaction medium to the top of the cylindrical section is about 71.3 meters, and the overall height of the reaction vessel is about 72.5 meters. The operating level is about 61.3 meters above the bottom of the reaction medium. The feed is again distributed within the reaction vessel near an elevation of 2 meters above the bottom of the reaction medium using a horizontal distributor assembly designed for a substantially uniform release of the feed over the area of cross section lying inside of a radius of 0.45* (inside diameter). The feed of air is again through an oxidant inlet distributor similar to the one shown in FIGS. 12-15, and all of the oxidant admission holes are located below the lower TL of the cylindrical section. The reflux solvent is distributed as droplets over essentially all of the cross sectional area of the disengaging zone.

The H:W ratio of the reaction medium is 12.3. The L:D ratio of the reaction vessel is 14.3. The volume occupied by the reaction medium is about 1,190 cubic meters, and the reaction vessel contains about 420,000 kilograms of slurry. The ratio of slurry mass to para-xylene feed rate is about 8.7 hours. The STR is about 41 kilograms of para-xylene fed per cubic meter of reaction medium per hour. The pressure differential from the bottom of the reaction medium to the overhead off-gas exiting the reaction vessel is about 0.21 megapascal. The upright surface area in contact with the reaction medium is about 975 square meters, which is about 3.18*Wmin*H. The ratio of the volume of reaction medium to upright surface area in contact with the reaction medium is about 1.22 meters. The relatively small value of D produces a superficial velocity of the gas phase at the mid-height of the reaction medium that is about 1.7 times the superficial velocity used in Examples 1 through 5. The gas hold-up at the mid-elevation of the reaction medium is in excess of 0.6. Under conditions of Example 6, it is estimated that decomposition of acetic acid in the reaction medium is desirably reduced below 0.03 kilograms per kilogram of produced CTA. This is owing to the reduced amount of slurry, more specifically acetic acid, in the reaction vessel compared to Example 3.

In this example, the H:W ratio is favorable for reduced end-to-end mixing and for beneficial staging of molecular oxygen and oxidizable compound. However, the axial velocities are higher than Example 1, accelerating end-to-end mixing for a given H:W. Fortunately, the lower STR reduces the volumetric demand for molecular oxygen transfer from gas to liquid; and the increased gas hold-up serves to increase the capability to transfer molecular oxygen from gas to liquid. On balance, the level of production of undesirable, colored byproducts is estimated to be comparable to Example 1.

Example 7

In this example, the reaction vessel is designed for yet higher gas superficial velocities and gas hold-up values according to the present invention. An enlarged, surmounting disengaging zone is used to limit entrainment of slurry in overhead off-gas.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 28 meters at a steady rate using an external de-aeration vessel.

The bubble column reaction vessel includes a vertical, cylindrical section, with the inside diameter equal to 4.60 meters. The height from lower TL to the upper end of the cylindrical section is 60 meters. At the upper end of this cylindrical section, a conical section diverges to an inside diameter of 7 meters while rising in height by 2 meters. The slope of the conical wall is thus about 31 degrees from vertical. Surmounting the conical section is a gas-disengaging cylindrical section with an inside diameter of 7 meters. The height of the upper cylindrical section is 7 meters. The vessel is fitted with 2:1 elliptical heads at the top and bottom. Thus, the combined height of the reaction vessel is about 71.9 meters. The operating level is about 61.2 meters above the bottom of the reaction medium, placing it near the conjunction of the main cylindrical body and the diverging conical section. The feed is again distributed within the reaction vessel near an elevation of 2 meters above the bottom of the reaction medium using a horizontal distributor assembly designed for a substantially uniform release of the feed over the area of cross section lying inside of a radius of 0.45* (inside diameter). The feed of air is again through an oxidant inlet distributor similar to the one shown in FIGS. 12-15, and all of the oxidant admission holes are located below the lower TL of the lower cylindrical section. The reflux solvent is distributed as droplets over essentially all of the cross sectional area of the expanded disengaging section.

The H:W ratio of the reaction medium and the L:D ratio of the reaction vessel are 13.3. The X:D ratio of the reaction vessel is 1.5. The L:Y ratio of the reaction vessel is 5.7. The volume occupied by the reaction medium is about 1,000 cubic meters, and the reaction vessel contains about 320,000 kilograms of slurry. The ratio of slurry mass to para-xylene feed rate is about 6.5 hours. The STR is about 49 kilograms of para-xylene fed per cubic meter of reaction medium per hour. The pressure differential from the bottom of the reaction medium to the overhead off-gas exiting the reaction vessel is about 0.19 megapascal. The upright surface area in contact with the reaction medium is about 896 square meters, which is about 3.19*Wmin*H. The ratio of the volume of reaction medium to upright surface area in contact with the reaction medium is about 1.12 meters. The relatively small value of D produces a superficial velocity of the gas phase at the mid-height of the reaction medium that is about 2 times the superficial velocity used in Examples 1 through 5. However, the superficial velocity of the gas phase in the expanded disengaging section is reduced to about 0.85 times the superficial velocity used in Examples 1 through 5. The gas hold-up at the mid-elevation of the reaction medium is about 0.7. Under conditions of this example, it is estimated that decomposition of acetic acid in the reaction medium is desirably reduced below 0.03 kilograms per kilogram of produced CTA. This is owing to the reduced amount of slurry, more specifically acetic acid, in the reaction vessel compared to Example 3. It is estimated that the level of undesirable colored byproducts is lower than in Example 6 owing to the improved staging and higher gas hold-up.

Example 8

In this example, the reaction vessel is the same as Example 7, but the operating level is raised to be about 63.2 meters above the bottom of the reaction medium, placing it near the conjunction of the diverging conical section and the expanded gas-disengaging cylindrical section. This provides various advantages versus controlling the level in the main cylindrical body section, including a reduced tendency for the top of the reaction medium to be foamy and too poorly circulating.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 28 meters at a steady rate using an external de-aeration vessel.

The H:W ratio of the reaction medium is about 13.7, and the L:D ratio of the reaction vessel is 13.3. The volume occupied by the reaction medium is about 1,060 cubic meters, and the reaction vessel contains about 330,000 kilograms of slurry. The ratio of slurry mass to para-xylene feed rate is about 6.8 hours. The STR is about 46 kilograms of para-xylene fed per cubic meter of reaction medium per hour. The pressure differential from the bottom of the reaction medium to the overhead off-gas exiting the reaction vessel is about 0.20 megapascal. The upright surface area in contact with the reaction medium is about 953 square meters, which is about 3.39*Wmin*H. The ratio of the volume of reaction medium to upright surface area in contact with the reaction medium is about 1.11 meters. The superficial velocity of the gas phase at the mid-height of the reaction medium is about 2 times the superficial velocity used in Examples 1 through 5. The gas hold-up at the mid-elevation of the reaction medium is about 0.7. Under conditions of this example, it is estimated that decomposition of acetic acid in the reaction medium is desirably reduced below 0.03 kilograms per kilogram of produced CTA. This is owing to the reduced amount of slurry, more specifically acetic acid, in the reaction vessel compared to Example 3. It is estimated that the level of undesirable colored byproducts is lower than in Example 6 owing to the improved staging and gas hold-up.

Example 9

In this example, the pressure containing members of the reaction vessel are the same as Example 7, but the internal members used to introduce the oxidant and the para-xylene are importantly modified to provide multiple vertically separated entries for each.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 28 meters at a steady rate using an external de-aeration vessel.

The bubble column reaction vessel includes the same oxidant distributor in the bottom head of the reaction vessel as in Example 8. However, only 70 percent of the total gas-phase oxidant stream is introduced via this lower distributor. The other 30 percent of the gas-phase oxidant is introduced via an elevated oxidant inlet distributor. This flow ratio is imposed by flow control loops using control valves and flow transmitters conveniently located on the supply conduits for the compressed air external to the reaction vessel. The elevated oxidant distributor comprises a horizontal, mitered, square-shaped flow conduit, rather than an octagonal one as is used in the lower elliptical head. The square-shaped conduit conveniently comprises nominal 14-inch Schedule 10S piping materials. The distance from the centroid of one side to the centroid of the opposite side is 1 meter. The elevated oxidant distributor comprises about sixty release holes for gas-phase oxidant, all 0.03 meters in diameter and near the bottom of the conduit about 14 meters above the bottom of the reaction medium. This elevated oxidant distributor serves at least two useful functions. Firstly, the oxidant flow injected downwards into the reaction medium disrupts the axial velocity profile rising along the vertical axis of symmetry of the cylindrical section. This imposes a useful hydraulic baffling to slow the spread of para-xylene into upper regions of the reaction medium, relating to overhead yield loss and to reducing demand for dissolved oxygen in upper regions. A few meters above the elevated oxidant inlet, the natural convention flow pattern re-organizes itself to race upwards along the central axis of symmetry, but the hydraulic baffling is nonetheless efficacious. Secondly, most of the heat of reaction is removed from the reaction medium via the evaporation of solvent, and most of this evaporation occurs near the oxidant feed locations. By separating vertically the location of introduction of parts of the gas-phase oxidant stream, the vertical profile of temperature in the reaction medium is adjusted.

The bubble column reaction vessel includes two para-xylene inlet distributors similar to the one in Example 8. The lower para-xylene inlet distributor is located to provide a substantially uniform release of 50 percent of the liquid-phase feed over the area of cross section lying inside of a radius of 0.45*(inside diameter) at a lower elevation of 2 meters above the bottom of the reaction medium. The upper para-xylene inlet distributor is located to provide a substantially uniform release of 50 percent of the liquid-phase feed over the area of cross section lying inside of a radius of 0.45*(inside diameter) at higher elevation of 10 meters above the bottom of the reaction medium. This flow ratio is imposed by flow control loops using control valves and flow transmitters conveniently located on the supply conduits for the liquid-phase feed external to the reaction vessel.

In this example, the operating level is raised to be about 63.7 meters above the bottom of the reaction medium, placing it just above the diverging conical section and into the expanded gas-disengaging cylindrical section. The H:W ratio of the reaction medium is about 13.8, and the L:D ratio of the reaction vessel is 13.3. The volume occupied by the reaction medium is about 1,070 cubic meters, and the reaction vessel contains about 340,000 kilograms of slurry. The ratio of slurry mass to para-xylene feed rate is about 6.9 hours. The STR is about 46 kilograms of para-xylene fed per cubic meter of reaction medium per hour. The pressure differential from the bottom of the reaction medium to the overhead off-gas exiting the reaction vessel is about 0.20 megapascal. The upright surface area in contact with the reaction medium is about 975 square meters, which is about 3.47*Wmin*H. The ratio of the volume of reaction medium to upright surface area in contact with the reaction medium is about 1.10 meters. The superficial velocity of the gas phase at the mid-height of the reaction medium is about 2 times the superficial velocity used in Examples 1 through 5.

Example 10

In this example, the reaction vessel is designed with three different cylindrical diameters at different elevations, with the mid-elevation diameter being smallest. This configuration benefits the lower cylindrical section, where the liquid feed stream and gas-phase oxidant first enter, with a relatively larger mass of liquid phase for initial dilution and reaction of para-xylene where oxygen is still more abundant; the middle cylindrical section, where molecular oxygen is increasingly depleted, with a relatively greater gas hold-up and gas-to-liquid mass transfer rate; and the top cylindrical section, which is a gas-disengaging zone, with relatively reduced gas-phase velocity to limit entrainment of slurry in overhead off-gas.

The feed rate of para-xylene is again 49,000 kilograms per hour—7 times larger than in Example 1. The other feed flows are increased with the same 7:1 ratio to Example 1. The compositions of the feeds are the same as in Example 1, providing the same concentrations of water, cobalt, bromine and manganese within the liquid phase of the reaction medium as in Example 1. The operating pressure of the reaction vessel overhead gas is again 0.52 megapascal gauge, and the operating temperature is again about 160° C. measured near the mid-elevation of the reaction medium. Reaction medium comprising CTA is removed from the side of the reaction vessel at an elevation of 28 meters at a steady rate using an external de-aeration vessel.

The bubble column includes three vertical, cylindrical sections of different diameters. The lowest cylindrical section has an inside diameter of 6.46 meters, giving a superficial velocity of the gas phase in this section approximately equal to the superficial velocity of Example 1. The height of this lower cylindrical section from lower TL to the upper end is 8 meters. At the upper end of this lower cylindrical section, a conical section converges to an inside diameter of 4.5 meters while rising in height by 1 meter. The slope of this conical wall is thus about 44 degrees from vertical. Surmounting the lower conical section, a middle cylindrical section has an inside diameter of 4.5 meters, giving a superficial velocity of the gas phase in this section about twice the superficial velocity in the lowest cylindrical section. The height of the middle cylindrical section is 45 meters. At the upper end of the middle cylindrical section, a conical section diverges to an inside diameter of 7 meters while rising in height by 2 meters. The slope of the conical wall is thus about 32 degrees from vertical. Surmounting the upper conical diverging section is a gas-disengaging cylindrical section with an inside diameter of 7 meters. The height of the upper cylindrical section is 7 meters. The vessel is fitted with 2:1 elliptical heads at the top and bottom. Thus, the combined height of the reaction vessel is about 66.4 meters. The operating level is about 57.6 meters above the bottom of the reaction medium, placing it near the conjunction of the diverging conical section and the upper cylindrical section. The feed is again distributed within the reaction vessel near an elevation of 2 meters above the bottom of the reaction medium using a horizontal distributor assembly designed for a substantially uniform release of the feed over the area of cross section lying inside of a radius of 0.45*(inside diameter). The feed of air is again through an oxidant inlet distributor similar to the one shown in FIGS. 12-15, and all of the oxidant admission holes are located below the lower TL of the lowest cylindrical section. The reflux solvent is distributed as droplets over essentially all of the cross sectional area of the top cylindrical section.

The volume occupied by the reaction medium is about 1,080 cubic meters, and the reaction vessel contains about 400,000 kilograms of slurry. The ratio of slurry mass to para-xylene feed rate is about 8.1 hours. The STR is about 45 kilograms of para-xylene fed per cubic meter of reaction medium per hour. The pressure differential from the bottom of the reaction medium to the overhead off-gas exiting the reaction vessel is about 0.20 megapascal. The upright surface area in contact with the reaction medium is about 944 square meters, which is about 3.64*Wmin*H and about 2.34*Wmax*H. The ratio of the volume of reaction medium to upright surface area in contact with the reaction medium is about 1.14 meters. The ratio of $L_l:D_l$ is about 1.5:1. The ratio of $L_u:D_u$ is about 10:1. The ratio of $L_l:L_u$ is about 0.21:1. The ratio of $X:D_l$ is about 1.1:1. The ratio of $L_u:Y$ is about 4.2:1. The ratio of $L_l:D_l$ is about 0.15:1.

The larger diameter at the base of the reactor provides a large slurry mass near the introduction zone for the feed para-xylene, where liquid flows and mixing are quite important to provide feed dilution to avoid coupled, colored aromatic impurities. Also, this larger diameter places a larger fraction of the reaction medium under more head pressure from the slurry above, promoting oxygen partial pressure and mass transfer of molecular oxygen from gas to liquid. The smaller diameter, elongated middle cylindrical section provides reactant staging and high gas hold-up; this improves the match of reaction demand for dissolved oxygen with the mass transfer supply from the rising gas phase, wherein oxygen is increasingly consumed and its partial pressure declining.

The invention has been described in detail with particular reference to preferred embodiments thereof, but will be understood that variations and modification can be effected within the spirit and scope of the invention.

We claim:

1. In a slurry bubble column reactor, the improvement comprising:

a vessel shell defining a reaction zone, wherein said reaction zone includes a normally-lower section having a first maximum horizontal cross-sectional area and a normally-upper section having a second maximum horizontal cross-sectional area, wherein said first maximum cross-sectional area is at least about 10 percent greater than said second maximum cross-sectional area; and a slurry outlet configured to substantially continuously withdraw slurry from said reaction zone;

wherein said normally-upper and normally-lower sections are substantially cylindrical and wherein said normally-lower section has a maximum height ($L_l$), a maximum diameter ($D_l$), and an $L_l:D_l$ ratio of at least about 0.5:1, wherein said normally-upper section has a maximum height ($L_u$), a minimum diameter ($D_u$), and an $L_u:D_u$ ratio of at least about 2:1; and wherein said reactor defines a disengagement zone located above said reaction zone, wherein said disengagement section has a maximum diameter (X), wherein said reactor has an $X:D_l$ ratio in the range of from about 0.8:1 to about 4:1.

2. The slurry bubble column reactor of claim 1 wherein said first maximum cross-sectional area is at least about 20 percent greater than said second maximum cross-sectional area.

3. The slurry bubble column reactor of claim 1 wherein said first maximum cross-sectional area in the range of from 30 to 150 percent greater than said second maximum cross-sectional area.

4. The slurry bubble column reactor of claim 1, wherein said $L_l:D_l$ ratio is in the range of from about 1:1 to about 10:1 and said $L_u:D_u$ ratio is in the range of from about 2.5:1 to about 20:1.

5. The slurry bubble column reactor of claim 1, wherein said $L_l$ is at least about 4 meters and said $L_u$ is at least about 4 meters, wherein the $L_l:L_u$ ratio is in the range of from about 0.05:1 to about 5:1.

6. The slurry bubble column reactor of claim 1, wherein said $L_l$ is in the range of from about 4 to about 50 meters and said $L_u$ in the range of from about 5 to about 80 meters, wherein the $L_l:L_u$ ratio is in the range of from about 0.1:1 to about 2.5:1.

7. The slurry bubble column reactor of claim 1, wherein said normally-upper and normally-lower sections are substantially aligned along a common central normally-upright axis.

8. The slurry bubble column reactor of claim 1, wherein said reaction zone further includes a transition section disposed between said upper and lower sections, wherein said transition section has a maximum diameter of $D_l$ and a minimum diameter of $D_u$.

* * * * *

UNITED STATES PATENT AND TRADEMARK OFFICE
CERTIFICATE OF CORRECTION

| | | |
|---|---|---|
| PATENT NO. | : 8,114,356 B2 | Page 1 of 1 |
| APPLICATION NO. | : 12/490442 | |
| DATED | : February 14, 2012 | |
| INVENTOR(S) | : Alan George Wonders et al. | |

It is certified that error appears in the above-identified patent and that said Letters Patent is hereby corrected as shown below:

On the title page, Item (75), the fourth inventor's name is omitted. Item (75) should read:

-- (75) Inventors: Alan George Wonders, Kingsport, TN (US); Lee Reynolds Partin, Kingsport, TN (US); Wayne Scott Strasser, Kingsport, TN (US); Marcel de Vreede, Barendrecht, (NL) --

Signed and Sealed this
Eighteenth Day of December, 2012

David J. Kappos
*Director of the United States Patent and Trademark Office*